(12) United States Patent
Bradner et al.

(10) Patent No.: US 10,407,441 B2
(45) Date of Patent: *Sep. 10, 2019

(54) COMPOSITIONS AND METHODS FOR TREATING NEOPLASIA, INFLAMMATORY DISEASE AND OTHER DISORDERS

(71) Applicant: Dana-Farber Cancer Institute, Inc., Boston, MA (US)

(72) Inventors: James Elliott Bradner, Weston, MA (US); Jun Qi, Sharon, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/886,559

(22) Filed: Feb. 1, 2018

(65) Prior Publication Data

US 2018/0237454 A1      Aug. 23, 2018

Related U.S. Application Data

(63) Continuation of application No. 15/061,576, filed on Mar. 4, 2016, now abandoned, which is a continuation of application No. 14/502,840, filed on Sep. 30, 2014, now Pat. No. 9,320,741, which is a continuation of application No. 13/698,010, filed as application No. PCT/US2011/036701 on May 16, 2011, now Pat. No. 8,981,083.

(60) Provisional application No. 61/334,991, filed on May 14, 2010, provisional application No. 61/370,745, filed on Aug. 4, 2010, provisional application No. 61/375,863, filed on Aug. 22, 2010, provisional application No. 61/467,376, filed on Mar. 24, 2011.

(51) Int. Cl.
| | | |
|---|---|---|
| *A61K 31/551* | (2006.01) | |
| *A61P 35/00* | (2006.01) | |
| *C07D 495/14* | (2006.01) | |
| *C07D 487/04* | (2006.01) | |
| *C07D 495/12* | (2006.01) | |
| *C07D 519/00* | (2006.01) | |
| *A61K 31/5517* | (2006.01) | |

(52) U.S. Cl.
CPC .......... *C07D 495/14* (2013.01); *A61K 31/551* (2013.01); *A61K 31/5517* (2013.01); *A61P 35/00* (2018.01); *C07D 487/04* (2013.01); *C07D 495/12* (2013.01); *C07D 519/00* (2013.01); *Y02A 50/411* (2018.01)

(58) Field of Classification Search
CPC .... A61K 31/5517; A61K 31/551; A61P 35/00
See application file for complete search history.

(56) References Cited

U.S. PATENT DOCUMENTS

| | | |
|---|---|---|
| 3,681,343 A | 8/1972 | Hester, Jr. |
| 3,709,898 A | 1/1973 | Hester, Jr. |
| 3,812,259 A | 5/1974 | Collins |
| 4,621,083 A | 11/1986 | Casals-Stenzel et al. |
| 5,104,543 A | 4/1992 | Brandt et al. |
| 5,593,988 A | 1/1997 | Tahara et al. |
| 5,712,274 A | 1/1998 | Sueoka et al. |
| 5,721,231 A | 2/1998 | Moriwaki et al. |
| 5,753,649 A | 5/1998 | Tahara et al. |
| 5,760,032 A | 6/1998 | Kitajima et al. |
| 5,854,238 A | 12/1998 | Kempen |
| 6,444,664 B1 | 9/2002 | Princen et al. |
| 6,861,422 B2 | 3/2005 | Hoffmann et al. |
| 7,015,213 B1 | 3/2006 | Bigg et al. |
| 7,528,143 B2 | 5/2009 | Noronha et al. |
| 7,528,153 B2 | 5/2009 | Aerts |
| 7,589,167 B2 | 9/2009 | Zhou et al. |
| 7,750,152 B2 | 7/2010 | Hoffman et al. |
| 7,786,299 B2 | 8/2010 | Hoffmann et al. |
| 7,816,530 B2 | 10/2010 | Grauert |
| 7,825,246 B2 | 11/2010 | Noronha et al. |
| 8,003,786 B2 | 8/2011 | Hoffmann et al. |
| 8,044,042 B2 | 10/2011 | Adachi et al. |
| 8,133,900 B2 | 3/2012 | Hood et al. |
| 8,138,199 B2 | 3/2012 | Noronha et al. |
| 8,338,464 B2 | 12/2012 | Melnick et al. |
| 8,476,260 B2 | 7/2013 | Miyoshi et al. |
| 8,604,042 B2 | 12/2013 | Noronha et al. |
| 8,981,083 B2 * | 3/2015 | Bradner ............ C07D 487/04 540/560 |
| 9,301,962 B2 | 4/2016 | Bradner et al. |
| 9,320,711 B2 | 4/2016 | Natoli et al. |

(Continued)

FOREIGN PATENT DOCUMENTS

| | | |
|---|---|---|
| CA | 2020806 A1 | 1/1991 |
| CA | 2710740 A1 | 7/2009 |

(Continued)

OTHER PUBLICATIONS

*Final Rejection for U.S. Appl. No. 13/697,963, "Compositions and Methods for Modulating Metabolism," dated Aug. 21, 2015.

(Continued)

*Primary Examiner* — Theodore R. West
(74) *Attorney, Agent, or Firm* — Foley Hoag LLP

(57) ABSTRACT

The invention features compositions and methods for treating or preventing a neoplasia. More specifically, the invention provides compositions and methods for disrupting the interaction of a BET family polypeptide comprising a bromodomain with chromatin (e.g., disrupting a bromodomain interaction with an acetyl-lysine modification present on a histone N-terminal tail).

18 Claims, 77 Drawing Sheets

Specification includes a Sequence Listing.

(56) References Cited

U.S. PATENT DOCUMENTS

| | | | |
|---|---|---|---|
| 9,320,741 B2 * | 4/2016 | Bradner | C07D 487/04 |
| 9,763,956 B2 | 9/2017 | Bernstein et al. | |
| 9,789,120 B2 | 10/2017 | Bradner et al. | |
| 9,815,849 B2 | 11/2017 | Bradner et al. | |
| 10,124,009 B2 | 11/2018 | Landau et al. | |
| 2002/0032200 A1 | 3/2002 | Cai et al. | |
| 2002/0169158 A1 | 11/2002 | Hunt et al. | |
| 2003/0130268 A1 | 7/2003 | Sagara et al. | |
| 2003/0216758 A1 | 11/2003 | Signore | |
| 2004/0043378 A1 | 3/2004 | Zhou et al. | |
| 2004/0176380 A1 | 9/2004 | Hoffmann et al. | |
| 2006/0074088 A1 | 4/2006 | Munzert et al. | |
| 2006/0142257 A1 | 6/2006 | Nieschlag et al. | |
| 2006/0223055 A1 | 10/2006 | Howley et al. | |
| 2007/0105839 A1 | 5/2007 | Imbach et al. | |
| 2007/0111933 A1 | 5/2007 | Kopchick et al. | |
| 2007/0179178 A1 | 8/2007 | Buettelmann et al. | |
| 2007/0218135 A1 | 9/2007 | Mukharya et al. | |
| 2008/0004308 A1 | 1/2008 | Dhanak et al. | |
| 2008/0081781 A1 | 4/2008 | Lippa et al. | |
| 2008/0305113 A1 | 12/2008 | Kwon et al. | |
| 2009/0012064 A1 | 1/2009 | Sagara et al. | |
| 2009/0238828 A1 | 9/2009 | Munzert et al. | |
| 2009/0280115 A1 | 11/2009 | Maier et al. | |
| 2009/0281191 A1 | 11/2009 | Rangwala et al. | |
| 2010/0041643 A1 | 2/2010 | Adachi et al. | |
| 2010/0227838 A1 | 9/2010 | Shah et al. | |
| 2010/0249412 A1 | 9/2010 | Linz et al. | |
| 2010/0286127 A1 * | 11/2010 | Miyoshi | C07D 495/14 |
| | | | 514/220 |
| 2011/0028405 A1 | 2/2011 | Harrison et al. | |
| 2011/0098288 A1 | 4/2011 | Major et al. | |
| 2011/0172231 A1 | 7/2011 | Baenteli et al. | |
| 2011/0201606 A1 | 8/2011 | Garcia-Echeverria et al. | |
| 2011/0212077 A1 | 9/2011 | Noronha et al. | |
| 2011/0245245 A1 | 10/2011 | Mortensen et al. | |
| 2012/0014979 A1 | 1/2012 | Dent | |
| 2012/0040961 A1 | 2/2012 | Gray et al. | |
| 2012/0202798 A1 | 8/2012 | Sagara et al. | |
| 2012/0244209 A1 | 9/2012 | Roth et al. | |
| 2012/0329803 A1 | 12/2012 | Linz et al. | |
| 2013/0184264 A1 | 7/2013 | Bradner et al. | |
| 2013/0210813 A1 | 8/2013 | Bradner et al. | |
| 2013/0245013 A1 | 9/2013 | Mohr et al. | |
| 2013/0252331 A1 | 9/2013 | Bradner et al. | |
| 2013/0261109 A1 | 10/2013 | Miyoshi et al. | |
| 2013/0274239 A1 | 10/2013 | Gangloff et al. | |
| 2013/0280332 A1 | 10/2013 | Moss et al. | |
| 2014/0011862 A1 | 1/2014 | Bradner et al. | |
| 2014/0243322 A1 | 8/2014 | Arnold et al. | |
| 2015/0335656 A1 | 11/2015 | Miyoshi et al. | |
| 2016/0033519 A1 | 2/2016 | Bradner et al. | |
| 2016/0168154 A1 | 6/2016 | Marineau et al. | |
| 2016/0231314 A1 | 8/2016 | Ryan et al. | |
| 2016/0279141 A1 | 9/2016 | Bradner et al. | |
| 2016/0332993 A1 | 11/2016 | Bradner et al. | |
| 2016/0347749 A1 | 12/2016 | Bradner et al. | |
| 2017/0008895 A1 | 1/2017 | Bradner et al. | |
| 2017/0029437 A1 | 2/2017 | Bradner et al. | |
| 2017/0209461 A1 | 7/2017 | Landau et al. | |
| 2017/0333444 A1 | 11/2017 | Landau et al. | |
| 2017/0360801 A1 | 12/2017 | Sotomayor et al. | |
| 2018/0193350 A1 | 7/2018 | Landau et al. | |
| 2018/0222917 A1 | 8/2018 | Bradner et al. | |
| 2018/0237454 A1 | 8/2018 | Bradner et al. | |

FOREIGN PATENT DOCUMENTS

| | | |
|---|---|---|
| CH | 622019 A5 | 3/1981 |
| CN | 1227555 A | 9/1999 |
| CN | 100348600 C | 11/2007 |
| CN | 101910182 A | 12/2010 |
| CN | 103037865 A | 4/2013 |
| DE | 3724164 A1 | 1/1988 |
| EP | 0 087 850 A1 | 9/1983 |
| EP | 0 368 175 A1 | 5/1990 |
| EP | 0 387 613 A1 | 9/1990 |
| EP | 0 934 940 A1 | 8/1999 |
| EP | 0 989 131 A1 | 3/2000 |
| EP | 1 297 836 A1 | 4/2003 |
| EP | 1 887 008 A1 | 2/2008 |
| EP | 2 239 264 A1 | 10/2010 |
| FR | 2329668 A1 | 5/1977 |
| JP | 1-299231 | 12/1989 |
| JP | 6-157316 | 6/1994 |
| JP | H10500998 A | 1/1998 |
| JP | 11-228576 | 8/1999 |
| JP | 11-512107 | 10/1999 |
| JP | 3001979 B2 | 1/2000 |
| JP | 3096299 B2 | 10/2000 |
| JP | 2006519236 A | 8/2006 |
| JP | 2008/156311 A | 7/2008 |
| JP | 2013510123 A | 3/2013 |
| JP | 2013/532130 A | 8/2013 |
| JP | 5913292 B2 | 4/2016 |
| JP | 61-87684 B2 | 8/2017 |
| KR | 10-2000-0016732 | 3/2000 |
| RU | 2294761 C2 | 3/2007 |
| TW | 201217382 A | 5/2012 |
| WO | WO-97/47622 A1 | 12/1997 |
| WO | WO-98/11111 A1 | 3/1998 |
| WO | WO-01/95912 A1 | 12/2001 |
| WO | WO-2006/129623 A1 | 12/2006 |
| WO | WO-2007/056117 A1 | 5/2007 |
| WO | WO-2007/095188 A2 | 8/2007 |
| WO | WO-2008/083056 A2 | 7/2008 |
| WO | WO-2008/137081 A1 | 11/2008 |
| WO | WO-2009084693 A1 * | 7/2009 ........... C07D 495/14 |
| WO | WO-2010/015387 A1 | 2/2010 |
| WO | WO-2010/049466 A1 | 5/2010 |
| WO | WO-2011/054553 A1 | 5/2011 |
| WO | WO-2011/054841 A1 | 5/2011 |
| WO | WO-2011/054843 A1 | 5/2011 |
| WO | WO-2011/054844 A1 | 5/2011 |
| WO | WO-2011/054845 A1 | 5/2011 |
| WO | WO-2011/054846 A1 | 5/2011 |
| WO | WO-2011/054848 A1 | 5/2011 |
| WO | WO-2011/143651 A1 | 11/2011 |
| WO | WO-2011/143657 A1 | 11/2011 |
| WO | WO-2011/143660 A2 | 11/2011 |
| WO | WO-2011/143669 A2 | 11/2011 |
| WO | WO-2011/161031 A1 | 12/2011 |
| WO | WO-2012/050907 A2 | 4/2012 |
| WO | WO-2012/075383 A2 | 6/2012 |
| WO | WO-2012/075456 A1 | 6/2012 |
| WO | WO-2012/095505 A1 | 7/2012 |
| WO | WO-2012/116170 A1 | 8/2012 |
| WO | WO-2012/118812 A2 | 9/2012 |
| WO | WO-2013/019710 A1 | 2/2013 |
| WO | WO-2013/033268 A2 | 3/2013 |
| WO | WO-2013/033269 A1 | 3/2013 |
| WO | WO-2013/033270 A2 | 3/2013 |
| WO | WO-2013/033420 A1 | 3/2013 |
| WO | WO-2013/097601 A1 | 7/2013 |
| WO | WO-2013/148197 A1 | 10/2013 |
| WO | WO-2013/192274 A2 | 12/2013 |
| WO | WO-2014/068402 A2 | 5/2014 |
| WO | WO-2014/071247 A1 | 5/2014 |
| WO | WO-2014/128070 A1 | 8/2014 |
| WO | WO-2014/128111 A1 | 8/2014 |
| WO | WO-2014/134583 A2 | 9/2014 |
| WO | WO-2014/144721 A2 | 9/2014 |
| WO | WO-2014/159392 A1 | 10/2014 |
| WO | WO-2014/193951 A1 | 12/2014 |
| WO | WO-2015/018521 A1 | 2/2015 |
| WO | WO-2015/018522 A1 | 2/2015 |
| WO | WO-2015/023938 A1 | 2/2015 |
| WO | WO-2015/054642 A2 | 4/2015 |
| WO | WO-2015/070020 A2 | 5/2015 |
| WO | WO-2015/081284 A1 | 6/2015 |
| WO | WO-2015/131113 A1 | 9/2015 |

(56) References Cited

FOREIGN PATENT DOCUMENTS

| WO | WO-2016/069578 A1 | 5/2016 |
|---|---|---|
| WO | WO-2016/210275 A1 | 12/2016 |
| WO | WO-2017/059319 A2 | 4/2017 |

OTHER PUBLICATIONS

*Final Rejection for U.S. Appl. No. 13/697,963, "Compositions and Methods for Modulating Metabolism," dated Jan. 18, 2017.
*Final Rejection for U.S. Appl. No. 13/934,843, "Compositions and Methods for Treating Leukemia," dated Oct. 30, 2015.
*Non-Final Rejection for U.S. Appl. No. 13/697,963, "Compositions and Methods for Modulating Metabolism," dated May 31, 2016.
*Non-Final Rejection for U.S. Appl. No. 13/934,843, "Compositions and Methods for Treating Leukemia," dated Jan. 25, 2017.
*Non-Final Rejection for U.S. Appl. No. 14/977,343, "Male Contraceptive Compositions and Methods of Use," dated Aug. 24, 2016.
*Non-Final Rejection for U.S. Appl. No. 15/034,922, "Combination Therapy for Cancer Using Bromodomain and Extra-Terminal (Bet) Protein Inhibitors," dated Mar. 8, 2018.
*Non-Final Rejection for U.S. Appl. No. 15/061,576, "Compositions and Methods for Treating Neoplasia, Inflammatory Disease and Other Disorders," dated Aug. 2, 2017.
*Non-Final Rejection for U.S. Appl. No. 15/121,964, "Treatment of Conditions Associated with Hyperinsulinaemia," dated Oct. 4, 2017.
*Notice of Allowance for U.S. Appl. No. 14/977,343, "Male Contraceptive Compositions and Methods of Use," dated Jun. 16, 2017.
*Notice of Allowance for U.S. Appl. No. 13/698,006, "Male Contraceptive Compositions and Methods of Use," dated Sep. 3, 2015.
*Notice of Allowance for U.S. Appl. No. 13/934,843 dated Jul. 13, 2017.
*Notice of Allowance for U.S. Appl. No. 14/977,343, "Male Contraceptive Compositions and Methods of Use," dated Feb. 13, 2017.
*Notice of Allowance, U.S. Appl. No. 13/698,010, dated Aug. 21, 2014.
*Notice of Allowance, U.S. Appl. No. 14/502,840, dated Dec. 4, 2015.
*Office Action, U.S. Appl. No. 13/697,963, dated Nov. 21, 2014.
*Office Action, U.S. Appl. No. 13/698,006, dated Apr. 10, 2014.
*Office Action, U.S. Appl. No. 13/698,006, dated Oct. 23, 2014.
*Office Action, U.S. Appl. No. 13/698,006, Dated: Sep. 26, 2013.
*Office Action, U.S. Appl. No. 13/934,843, Dated: Mar. 23, 2015.
*Office Action, U.S. Appl. No. 15/522,222, dated Mar. 2, 2018.
*Requirement for Restriction/Election for U.S. Appl. No. 13/697,963, "Compositions and Methods for Modulating Metabolism," dated Mar. 20, 2014.
*Requirement for Restriction/Election for U.S. Appl. No. 13/934,843, "Compositions and Methods for Treating Leukemia," dated Jul. 1, 2014.
*Requirement for Restriction/Election for U.S. Appl. No. 15/034922, "Combination Therapy for Cancer Using Bromodomain and Extra-Terminal (BET) Protein Inhibitors," dated Apr. 21, 2017.
*Requirement for Restriction/Election for U.S. Appl. No. 15/061,576, "Compositions and Methods for Treating Neoplasia, Inflammatory Disease and Other Disorders," dated Feb. 15, 2017.
*Requirement for Restriction/Election for U.S. Appl. No. 15/886,559 dated Jul. 16, 2018.
Abbate, et al., "Structure of the papillomavirus DNA-tethering complex E2:Brd4 and a peptide that ablates HPV chromosomal association," Mol Cell, 24(6): 877-889, (2006).
Acosta et al., "Amifostine Impairs p53-mediated Apoptosis of Human Myeloid Leukemia Cells," Molecular Cancer Therapeutics, 2: 893-900 (2003).
Anders et al., "Genome-wide Localization of Small Molecules," Nat Biotechnol, 32(1): 92-96 (2014).

Arango, et al., "Reversible Azoospermia in a Patient Treated with Triazolam," Eur J Contracept Reprod Health Care, 1(3): 293-294 (1996).
Bartholomeeusen et al., "Bromodomain and Extra-terminal (BET) Bromodomain Inhibition Activate Transcription via Transient Release of Positive Transcription Elongation Factor b (P-TEFb) from 75K Small Nuclear Ribonucleoprotein," J Biol Chem, 287(43): 36609-36619 (2012).
Baud et al., "Chemical Biology. A Bump-and-hole Approach to Engineer Controlled Selectivity of BET Bromodomain Chemical Probes," Science, 346(6209): 638-641 (2014).
Bendas et al., "Cancer Cell Adhesion and Metastasis: Selectins, Integrins, and the Inhibitory Potential of Heparins," International Journal of Cell Biology, 2012:1-10 (2012).
Berge et al., "Pharmaceutical Salts," J Pharm Sci, 66(1): 1-19 (1977).
Berkovits, et al., "The First Bromodomain of the Testis-Specific Double Bromodomain Protein Brdt is Required for Chromocenter Organization That is Modulated by Genetic Background," Dev Biol, 360(2): 358-368 (2011).
Berkovits, et al., "The Role of the Double Bromodomain-Containing BET Genes During Mammalian Spermatogenesis," Curr Top Dev Biol, 102: 293-326 (2013).
Buchdunger, et al., "Inhibition of the Abl Protein-Tyrosine Kinase In Vitro and In Vivo by A 2-Phenylaminopyrimidine Derivative," Cancer Res, 56(1): 100-104 (1996).
Buchdunger, et al., "Selective inhibition of the platelet-derived growth factor signal transduction pathway by a protein-tyrosine kinase inhibitor of the 2-phenylaminopyrimidine class," Proc Natl Acad Sci, 92(7): 2558-2562 (1995).
Bullock, et al., "Structural Basis of Inhibitor Specificity of the Human Protooncogene Proviral Insertion Site in Moloney Murine ILeukemia Virus (PIM-1) kinase," J Med Chem, 48(24): 7604-7614 (2005).
Cellai, et al., "Mechanistic Insight Into WEB-2170-induced Apoptosis in Human Acute Myelogenous Leukemia Cells: the Crucial Role of PTEN," Exp Hematol, 37(10): 1176-1185 (2009).
Cellai, et al., "Specific PAF Antagonist WEB-2086 Induces Terminal Differentiation of Murine and Human Leukemia Cells," FASEB J, 16(7): 635-759 (2002).
Chaidos et al., "Protent Antimyeloma Activity of the Novel Bromodomain Inhibitors I-BET151 and I-BET762," Blood, 123(5): 697-705 (2014).
Cheng et al., "Adjudin Disrupts Spermatogenesis via the Action of Some Unlikely Partners: Eps8, Arp2/3 complex, drebrin E, PAR6 and 14-3-3," Spermatogenesis, 1(4): 291-297 (2011).
Chesi et al., "Drug Response in a Genetically Engineered Mouse Model of Multiple Myeloma is Predictive of Clinical Efficacy," Blood, 120(2): 376-385 (2012).
Choi et al., "Brain Penetrant LRRK2 Inhibitor," ACS Med Chem Lett, 3(8): 658-662 (2012).
Cole, "Chemical probes for histone-modifying enzymes," Nat Chem Biol, 4: 590-597 (2008).
Crawford, et al., "Bromodomain 4 activation predicts breast cancer survival," Proc Natl Acad Sci, 105(17): 6380-6385 (2008).
Dawson et al., "Inhibition of BET Recruitment to Chromatin as an Effective Treatment for MLL-fusion Leukaemia," Nature, 478(7370): 529-533 (2011).
Delbroek et al., "Development of an Enzyme-linked Immunosorbent Assay for Detection of Cellular and in Vivo LRRK2 S935 Phosphorylation," J Pharm Biomed Anal, 76: 49-58 (2013).
Delmore et al., "BET Bromodomain Inhibition as a Therapeutic Strategy to Target c-Myc," Cell, 146(6): 904-917 (2011).
Deng et al., "Structural Determinants for ERK5 (MAPK7) and Leucine Rich Repeat Kinase 2 Activities of Benzo[e]pyrimido-[5,4-b]diazepine-6(11H)-ones," Eur J Med Chem, 70: 758-767 (2013).
Denis, et al., "An Emerging Role for Bromodomain-Containing Proteins in Chromatin Regulation and Transcriptional Control of Adipogenesis," FEBS Lett, 584(15): 3260-3268 (2010).
Dey, et al., "Brd4 Marks Select Genes on Mitotic Chromatin and Directs Postmitotic Transcription," Mol Biol Cell, 20(23): 4899-4909 (2009).

(56) References Cited

OTHER PUBLICATIONS

Diamanti-Kandarakis et al., "Therapeutic Effects of Metformin on Insulin Resistance and Hyperandrogenism in Polycystic Ovary Syndrome," European Journal of Endocrinology, 138: 269-274 (1998).
Dittmann et al., "The Commonly Used PI3-Kinase Probe LY294002 Is an Inhibitor of BET Bromodomains," ACS Chem Biol, 9(2):495-502 (2014).
Druker, et al., "Effects of a selective inhibitor of the Abl tyrosine kinase on the growth of Bcr-Abl positive cells," Nat Med, 2(5): 561-566 (1996).
Druker, et al., "Efficacy and safety of a specific inhibitor of the BCR-ABL tyrosine kinase in chronic myeloid leukemia," N Engl J Med, 344: 1031-1037 (2001).
Elkins et al., "X-ray Crystal Structure of ERK5 (MAPK7) in Complex with a Specific Inhibitor," J Med Chem, 56(11): 4413-4421 (2013).
Examination Report, AU Application No. 2011252808, dated: Aug. 5, 2013.
Extended European Search Report for European Patent Application No. 14860080.2 dated May 3, 2017.
Extended European Search Report for European Patent Application No. EP14828728 dated Jan. 31, 2017.
Fedorov, et al., "A Systematic Interaction Map of Validated Kinase Inhibitors with Ser/Thr kinases," Proc Natl Acad Sci, 104(51): 20523-20528 (2007).
Filippakopoulos et al., "Targeting Bromodomains: Epigenetic Readers of Lysine Acetylation," Nat Rev Drug Discov, 13(5): 337-356 (2014).
Filippakopoulos, et al., "Selective Inhibition of BET Bromodomains," Nature, 468(7327): 1067-1073 (2010).
French, "Demystified Molecular pathology of NUT Midline Carcinomas," J Clin Pathol, 63: 492-496 (2010).
French, et al. "BRD4-NUT Fusion Oncogene: a Novel Mechanism in Aggressive Carcinoma," Cancer Res, 63(2): 304-307 (2003).
French, et al., "BRD-NUT Oncoproteins: a Family of Closely Related Nuclear Proteins that Block Epithelial Differentiation and Maintain the Growth of Carcinoma Cells," Oncogene, 27: 2237-2242 (2008).
French, et al., "BRD4 Bromodomain Gene Rearrangement in Aggressive Carcinoma with Translocation t(15;19)," Am J Pathol, 159(6): 1987-1992 (2001).
GENBANK Submission; NH/NCBI, Accession No. H86170.
GENBANK Submission; NH/NCBI, Accession No. NP_001003694.
GENBANK Submission; NH/NCBI, Accession No. NP_001420.
GENBANK Submission; NH/NCBI, Accession No. NP_001717.
GENBANK Submission; NH/NCBI, Accession No. NP_003061.
GENBANK Submission; NH/NCBI, Accession No. NP_003063.
GENBANK Submission; NH/NCBI, Accession No. NP_003843.
GENBANK Submission; NH/NCBI, Accession No. NP_003875.
GENBANK Submission; NH/NCBI, Accession No. NP_004371.
GENBANK Submission; NH/NCBI, Accession No. NP_004597.
GENBANK Submission; NH/NCBI, Accession No. NP_005095.
GENBANK Submission; NH/NCBI, Accession No. NP_005753.
GENBANK Submission; NH/NCBI, Accession No. NP_009168.
GENBANK Submission; NH/NCBi, Accession No. NP_031397.
GENBANK Submission; NH/NCBI, Accession No. NP_038478.
GENBANK Submission; NH/NCBI, Accession No. NP_054828.
GENBANK Submission; NH/NCBI, Accession No. NP_055392.
GENBANK Submission; NH/NCBI, Accession No. NP_060404.
GENBANK Submission; NH/NCBI, Accession No. NP_060635.
GENBANK Submission; NH/NCBI, Accession No. NP_060959.
GENBANK Submission; NH/NCBI, Accession No. NP_061836.
GENBANK Submission; NH/NCBI, Accession No. NP_066564.
GENBANK Submission; NH/NCBI, Accession No. NP_076413.
GENBANK Submission; NH/NCBI, Accession No. NP_612411.
GENBANK Submission; NH/NCBI, Accession No. NP_722516.
GENBANK Submission; NH/NCBI, Accession No. NP_872579.
GENBANK Submission; NH/NCBI Accession No. NT_039676.

Gonzalez-Barrosa et al., "Mutations in UCP2 in Congenital Hyperinsulism Reveal a Role for Regulation of Insulin Secretion," PLoS One, 3(1): 1-8 (2008).
Greenwald, et al., "Eμ-BRD2 Transgenic Mice Develop B-Cell Lymphoma and Leukemia," Blood, 103(4): 1475-1484 (2004).
Haack, et al., "Diagnosis of NUT Midline Carcinoma Using a NUT-specific Monoclonal Antibody," Am J Surg Pathol, 33(7): 984-991 (2009).
He et al., "The Histone Methyltransferase Ezh2 is a Crucial Epigenetic Regulator of Allogeneic T-cell Responses Mediating Graft-versus-host Disease," Blood, 122(25): 4119-4128 (2013).
Hedrington et al., "Effects of Antecedent GABAA Activation with Alprazolam on Counterregulatory Responses to Hypoglycemia in Healthy Humans," Diabetes, 59(4): 1074-1081 (2010).
Houzelstein et al., "Growth and Early Postimplantation Defects in Mice Deficient for the Bromodomain-containing Protein Brd4," Mol Cell Biol, 22(11): 3794-3802 (2002).
Hsu et al., "Metabolic Syndrome, Hyperinsulinemia and Cancer," The American Journal of Clinical Nutrition, 86(3): 867S-871S (2007).
Hu, et al., "Adjudin Targeting Rabbit Germ Cell Adhesion as a Male Contraceptive: A Pharmacokinetics Study," J Androl, 30(1): 87-93 (2009).
Huang, et al., "Brd4 Coactivates Transcriptional Activation of NF-κB via Specific Binding to Acetylated RelA," Mol Cell Biol, 29(5): 1375-1387 (2009).
International Preliminary Report on Patentability for International Application No. PCT/US14/64549 dated May 10, 2016.
International Preliminary Report on Patentability for International Application No. PCT/US2015/018118 dated Sep. 6, 2016.
International Preliminary Report on Patentability for International Application No. PCT/US2015/057538 dated May 2, 2017.
International Preliminary Report on Patentability for International Application No. PCT/US2016/039270 dated Dec. 26, 2017.
International Preliminary Report on Patentability for International Application No. PCT/US2016/054924 dated Apr. 3, 2018.
International Preliminary Report on Patentability for PCT/US2014/023386, dated Sep. 15, 2015.
International Preliminary Report on Patentability for PCT/US2014/48230, dated Jan. 26, 2016.
International Preliminary Report on Patentability for PCT/US2015/044180, dated Feb. 14, 2017.
International Preliminary Report on Patentability for PCT/US2015/044303, dated Feb. 14, 2017.
International Preliminary Report on Patentability for PCT/US2015/14039, dated Aug. 2, 2016.
International Preliminary Report on Patentability for PCT/US2015/14044, dated Aug. 2, 2016.
International Preliminary Report on Patentability for PCT/US2015/14109, dated Aug. 2, 2016.
International Preliminary Report on Patentability for PCT/US2015/14120, dated Aug. 2, 2016.
International Search Report and Written Opinion for International Application No. PCT/US14/64549 dated Mar. 11, 2015.
International Search Report and Written Opinion for International Application No. PCT/US2015/018118 dated May 19, 2015.
International Search Report and Written Opinion for International Application No. PCT/US2015/057538 dated Jan. 21, 2016.
International Search Report and Written Opinion for International Application No. PCT/US2016/039270 dated Oct. 18, 2016.
International Search Report and Written Opinion for International Application No. PCT/US2016/054924 dated Sep. 5, 2017.
International Search Report for International Application No. PCT/US2014/023386 dated Jul. 9, 2014.
International Search Report for International Application No. PCT/US2014/14120, dated Apr. 23, 2015.
International Search Report for International Application No. PCT/US2014/48230, dated Jan. 30, 2015.
International Search Report for International Application No. PCT/US2015/044180, dated Nov. 5, 2015.
International Search Report for International Application No. PCT/US2015/044303, dated Dec. 31, 2015.

(56) References Cited

OTHER PUBLICATIONS

International Search Report for International Application No. PCT/US2015/059551, dated Jan. 13, 2016.
International Search Report for International Application No. PCT/US2015/059622, dated Mar. 30, 2016.
International Search Report for International Application No. PCT/US2015/14039, dated Apr. 23, 2015.
International Search Report for International Application No. PCT/US2015/14044, dated Apr. 23, 2015.
International Search Report for International Application No. PCT/US2015/14109, dated Jul. 6, 2015.
International Search Report for International Application No. PCT/US2016/051017, dated Jan. 10, 2017.
International Search Report for International Application No. PCT/US2016/051107, dated Nov. 22, 2016.
Kadota, et al. "Identification of Novel Gene Amplifications in Breast Cancer and Coexistence of Gene Amplification With an Activating Mutation of PIK3CA," Cancer Res, 69(18): 7357-7365 (2009).
Kavanagh et al., "The Development of CNS-active LRRK2 Inhibitors Using Property-directed Optimisation," Bioorg Med Chem Lett, 23(13): 3690-3696 (2013).
Kim, et al., "Berberine Improves Lipid Dysregulation in Obesity by Controlling Central and Peripheral AMPK Activity," Am J Physiol Endocrinol Metab, 296(4): E812-E819 (2009).
Konze et al., "An Orally Bioavailable Chemical Probe of the Lysine Methyltransferases EZH2 and EZH1," ACS Chem Biol, 8(6): 1324-1334 (2013).
Krueger et al., "The Mechanism of Release of P-TEFb and HEXIM1 from the 7SK snRNP by Viral and Cellular Activators Includes a Conformational change in 7SK," PLoS One, 5(8): e12335 (2010).
Lawless, et al., "Histone Deacetylase Inhibitors Target Diabetes Via Chromatin Remodeling or as Chemical Chaperones?" Curr Diabetes Rev, 5(3): 201-209 (2009).
le Coutre, et al., "In vivo eradication of human BCR/ABL-positive leukemia cells with an ABL kinase inhibitor," J Natl Cancer Inst, 91(2): 163-168 (1999).
Lee et al., "Synergistic effect of JQ1 and rapamycin for treatment of human osteosarcoma," Int J Cancer, 136(9):2055-2064 (2014).
Lee, et al., "Berberine, a Natural Plant Product, Activates AMP-Activated Protein Kinase with Beneficial Metabolic Effects in Diabetic and Insulin-Resistant States," Diabetes, 55(8): 2256-2264 (2006).
Lotti et al., "Ultrasound of the Male Genital Tract in Relation to Male Reproductive Health," Hum Reprod Update, 21(1): 56-83 (2015).
Loven et al., "Selective Inhibition of Tumor Oncogenes by Disruption of Super-Enhancers," Cell 153: 320-334 (2013).
Marushige, "Activation of Chromatin by Acetylation of Histone Side Chains," Proc Natl Acad Sci, 73(11): 3937-3941 (1976).
Matzuk, et al., "Small-Molecule Inhibition of BRDT for Male Contraception," Cell, 150(4): 673-684 (2012).
McKeown et al., "Biased Multicomponent Reactions to Develop Novel Bromodomain Inhibitors," J Med Chem, 57(21): 9019-9027 (2014).
Meguro, et al., "Heterocycles. VI.1) Synthesis of 4H-s-Triazolo[4,3-α][1,4]benzodiazepines, Novel Tricyclic Psychosedatives," Chem Pharm Bull, 21(11): 2382-2390 (1973).
Meng-er, et al., "Use of All-Trans Retinoic Acid in the Treatment of Acute Promyelocytic Leukemia," Blood, 72(2): 567-572 (1988).
Mertz et al., "Targeting MYC Dependence in Cancer by Inhibiting BET Bromodomains," PNAS, 108(40): 16669-16674 (2011).
Mochizuki, et al., "The Bromodomain Protein Brd4 Stimulates G1 Gene Transcription and Promotes Progression to S Phase," J Biol Chem, 283(14): 9040-9048 (2008).
Moros et al., "Synergistic Anti-tumor Activity of Lenalidomide with the BET Bromodomain Inhibitor CPI203 in Bortezomib-resistant Mantle Cell Lymphoma," Leukemia 28(10): 2049-2059 (2014).
Moros et al., "Synergistic antitumor activity of lenalidomide with the BET bromodomain inhibitor CPI203 in bortezomib-resistant mantle cell lymphoma," Leukemia, 28: 2049-2059 (2014).
Niesen, et al., "The use of Differential Scanning Fluorimetry to Detect Ligand Interactions that Promote Protein Stability," Nat Protoc, 2(9): 2212-2221 (2007).
Nishimura et al., "Fertility and Reproduction Studies of Apafant (WEB 2086 BS) in Rats Dosed Orally," Oyo Yakuri/Pharmacometrics, 52(3/4): 185-200 (1996).
Notice of Allowance, U.S. Appl. No. 14/504,840, dated Dec. 4, 2015.*.
Novus Biologicals, "CD11b Expression, Leukocyte Adhesion and the Innate Immune System," Nobusbio.com, (2011).
Owen, et al., "The Structural Basis for the Recognition of Acetylated Histone R4 by the Bromodomain of Histone Acetyltransferase Gcn5p," The EMBO Journal, 19(22): 6141-6149 (2000).
Patani, et al., "Bioisosterism: A Rational Approach in Drug Design," Chem Rev, 96(8): 3147-3176 (1996).
Phelps, et al., "Clinical Response and Pharmacokinetics from a Phase 1 Study of an Active Dosing Schedule of Flavopiridol in Relapsed Chronic Lymphocytic Leukemia," Blood, 113(12): 2637-2645 (2009).
Preisler, et al., "Assessment of c-myc Expression in Individual Leukemic Cells," Leuk Res, 12(6): 507-516 (1988).
Ptashne, "Binding Reactions: Epigenetic Switches, Signal Transduction and Cancer," Curr Biol, 19(6): R234-R241 (2009).
PubChem CID 5325760. Jan. 25, 2006.
PubChem CID-55504609. Jan. 25, 2012.
PubChem CID-56267130. Jan. 25, 2012.
PubChem SID 225027960. Feb. 2, 2015.
PubChem SID 235048169. Feb. 13, 2015.
PubChem SID 235671906. Feb. 13, 2015.
Quinn, et al., "A homogeneous method for investigation of methylation-dependent protein-protein interactions in epigenetics," Nucleic Acids Res, 38(2): e11(1-10) (2010).
Rahl, et al., "c-Myc Regulates Transcriptional Pause Release," Cell, 141(3): 432-445 (2010).
Rhein et al., "CD11 b is a Therapy Resistance and Minimal Residual Disease-Specific Marker in Precursor B-cell Acute Lymphoblastic Leukemia," Blood, 115(18): 3763-3771 (2010).
Roberts et al., "A Bead-Based Proximity Assay for BRD4 Ligand Discovery," Curr Protoc Chem Biol, 7(4): 263-278 (2016).
Santillan, et al., "Bromodomain and Histone Acetyltransferase Domain Specificities Control Mixed Lineage Leukemia Phenotype," Cancer Res, 66(20): 10032-10039 (2006).
Schindler, et al. "Structural mechanism for STI-571 Inhibition of Abelson Tyrosine kinase. Science," 289(5486): 1938-1942 (2000).
Schreiber, et al., "Signaling Network Model of Chromatin," Cell, 111(6): 771-778 (2002).
Schroder et al., "Two-pronged Binding with Bromodomain-containing Protein 4 Liberates Positive Transcription Elongation Factor b from Inactive Ribonucleoprotein Complexes," J Biol Chem, 287(2): 1090-1099 (2012).
Seyrig, et al., "Effects of a Chronic Administration of Two Benzodiazepines on Food Intake in Rats Given a Highly Palatable Diet," Pharmacology Biochemistry & Behavior, 25(4): 913-918 (1986).
Shang, et al., "The First Bromodomain of Brdt, a Testis-Specific Member of the BET Sub-Family of Double-Bromodomain-Containing Proteins, is Essential for Male Germ Cell Differentiation," Development, 134: 3507-3515 (2007).
Shanik et al., "Insulin Resistance and Hyperinsulinemia," Diabetes Care, 31(2): S262-S268 (2008).
Smith et al., "The Bromodomain: A New Target in Emerging Epigenetic Medicine," ACS Chem Biol, 11(3): 598-608 (2016).
Souers et al., "ABT-199, a Potent and Selective BCL-2 Inhibitor, Achieves Antitumor Activity While Sparing Platelets," Nature Medicine, 19(2): 202-210 (2013).
Tanaka et al., "Inhibitors of Emerging Epigenetic Targets for Cancer Therapy: A Patient Review (2010-2014)," Pharm Pat Anal, 4(4): 261-284 (2015).
Taskinen, et al., "A High Tumor-Associated Macrophage Content Predicts Favorable Outcome in Follicular Lymphoma Patients Treated

(56) References Cited

OTHER PUBLICATIONS with Rituximab and Cyclophosphamide-Doxorubicin-Vincristine-Prednisone," Clin Cancer Res, 13(19): 5784-5789 (2007).
Tse et al., "ABT-263: A Potent and Orally Bioavaliable Bcl-2 Family Inhibitor," Cancer Res, 68(9): 3421-3428 (2008).
Verma et al., "Identification of Potent, Selective, Cell-Active Inhibitors of the Histone Lysine Methyltransferase EZH2," ACS Med Chem Lett, 3(12): 1091-1096 (2012).
Vollmuth, et al., "Structures of the dual bromodomains of the P-TEFb-activating protein Brd4 at atomic resolution," J Biol Chem, 284(52): 36547-36556 (2009).
VonVoigtlander, et al., "Alprazolam: Review of Pharmacological, Pharmacokinetic and Clinical Data," Drug Dev Res, 6(1): 1-12 (1985).
Wang et al., "Activation of SOX2 Expression BRD4-NUT Oncogenic Fusion Drives Neoplastic Transformation in NUT Midline Carcinoma," Cancer Research, 74(12): 3332-3343 (2014).
Wang, et al., "A Seamless Trespass: Germ Cell Migration Across the Seminiferous Epithelium During Spermatogenesis," J Cell Biol, 178(4): 549-556 (2007).
Wang, et al., "Brd2 Disruption in Mice Causes Severe Obesity Without Type 2 Diabetes," Biochem J, 425(1): 71-83 (2010).
Wass et al., "Crizotinib in ALK-Positive Diffuse Large B-Cell Lymphoma: A Case Report," Blood, 120(21): 4862 (2012).
Wehner et al., "Effects of Natlizumab, an Alpha4 Integrin Inhibitor, on Fertility in Male and Female Guinea Pigs," Birth Defects Reg. Pat BI, 86(2): 108-116 (2009).
Yang, "Multisite Protein Modification and Intramolecular Signaling," Oncogene, 24: 1653-1662 (2005).
Yang, et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo," Blood, 110(6): 2034-2040 (2007).
Yang, et al., "Brd4 recruits P-TEFb to chromosomes at late mitosis to promote G1 gene expression and cell cycle progression," Mol Cell Biol, 28(3): 967-976 (2008).
Yang, et al., "Recruitment of P-TEFb for Stimulation of Transcriptional Elongation by the Bromodomain Protein Brd4," Mol Cell, 19(4): 535-545 (2005).
You, et al., "Kaposi's sarcoma-associated herpesvirus latency-associated nuclear antigen interacts with bromodomain protein Brd4 on host mitotic chromosomes," J Virol, 80(18): 8909-8919 (2006).
You, et al., "Regulation of Aurora B Expression by the Bromodomain Protein Brd4," Mol Cell Biol, 29: 5094-5103 (2009).
Zeng, et al., "Bromodomain: an Acetyl-lysine Binding Domain," FEBS Lett, 513(1): 124-128 (2002).
Zhang, et al., "Down-Regulation of NF-κB Transcriptional Activity in HIV-Associated Kidney Disease by BRD4 Inhibition," J Biol Chem, 287(34): 28840-28851 (2012).
Zhang, et al., "Down-Regulation of NF-κB Transcriptional Activity in HIV-Associated Kidney Disease by BRD4 Inhibition," J Biol Chem, 287(46): 38956 (2012).
Zhao, et al., "Research Development on Fusion Protein Transcription Factor siRNA Specifically Targeting Leukemia," Sciencepaper Online: 1-6 and J Med Res, 39(2): 6-9 (2010) (English-language translation entitled "Progress of Research on siRNA that Targets Leukemia Specific Transcription Regulation Factor Fusion Proteins," 1-10).
Zuber, et al., "RNAi Screen Identifies Brd4 as a Therapeutic Target in Acute Myeloid Leukaemia," Nature, 478(7370): 524-528 (2011), with "Supplementary Information" from www.nature.com/nature/journal/v478/n7370/extref/nature10334-s1.pdf, pp. 1-33.
Zuercher et al., "Identification and Structure-activity Relationship of Phenolic Acyl Hydrazones as Selective Agonists for the Estrogen-related Orphan Nuclear Receptors ERRbeta and ERRgamma," J Med Chem, 48(9): 3107-3109 (2005).

\* cited by examiner

FIG. 4L
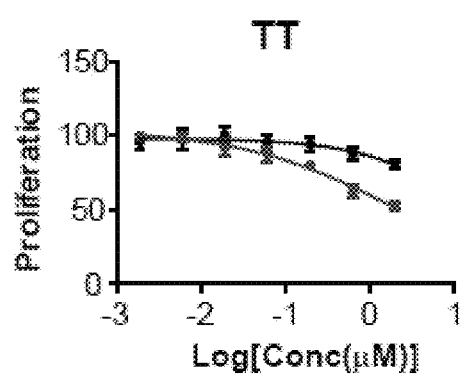
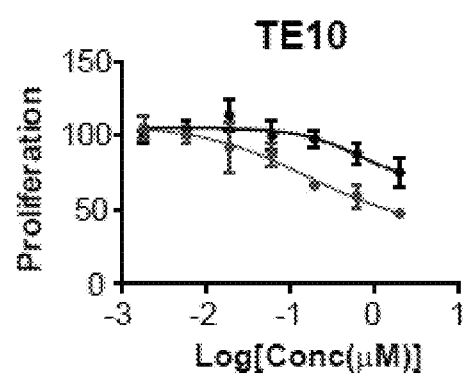

FIG. 10A
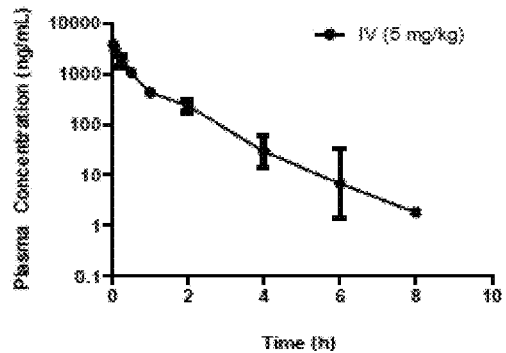
FIG. 10B
| PK Parameter | Unit | Estimate |
|---|---|---|
| CL | L/hr/kg | 2.35 |
| $V_{ss}$ | L/kg | 2.02 |
| $T_{1/2}$ | hr | 0.897 |
| $AUC_{last}$ | hr*ng/mL | 2130 |
| $AUC_{INF}$ | hr*ng/mL | 2130 |
| $MRT_{INF}$ | hr | 0.861 |
FIG. 10C
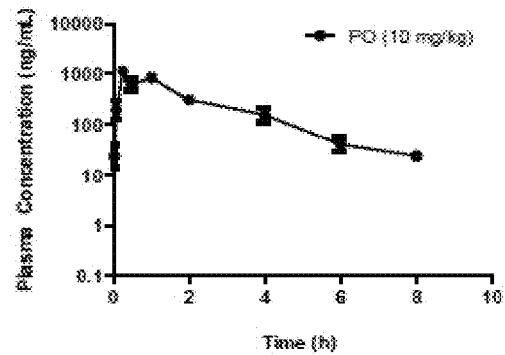
FIG. 10D
| PK Parameter | Unit | Estimate |
|---|---|---|
| $T_{max}$ | hr | 0.250 |
| $C_{max}$ | ng/mL | 1180 |
| $T_{1/2}$ | hr | 1.39 |
| $AUC_{last}$ | hr*ng/mL | 2040 |
| $AUC_{INF}$ | hr*ng/mL | 2090 |
| F | % | 49.1 |

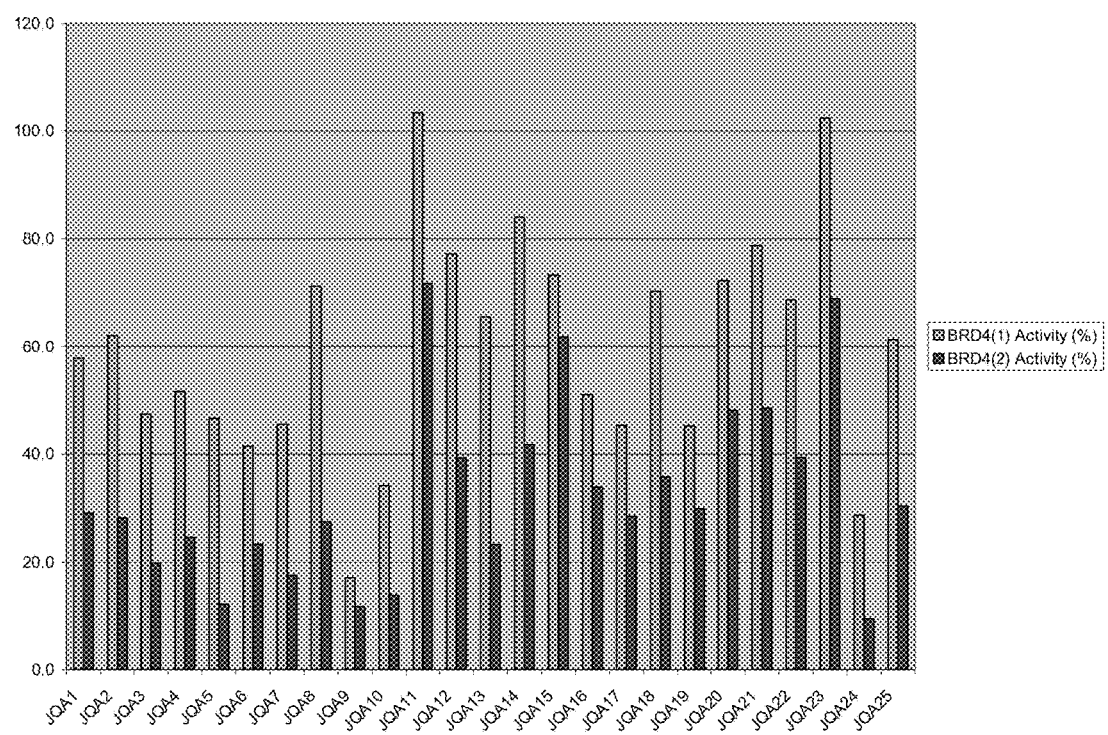
FIG. 16A: BRD4(1) and BRD4(2) Binding Activity Inhibition at 5 μM compound

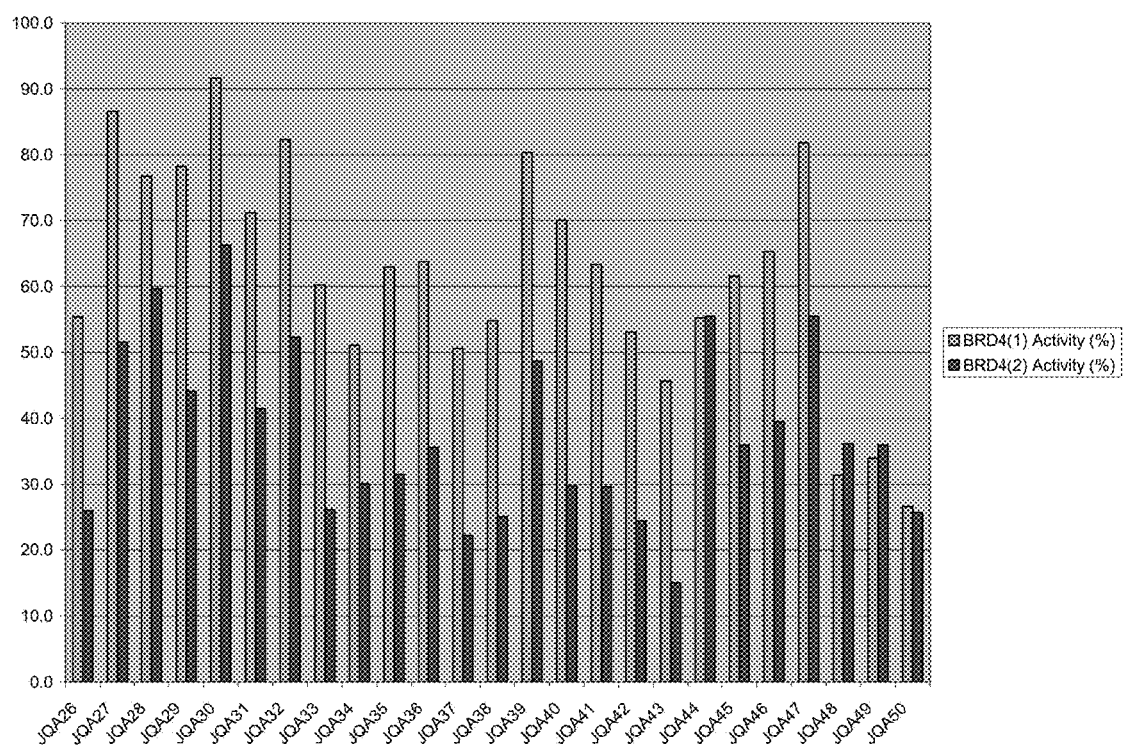
FIG. 16B: BRD4(1) and BRD4(2) Binding Activity Inhibition at 5 μM compound FIG. 16C: BRD4(1) and BRD4(2) Binding Activity Inhibition at 5 μM compound
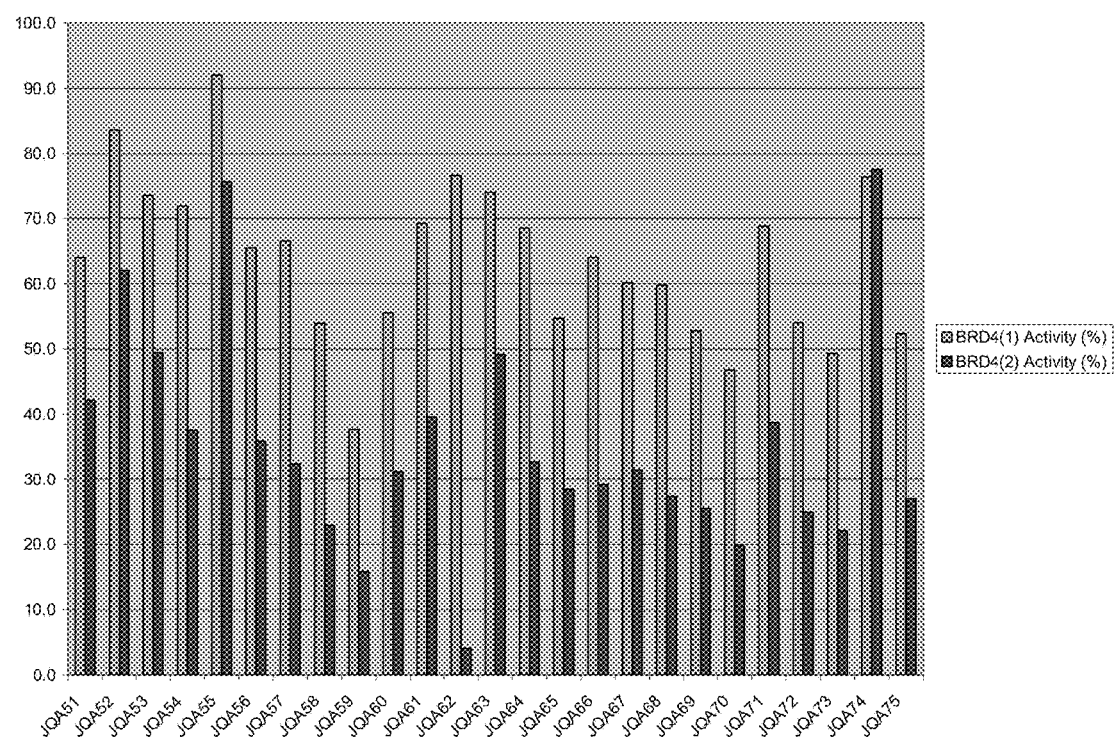

FIG. 16D: BRD4(1) and BRD4(2) Binding Activity Inhibition at 5 µM compound
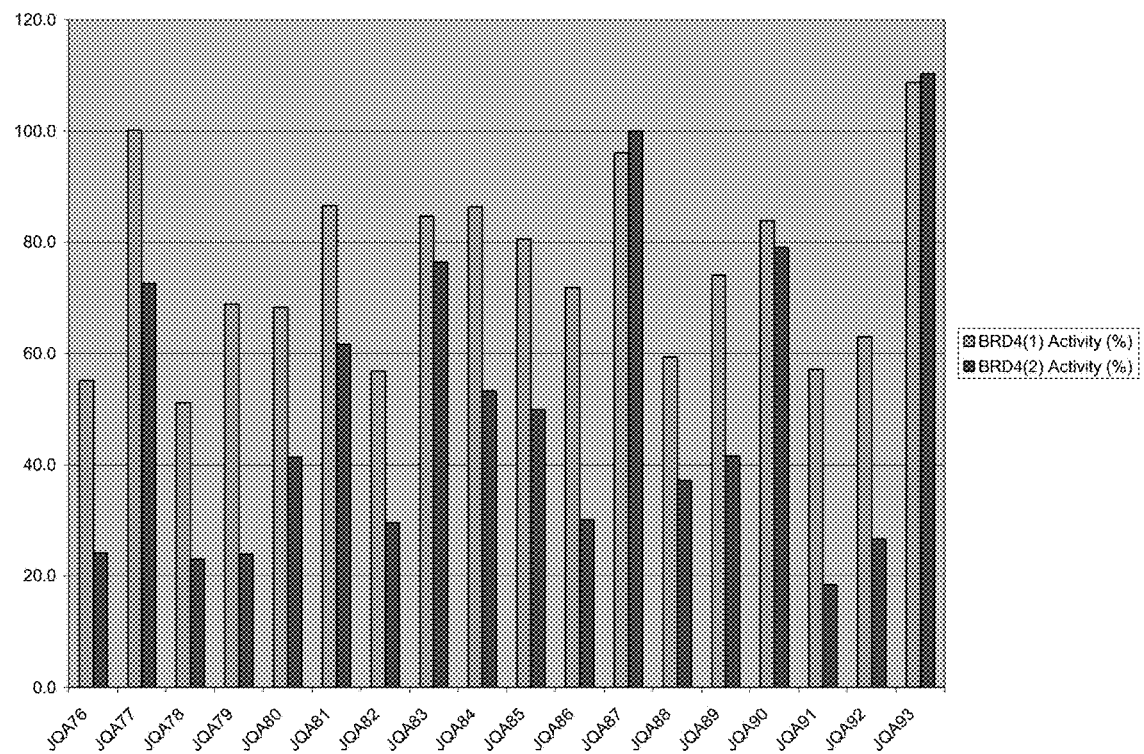

FIG. 17A: NMC Cell Viability % at 2 μM compound
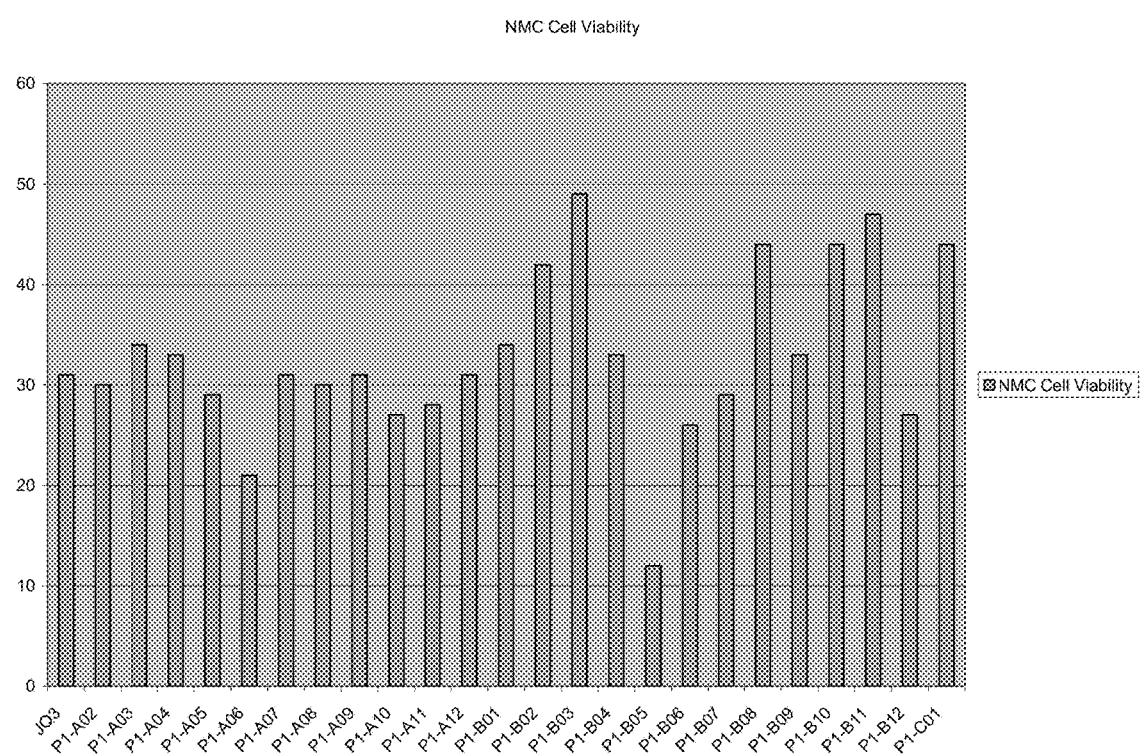

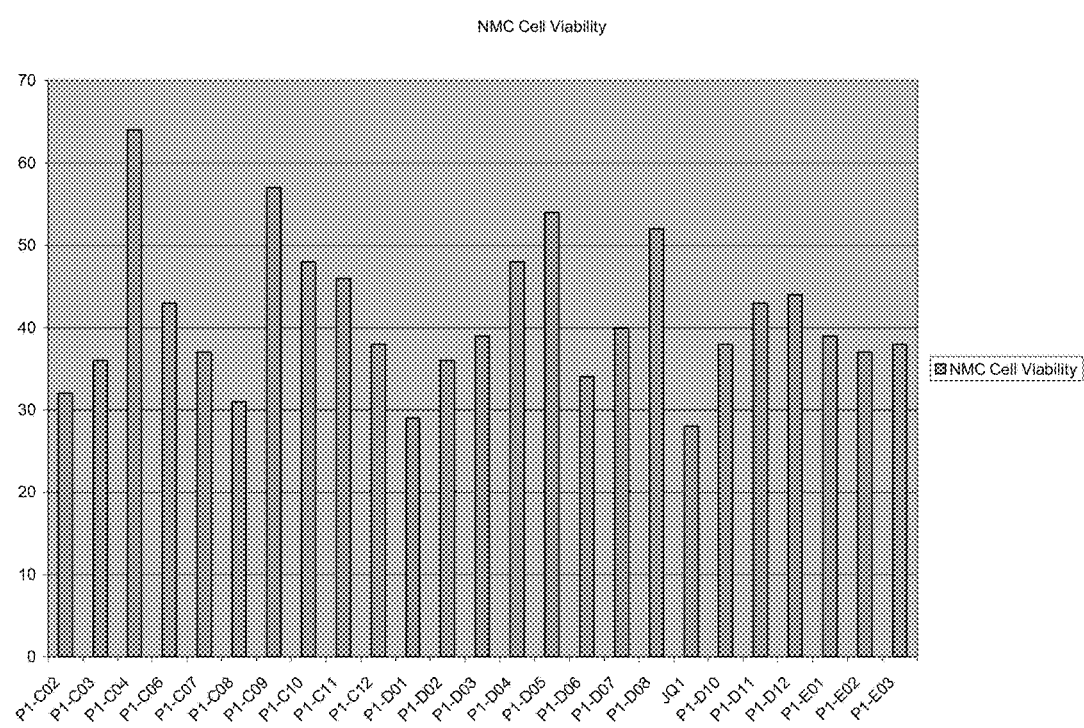
FIG. 17B: NMC Cell Viability % at 2 µM compound

FIG. 17C: NMC Cell Viability % at 2 μM compound
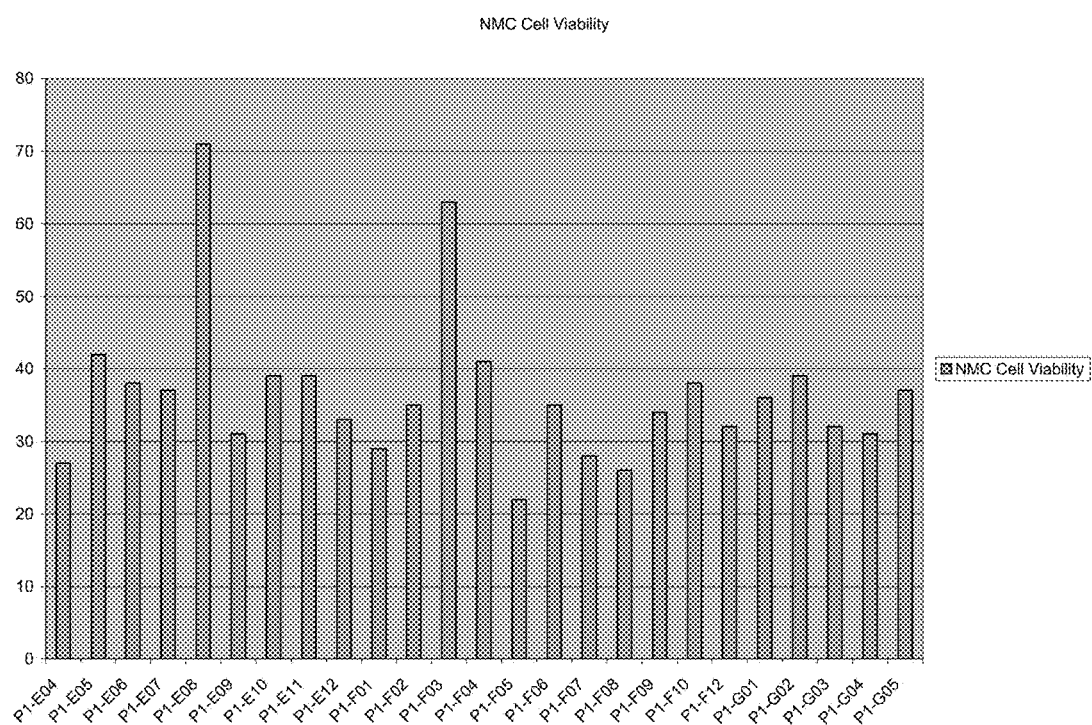

FIG. 17D: NMC Cell Viability % at 2 μM compound
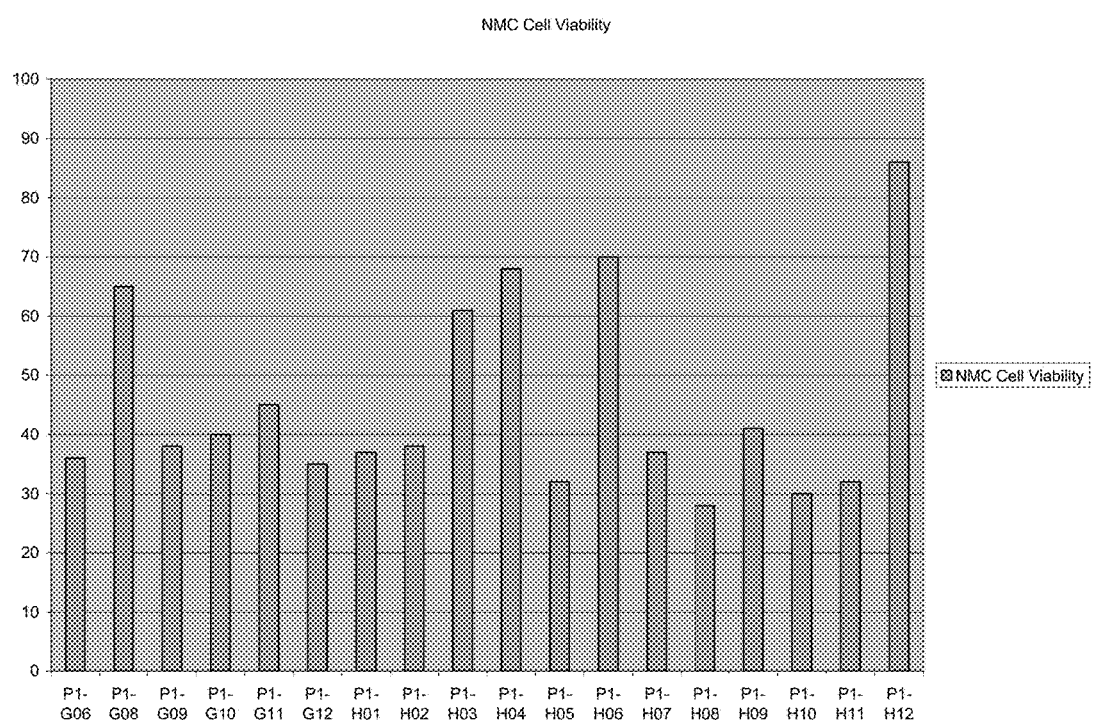

With BRD4.1

With BRD4.2

With 797 Cell Line

With 10326 Cell Line

SEQUENCE LISTING

<160> NUMBER OF SEQ ID NOS: 6

<210> SEQ ID NO 1
<211> LENGTH: 801
<212> TYPE: PRT
<213> ORGANISM: Homo sapiens

<400> SEQUENCE: 1

```
Met Leu Gln Asn Val Thr Pro His Asn Lys Leu Pro Gly Glu Gly Asn
1               5                   10                  15

Ala Gly Leu Leu Gly Leu Gly Pro Glu Ala Ala Pro Gly Lys Arg
            20                  25                  30

Ile Arg Lys Pro Ser Leu Leu Tyr Glu Gly Phe Glu Ser Pro Thr Met
            35                  40                  45

Ala Ser Val Pro Ala Leu Gln Leu Thr Pro Ala Asn Pro Pro Pro Pro
50                  55                  60

Glu Val Ser Asn Pro Lys Lys Pro Gly Arg Val Thr Asn Gln Leu Gln
65                  70                  75                  80

Tyr Leu His Lys Val Val Met Lys Ala Leu Trp Lys His Gln Phe Ala
                85                  90                  95

Trp Pro Phe Arg Gln Pro Val Asp Ala Val Lys Leu Gly Leu Pro Asp
                100                 105                 110

Tyr His Lys Ile Ile Lys Gln Pro Met Asp Met Gly Thr Ile Lys Arg
            115                 120                 125

Arg Leu Glu Asn Asn Tyr Tyr Trp Ala Ala Ser Glu Cys Met Gln Asp
        130                 135                 140

Phe Asn Thr Met Phe Thr Asn Cys Tyr Ile Tyr Asn Lys Pro Thr Asp
145                 150                 155                 160

Asp Ile Val Leu Met Ala Gln Thr Leu Glu Lys Ile Phe Leu Gln Lys
                165                 170                 175

Val Ala Ser Met Pro Gln Glu Glu Gln Glu Leu Val Val Thr Ile Pro
            180                 185                 190

Lys Asn Ser His Lys Lys Gly Ala Lys Leu Ala Ala Leu Gln Gly Ser
        195                 200                 205

Val Thr Ser Ala His Gln Val Pro Ala Val Ser Ser Val Ser His Thr
    210                 215                 220

Ala Leu Tyr Thr Pro Pro Pro Glu Ile Pro Thr Thr Val Leu Asn Ile
225                 230                 235                 240

Pro His Pro Ser Val Ile Ser Ser Pro Leu Leu Lys Ser Leu His Ser
                245                 250                 255

Ala Gly Pro Pro Leu Leu Ala Val Thr Ala Ala Pro Pro Ala Gln Pro
            260                 265                 270

Leu Ala Lys Lys Lys Gly Val Lys Arg Lys Ala Asp Thr Thr Thr Pro
        275                 280                 285

Thr Pro Thr Ala Ile Leu Ala Pro Gly Ser Pro Ala Ser Pro Pro Gly
    290                 295                 300

Ser Leu Glu Pro Lys Ala Ala Arg Leu Pro Pro Met Arg Arg Glu Ser
```

```
            305                 310                 315                 320
      Gly Arg Pro Ile Lys Pro Pro Arg Lys Asp Leu Pro Asp Ser Gln Gln
                          325                 330                 335

Gln His Gln Ser Ser Lys Lys Gly Lys Leu Ser Glu Gln Leu Lys His
                          340                 345                 350

Cys Asn Gly Ile Leu Lys Glu Leu Leu Ser Lys Lys His Ala Ala Tyr
                          355                 360                 365

Ala Trp Pro Phe Tyr Lys Pro Val Asp Ala Ser Ala Leu Gly Leu His
                          370                 375                 380

Asp Tyr His Asp Ile Ile Lys His Pro Met Asp Leu Ser Thr Val Lys
      385                 390                 395                 400

Arg Lys Met Glu Asn Arg Asp Tyr Arg Asp Ala Gln Glu Phe Ala Ala
                          405                 410                 415

Asp Val Arg Leu Met Phe Ser Asn Cys Tyr Lys Tyr Asn Pro Pro Asp
                          420                 425                 430

His Asp Val Val Ala Met Ala Arg Lys Leu Gln Asp Val Phe Glu Phe
                          435                 440                 445

Arg Tyr Ala Lys Met Pro Asp Glu Pro Leu Glu Pro Gly Pro Leu Pro
                          450                 455                 460

Val Ser Thr Ala Met Pro Pro Gly Leu Ala Lys Ser Ser Ser Glu Ser
      465                 470                 475                 480

Ser Ser Glu Glu Ser Ser Ser Glu Ser Ser Glu Glu Glu Glu Glu Glu
                          485                 490                 495

Glu Asp Glu Glu Asp Glu Glu Glu Glu Ser Glu Ser Ser Asp Ser
                          500                 505                 510

Glu Glu Glu Arg Ala His Arg Leu Ala Glu Leu Gln Glu Gln Leu Arg
                          515                 520                 525

Ala Val His Glu Gln Leu Ala Ala Leu Ser Gln Gly Pro Ile Ser Lys
                          530                 535                 540

Pro Lys Arg Lys Arg Glu Lys Glu Lys Lys Lys Arg Lys Ala
      545                 550                 555                 560

Glu Lys His Arg Gly Arg Ala Gly Ala Asp Glu Asp Lys Gly Pro
                          565                 570                 575

Arg Ala Pro Arg Pro Gln Pro Lys Lys Ser Lys Lys Ala Ser Gly
                          580                 585                 590

Ser Gly Gly Gly Ser Ala Ala Leu Gly Pro Ser Gly Phe Gly Pro Ser
                          595                 600                 605

Gly Gly Ser Gly Thr Lys Leu Pro Lys Lys Ala Thr Lys Thr Ala Pro
                          610                 615                 620

Pro Ala Leu Pro Thr Gly Tyr Asp Ser Glu Glu Glu Glu Glu Ser Arg
      625                 630                 635                 640

Pro Met Ser Tyr Asp Glu Lys Arg Gln Leu Ser Leu Asp Ile Asn Lys
                          645                 650                 655

Leu Pro Gly Glu Lys Leu Gly Arg Val Val His Ile Ile Gln Ala Arg
                          660                 665                 670

Glu Pro Ser Leu Arg Asp Ser Asn Pro Glu Glu Ile Glu Ile Asp Phe
                          675                 680                 685

Glu Thr Leu Lys Pro Ser Thr Leu Arg Glu Leu Glu Arg Tyr Val Leu
                          690                 695                 700

Ser Cys Leu Arg Lys Lys Pro Arg Lys Pro Tyr Thr Ile Lys Lys Pro
      705                 710                 715                 720

Val Gly Lys Thr Lys Glu Glu Leu Ala Leu Glu Lys Lys Arg Glu Leu
                          725                 730                 735
```

```
Glu Lys Arg Leu Gln Asp Val Ser Gly Gln Leu Asn Ser Thr Lys Lys
                740                 745                 750

Pro Pro Lys Lys Ala Asn Glu Lys Thr Glu Ser Ser Ser Ala Gln Gln
            755                 760                 765

Val Ala Val Ser Arg Leu Ser Ala Ser Ser Ser Ser Asp Ser Ser
        770                 775                 780

Ser Ser Ser Ser Ser Ser Ser Ser Asp Thr Ser Asp Ser Asp Ser
785                 790                 795                 800

Gly

<210> SEQ ID NO 2
<211> LENGTH: 726
<212> TYPE: PRT
<213> ORGANISM: Homo sapiens

<400> SEQUENCE: 2

Met Ser Thr Ala Thr Val Ala Pro Ala Gly Ile Pro Ala Thr Pro
1               5                   10                  15

Gly Pro Val Asn Pro Pro Pro Glu Val Ser Asn Pro Ser Lys Pro
                20                  25                  30

Gly Arg Lys Thr Asn Gln Leu Gln Tyr Met Gln Asn Val Val Lys
            35                  40                  45

Thr Leu Trp Lys His Gln Phe Ala Trp Pro Phe Tyr Gln Pro Val Asp
50                  55                  60

Ala Ile Lys Leu Asn Leu Pro Asp Tyr His Lys Ile Ile Lys Asn Pro
65                  70                  75                  80

Met Asp Met Gly Thr Ile Lys Lys Arg Leu Glu Asn Asn Tyr Tyr Trp
                85                  90                  95

Ser Ala Ser Glu Cys Met Gln Asp Phe Asn Thr Met Phe Thr Asn Cys
                100                 105                 110

Tyr Ile Tyr Asn Lys Pro Thr Asp Asp Ile Val Leu Met Ala Gln Ala
                115                 120                 125

Leu Glu Lys Ile Phe Leu Gln Lys Val Ala Gln Met Pro Gln Glu Glu
130                 135                 140

Val Glu Leu Leu Pro Pro Ala Pro Lys Gly Lys Gly Arg Lys Pro Ala
145                 150                 155                 160

Ala Gly Ala Gln Ser Ala Gly Thr Gln Gln Val Ala Ala Val Ser Ser
                165                 170                 175

Val Ser Pro Ala Thr Pro Phe Gln Ser Val Pro Pro Thr Val Ser Gln
                180                 185                 190

Thr Pro Val Ile Ala Ala Thr Pro Val Pro Thr Ile Thr Ala Asn Val
                195                 200                 205

Thr Ser Val Pro Val Pro Ala Ala Ala Pro Pro Pro Ala Thr
                210                 215                 220

Pro Ile Val Pro Val Val Pro Thr Pro Pro Val Val Lys Lys
225                 230                 235                 240

Gly Val Lys Arg Lys Ala Asp Thr Thr Thr Pro Thr Thr Ser Ala Ile
                245                 250                 255

Thr Ala Ser Arg Ser Glu Ser Pro Pro Pro Leu Ser Asp Pro Lys Gln
                260                 265                 270

Ala Lys Val Val Ala Arg Arg Glu Ser Gly Gly Arg Pro Ile Lys Pro
            275                 280                 285

Pro Lys Lys Asp Leu Glu Asp Gly Glu Val Pro Gln His Ala Gly Lys
                290                 295                 300
```

```
Lys Gly Lys Leu Ser Glu His Leu Arg Tyr Cys Asp Ser Ile Leu Arg
305                 310                 315                 320

Glu Met Leu Ser Lys His Ala Ala Tyr Ala Trp Pro Phe Tyr Lys
            325                 330                 335

Pro Val Asp Ala Glu Ala Leu Glu Leu His Asp Tyr His Asp Ile Ile
                340                 345                 350

Lys His Pro Met Asp Leu Ser Thr Val Lys Arg Lys Met Asp Gly Arg
            355                 360                 365

Glu Tyr Pro Asp Ala Gln Gly Phe Ala Ala Asp Val Arg Leu Met Phe
    370                 375                 380

Ser Asn Cys Tyr Lys Tyr Asn Pro Pro Asp His Glu Val Val Ala Met
385                 390                 395                 400

Ala Arg Lys Leu Gln Asp Val Phe Glu Met Arg Phe Ala Lys Met Pro
                405                 410                 415

Asp Glu Pro Val Glu Ala Pro Ala Leu Pro Ala Pro Ala Ala Pro Met
            420                 425                 430

Val Ser Lys Gly Ala Glu Ser Ser Arg Ser Ser Glu Ser Ser Ser
            435                 440                 445

Asp Ser Gly Ser Ser Asp Ser Glu Glu Glu Arg Ala Thr Arg Leu Ala
450                 455                 460

Glu Leu Gln Glu Gln Leu Lys Ala Val His Glu Gln Leu Ala Ala Leu
465                 470                 475                 480

Ser Gln Ala Pro Val Asn Lys Pro Lys Lys Lys Glu Lys Glu
                485                 490                 495

Lys Glu Lys Lys Lys Lys Asp Lys Glu Lys Glu Lys Glu Lys His Lys
            500                 505                 510

Val Lys Ala Glu Glu Lys Lys Ala Lys Val Ala Pro Pro Ala Lys
            515                 520                 525

Gln Ala Gln Gln Lys Lys Ala Pro Ala Lys Lys Ala Asn Ser Thr Thr
    530                 535                 540

Thr Ala Gly Arg Gln Leu Lys Lys Gly Gly Lys Gln Ala Ser Ala Ser
545                 550                 555                 560

Tyr Asp Ser Glu Glu Glu Glu Gly Leu Pro Met Ser Tyr Asp Glu
                565                 570                 575

Lys Arg Gln Leu Ser Leu Asp Ile Asn Arg Leu Pro Gly Glu Lys Leu
            580                 585                 590

Gly Arg Val Val His Ile Ile Gln Ser Arg Glu Pro Ser Leu Arg Asp
        595                 600                 605

Ser Asn Pro Asp Glu Ile Glu Ile Asp Phe Glu Thr Leu Lys Pro Thr
610                 615                 620

Thr Leu Arg Glu Leu Glu Arg Tyr Val Lys Ser Cys Leu Gln Lys Lys
625                 630                 635                 640

Gln Arg Lys Pro Phe Ser Ala Ser Gly Lys Lys Gln Ala Ala Lys Ser
                645                 650                 655

Lys Glu Glu Leu Ala Gln Glu Lys Lys Lys Glu Leu Glu Lys Arg Leu
            660                 665                 670

Gln Asp Val Ser Gly Gln Leu Ser Ser Lys Lys Pro Ala Arg Lys
            675                 680                 685

Glu Lys Pro Gly Ser Ala Pro Ser Gly Gly Pro Ser Arg Leu Ser Ser
    690                 695                 700

Ser Ser Ser Ser Glu Ser Gly Ser Ser Ser Ser Gly Ser Ser Ser
705                 710                 715                 720
```

```
Asp Ser Ser Asp Ser Glu
                725

<210> SEQ ID NO 3
<211> LENGTH: 722
<212> TYPE: PRT
<213> ORGANISM: Homo sapiens

<400> SEQUENCE: 3

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
            20                  25                  30

Ala Gln Pro Gln Pro Ala Asn Ala Ala Ser Thr Asn Pro Pro Pro Pro
        35                  40                  45

Glu Thr Ser Asn Pro Asn Lys Pro Lys Arg Gln Thr Asn Gln Leu Gln
    50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
                85                  90                  95

Tyr Tyr Lys Ile Ile Lys Thr Pro Met Asp Met Gly Thr Ile Lys Lys
            100                 105                 110

Arg Leu Glu Asn Asn Tyr Tyr Trp Asn Ala Gln Glu Cys Ile Gln Asp
        115                 120                 125

Phe Asn Thr Met Phe Thr Asn Cys Tyr Ile Tyr Asn Lys Pro Gly Asp
    130                 135                 140

Asp Ile Val Leu Met Ala Glu Ala Leu Glu Lys Leu Phe Leu Gln Lys
145                 150                 155                 160

Ile Asn Glu Leu Pro Thr Glu Glu Thr Glu Ile Met Ile Val Gln Ala
                165                 170                 175

Lys Gly Arg Gly Arg Gly Arg Lys Glu Thr Gly Thr Ala Lys Pro Gly
            180                 185                 190

Val Ser Thr Val Pro Asn Thr Thr Gln Ala Ser Thr Pro Pro Gln Thr
        195                 200                 205

Gln Thr Pro Gln Pro Asn Pro Pro Val Gln Ala Thr Pro His Pro
    210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
                245                 250                 255

Pro Gln Pro Pro Pro Ala Pro Ala Pro Gln Pro Val Gln Ser His Pro
            260                 265                 270

Pro Ile Ile Ala Ala Thr Pro Gln Pro Val Lys Thr Lys Lys Gly Val
        275                 280                 285

Lys Arg Lys Ala Asp Thr Thr Thr Pro Thr Thr Ile Asp Pro Ile His
    290                 295                 300

Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Pro Lys Lys Asp Val Pro
                325                 330                 335

Asp Ser Gln Gln His Pro Ala Pro Glu Lys Ser Ser Lys Val Ser Glu
            340                 345                 350

Gln Leu Lys Cys Cys Ser Gly Ile Leu Lys Glu Met Phe Ala Lys Lys
        355                 360                 365
```

His Ala Ala Tyr Ala Trp Pro Phe Tyr Lys Pro Val Asp Val Glu Ala
        370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                405                 410                 415

Glu Phe Gly Ala Asp Val Arg Leu Met Phe Ser Asn Cys Tyr Lys Tyr
            420                 425                 430

Asn Pro Pro Asp His Glu Val Val Ala Met Ala Arg Lys Leu Gln Asp
                435                 440                 445

Val Phe Glu Met Arg Phe Ala Lys Met Pro Asp Glu Pro Glu Glu Pro
450                 455                 460

Val Val Ala Val Ser Ser Pro Ala Val Pro Pro Thr Lys Val Val
465                 470                 475                 480

Ala Pro Pro Ser Ser Ser Asp Ser Ser Ser Asp Ser Ser Ser Asp Ser
                485                 490                 495

Asp Ser Ser Thr Asp Asp Ser Glu Glu Glu Arg Ala Gln Arg Leu Ala
                500                 505                 510

Glu Leu Gln Glu Gln Leu Lys Ala Val His Glu Gln Leu Ala Ala Leu
            515                 520                 525

Ser Gln Pro Gln Gln Asn Lys Pro Lys Lys Glu Lys Asp Lys Lys
            530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Lys Lys Thr Lys Lys Asn
                565                 570                 575

Asn Ser Ser Asn Ser Asn Val Ser Lys Lys Glu Pro Ala Pro Met Lys
                580                 585                 590

Ser Lys Pro Pro Pro Thr Tyr Glu Ser Glu Glu Glu Asp Lys Cys Lys
                595                 600                 605

Pro Met Ser Tyr Glu Glu Lys Arg Gln Leu Ser Leu Asp Ile Asn Lys
610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
                660                 665                 670

Ser Cys Leu Arg Lys Lys Arg Lys Pro Gln Ala Glu Lys Val Asp Val
            675                 680                 685

Ile Ala Gly Ser Ser Lys Met Lys Gly Phe Ser Ser Ser Glu Ser Glu
690                 695                 700

Ser Ser Ser Glu Ser Ser Ser Ser Asp Ser Glu Asp Ser Glu Thr Gly
705                 710                 715                 720

Pro Ala

<210> SEQ ID NO 4
<211> LENGTH: 947
<212> TYPE: PRT
<213> ORGANISM: Homo sapiens

<400> SEQUENCE: 4

Met Ser Leu Pro Ser Arg Gln Thr Ala Ile Ile Val Asn Pro Pro Pro
1               5                   10                  15

```
Pro Glu Tyr Ile Asn Thr Lys Lys Asn Gly Arg Leu Thr Asn Gln Leu
            20                  25                  30

Gln Tyr Leu Gln Lys Val Val Leu Lys Asp Leu Trp Lys His Ser Phe
        35                  40                  45

Ser Trp Pro Phe Gln Arg Pro Val Asp Ala Val Lys Leu Gln Leu Pro
50                  55                  60

Asp Tyr Tyr Thr Ile Ile Lys Asn Pro Met Asp Leu Asn Thr Ile Lys
65                  70                  75                  80

Lys Arg Leu Glu Asn Lys Tyr Tyr Ala Lys Ala Ser Glu Cys Ile Glu
                85                  90                  95

Asp Phe Asn Thr Met Phe Ser Asn Cys Tyr Leu Tyr Asn Lys Pro Gly
            100                 105                 110

Asp Asp Ile Val Leu Met Ala Gln Ala Leu Glu Lys Leu Phe Met Gln
        115                 120                 125

Lys Leu Ser Gln Met Pro Gln Glu Glu Gln Val Val Gly Val Lys Glu
130                 135                 140

Arg Ile Lys Lys Gly Thr Gln Gln Asn Ile Ala Val Ser Ser Ala Lys
145                 150                 155                 160

Glu Lys Ser Ser Pro Ser Ala Thr Glu Lys Val Phe Lys Gln Gln Glu
                165                 170                 175

Ile Pro Ser Val Phe Pro Lys Thr Ser Ile Ser Pro Leu Asn Val Val
            180                 185                 190

Gln Gly Ala Ser Val Asn Ser Ser Ser Gln Thr Ala Ala Gln Val Thr
        195                 200                 205

Lys Gly Val Lys Arg Lys Ala Asp Thr Thr Thr Pro Ala Thr Ser Ala
210                 215                 220

Val Lys Ala Ser Ser Glu Phe Ser Pro Thr Phe Thr Glu Lys Ser Val
225                 230                 235                 240

Ala Leu Pro Pro Ile Lys Glu Asn Met Pro Lys Asn Val Leu Pro Asp
                245                 250                 255

Ser Gln Gln Gln Tyr Asn Val Val Lys Thr Val Lys Val Thr Glu Gln
            260                 265                 270

Leu Arg His Cys Ser Glu Ile Leu Lys Glu Met Leu Ala Lys Lys His
        275                 280                 285

Phe Ser Tyr Ala Trp Pro Phe Tyr Asn Pro Val Asp Val Asn Ala Leu
290                 295                 300

Gly Leu His Asn Tyr Tyr Asp Val Val Lys Asn Pro Met Asp Leu Gly
305                 310                 315                 320

Thr Ile Lys Glu Lys Met Asp Asn Gln Glu Tyr Lys Asp Ala Tyr Lys
                325                 330                 335

Phe Ala Ala Asp Val Arg Leu Met Phe Met Asn Cys Tyr Lys Tyr Asn
            340                 345                 350

Pro Pro Asp His Glu Val Val Thr Met Ala Arg Met Leu Gln Asp Val
        355                 360                 365

Phe Glu Thr His Phe Ser Lys Ile Pro Ile Glu Pro Val Glu Ser Met
370                 375                 380

Pro Leu Cys Tyr Ile Lys Thr Asp Ile Thr Glu Thr Thr Gly Arg Glu
385                 390                 395                 400

Asn Thr Asn Glu Ala Ser Ser Glu Gly Asn Ser Ser Asp Asp Ser Glu
                405                 410                 415

Asp Glu Arg Val Lys Arg Leu Ala Lys Leu Gln Glu Gln Leu Lys Ala
            420                 425                 430
```

-continued

Val His Gln Gln Leu Gln Val Leu Ser Gln Val Pro Phe Arg Lys Leu
            435                 440                 445

Asn Lys Lys Lys Glu Lys Ser Lys Lys Glu Lys Lys Glu Lys Val
450                 455                 460

Asn Asn Ser Asn Glu Asn Pro Arg Lys Met Cys Glu Gln Met Arg Leu
465                 470                 475                 480

Lys Glu Lys Ser Lys Arg Asn Gln Pro Lys Arg Lys Gln Gln Phe
            485                 490                 495

Ile Gly Leu Lys Ser Glu Asp Glu Asp Asn Ala Lys Pro Met Asn Tyr
            500                 505                 510

Asp Glu Lys Arg Gln Leu Ser Leu Asn Ile Asn Lys Leu Pro Gly Asp
            515                 520                 525

Lys Leu Gly Arg Val Val His Ile Ile Gln Ser Arg Glu Pro Ser Leu
            530                 535                 540

Ser Asn Ser Asn Pro Asp Glu Ile Glu Ile Asp Phe Glu Thr Leu Lys
545                 550                 555                 560

Ala Ser Thr Leu Arg Glu Leu Glu Lys Tyr Val Ser Ala Cys Leu Arg
            565                 570                 575

Lys Arg Pro Leu Lys Pro Ala Lys Lys Ile Met Met Ser Lys Glu
            580                 585                 590

Glu Leu His Ser Gln Lys Gln Glu Leu Glu Lys Arg Leu Leu Asp
            595                 600                 605

Val Asn Asn Gln Leu Asn Ser Arg Lys Arg Gln Thr Lys Ser Asp Lys
            610                 615                 620

Thr Gln Pro Ser Lys Ala Val Glu Asn Val Ser Arg Leu Ser Glu Ser
625                 630                 635                 640

Ser Ser Ser Ser Ser Ser Ser Glu Ser Glu Ser Ser Ser Asp
            645                 650                 655

Leu Ser Ser Ser Asp Ser Ser Asp Ser Glu Ser Glu Met Phe Pro Lys
            660                 665                 670

Phe Thr Glu Val Lys Pro Asn Asp Ser Pro Ser Lys Glu Asn Val Lys
            675                 680                 685

Lys Met Lys Asn Glu Cys Ile Leu Pro Glu Gly Arg Thr Gly Val Thr
690                 695                 700

Gln Ile Gly Tyr Cys Val Gln Asp Thr Thr Ser Ala Asn Thr Thr Leu
705                 710                 715                 720

Val His Gln Thr Thr Pro Ser His Val Met Pro Asn His His Gln
            725                 730                 735

Leu Ala Phe Asn Tyr Gln Glu Leu Glu His Leu Gln Thr Val Lys Asn
            740                 745                 750

Ile Ser Pro Leu Gln Ile Leu Pro Pro Ser Gly Asp Ser Glu Gln Leu
            755                 760                 765

Ser Asn Gly Ile Thr Val Met His Pro Ser Gly Asp Ser Asp Thr Thr
770                 775                 780

Met Leu Glu Ser Glu Cys Gln Ala Pro Val Gln Lys Asp Ile Lys Ile
785                 790                 795                 800

Lys Asn Ala Asp Ser Trp Lys Ser Leu Gly Lys Pro Val Lys Pro Ser
            805                 810                 815

Gly Val Met Lys Ser Ser Asp Glu Leu Phe Asn Gln Phe Arg Lys Ala
            820                 825                 830

Ala Ile Glu Lys Glu Val Lys Ala Arg Thr Gln Glu Leu Ile Arg Lys
            835                 840                 845

His Leu Glu Gln Asn Thr Lys Glu Leu Lys Ala Ser Gln Glu Asn Gln

```
                850                 855                 860
Arg Asp Leu Gly Asn Gly Leu Thr Val Glu Ser Phe Ser Asn Lys Ile
865                 870                 875                 880

Gln Asn Lys Cys Ser Gly Glu Glu Gln Lys Glu His Gln Gln Ser Ser
                885                 890                 895

Glu Ala Gln Asp Lys Ser Lys Leu Trp Leu Leu Lys Asp Arg Asp Leu
                900                 905                 910

Ala Arg Gln Lys Glu Gln Glu Arg Arg Arg Glu Ala Met Val Gly
            915                 920                 925

Thr Ile Asp Met Thr Leu Gln Ser Asp Ile Met Thr Met Phe Glu Asn
        930                 935                 940

Asn Phe Asp
945

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: 5, 8, 12, 16
<223> OTHER INFORMATION: Lys(Ac)
<220> FEATURE:
<221> NAME/KEY: MOD_RES
<222> LOCATION: (20)...(20)
<223> OTHER INFORMATION: Lys(Biotin)-OH

<400> SEQUENCE: 5

Ser Gly Arg Gly Lys Gly Gly Lys Gly Leu Gly Lys Gly Gly Ala Lys
1               5                   10                  15

Arg His Arg Lys
            20

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)...(1)
<223> OTHER INFORMATION: Biotin-Lys
<220> FEATURE:
<221> NAME/KEY: MOD_RES
<222> LOCATION: (10)...(10)
<223> OTHER INFORMATION: Lys(Ac)
<220> FEATURE:
<221> NAME/KEY: MOD_RES
<222> LOCATION: (19)...(19)
<223> OTHER INFORMATION: Thr-OH

<400> SEQUENCE: 6

Lys Ser Ala Pro Ala Thr Gly Gly Val Lys Lys Pro His Arg Tyr Arg
1               5                   10                  15

Pro Gly Thr
```

COMPOSITIONS AND METHODS FOR TREATING NEOPLASIA, INFLAMMATORY DISEASE AND OTHER DISORDERS

RELATED APPLICATIONS

This application is a continuation of U.S. application Ser. No. 15/061,576, filed Mar. 4, 2016, which is a continuation of U.S. application Ser. No. 14/502,840, filed Sep. 30, 2014, which is a continuation of U.S. application Ser. No. 13/698,010, which is the U.S. National Stage of International Application No. PCT/US2011/036701, filed May 16, 2011, which designates the U.S., published in English, and claims the benefit of U.S. Provisional Application No. 61/334,991, filed May 14, 2010, U.S. Provisional Application No. 61/370,745, filed Aug. 4, 2010, U.S. Provisional Application No. 61/375,863, filed Aug. 22, 2010, and U.S. Provisional Application No. 61/467,376, filed Mar. 24, 2011. The contents of each of these applications are incorporated herein by reference in their entirety.

STATEMENT OF RIGHTS TO INVENTIONS MADE UNDER FEDERALLY SPONSORED RESEARCH

This invention was made with government support under grant number K08 CA128972 awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

a) File name: TDQ-10021_SEQLISTING.txt; created Feb. 1, 2018, 28 KB in size.

BACKGROUND OF THE INVENTION

Histone N-terminal tails maintain chromatin stability and are subject to modifications associated with transcriptional regulation. The best characterized of these modifications are acetylation, methylation and phosphorylation For each modification, enzymes exist that either lay down the appropriate mark or remove it. These modifications must then be interpreted by the transcriptional machinery. Acetyl-lysine recognition is principally mediated by bromodomains, which are commonly components of transcription factor complexes. The bromodomain and extra-terminal (BET)-family (e.g., BRD2, BRD3, BRD4 and BRDT) share a common domain architecture comprising two N-terminal bromodomains which exhibit a high level of sequence conservation, and a more divergent C-terminal domain which is implicated in protein-protein interactions. Aberrant regulation of histone modification can affect gene activity and play a role in oncogenesis. Lysine sidechain acetylation is an important regulatory event in the function of non-histone proteins, including but not limited to Hsp90, p53, STAT transcription factors, cortactin, beta-catenin and alpha-tubulin. Thus, modulation of lysine sidechain recognition would be expected to exert important phenotypic and therapeutic effects broadly in development and disease. Despite the importance of acetyl-lysine recognition to oncogenesis, few modulators of acetyl-lysine recognition have been identified.

SUMMARY OF THE INVENTION

As described below, the present invention features compositions and methods for treating or preventing a neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility. In particular embodiments, compounds of the invention are used to overcome drug resistance in neoplasia (e.g., cancer and non-malignant diseases). Further uses of the compositions of the invention include, but are not limited to, use in organ transplantation, modulation of cell state for regenerative medicine (i.e., by promoting or inhibiting cellular differentiation), and facilitating pluripotency. More specifically, the invention provides compositions and methods for disrupting the interaction of a BET family polypeptide comprising a bromodomain with acetyl-lysine and/or chromatin (e.g., disrupting a bromodomain interaction with an acetyl-lysine modification present on a histone N-terminal tail) and inhibiting oncogenesis. In another embodiment, the invention prevents or treats an inflammatory disease.

In one aspect, the invention provides a compound of Formula I:

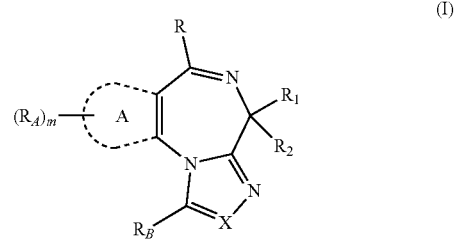

wherein
X is N or $CR_5$;
  $R_5$ is H, alkyl, cycloalkyl, heterocycloalkyl, aryl, or heteroaryl, each of which is optionally substituted;
  $R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
  each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
R is alkyl, cycloalkyl, heterocycloalkyl, aryl, or heteroaryl; each of which is optionally substituted;
$R_1$ is —$(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, optionally substituted aryl, or optionally substituted heteroaryl;
$R_2$ is H, D, halogen, or optionally substituted alkyl;
each $R_3$ is independently selected from the group consisting of:
  (i) H, aryl, substituted aryl, heteroaryl, or substituted heteroaryl;
  (ii) heterocycloalkyl or substituted heterocycloalkyl;
  (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) $NH_2$, $N=CR_4R_6$;
  each $R_4$ is independently H, alkyl, alkyl, cycloalkyl, heterocycloalkyl, aryl, or heteroaryl, each of which is optionally substituted;
  or $R_3$ and $R_4$ are taken together with the nitrogen atom to which they are attached to form a 4-10-membered ring;
  $R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;
m is 0, 1, 2, or 3;
provided that (a) if ring A is thienyl, X is N, R is phenyl or substituted phenyl, $R_2$ is H, $R_B$ is methyl, and $R_1$ is —$(CH_2)_n$-L, in which n is 1 and L is —CO—$N(R_3R_4)$, then $R_3$ and $R_4$ are not taken together with the nitrogen atom to which they are attached to form a morpholino ring;

(b) if ring A is thienyl, X is N, R is substituted phenyl, $R_2$ is H, $R_B$ is methyl, and $R_1$ is —$(CH_2)_n$-L, in which n is 1 and L is —CO—$N(R_3R_4)$, and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if ring A is thienyl, X is N, R is substituted phenyl, $R_2$ is H, $R_B$ is methyl, and $R_1$ is —$(CH_2)_n$-L, in which n is 1 and L is —COO—$R_3$, then $R_3$ is not methyl or ethyl;

or a salt, solvate or hydrate thereof.

In certain embodiments, R is aryl or heteroaryl, each of which is optionally substituted.

In certain embodiments, L is H, —COO—$R_3$, —CO—N($R_3R_4$), —$S(O)_2$—$R_3$, —$S(O)_2$—$N(R_3R_4)$, $N(R_3R_4)$, $N(R_4)C(O)R_3$ or optionally substituted aryl. In certain embodiments, each $R_3$ is independently selected from the group consisting of: H, —$C_1$-$C_8$ alkyl, containing 0, 1, 2, or 3 heteroatoms selected from O, S, or N; or $NH_2$, $N=CR_4R_6$.

In certain embodiments, $R_1$ is —$(CH_2)_n$-L, in which n is 1 and L is —CO—$N(R_3R_4)$, and one of $R_3$ and $R_4$ is H, and the other of $R_3$ and $R_4$ is $(CH_2)_p$—Y, in which p is 1-3 (e.g., p is 2) and Y is a nitrogen-containing ring (which may be aromatic or non-aromatic).

In certain embodiments, $R_2$ is H, D, halogen or methyl.

In certain embodiments, $R_B$ is alkyl, hydroxyalkyl, haloalkyl, or alkoxy; each of which is optionally substituted.

In certain embodiments, $R_B$ is methyl, ethyl, hydroxy methyl, methoxymethyl, trifluoromethyl, COOH, COOMe, COOEt, or $COOCH_2OC(O)CH_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.

In certain embodiments, m is 1 or 2, and at least one occurrence of $R_A$ is methyl.

In certain embodiments, each $R_A$ is independently H, an optionally substituted alkyl, or any two $R_A$ together with the atoms to which each is attached, can form an aryl.

In another aspect, the invention provides a compound of Formula II:

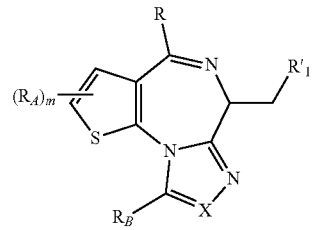

(II)

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
R is alkyl, cycloalkyl, heterocycloalkyl, aryl, or heteroaryl, each of which is optionally substituted;
$R'_1$ is H, —COO—$R_3$, —CO—$R_3$, optionally substituted aryl, or optionally substituted heteroaryl;
each $R_3$ is independently selected from the group consisting of:
  (i) H, aryl, substituted aryl, heteroaryl, substituted heteroaryl;
  (ii) heterocycloalkyl or substituted heterocycloalkyl;
  (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl; each of which may be optionally substituted;

m is 0, 1, 2, or 3;
provided that if $R'_1$ is —COO—$R_3$, X is N, R is substituted phenyl, and $R_B$ is methyl, then $R_3$ is not methyl or ethyl;
or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, $R'_1$ is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, $R'_1$ is —COO—$R_3$, and $R_3$ is methyl, ethyl, propyl, i-propyl, butyl, sec-butyl, or t-butyl; or $R'_1$ is H or optionally substituted phenyl.

In certain embodiments, $R_B$ is methyl, ethyl, hydroxy methyl, methoxymethyl, trifluoromethyl, COOH, COOMe, COOEt, $COOCH_2OC(O)CH_3$.

In certain embodiments, $R_B$ is methyl, ethyl, hydroxy methyl, methoxymethyl, trifluoromethyl, COOH, COOMe, COOEt, or $COOCH_2OC(O)CH_3$.

In certain embodiments, each $R_A$ is independently an optionally substituted alkyl, or any two $R_A$ together with the atoms to which each is attached, can form a fused aryl.

In certain embodiments, each $R_A$ is methyl.

In another aspect, the invention provides a compound of formula III:

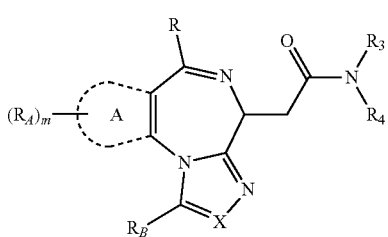

(III)

wherein
X is N or $CR_5$;
  $R_5$ is H, alkyl, cycloalkyl, heterocycloalkyl, aryl, or heteroaryl, each of which is optionally substituted;
  $R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
  each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
R is alkyl, cycloalkyl, heterocycloalkyl, aryl, or heteroaryl, each of which is optionally substituted;
each $R_3$ is independently selected from the group consisting of:
  (i) H, aryl, substituted aryl, heteroaryl, or substituted heteroaryl;
  (ii) heterocycloalkyl or substituted heterocycloalkyl;
  (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
  (iv) $NH_2$, $N=CR_4R_6$;
each $R_4$ is independently H, alkyl, alkyl, cycloalkyl, heterocycloalkyl, aryl, or heteroaryl, each of which is optionally substituted;
or $R_3$ and $R_4$ are taken together with the nitrogen atom to which they are attached to form a 4-10-membered ring;
$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;
m is 0, 1, 2, or 3;
provided that:
  (a) if ring A is thienyl, X is N, R is phenyl or substituted phenyl, $R_B$ is methyl, then $R_3$ and $R_4$ are not taken together with the nitrogen atom to which they are attached to form a morpholino ring; and
  (b) if ring A is thienyl, X is N, R is substituted phenyl, $R_2$ is H, $R_B$ is methyl, and one of $R_3$ and $R_4$ is H, then the other of $R_3$ and $R_4$ is not methyl, hydroxyethyl, alkoxy, phenyl, substituted phenyl, pyridyl or substituted pyridyl; or a salt, solvate or hydrate thereof.

In certain embodiments, R is aryl or heteroaryl, each of which is optionally substituted. In certain embodiments, R is phenyl or pyridyl, each of which is optionally substituted.

In certain embodiments, R is p-Cl-phenyl, o-Cl-phenyl, m-Cl-phenyl, p-F-phenyl, o-F-phenyl, m-F-phenyl or pyridinyl. In certain embodiments, $R_3$ is H, $NH_2$, or $N=CR_4R_6$.

In certain embodiments, each $R_4$ is independently H, alkyl, cycloalkyl, heterocycloalkyl, aryl, heteroaryl; each of which is optionally substituted.

In certain embodiments, $R_6$ is alkyl, alkenyl, cycloalkyl, cycloalkenyl, heterocycloalkyl, aryl, or heteroaryl, each of which is optionally substituted.

In certain embodiments, one of $R_3$ and $R_4$ is H, and the other of $R_3$ and $R_4$ is $(CH_2)_p$—Y, in which p is 1-3 (e.g., p is 2) and Y is a nitrogen-containing ring (which may be aromatic or non-aromatic).

In another aspect, the invention provides a compound of formula IV:

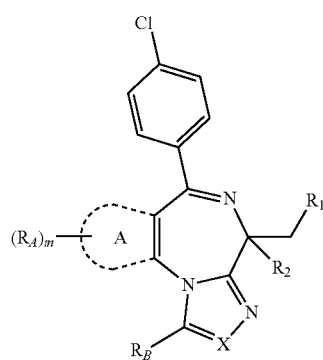

(IV)

wherein
X is N or $CR_5$;
  $R_5$ is H, alkyl, cycloalkyl, heterocycloalkyl, aryl, or heteroaryl, each of which is optionally substituted;
  $R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
  each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
$R_1$ is —$(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, optionally substituted aryl, or optionally substituted heteroaryl;
$R_2$ is H, D, halogen, or optionally substituted alkyl;
each $R_3$ is independently selected from the group consisting of:
  (i) H, aryl, substituted aryl, heteroaryl, or substituted heteroaryl;
  (ii) heterocycloalkyl or substituted heterocycloalkyl;
  (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
  (iv) $NH_2$, $N=CR_4R_6$;
each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that
  (a) if ring A is thienyl, X is N, $R_2$ is H, $R_B$ is methyl, and $R_1$ is —$(CH_2)_n$-L, in which n is 0 and L is —CO—$N(R_3R_4)$, then $R_3$ and $R_4$ are not taken together with the nitrogen atom to which they are attached to form a morpholino ring;
  (b) if ring A is thienyl, X is N, $R_2$ is H, $R_B$ is methyl, and $R_1$ is —$(CH_2)_n$-L, in which n is 0 and L is —CO—$N(R_3R_4)$, and one of $R_3$ and $R_4$ is H, then the other of $R_3$ and $R_4$ is not methyl, hydroxyethyl, alkoxy, phenyl, substituted phenyl, pyridyl or substituted pyridyl; and
  (c) if ring A is thienyl, X is N, $R_2$ is H, $R_B$ is methyl, and $R_1$ is —$(CH_2)_n$-L, in which n is 0 and L is —COO—$R_3$, then $R_3$ is not methyl or ethyl; or
a salt, solvate or hydrate thereof.

In certain embodiments, $R_1$ is —$(CH_2)_n$-L, in which n is 0-3 and L is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, n is 1 or 2 and L is alkyl or —COO—$R_3$, and $R_3$ is methyl, ethyl, propyl, i-propyl, butyl, sec-butyl, or t-butyl; or n is 1 or 2 and L is H or optionally substituted phenyl.

In certain embodiments, $R_1$ is —$(CH_2)_n$-L, in which n is 0 and L is —CO—$N(R_3R_4)$, and one of $R_3$ and $R_4$ is H, and the other of $R_3$ and $R_4$ is $(CH_2)_p$—Y, in which p is 1-3 (e.g., p is 2) and Y is a nitrogen-containing ring (which may be aromatic or non-aromatic).

In certain embodiments, $R_2$ is H or methyl.

In certain embodiments, $R_B$ is methyl, ethyl, hydroxymethyl, methoxymethyl, trifluoromethyl, COOH, COOMe, COOEt, $COOCH_2OC(O)CH_3$.

In certain embodiments, ring A is phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, each $R_A$ is independently an optionally substituted alkyl, or any two $R_A$ together with the atoms to which each is attached, can form an aryl.

The invention also provides compounds of Formulae V-XXII herein, and any compound described herein.

In another aspect, the invention provides a method for treating or preventing a neoplasia in a subject, the method comprising administering to the subject an effective amount of a compound of any of Formulae I-XXII, or any compound described herein.

In certain embodiments, the compound is a compound of any of Formulas I-IV.

In another aspect, the invention provides a method for reducing the growth, proliferation or survival of a neoplastic cell, the method comprising contacting the cell with an effective amount of a compound of any of Formulae I-XXII, or any compound described herein, thereby reducing the growth, proliferation or survival of a neoplastic cell.

In another aspect, the invention provides a method of inducing differentiation in a neoplastic cell, the method comprising contacting the cell with a compound of any of Formulae I-XXII, or any compound described herein, thereby inducing differentiation in the neoplastic cell.

In another aspect, the invention provides a method of inducing cell death in a neoplastic cell, the method comprising contacting the cell with a therapeutically effective amount of a compound of any of Formulae I-XXII, or any compound described herein, thereby inducing cell death in the neoplastic cell.

In certain embodiments, the methods further comprise selecting the compound for binding to a bromodomain of the BET family.

In certain embodiments, the methods further comprise selecting the compound for inhibiting bromodomain binding to chromatin in a cellular environment.

In certain embodiments, the methods further comprise selecting the compound for binding specificity using differential scanning fluorimetry (DSF), Isothermal Titration Calorimetry, and/or a luminescence proximity homogeneous assay (ALPHA-screen). In certain embodiments, the compound increases the thermal stability of the bromodomain in said assay.

In certain embodiments of the methods, the BET family member is BRD2, BRD3, BRD4 or BRDT.

In certain embodiments of the methods, the cell is in a subject.

In another aspect, the invention provides a method of preventing or treating a neoplasia in a subject, the method comprising administering to a subject in need thereof an effective amount of a compound of any of Formulae I-XXII, or any compound described herein, thereby preventing or treating neoplasia in a subject.

In certain embodiments, the subject is a mammal. In certain embodiments, the subject is a human patient.

In certain embodiments, the method reduces the growth or proliferation of a neoplasia in a subject.

In certain embodiments, the neoplasia is driven by a transcriptional activator. In certain embodiments, the transcriptional activator is myc.

In certain embodiments, the subject has a neoplasia selected from the group consisting of Burkitt's lymphoma, small cell lung cancer, breast cancer, colon cancer, neuroblastoma, glial blastoma multiforme, MLL driven leukemia, chronic lymphocytic leukemia, NUT midline carcinoma, squamous cell carcinoma or any other carcinoma associated with a NUT rearrangement.

In another aspect, the invention provides a composition comprising a therapeutically effective amount of a compound of any of Formulae I-XXII, or any compound described herein, and a pharmaceutically acceptable excipient or carrier therefor.

In another aspect, the invention provides a packaged pharmaceutical comprising a therapeutically effective amount of a compound of any of Formulae I-XXII, or any compound described herein, and written instructions for administration of the compound.

In another aspect, the invention provides a method of preventing or treating a neoplasia in a subject, the method comprising administering to the subject a therapeutically effective amount of a compound of any of Formulae I-XXII, or any compound described herein, wherein the compound disrupts bromodomain binding to acetyl-lysine or otherwise displaces a BET family member from chromatin, thereby preventing or treating said neoplasia.

In certain embodiments, the compound inhibits Histone H4 Kac peptide binding to a BET family member.

In certain embodiments, the BET family member is BRD2, BRD3, BRD4 or BRDT.

In certain embodiments, the compound binds to a Kac binding site of a BET-family bromodomain.

In another aspect, the invention provides a method of identifying a compound for the treatment of a neoplasia, the method comprising contacting a test compound with a BET family member comprising a bromodomain; and detecting specific binding to the bromodomain, thereby identifying the test compound as useful for the treatment of a neoplasia.

In certain embodiments, binding specificity is assayed using differential scanning fluorimetry (DSF).

In certain embodiments, binding increases the thermal stability of said bromodomain.

In certain embodiments, binding is detected using Isothermal Titration Calorimetry.

In certain embodiments, binding is detected using a luminescence proximity homogeneous assay (ALPHA-screen).

In certain embodiments, the compound inhibits Histone H4 Kac peptide binding to said bromodomain.

In certain embodiments, the compound forms a hydrogen bond with an evolutionarily conserved asparagine in said bromodomain.

In certain embodiments, said BET family member is BRD4 or BRD2 and the asparagine is Asn140 in BRD4(1) and Asn429 in BRD2(2).

In certain embodiments, the compound binds competitively with chromatin in a cellular environment.

In certain embodiments, competitive binding with chromatin is detected using fluorescence recovery after photobleaching (FRAP).

In certain embodiments, the method is carried out in a neoplastic cell in vitro.

In certain embodiments, the method further comprises detecting a decrease in cell proliferation, an increase in cell death, or an increase in cell differentiation.

In certain embodiments, cell death is apoptotic cell death.

In certain embodiments, cell differentiation is identified by detecting an increase in cytokeratin expression.

In certain embodiments, the method further comprises detecting a reduction in transcriptional elongation.

In another aspect, the invention provides a method for treating or preventing neoplasia in a subject, the method comprising administering to said subject an effective amount of a compound of any of Formulae I-XXII, or any compound described herein, wherein said compound is capable of binding a BET family bromodomain and disrupting said bromodomains interaction with chromatin, thereby preventing or treating said cancer.

In certain embodiments, the method induces cell death or differentiation in a neoplastic cell of said subject.

In another aspect, the invention provides a composition for the treatment or prevention of a neoplasia, the composition comprising an effective amount of a compound selected from the group consisting of the compound of any of Formulae I-XXII, or any compound described herein, and a pharmaceutically acceptable excipient, wherein said compound inhibits Histone H4 Kac peptide binding to a BET family bromodomain.

In another aspect, the invention provides a method for reducing inflammation in a subject, the method comprising administering to the subject an effective amount of a compound of any of Formulae I-XXII, or any compound described herein.

In another aspect, the invention provides a method of preventing or treating an inflammatory disease in a subject, the method comprising administering to a subject in need thereof an effective amount of a compound of any of Formulae I-XXII, or any compound described herein.

In certain embodiments, the subject is a mammal. In certain embodiments, the subject is a human patient.

In certain embodiments, the method reduces cytokine level, histamine release, or the biological activity of an immunoresponsive cell.

In another aspect, the invention provides a method of identifying a compound for the treatment of inflammation, the method comprising contacting a test compound with a BET family member comprising a bromodomain; and detecting specific binding to the bromodomain, thereby identifying the test compound as useful for the treatment of inflammation.

Other features and advantages of the invention will be apparent from the detailed description, and from the claims.

Definitions

By "agent" is meant any small molecule chemical compound, antibody, nucleic acid molecule, or polypeptide, or fragments thereof.

As used herein, the term an "aromatic ring" or "aryl" means a monocyclic or polycyclic-aromatic ring or ring radical comprising carbon and hydrogen atoms.

Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or optionally is substituted with one or more substituents, e.g., substituents as described herein for alkyl groups (including without limitation alkyl (preferably, lower alkyl or alkyl substituted with one or more halo), hydroxy, alkoxy (preferably, lower alkoxy), alkylthio, cyano, halo, amino, boronic acid ($—B(OH)_2$, and nitro). In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be unsubstituted, or optionally substituted with one or more substituents, such as amino, alkylamino, arylamino, heteroarylamino, alkoxy, alkylthio, oxo, halo, acyl, nitro, hydroxyl, cyano, aryl, heteroaryl, alkylaryl, alkylheteroaryl, aryloxy, heteroaryloxy, arylthio, heteroarylthio, arylamino, heteroarylamino, carbocyclyl, carbocyclyloxy, carbocyclylthio, carbocyclylamino, heterocyclyl, heterocyclyloxy, heterocyclylamino, heterocyclylthio, and the like. Lower alkyls are typically preferred for the compounds of this invention.

By "bromodomain" is meant a portion of a polypeptide that recognizes acetylated lysine residues. In one embodiment, a bromodomain of a BET family member polypeptide comprises approximately 110 amino acids and shares a conserved fold comprising a left-handed bundle of four alpha helices linked by diverse loop regions that interact with chromatin.

By "BET family polypeptide" is meant a polypeptide comprising two bromodomains and an extraterminal (ET) domain or a fragment thereof having transcriptional regulatory activity or acetylated lysine binding activity. Exemplary BET family members include BRD2, BRD3, BRD4 and BRDT.

By "BRD2 polypeptide" is meant a protein or fragment thereof having at least 85% identity to NP_005095 that is capable of binding chromatin or regulating transcription.

The sequence (SEQ ID NO: 1) of an exemplary BRD2 polypeptide follows:

MLQNVTPHNKLPGEGNAGLLGLGPEAAAPGKRIRKPSLLYEGFESPTMAS
VPALQLTPANPPPPEVSNPKKPGRVTNQLQYLHKVVMKALWKHQFAWPFR
QPVDAVKLGLPDYHKIIKQPMDMGTIKRRLENNYYWAASECMQDENTMET
NCYIYNKPTDDIVLMAQTLEKIFLQKVASMPQEEQELVVTIPKNSHKKGA
KLAALQGSVTSAHQVPAVSSVSHTALYTPPPEIPTTVLNIPHPSVISSPL
LKSLHSAGPPLLAVTAAPPAQPLAKKKGVKRKADTTTPTPTAILAPGSPA

-continued
SPPGSLEPKAARLPPMRRESGRPIKPPRKDLPDSQQQHQSSKKGKLSEQL
KHCNGILKELLSKKHAAYAWPFYKPVDASALGLHDYHDIIKHPMDLSTVK -continued
RKMENRDYRDAQEFAADVRLMFSNCYKYNPPDHDVVAMARKLQDVFEFRY
AKMPDEPLEPGPLPVSTAMPPGLAKSSSESSSEESSSESSSEEEEEEDEE
DEEEEESESSDSEEERAHRLAELQEQLRAVHEQLAALSQGPISKPKRKRE
KKEKKKKRKAEKHRGRAGADEDDKGPRAPRPPQPKKSKKASGSGGGSAAL
GPSGFGPSGGSGTKLPKKATKTAPPALPTGYDSEEEEESRPMSYDEKRQL
SLDINKLPGEKLGRVVHITQAREPSLRDSNPEETEIDFETLKPSTLRELE
RYVLSCLRKKPRKPYTIKKPVGKTKEELALEKKRELEKRLQDVSGQLNST
KKPPKKANEKTESSSAQQVAVSRLSASSSSSDSSSSSSSSSSSDTSDSDS
G By "BRD2 nucleic acid molecule" is meant a polynucleotide encoding a BRD2 polypeptide or fragment thereof.

By "BRD3 polypeptide" is meant a protein or fragment thereof having at least 85% identity to NP_031397.1 that is capable of binding chromatin or regulating transcription.

The sequence (SEQ ID NO: 2) of an exemplary BRD3 polypeptide follows:

```
  1  mstattvapa gipatpgpvn ppppevsnps kpgrktnqlq ymqnvvvktl wkhqfawpfy
 61  qpvdaiklnl pdyhkiiknp mdmgtikkrl ennyywsase cmqdfntmft ncyiynkptd
121  divlmaqale kiflqkvaqm pqeevellpp apkgkgrkpa agaqsagtqg vaavssvspa
181  tpfqsvpptv sqtpviaatp vptitanvts vpvppaaapp ppatpivpvv pptppvvkkk
241  gvkrkadttt pttsaitasr sesppplsdp kqakvvarre sggrpikppk kdledgevpq
301  hagkkgklse hlrycdsilr emlskkhaay awpfykpvda ealelhdyhd iikhpmdlst
361  vkrkmdgrey pdaqgfaadv rlmfsncyky nppdhevvam arklqdvfem rfakmpdepv
421  eapalpapaa pmvskgaess rsseesssds gssdseeera trlaelqeql kavheqlaal
481  sqapvnkpkk kkekkekekk kkdkekekek hkvkaeeekk akvappakqa qqkkapakka
541  nstttagrql kkggkqasas ydseeeeegl pmsydekrql sldinrlpge klgrvvhiiq
601  srepslrdsn pdeieidfet lkpttlrele ryvksclqkk qrkpfsasgk kqaakskeel
661  aqekkkelek rlqdvsgqls sskkparkek pgsapsggps rlsssssses gssssgsss
721  dssdse
```

By "Brd3 nucleic acid molecule" is meant a polynucleotide encoding a BRD3 polypeptide.

By "BRD4 polypeptide" is meant a protein or fragment thereof having at least 85% identity to NP_055114 (SEQ ID NO: 3) that is capable of binding chromatin or regulating transcription.

```
  1  msaesgpgtr lrnlpvmgdg letsqmsttq aqaqpqpana astnppppet snpnkpkrqt
 61  nqlqyllrvv lktlwkhqfa wpfqqpvdav klnlpdyyki iktpmdmgti kkrlennyyw
```

```
121  naqeciqdfn  tmftncyiyn  kpgddivlma  ealeklflqk  inelpteete  imivqakgrg 181  rgrketgtak  pgvstvpntt  qastppqtqt  pqpnpppvqa  tphpfpavtp  dlivqtpvmt 241  vvppqplqtp  ppvppqpqpp  papapqpvqs  hppiiaatpq  pvktkkgvkr  kadtttptti 301  dpihseppslp  pepkttklgq  rressrpvkp  pkkdvpdsqq  hpapeksskv  seqlkccsgi 361  lkemfakkha  ayawpfykpv  dvealglhdy  cdiikhpmdm  stiksklear  eyrdaqefga 421  dvrlmfsncy  kynppdhevv  amarklqdvf  emrfakmpde  peepvvavss  pavppptkvv 481  appsssdsss  dsssdsdsst  ddseeeraqr  laelqeqlka  vheqlaalsq  pqqnkpkkke 541  kdkkekkkek  hkrkeeveen  kkskakeppp  kktkknnssn  snvskkepap  mkskppptye 601  seeedkckpm  syeekrqlsl  dinklpgekl  grvvhiiqsr  epslknsnpd  eieidfetlk 661  pstlrelery  vtsclrkkrk  pqaekvdvia  gsskmkgfss  sesesssess  ssdsedsetg 721  pa
```

By "Brd4 nucleic acid molecule" is meant a polynucleotide that encodes a BRD4 polypeptide.

By "BRDT polypeptide is meant a protein or fragment thereof having at least 85% identity to NP_001717 (SEQ ID NO: 4) that is capable of binding chromatin or regulating transcription.

By "analog" is meant a molecule that is not identical, but has analogous functional or structural features. For example, a polypeptide analog retains at least some of the biological activity of a corresponding naturally-occurring polypeptide, while having certain biochemical modifications that enhance the analog's function relative to a naturally occurring poly-

```
  1  mslpsrqtai  ivnppppeyi  ntkkngrltn  qlqylqkvvl  kdlwkhsfsw  pfqrpvdavk 61  lqlpdyytii  knpmdlntik  krlenkyyak  aseciedfnt  mfsncylynk  pgddivlmaq 121  aleklfmqkl  sqmpqeeqvv  gvkerikkgt  qqniavssak  eksspsatek  vfkqqeipsv 181  fpktsispln  vvqgasvnss  sqtaaqvtkg  vkrkadtttp  atsavkasse  fsptfteksv 241  alppikenmp  knvlpdsqqq  ynvvktvkvt  eqlrhcseil  kemlakkhfs  yawpfynpvd 301  vnalglhnyy  dvvknpmdlg  tikekmdnqe  ykdaykfaad  vrlmfmncyk  ynppdhevvt 361  marmlqdvfe  thfskipiep  vesmplcyik  tditettgre  ntneassegn  ssddsederv 421  krlaklqeql  kavhqqlqvl  sqvpfrklnk  kkekskkekk  kekvnnsnen  prkmcegmrl 481  kekskrnqpk  krkqqfiglk  sedednakpm  nydekrqlsl  ninklpgdkl  grvvhiiqsr 541  epslsnsnpd  eieidfetlk  astlreleky  vsaclrkrpl  kppakkimms  keelhsqkkq 601  elekrlldvn  nqlnsrkrqt  ksdktqpska  venvsrlses  sssssssses  esssssdlsss 661  dssdsesemf  pkftevkpnd  spskenvkkm  knecilpegr  tgvtqigycv  qdttsanttl 721  vhqttpshvm  ppnhhglafn  yqelehlqtv  knisplqilp  psgdseqlsn  gitvmhpsgd 781  sdttmlesec  qapvqkdiki  knadswkslg  kpvkpsgvmk  ssdelfnqfr  kaaiekevka 841  rtqelirkhl  eqntkelkas  qenqrdlgng  ltvesfsnki  qnkcsgeeqk  ehqqsseaqd 901  ksklwllkdr  dlargkeqer  rrreamvgti  dmtlqsdimt  mfennfd
```

By "BRDT nucleic acid molecule" is meant a polynucleotide encoding a BRDT polypeptide.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

peptide. Such biochemical modifications could increase the analog's protease resistance, membrane permeability, or half-life, without altering, for example, ligand binding. An analog may include an unnatural amino acid.

By "compound" is meant any small molecule chemical compound, antibody, nucleic acid molecule, or polypeptide, or fragments thereof.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents as for aryl groups. Examples of heteroaryl groups include, but are not limited to, pyridyl, furanyl, benzodioxolyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heterocyclic" as used herein, refers to organic compounds that contain at least at least one atom other than carbon (e.g., S, O, N) within a ring structure. The ring structure in these organic compounds can be either aromatic or non-aromatic. Some examples of heterocyclic moeities include, are not limited to, pyridine, pyrimidine, pyrrolidine, furan, tetrahydrofuran, tetrahydrothiophene, and dioxane.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom ($C^{12}$) would be one in which the carbon atom of the compound is replaced with the $C^{13}$ isotope.

The term "neoplastic" refers to those cells having the capacity for autonomous growth, i.e., an abnormal state or condition characterized by rapidly proliferating cell growth. A neoplastic disease state may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Illustrative neoplasms amenable to treatment with a compound of the invention include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, mixed lineage leukemia, chronic leukemia, chronic myelocytic leukemia, chronic lymphocytic leukemia), multiple myeloma, polycythemia vera, cutaneous T-cell lymphoma (CTCL), lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, non-small cell lung carcinoma, bladder carcinoma, epithelial carcinoma, glioma, glioblastoma, glioblastoma multiforme, astrocytoma, medulloblastoma, craniopharyngioma, ependymoma, pinealoma, hemangioblastoma, acoustic neuroma, neuroendocrine tumor, oligodenroglioma, schwannoma, meningioma, melanoma, neuroblastoma, and retinoblastoma).

In one embodiment, the neoplasia is driven by a dominant transcriptional activator, such as myc. Such cancers include, but are not limited to, Burkitt's lymphoma, small cell lung cancer, breast cancer, colon cancer, neuroblastoma, glial blastoma multiforme, MLL driven leukemias, chronic lymphocytic leukemias, squamous cell carcinoma involving a NUT rearrangement, as well as other cancers involving bromodomain-containing proteins or NUT reaarrangements.

The language "inhibiting the growth" of the neoplasm includes the slowing, interrupting, arresting or stopping its growth and metastases and does not necessarily indicate a total elimination of the neoplastic growth.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model.

By a "computer system" is meant the hardware means, software means and data storage means used to analyse atomic coordinate data. The minimum hardware means of the computer-based systems of the present invention comprises a central processing unit (CPU), input means, output means and data storage means. Desirably a monitor is provided to visualise structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

By "computer readable media" is meant any media which can be read and accessed directly by a computer e.g. so that the media is suitable for use in the above-mentioned computer system. The media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases susceptible to treatment with compounds delineated herein include a neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency.

By "effective amount" is meant the amount of an agent required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents, e.g., substituents as described herein for aryl groups. Examples of heteroaryl groups include, but are not limited to, pyridyl, furanyl, benzodioxolyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heterocyclic" as used herein, refers to organic compounds that contain at least at least one atom other than carbon (e.g., S, O, N) within a ring structure. The ring structure in these organic compounds can be either aromatic or, in certain embodiments, non-aromatic. Some examples of heterocyclic moeities include, are not limited to, pyridine, pyrimidine, pyrrolidine, furan, tetrahydrofuran, tetrahydrothiophene, and dioxane.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom ($C^{12}$) would be one in which the carbon atom of the compound is replaced with the $C^{13}$ isotope.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fitting" is meant determining by automatic, or semi-automatic means, interactions between one or more atoms of an agent molecule and one or more atoms or binding sites of a BET family member (e.g., a bromodomain of BRD2, BRD3, BRD4 and BRDT), and determining the extent to which such interactions are stable. Various computer-based methods for fitting are described further herein.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

The term "neoplastic" refers to those cells having the capacity for autonomous growth, i.e., an abnormal state or condition characterized by rapidly proliferating cell growth. A neoplastic disease state may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The language "inhibiting the growth" of the neoplasm includes the slowing, interrupting, arresting or stopping its growth and metastases and does not necessarily indicate a total elimination of the neoplastic growth.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the term neoplasia generally refers to cells experiencing abnormal cell growth rates. Neoplasias include "tumors," which may be either benign, premalignant or malignant.

The term "obtaining" as in "obtaining compound" is intended to include purchasing, synthesizing or otherwise acquiring the compound.

The term "optical isomers" as used herein includes molecules, also known as chiral molecules, that are exact non-superimposable mirror images of one another.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "polymorph" as used herein, refers to solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

Furthermore the indication of stereochemistry across a carbon-carbon double bond is also opposite from the general chemical field in that "Z" refers to what is often referred to as a "cis" (same side) conformation whereas "E" refers to what is often referred to as a "trans" (opposite side) conformation. Both configurations, cis/trans and/or Z/E are encompassed by the compounds of the present invention.

With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 85% identity to a reference amino acid sequence (for example, any one of the amino acid sequences described herein) or nucleic acid sequence (for example, any one of the nucleic acid sequences described herein). Preferably, such a sequence is at least 85%, 90%, 95%, 99% or even 100% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e.sup.-3 and e.sup.-100 indicating a closely related sequence.

By "reduces" or "increases" is meant a negative or positive alteration, respectively, of at least about 10%, 25%, 50%, 75%, or 100% relative to a reference.

By "root mean square deviation" is meant the square root of the arithmetic mean of the squares of the deviations from the mean.

By "reducing cell survival" is meant to inhibit the viability of a cell or to induce cell death relative to a reference cell.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "subject" is meant a mammal, including, but not limited to, a human or non-human mammal, such as a bovine, equine, canine, ovine, or feline.

By "specifically binds" is meant a compound or antibody that recognizes and binds a polypeptide of the invention, but which does not substantially recognize and bind other molecules in a sample, for example, a biological sample, which naturally includes a polypeptide of the invention.

The term "sulfhydryl" or "thiol" means —SH.

As used herein, the term "tautomers" refers to isomers of organic molecules that readily interconvert by tautomerization, in which a hydrogen atom or proton migrates in the reaction, accompanied in some occasions by a switch of a single bond and an adjacent double bond.

As used herein, the terms "treat," "treating," "treatment," and the like refer to reducing or ameliorating a disorder and/or symptoms associated therewith. By "ameliorate" is meant decrease, suppress, attenuate, diminish, arrest, or stabilize the development or progression of a disease. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

"An effective amount" refers to an amount of a compound, which confers a therapeutic effect on the treated subject. The therapeutic effect may be objective (i.e., measurable by some test or marker) or subjective (i.e., subject gives an indication of or feels an effect). An effective amount of a compound described herein may range from about 1 mg/Kg to about 5000 mg/Kg body weight. Effective doses will also vary depending on route of administration, as well as the possibility of co-usage with other agents.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2A shows that fluorescence recovery after photobleaching (FRAP) of GFP-BRD4 is unaffected by the presence of (−)-JQ1 (250 nM, 5 h) compared to vehicle control. Data represent the mean±s.d. (n=5). FIG. 2B shows that expressed GFP-BRD4 demonstrates enhanced recovery in the presence of (+)-JQ1 (250 nM, 5 h), in a parallel comparative study. Data represent the mean±s.d. (n=5). FIG. 2C provides a quantitative comparison of the mobile fraction of GFP-BRD4 observed in FRAP studies (a,b). Data represent the mean±s.d. (n=5) and are annotated with p-values as obtained from a two-tailed t-test comparing ligand treated samples to vehicle controls.

FIG. 3A shows fluorescence recovery after photobleaching (FRAP) of GFP-BRD4 that demonstrates enhanced recovery in the presence of JQ1. Nuclei are false-colored in proportion to fluorescence intensity. White circles indicate regions of photobleaching. FIGS. 3B-3D show that JQ1 accelerates fluorescence recovery in FRAP experiments performed with transfected (FIG. 3B) GFP-BRD4 and (FIG. 3C) GFP-BRD4-NUT, but has no effect on recovery of nuclear GFP-NUT (FIG. 3D). FIG. 3E shows a quantitative comparison of time to half-maximal fluorescence recovery for FRAP studies (FIGS. 3B-3D). Data represent the mean±s.d. (n=5), and are annotated with p-values as obtained from a two-tailed t-test. FIG. 3F JQ1 (500 nM, 48 h) prompts a loss of focal nuclear staining for NUT (anti-NUT; 40×). FIG. 3G shows that NMC cells treated with JQ1 (500 nM, 48 h) demonstrate cytological signs of squamous differentiation (H&E; 40×). FIG. 3H shows that the differentiation of NMC cells by JQ1 (500 nM) is prompt, time-dependent and characterized by a marked increase in cytokeratin expression (AE1/AE3; 40×). FIGS. 3I-3J show that JQ1 attenuates rapid proliferation of (FIG. 3I) 797 and (FIG. 3J) Per403 NMC cell lines in vitro (Ki67; 40×).

FIG. 4A shows that NMC 797 cells treated with JQ1 (500 nM) demonstrate time-dependent cytologic signs of squamous differentiation (H&E; 40× and 100×, as shown), exemplified by cell spindling, flattening and the development of open chromatin. FIG. 4B shows that NMC Per403 cells treated with JQ1 (500 nM, 48 h) exhibit comparable signs of squamous differentiation. Cell spindling and cytosolic keratinization is illustrated by H&E and keratin staining, respectively (40×). FIG. 4C show that the non-NMC squamous carcinoma cell line TE10 fails to differentiate in response to JQ1 (500 nM), illustrated by H&E and keratin (AE1/AE3) staining (40×).

FIG. 4D includes two micrographs showing that JQ1 attenuates rapid proliferation of NMC Per403 cell lines in vitro (Ki67; 40×). Images are shown at identical magnification. FIG. 4E is a graph showing the effect of JQ1 on cellular proliferation (Ki67 staining and positivity; %) as measured by IHC as carried out in (4D) and FIG. 3J. Cells were manually scored as Ki67 positive (dark staining nuclei) or negative (pale blue staining nuclei) in five high-powered fields. Data represent the mean±s.d. (n=5), and are annotated with p-values as obtained from a two-tailed t-test.

FIG. 4F includes six micrographs, which show that NMC 797 cells treated in chamber slides with (−)-JQ1 (100 nM) exhibited comparable cytosolic phenotypes compared to vehicle-treated controls. (+)-JQ1 (100 nM, 48 h) prompted squamous differentiation exhibited by cell spindling, flattening and increased expression of keratin. FIG. 4G shows that NMC 797 cells treated with JQ1 enantiomers or vehicle were centrifuged, fixed, sectioned and stained for keratin expression (left; AE1/AE3, 20×). Image-based analysis of keratin expression was performed on concurrently prepared slides using unbiased masking and quantification algorithms capable of scoring nuclei for staining intensity (right; 20×). FIG. 4H shows that (+)-JQ1 (250 nM) induced rapid expression of keratin in treated NMC 797 cells compared to (−)-JQ1 (250 nM) and vehicle controls, as determined by quantitative immunohistochemistry. Percent positive nuclei per treatment condition are presented. Data represent the mean±s.d. (n=3) and are annotated with p-values as obtained from a two-tailed t-test. FIG. 4I, (+)-JQ1 (250 nM) elicits a time-dependent induction of strong (3+) keratin staining of treated NMC 797 cells, compared to (−)-JQ1 (250 nM). Percent positive nuclei per treatment condition are presented. Data represent the mean±s.d. (n=3) and are annotated with p-values as obtained from a two-tailed t-test. Grouped images are shown at identical magnification.

FIGS. 4J-4L show that squamous carcinoma cell lines which do not possess the BRD4-NUT translocation are less sensitive to treatment with JQ1. Gastrointestinal squamous carcinoma cell lines (TT and TE10) were cultured in the presence of (+)-JQ1 (250 nM, red circles) or (−)-JQ1 (250 nM, black circles) for 72 hours. Minimal effects observed on cell proliferation with JQ1 is consistent with a plausible role in cell cycle progression in mitotic cells[7]. Data is presented as mean±s.d. (n=3). $IC_{50}$ values were calculated by logistic regression.

FIG. 5A shows the growth effects of BRD4 inhibition on BRD4-NUT dependent cell lines. Cells were incubated with (+)-JQ1 (red circles) or (−)-JQ1 (black circles) and monitored for proliferation after 72 hours. (+)-JQ1 uniquely attenuated proliferation by NMC cell lines. Data is presented as mean±s.d. (n=3). $IC_{50}$ values were calculated by logistic regression. FIG. 5B shows the progressive antiproliferative effects of (+)-JQ1 on NMC 797 cells over time were demonstrated on days 1, 3, 7 and 10. Data points are mean±s.d. (n=3). FIG. 5C shows results of flow cytometry for DNA content in NMC 797 cells. (+)-JQ1 (250 nM, 48 h) induced a G1 arrest compared to (−)-JQ1 (250 nM) and vehicle control. FIG. 5D shows the results of a flow cytometric analysis of NMC 797 squamous carcinoma cells treated with vehicle, JQ1 or staurosporine (STA), as indicated. PI, propidium iodide. AV, annexin-V. FIG. 5E shows the results of PET imaging of murine NMC 797 xenografts. FDG uptake in hind limb xenografts is reduced by 50 mg $kg^{-1}$ JQ1 treatment compared to vehicle control. FIG. 5F shows that tumor volume is reduced in mice with established disease (NMC 797 xenografts) treated with 50 mg $kg^{-1}$ daily JQ1 compared to vehicle control. A significant response to therapy is observed by two-tailed t-test at 14 days (p=0.039). Data represent the mean±s.d. (n=7). FIG. 5G shows a histopathological analysis of NMC 797 tumors excised from animals treated with JQ1 reveals induction of keratin expression (AE1/AE3, 40×) and impaired proliferation (Ki67, 40×), as compared to vehicle-treated animals (scale bar is 20 μm). FIG. 5H shows that the viability of patient-derived NMC 11060 xenografts was confirmed by PET imaging. FIG. 5I shows the therapeutic response of primary 11060 NMC xenografts to (+)-JQ1 (50 mg $kg^{-1}$ daily for four days) was demonstrated by PET imaging. FIG. 5J shows a histopathological analysis of primary NMC 11060 tumors excised from animals treated with (+)-JQ1 reveals induction of keratin expression (AE1/AE3, 20×; scale bar is 20 μm), as compared to vehicle-treated animals. Quantitative analysis of keratin induction was performed using image masking (FIG. 5J, right panel) and pixel positivity analysis (FIG. 5K). A significant response to therapy is observed by two-tailed t-test (p=0.0001). Data represent the mean±s.d. of three independent wide microscopic fields. Comparative images of stained excised tumors and quantitative masks are provided in FIG. 9.

FIG. 5L shows that treatment of NMC 797 xenograft-bearing mice with JQ1 (50 mg $kg^{-1}$ per day) reduced tumor burden over 14 days of therapy. Data represent the mean±s.d. (n=7). FIG. 5M shows that JQ1 did not produce adverse symptoms or weight loss. Data represent the mean±s.d. (n=7).

FIG. 7A provides the results of FACS analysis. NMC Per403 cells treated with JQ1 (500 nM, 24 or 48 h) exhibit induction of apoptosis by flow cytometry, in contrast to non-NMC squamous carcinoma cell lines TE10 and TT. PI, propidium iodide, AV, annexin V. FIG. 7B shows a quantification and comparison of annexin-V positive cells by flow cytometry as performed in FIGS. 5B and 5A. JQ1 (500 nM) exhibited a prompt and time-dependent induction of apoptosis in NMC cell lines compared to non-NMC squamous carcinoma cell lines. Data represent the mean±s.d. (n=3), and are annotated with p-values as obtained from a two-tailed t-test.

FIG. 8A shows results from the analysis of patient-derived NMC 11060 cells. The cells were isolated from discarded clinical material and grown in short-term cultures for in vitro studies. Antiproliferative effects of BRD4 inhibition on NMC 11060 cells were measured after 72 hours of incubation with (+)-JQ1 (red circles) or (−)-JQ1 (black circles). NMC 11060 cells are uniquely sensitive to the (+)-JQ1 enantiomer. Data is presented as mean±s.d. (n=3). $IC_{50}$ values were calculated by logistic regression. FIG. 8B shows the progressive antiproliferative effects of (+)-JQ1 on patient-derived NMC 11060 cells over time as demonstrated on days 1, 3, 7 and 10. Data points are mean±s.d. (n=3). FIG. 8C shows results of Flow cytometry for DNA content in NMC 11060 cells. (+)-JQ1 (250 nM, 48 h) induces a G1 arrest compared to (−)-JQ1 (250 nM) and vehicle control.

FIG. 9A shows a low magnification (0.8×) image of an excised NMC 11060 primary xenograft derived from a vehicle-treated animal, sectioned and stained for keratin expression (AE1/AE3; left). Overall staining for keratin is low throughout the sectioned tumor. Image-based analysis of keratin expression was performed using unbiased masking and quantification algorithms capable of scoring individual pixels for staining intensity (right). FIG. 9B shows a low magnification (0.8×) image of an excised NMC 11060 primary xenograft derived from a (+)-JQ1-treated animal (50 mg kg$^{-1}$ daily for four days), sectioned and stained for keratin expression (AE1/AE3; left). Diffuse staining consistent with a uniform effect on keratin induction in JQ1-treated tumors is observed. Image-based analysis of keratin expression was performed using unbiased masking and quantification algorithms capable of scoring individual pixels for staining intensity (right). Pixel positivity is scored quantitatively and reported visually as blue (0), yellow (1+), orange (2+) and red (3+). All paired images are shown at identical magnification.

FIG. 10 shows that JQ1 exhibits excellent oral bioavailability and adequate pharmacokinetic exposure in rodents. Pharmacokinetic studies of (+)-JQ1 were performed in CD1 mice following intravenous (FIGS. 10A-10B) and oral (FIGS. 10B-10C) administration. a, Mean plasma concentration-time profiles of (+)-JQ1 after intravenous dosing (5 mg kg$^{-1}$). Data represent the mean and s.d. (n=3). FIG. 10B shows calculated pharmacokinetic parameters for intravenous (+)-JQ1 demonstrate excellent drug exposure [Area under the curve (AUC)=2090 hr*ng/mL] and an approximately one hour half-life ($T_{1/2}$). FIG. 10C shows mean plasma concentration-time profiles of (+)-JQ1 after oral dosing (10 mg kg$^{-1}$). Data represent the mean and s.d. (n=3). FIG. 10D shows calculated pharmacokinetic parameters for oral (+)-JQ1 demonstrate excellent oral bioavailability (F=49%), peak plasma concentration (Cmax=1180 ng/mL) and drug exposure (AUC=2090 hr*ng/mL). CL, clearance; Vss, volume in steady-state; $MRT_{INF}$, mean residence time extrapolated to infinity; $T_{max}$, time to maximum concentration.

FIG. 15A shows that JQ1 reduced tumor burden in a murine xenograph model of Nut midline carcinoma. FIG. 15B shows the weight of mice treated with JQ1.

FIGS. 16A-16D are graphs showing the BRD4(1) and BRD4(2) binding activity of JQ1 and derivatives thereof.

FIGS. 17A-17D are graphs showing the effect of JQ1 and derivatives thereof on Nut midline carcinoma (NMC) cell viability.

DETAILED DESCRIPTION OF THE INVENTION

Figure 1:
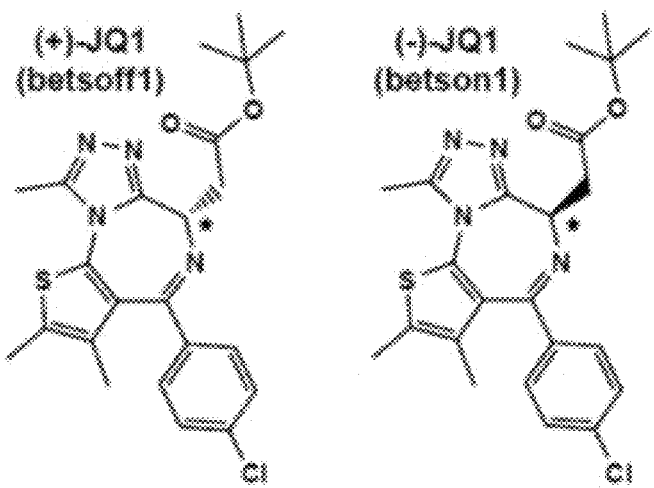
FIG. 1 shows the structure of the two JQ1 stereo-isomers. The stereocentre at C6 is indicated by an asterix (*).

The invention features compositions and methods that are useful for the treatment or prevention of a neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency.

The invention is based, at least in part, on the discovery of a cell-permeable, potent small-molecule inhibitor (JQ1) with biochemical selectivity for the BET-family of bromodomains, and related compounds capable of regulating the bromodomain family, which are a family of polypeptides that contain a bromodomain that recognizes acetyl-lysine residues on nuclear chromatin. Lysine acetylation has emerged as a signaling modification of broad relevance to cellular and disease biology. Targeting the enzymes which reversibly mediate side-chain acetylation has been an active area of drug discovery research for many years. To date, successful efforts have been limited to the "writers" (acetyltransferases) and "erasers" (histone deacetylases) of covalent modifications arising in the context of nuclear chromatin. Potent inhibitors of acetyl-lysine recognition modules, or bromodomains, have not yet been described. The recent characterization of a high-resolution co-crystal structures with BRD4 revealed excellent shape complementarity with the acetyl-lysine binding cavity. Binding of JQ1 to the tandem bromodomains of BRD4 is acetyl-lysine competitive and displaces BRD4 from chromatin in human cells. Recurrent translocation of BRD4 is observed in an incurable, genetically-defined subtype of human squamous carcinoma. Competitive binding of JQ1 to the BRD4 fusion oncoprotein results in immediate squamous differentiation and specific anti-proliferative effects in patient-derived cell lines and in a murine model of BRD4-dependent carcinoma. These data establish the feasibility of targeting protein-protein interactions of epigenetic "readers" and reports a versatile chemical scaffold for the development of chemical probes more broadly throughout the bromodomain family.

Bromodomain-Containing Proteins

Gene regulation is fundamentally governed by reversible, non-covalent assembly of macromolecules. Signal transduction to RNA polymerase requires higher-ordered protein complexes, spatially regulated by assembly factors capable of interpreting the post-translational modification states of chromatin. Epigenetic readers are structurally diverse proteins each possessing one or more evolutionarily conserved effector modules, which recognize covalent modifications of histone proteins or DNA. The ε-N-acetylation of lysine residues (Kac) on histone tails is associated with an open chromatin architecture and transcriptional activation[3]. Context-specific molecular recognition of acetyl-lysine is principally mediated by bromodomains.

Bromodomain-containing proteins are of substantial biological interest, as components of transcription factor complexes (TAF1, PCAF, Gcn5 and CBP) and determinants of epigenetic memory[4]. There are 41 human proteins containing a total of 57 diverse bromodomains. Despite large sequence variations, all bromodomains share a conserved fold comprising a left-handed bundle of four alpha helices ($\alpha_Z$, $\alpha_A$, $\alpha_B$, $\alpha_C$), linked by diverse loop regions (ZA and BC loops) that determine substrate specificity. Co-crystal structures with peptidic substrates showed that the acetyl-lysine is recognized by a central hydrophobic cavity and is anchored by a hydrogen bond with an asparagine residue present in most bromodomains[5]. The bromodomain and extra-terminal (BET)-family (BRD2, BRD3, BRD4 and BRDT) shares a common domain architecture comprising two N-terminal bromodomains that exhibit high level of sequence conservation, and a more divergent C-terminal recruitment domain (see, Zeng, L. & Zhou, M. M. Bromodomain: an acetyl-lysine binding domain. *FEBS Lett* 513, 124-128, (2002).

BRD4

Recent research has established a compelling rationale for targeting BRD4, in cancer. BRD4 functions to facilitate cell cycle progression and knock-down in cultured cancer cell lines prompts G1 arrest. BRD4 is an important mediator of transcriptional elongation, functioning to recruit the positive transcription elongation factor complex (P-TEFb)[7,8]. Cyclin dependent kinase-9, a core component of P-TEFb, is a validated target in chronic lymphocytic leukemia[9], and has recently been linked to c-Myc dependent transcription[10]. Bromodomains present in BRD4 recruit P-TEFb to mitotic chromosomes resulting in increased expression of growth promoting genes[11]. BRD4 remains bound to transcriptional start sites of genes expressed during M/G1 but has not been found present at start sites that are expressed later in the cell cycle. Knockdown of BRD4 in proliferating cells has been shown to lead to G1 arrest and apoptosis[12] by decreasing expression levels of genes important for mitotic progression[13] and survival[14].

Most importantly, BRD4 has recently been identified as a component of a recurrent t(15; 19) chromosomal translocation in an aggressive form of human squamous carcinoma[15, 16]. Such translocations express the tandem N-terminal bromodomains of BRD4 as an in-frame chimera with the NUT (nuclear protein in testis) protein, genetically defining the so-called NUT midline carcinoma (NMC). Functional studies in patient-derived NMC cell lines have validated the essential role of the BRD4-NUT oncoprotein in maintaining the characteristic proliferation advantage and differentiation block of this uniformly fatal malignancy[17]. Notably, RNA silencing of BRD4-NUT gene expression arrests proliferation and prompts squamous differentiation with a marked increase in cytokeratin expression. These observations underscore the broad utility and immediate therapeutic potential of a direct-acting inhibitor of human bromodomain proteins.

The invention features compositions and methods that are useful for inhibiting human bromodomain proteins.

Compounds of the Invention

The invention provides compounds (e.g., JQ1 and compounds of formulas delineated herein) that bind in the binding pocket of the apo crystal structure of the first bromodomain of a BET family member (e.g., BRD4). Without wishing to be bound by theory, these compounds may be particularly effective in inhibiting the growth, proliferation, or survival of proliferating neoplastic cells or of inducing the differentiation of such cells. In one approach, compounds useful for the treatment of a neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility or for use in organ transplantation, modulation of cell state for regenerative medicine (i.e., by promoting or inhibiting cellular differentiation), and facilitating pluripotency are selected using a molecular docking program to identify compounds that are expected to bind to a bromodomain structural binding pocket. In certain embodiments, a compound of the invention can bind to a BET family member and reduce the biological activity of the BET family member (e.g., reduce elongation) and/or disrupt the subcellular localization of the BET family member (e.g., reduce chromatin binding).

In certain embodiments, a compound of the invention can prevent, inhibit, or disrupt, or reduce by at least 10%, 25%, 50%, 75%, or 100% the biological activity of a BET family member (e.g., BRD2, BRD3, BRD4, BRDT) and/or disrupt the subcellular localization of such proteins, e.g., by binding to a binding site in a bromodomain apo binding pocket.

In certain embodiments, a compound of the invention is a small molecule having a molecular weight less than about 1000 daltons, less than 800, less than 600, less than 500, less than 400, or less than about 300 daltons. Examples of compounds of the invention include JQ1 and other compounds that bind the binding pocket of the apo crystal structure of the first bromodomain of a BET family member (e.g., BRD4 (hereafter referred to as BRD4(1); PDB ID 2OSS). JQ1 is a novel thieno-triazolo-1,4-diazepine. The invention further provides pharmaceutically acceptable salts of such compounds.

In one aspect, the invention provides a compound of Formula I:

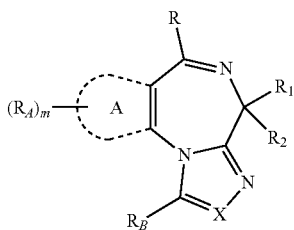

(I)

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
R is alkyl, cycloalkyl, heterocycloalkyl, aryl, or heteroaryl; each of which is optionally substituted;
$R_1$ is —$(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, optionally substituted aryl, or optionally substituted heteroaryl;
$R_2$ is H, D (deuterium), halogen, or optionally substituted alkyl;
each $R_3$ is independently selected from the group consisting of:
(i) H, aryl, substituted aryl, heteroaryl, or substituted heteroaryl;
(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
(iv) $NH_2$, $N=CR_4R_6$;
each $R_4$ is independently H, alkyl, alkyl, cycloalkyl, heterocycloalkyl, aryl, or heteroaryl, each of which is optionally substituted;
or $R_3$ and $R_4$ are taken together with the nitrogen atom to which they are attached to form a 4-10-membered ring;
$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;
m is 0, 1, 2, or 3;
provided that
(a) if ring A is thienyl, X is N, R is phenyl or substituted phenyl, $R_2$ is H, $R_B$ is methyl, and $R_1$ is —$(CH_2)_n$-L, in which n is 1 and L is —CO—$N(R_3R_4)$, then $R_3$ and $R_4$ are not taken together with the nitrogen atom to which they are attached to form a morpholino ring;
(b) if ring A is thienyl, X is N, R is substituted phenyl, $R_2$ is H, $R_B$ is methyl, and $R_1$ is —$(CH_2)_n$-L, in which n is 1 and L is —CO—$N(R_3R_4)$, and one of $R_3$ and $R_4$ is H, then the other of $R_3$ and $R_4$ is not methyl, hydroxyethyl, alkoxy, phenyl, substituted phenyl, pyridyl or substituted pyridyl; and
(c) if ring A is thienyl, X is N, R is substituted phenyl, $R_2$ is H, $R_B$ is methyl, and $R_1$ is —$(CH_2)_n$-L, in which n is 1 and L is —COO—$R_3$, then $R_3$ is not methyl or ethyl;
or a salt, solvate or hydrate thereof.

In certain embodiments, R is aryl or heteroaryl, each of which is optionally substituted.

In certain embodiments, L is H, —COO—$R_3$, —CO—$N(R_3R_4)$, —$S(O)_2$—$R_3$, —$S(O)_2$—$N(R_3R_4)$, $N(R_3R_4)$, $N(R_4)C(O)R_3$ or optionally substituted aryl. In certain embodiments, each $R_3$ is independently selected from the group consisting of: H, —$C_1$-$C_8$ alkyl, which is optionally substituted, containing 0, 1, 2, or 3 heteroatoms selected from O, S, or N; or $NH_2$, $N=CR_4R_6$.

In certain embodiments, $R_2$ is H, D, halogen or methyl.

In certain embodiments, $R_B$ is alkyl, hydroxyalkyl, haloalkyl, or alkoxy; each of which is optionally substituted.

In certain embodiments, $R_B$ is methyl, ethyl, hydroxymethyl, methoxymethyl, trifluoromethyl, COOH, COOMe, COOEt, or $COOCH_2OC(O)CH_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.

In certain embodiments, m is 1 or 2, and at least one occurrence of $R_A$ is methyl.

In certain embodiments, each $R_A$ is independently H, an optionally substituted alkyl, or any two $R_A$ together with the atoms to which each is attached, can form an aryl.

In another aspect, the invention provides a compound of Formula II:

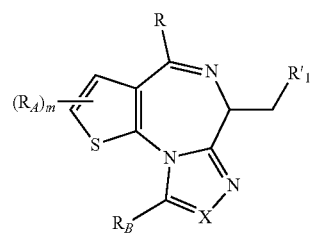

(II)

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
R is alkyl, cycloalkyl, heterocycloalkyl, aryl, or heteroaryl, each of which is optionally substituted;

R'$_1$ is H, —COO—R$_3$, —CO—R$_3$, optionally substituted aryl, or optionally substituted heteroaryl;

each R$_3$ is independently selected from the group consisting of:
(i) H, aryl, substituted aryl, heteroaryl, substituted heteroaryl;
(ii) heterocycloalkyl or substituted heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl; —C$_3$-C$_{12}$ cycloalkenyl, or substituted —C$_3$-C$_{12}$ cycloalkenyl; each of which may be optionally substituted;

m is 0, 1, 2, or 3;

provided that if R'$_1$ is —COO—R$_3$, X is N, R is substituted phenyl, and R$_B$ is methyl, then R$_3$ is not methyl or ethyl;

or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, R'$_1$ is —COO—R$_3$, optionally substituted aryl, or optionally substituted heteroaryl; and R$_3$ is —C$_1$-C$_8$ alkyl, which contains 0, 1, 2, or 3 heteroatoms selected from O, S, or N, and which may be optionally substituted. In certain embodiments, R'$_1$ is —COO—R$_3$, and R$_3$ is methyl, ethyl, propyl, i-propyl, butyl, sec-butyl, or t-butyl; or R'$_1$ is H or optionally substituted phenyl.

In certain embodiments, R$_B$ is methyl, ethyl, hydroxy methyl, methoxymethyl, trifluoromethyl, COOH, COOMe, COOEt, COOCH$_2$OC(O)CH$_3$.

In certain embodiments, R$_B$ is methyl, ethyl, hydroxy methyl, methoxymethyl, trifluoromethyl, COOH, COOMe, COOEt, or COOCH$_2$OC(O)CH$_3$.

In certain embodiments, each R$_A$ is independently an optionally substituted alkyl, or any two R$_A$ together with the atoms to which each is attached, can form a fused aryl.

In certain embodiments, each R$_A$ is methyl.

In another aspect, the invention provides a compound of formula III:

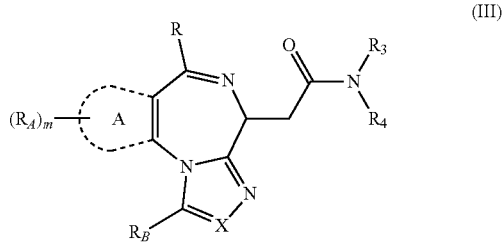

(III)

wherein
X is N or CR$_5$;
R$_5$ is H, alkyl, cycloalkyl, heterocycloalkyl, aryl, or heteroaryl, each of which is optionally substituted;
R$_B$ is H, alkyl, hydroxylalkyl, aminoalkyl, alkoxyalkyl, haloalkyl, hydroxy, alkoxy, or —COO—R$_3$, each of which is optionally substituted;
ring A is aryl or heteroaryl;
each R$_A$ is independently alkyl, cycloalkyl, heterocycloalkyl, aryl, or heteroaryl, each of which is optionally substituted; or any two R$_A$ together with the atoms to which each is attached, can form a fused aryl or heteroaryl group;
R is alkyl, cycloalkyl, heterocycloalkyl, aryl, or heteroaryl, each of which is optionally substituted;

each R$_3$ is independently selected from the group consisting of:
(i) H, aryl, substituted aryl, heteroaryl, or substituted heteroaryl;
(ii) heterocycloalkyl or substituted heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted; and
(iv) NH$_2$, N=CR$_4$R$_6$;

each R$_4$ is independently H, alkyl, alkyl, cycloalkyl, heterocycloalkyl, aryl, or heteroaryl, each of which is optionally substituted;

or R$_3$ and R$_4$ are taken together with the nitrogen atom to which they are attached to form a 4-10-membered ring;

R$_6$ is alkyl, alkenyl, cycloalkyl, cycloalkenyl, heterocycloalkyl, aryl, or heteroaryl, each of which is optionally substituted; or R$_4$ and R$_6$ are taken together with the carbon atom to which they are attached to form a 4-10-membered ring;

m is 0, 1, 2, or 3;

provided that:
(a) if ring A is thienyl, X is N, R is phenyl or substituted phenyl, R$_B$ is methyl, then R$_3$ and R$_4$ are not taken together with the nitrogen atom to which they are attached to form a morpholino ring; and
(b) if ring A is thienyl, X is N, R is substituted phenyl, R$_2$ is H, R$_B$ is methyl, and one of R$_3$ and R$_4$ is H, then the other of R$_3$ and R$_4$ is not methyl, hydroxyethyl, alkoxy, phenyl, substituted phenyl, pyridyl or substituted pyridyl; or a salt, solvate or hydrate thereof.

In certain embodiments, R is aryl or heteroaryl, each of which is optionally substituted. In certain embodiments, R is phenyl or pyridyl, each of which is optionally substituted.

In certain embodiments, R is p-Cl-phenyl, o-Cl-phenyl, m-Cl-phenyl, p-F-phenyl, o-F-phenyl, m-F-phenyl or pyridinyl. In certain embodiments, R$_3$ is H, NH$_2$, or N=CR$_4$R$_6$.

In certain embodiments, each R$_4$ is independently H, alkyl, cycloalkyl, heterocycloalkyl, aryl, heteroaryl; each of which is optionally substituted.

In certain embodiments, R$_6$ is alkyl, alkenyl, cycloalkyl, cycloalkenyl, heterocycloalkyl, aryl, or heteroaryl, each of which is optionally substituted.

In another aspect, the invention provides a compound of formula IV:

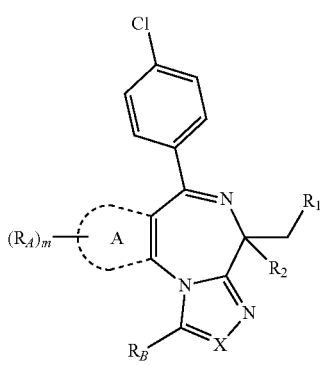

(IV)

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
$R_1$ is —$(CH_2)_n$-L, in which n is 0-3 and L is H, —COO—$R_3$, —CO—$R_3$, —CO—N($R_3R_4$), —S(O)$_2$—$R_3$, —S(O)$_2$—N($R_3R_4$), N($R_3R_4$), N($R_4$)C(O)$R_3$, optionally substituted aryl, or optionally substituted heteroaryl;
$R_2$ is H, D, halogen, or optionally substituted alkyl;
each $R_3$ is independently selected from the group consisting of:
(i) H, aryl, substituted aryl, heteroaryl, or substituted heteroaryl;
(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
(iv) $NH_2$, N=$CR_4R_6$;
each $R_4$ is independently H, alkyl, alkyl, cycloalkyl, heterocycloalkyl, aryl, or heteroaryl, each of which is optionally substituted;
or $R_3$ and $R_4$ are taken together with the nitrogen atom to which they are attached to form a 4-10-membered ring;
$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;
m is 0, 1, 2, or 3;
provided that
(a) if ring A is thienyl, X is N, $R_2$ is H, $R_B$ is methyl, and $R_1$ is —$(CH_2)_n$-L, in which n is 0 and L is —CO—N($R_3R_4$), then $R_3$ and $R_4$ are not taken together with the nitrogen atom to which they are attached to form a morpholino ring;
(b) if ring A is thienyl, X is N, $R_2$ is H, $R_B$ is methyl, and $R_1$ is —$(CH_2)_n$-L, in which n is 0 and L is —CO—N($R_3R_4$), and one of $R_3$ and $R_4$ is H, then the other of $R_3$ and $R_4$ is not methyl, hydroxyethyl, alkoxy, phenyl, substituted phenyl, pyridyl or substituted pyridyl; and
(c) if ring A is thienyl, X is N, $R_2$ is H, $R_B$ is methyl, and $R_1$ is —$(CH_2)_n$-L, in which n is 0 and L is —COO—$R_3$, then $R_3$ is not methyl or ethyl; or
a salt, solvate or hydrate thereof.

In certain embodiments, $R_1$ is —$(CH_2)_n$-L, in which n is 0-3 and L is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, n is 1 or 2 and L is alkyl or —COO—$R_3$, and $R_3$ is methyl, ethyl, propyl, i-propyl, butyl, sec-butyl, or t-butyl; or n is 1 or 2 and L is H or optionally substituted phenyl.

In certain embodiments, $R_2$ is H or methyl.

In certain embodiments, $R_B$ is methyl, ethyl, hydroxymethyl, methoxymethyl, trifluoromethyl, COOH, COOMe, COOEt, COOCH$_2$OC(O)CH$_3$.

In certain embodiments, ring A is phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, each $R_A$ is independently an optionally substituted alkyl, or any two $R_A$ together with the atoms to which each is attached, can form an aryl.

The invention also provides compounds of Formulae V-XXII, and any compound described herein.

In another aspect, the invention provides a compound represented by the formula:

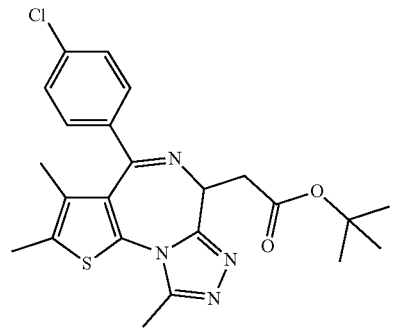 [SMILES: Cc1sc2c(c1C)C(c1ccc(Cl)cc1)=NC(CC(=O)OC(C)(C)C)c1nnc(C)n1-2]

a salt, solvate or hydrate thereof.
In certain embodiments, the compound is (+)-JQ1:

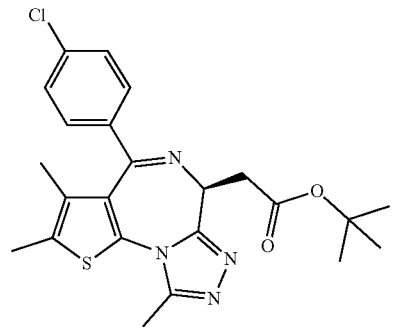 [SMILES: Cc1sc2c(c1C)C(c1ccc(Cl)cc1)=N[C@@H](CC(=O)OC(C)(C)C)c1nnc(C)n1-2]

a salt, solvate or hydrate thereof.

In another aspect, the invention provides a compound represented by the formula:
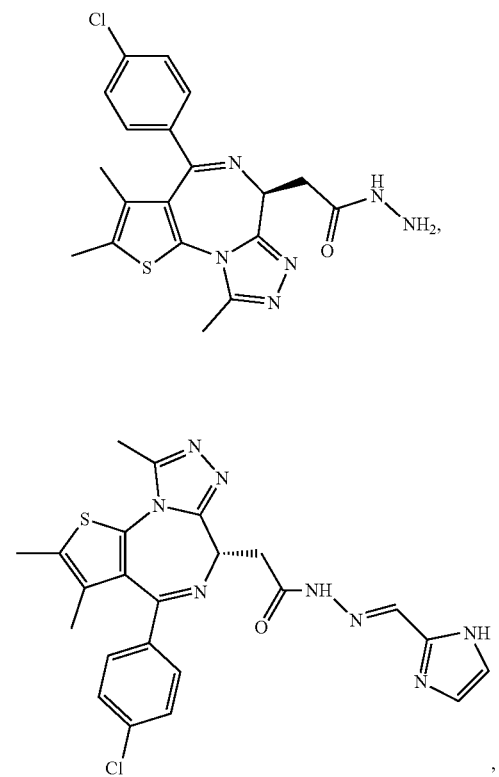
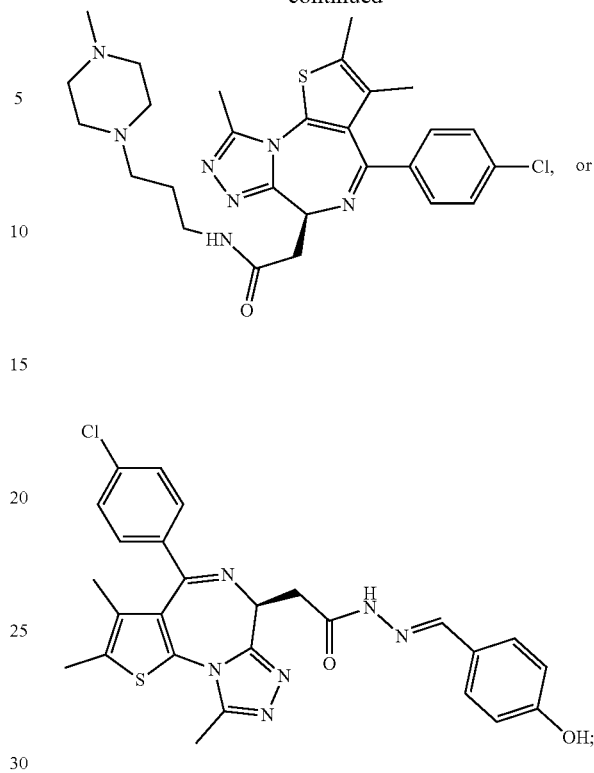
a salt, solvate or hydrate thereof.
In another aspect, the invention provides a compound represented by the formula:
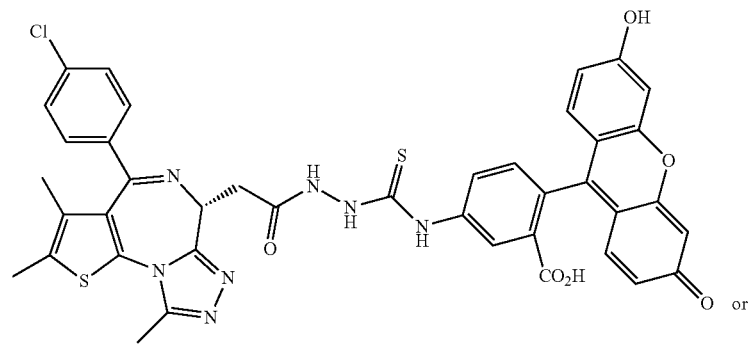
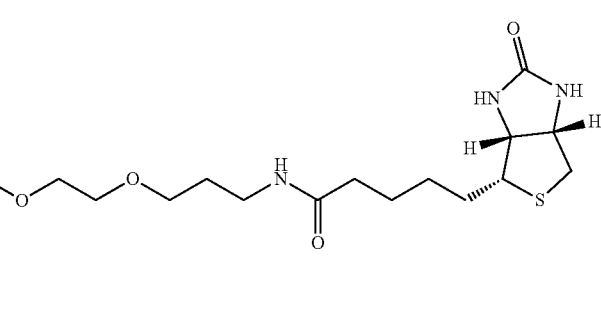
a salt, solvate or hydrate thereof.

In another aspect, the invention provides a compound represented by any one of the following formulae:
JQ1S
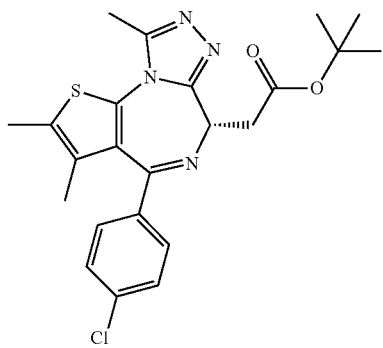
JQ6
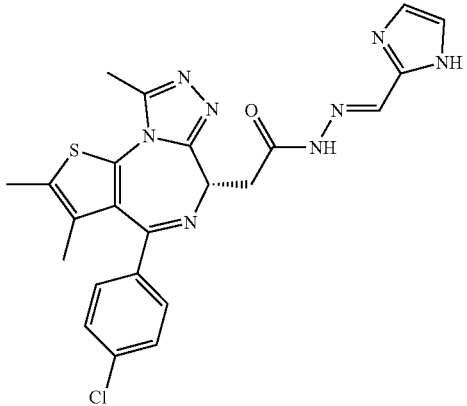
JQ11
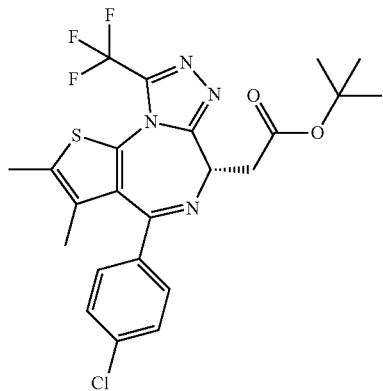
JQ1R
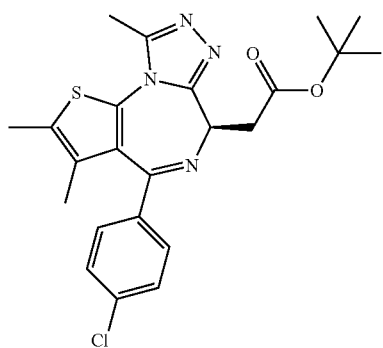
JQ13
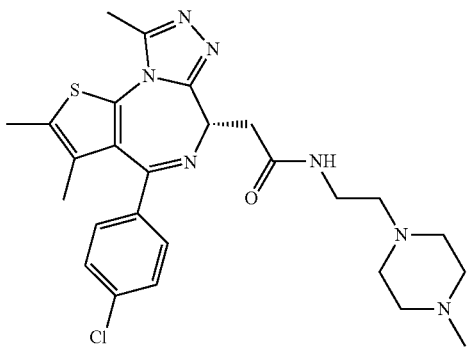
JQ21
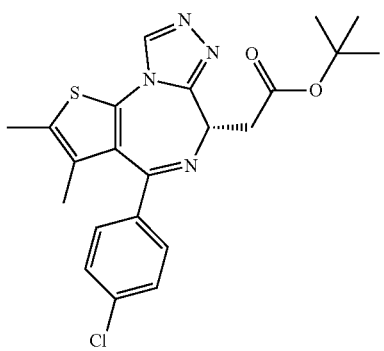
JQ20
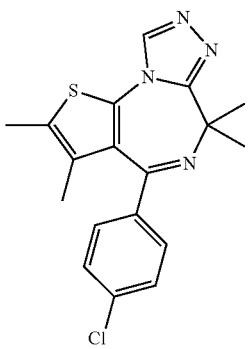
JQ19
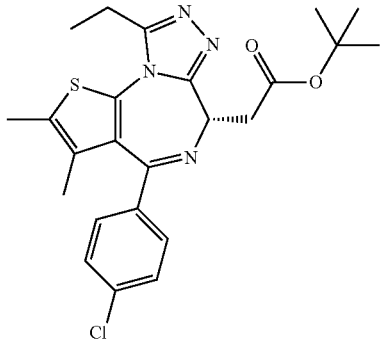

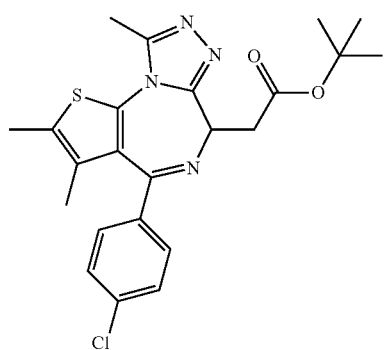
JQ8
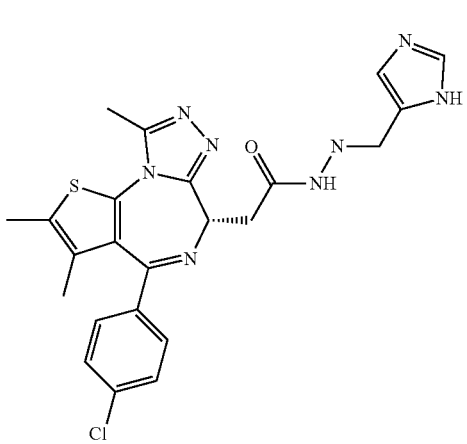
JQ18
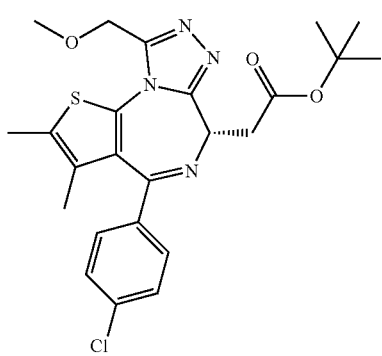
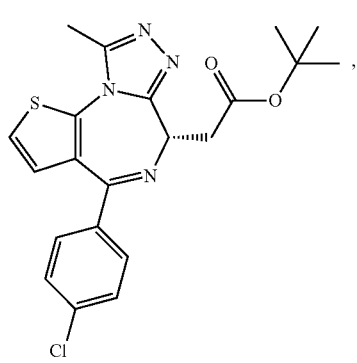
or a salt, solvate or hydrate thereof.
In another aspect, the invention provides a compound represented by any one of the following formulae:
JQ24B
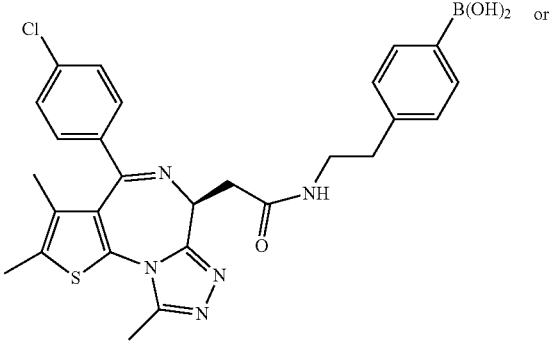
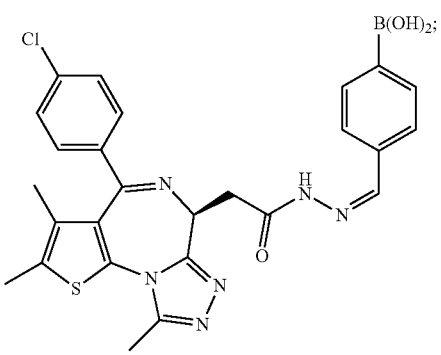
or
a salt, solvate or hydrate thereof.
In another aspect, the invention provides a compound represented by any one of the following structures:
KS1
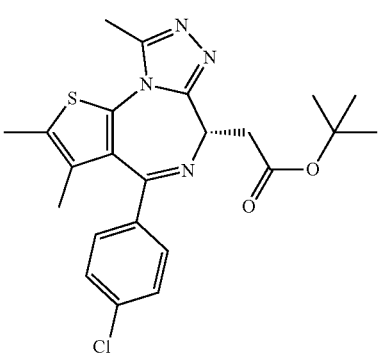
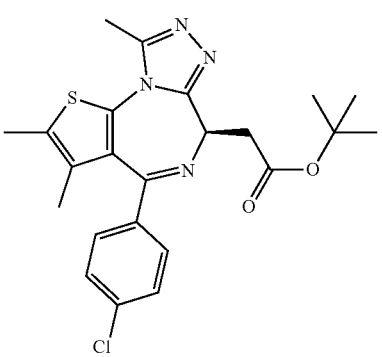

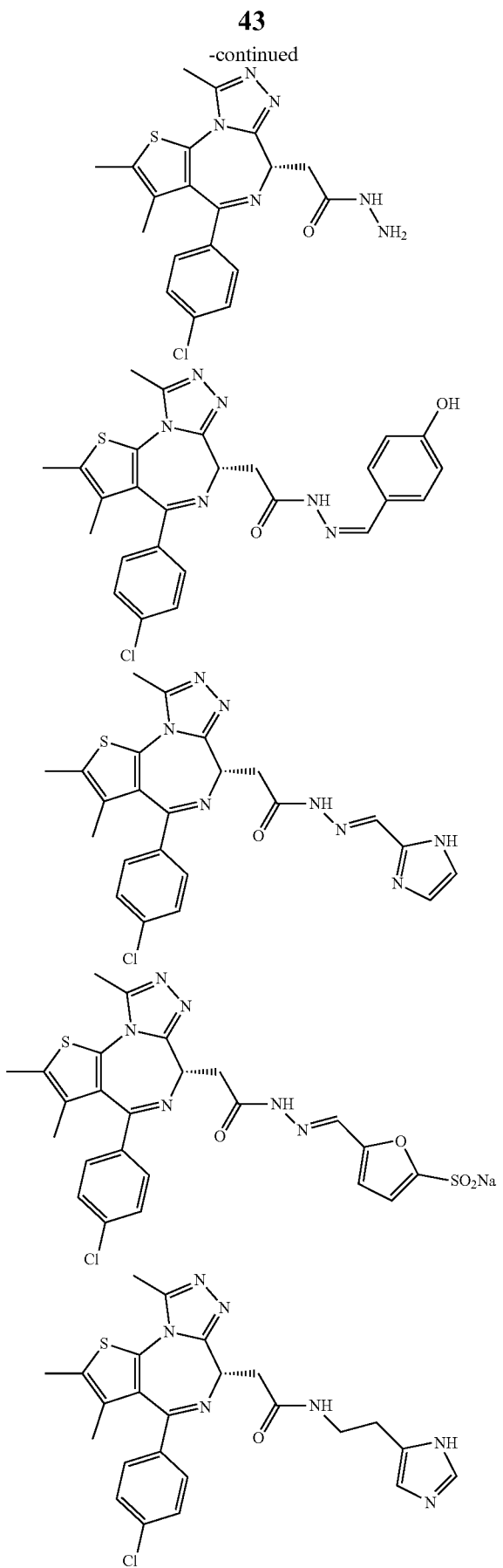
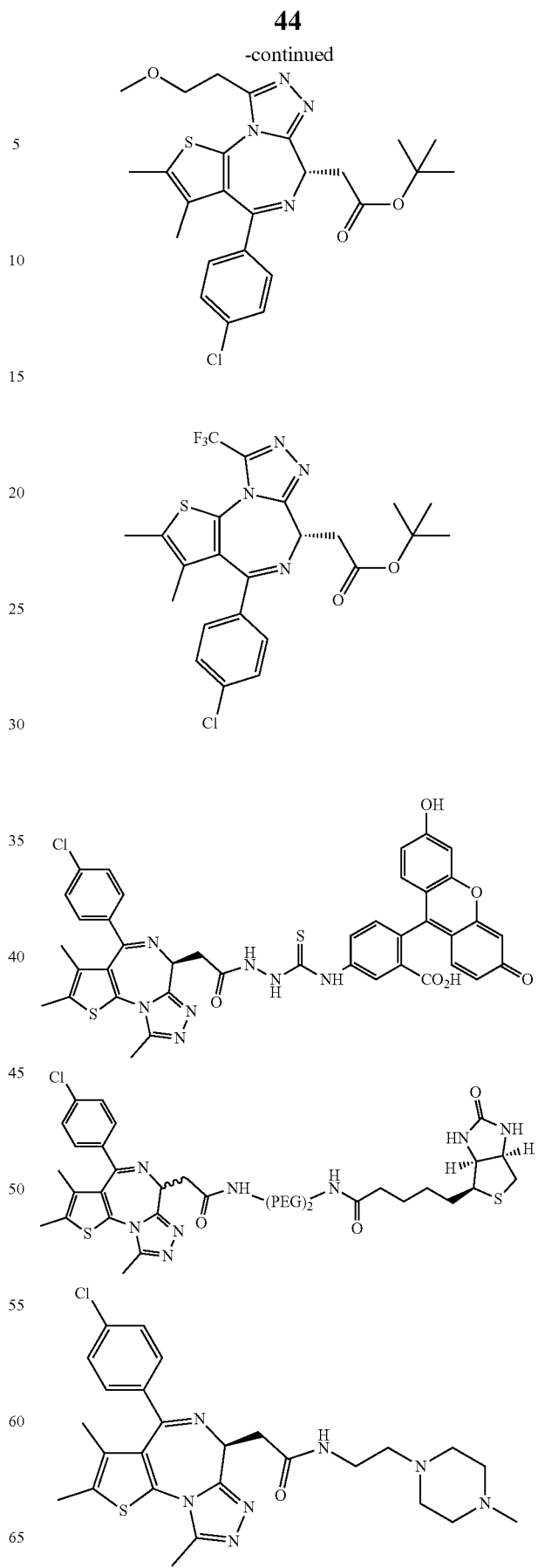

45
-continued
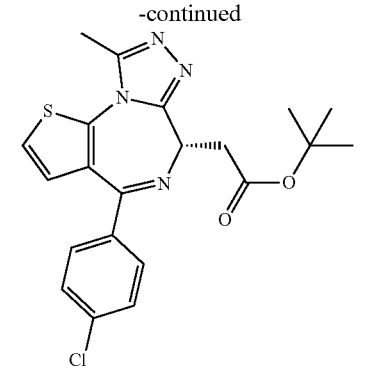
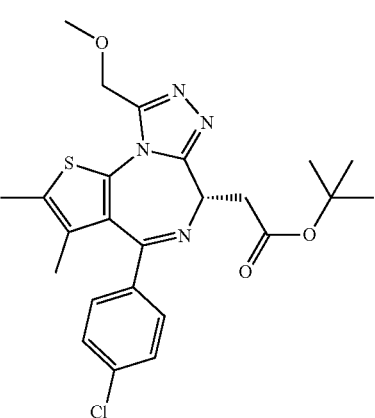
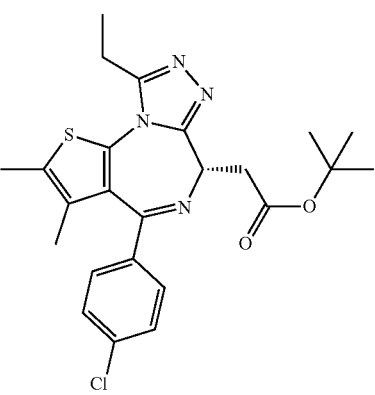
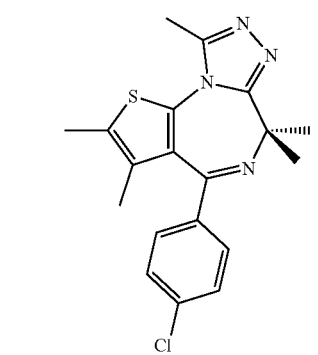
46
-continued
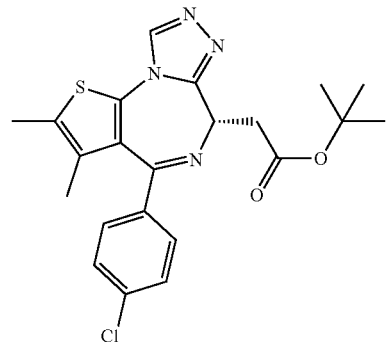
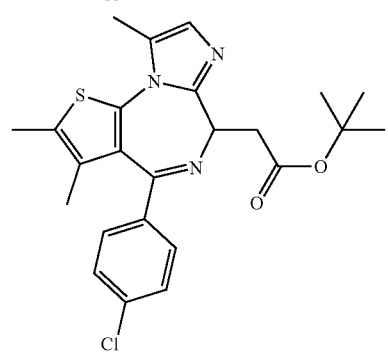
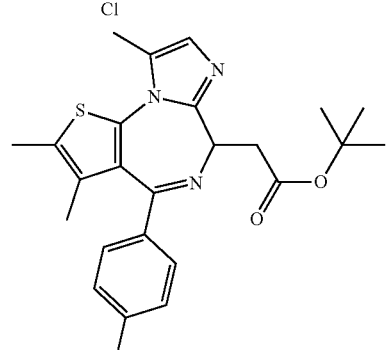
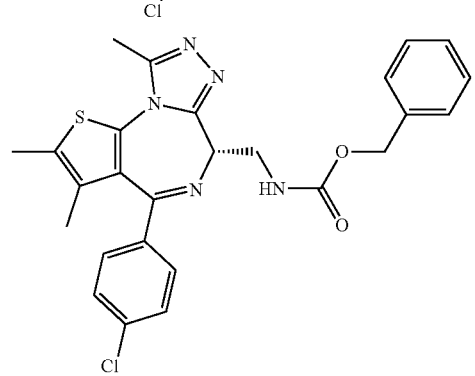
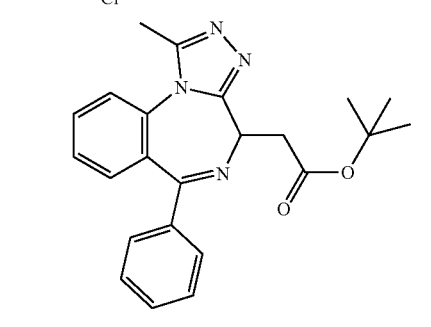

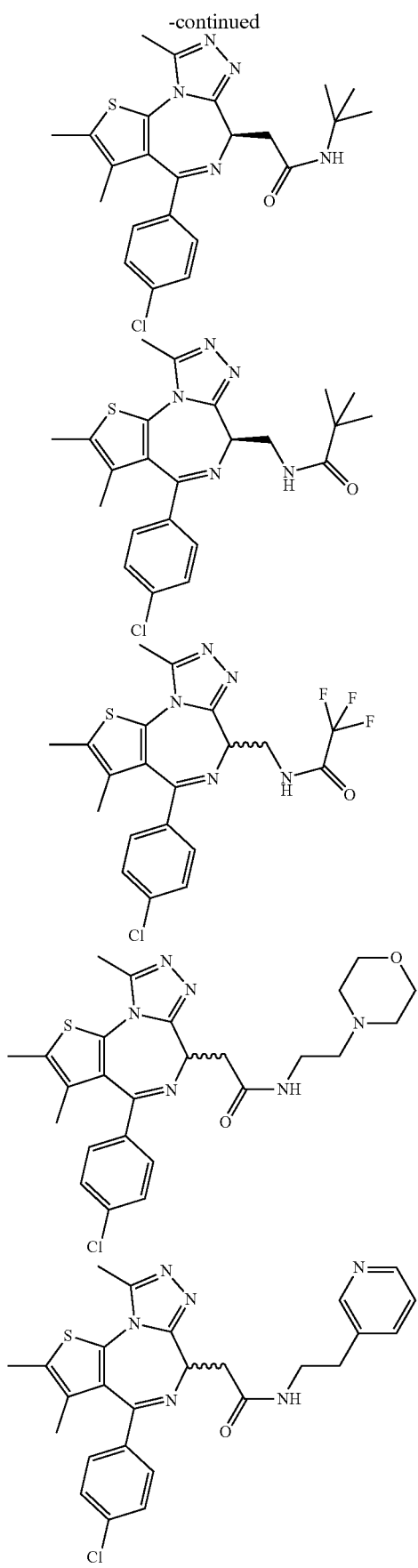
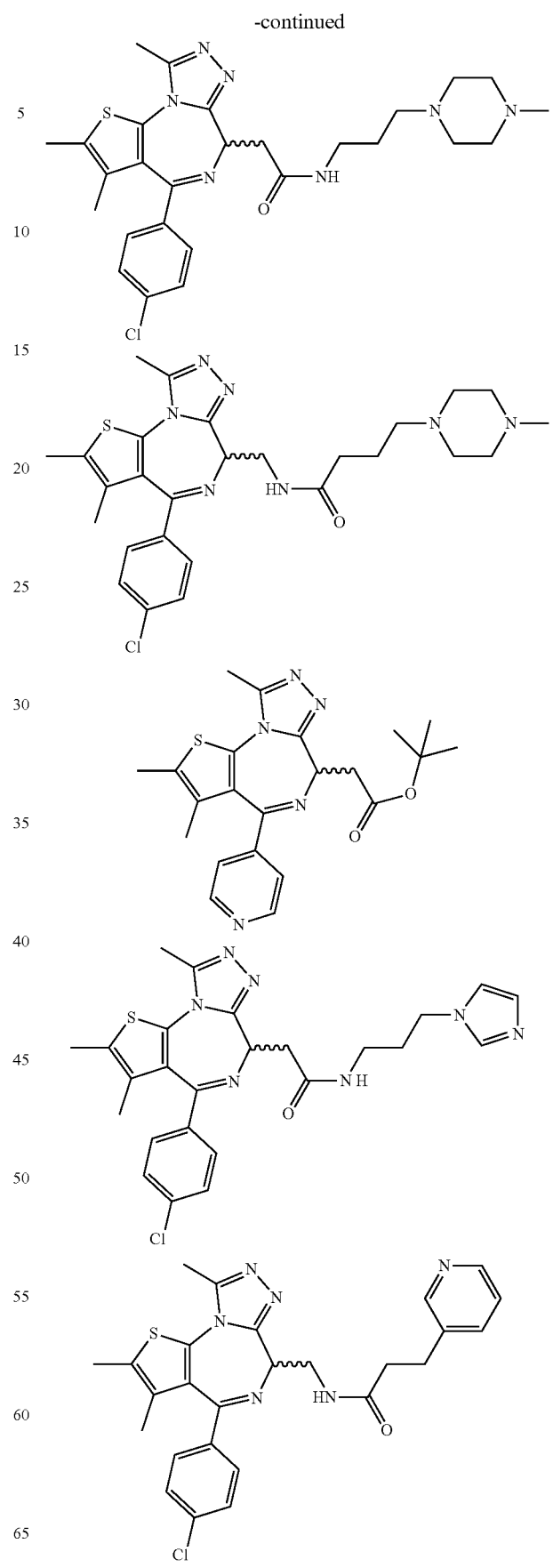

49
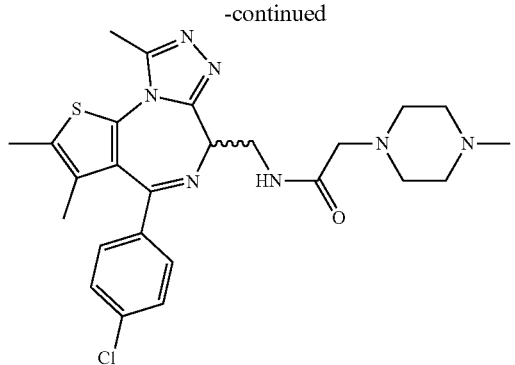
or
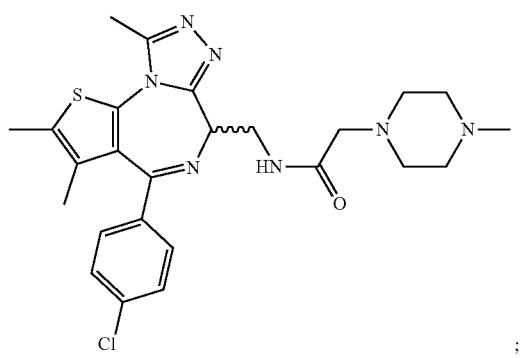
;
or a salt, solvate or hydrate thereof.
In certain embodiments, a compound of the invention can be represented by one of the following structures:
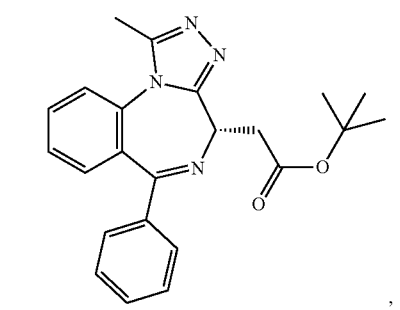
,
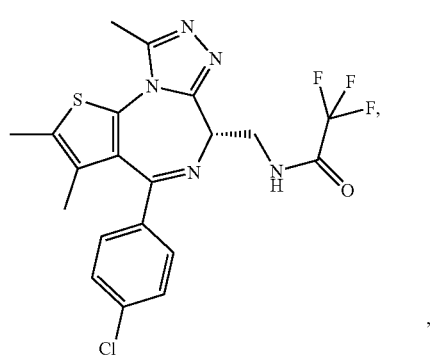
,
50
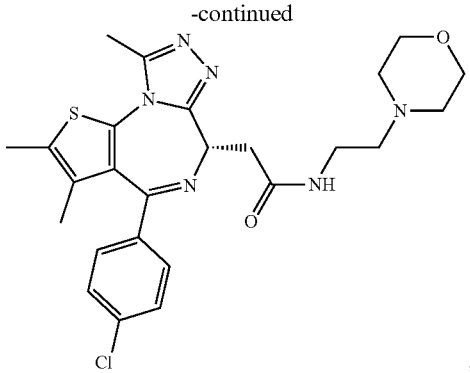
,
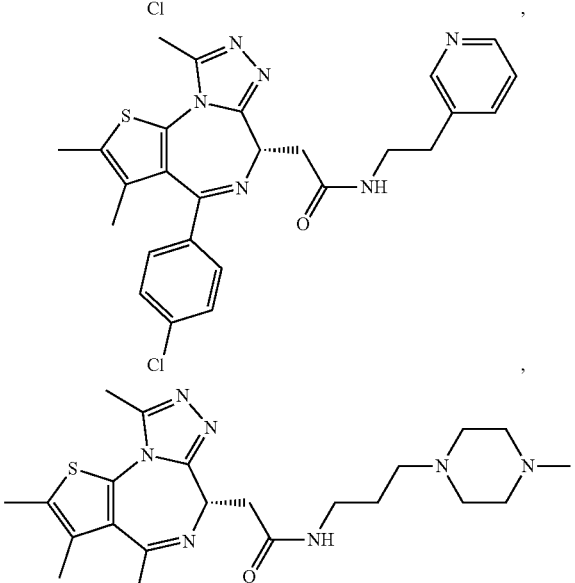
,
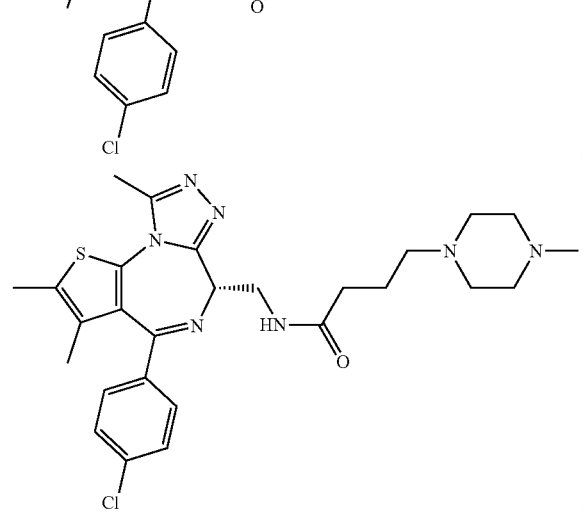
,
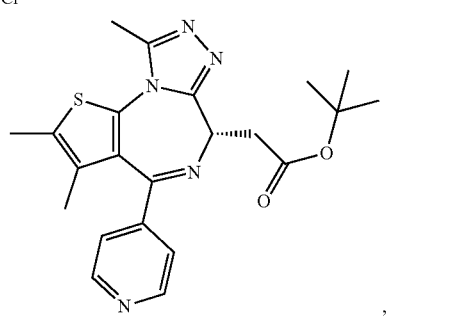
, 51
-continued
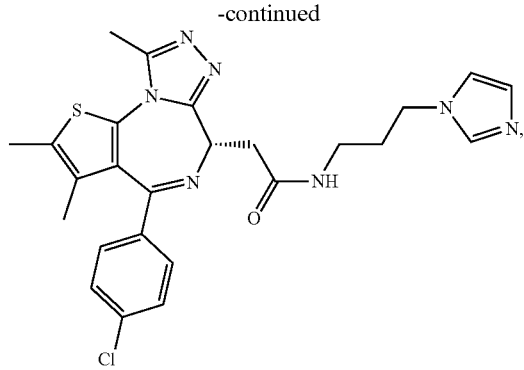
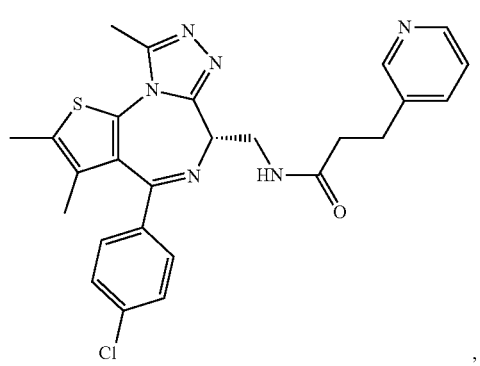
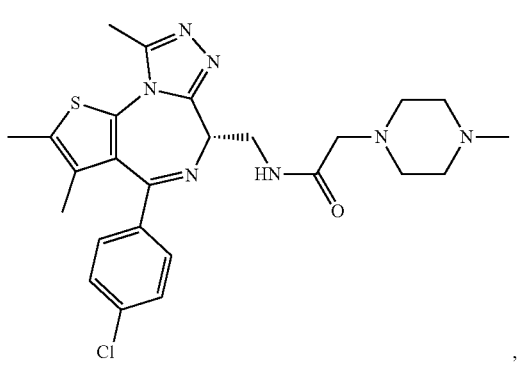
52
-continued
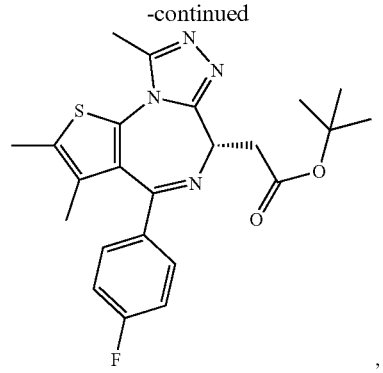
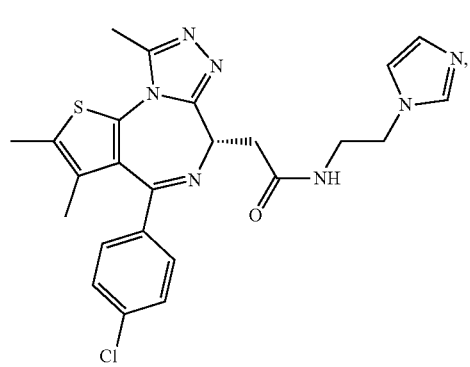
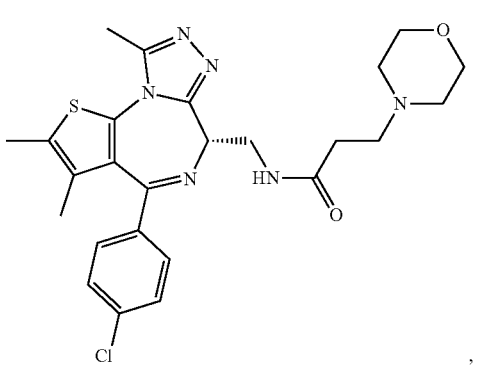
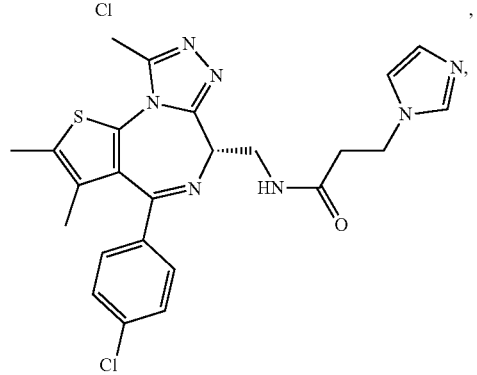

-continued
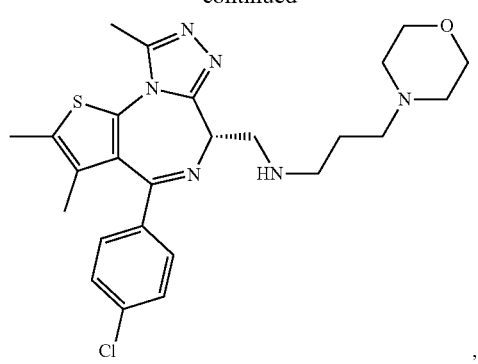
,
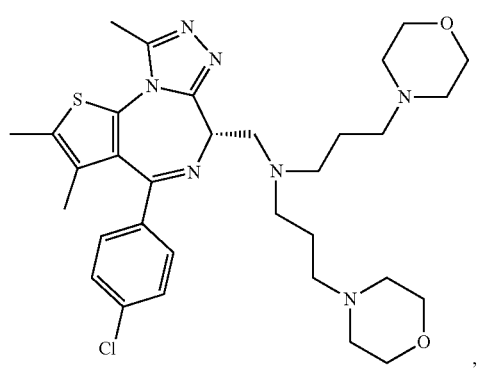
,
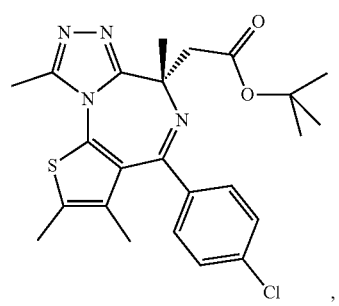
,
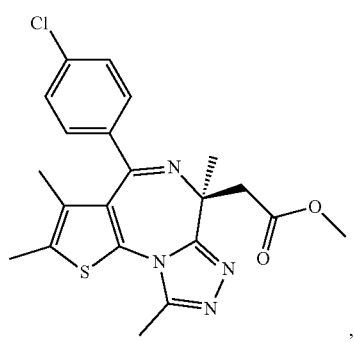
,
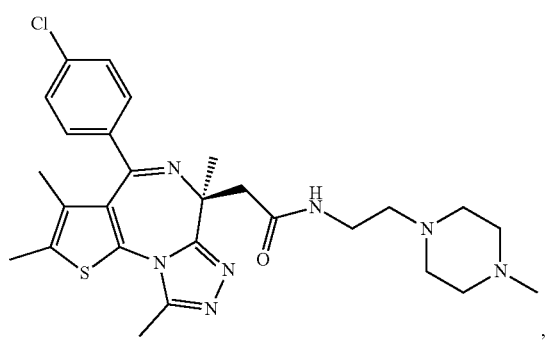
,
-continued
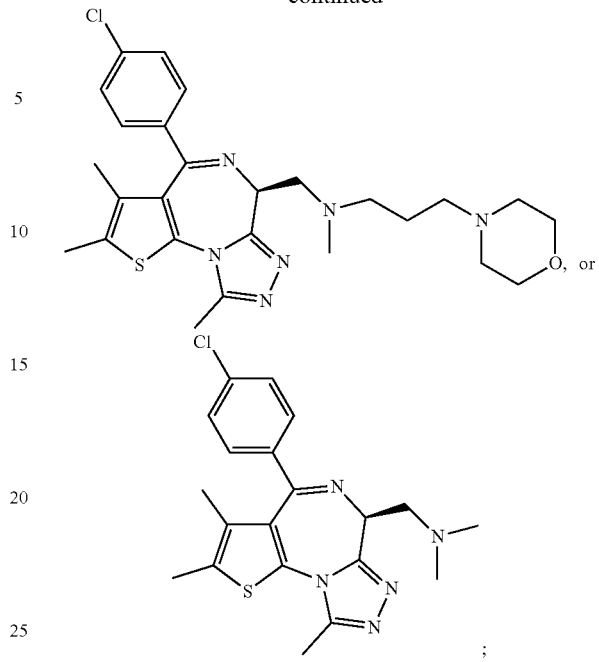
or a salt, solvate or hydrate thereof.
In one embodiment, the compound is represented by the structure:
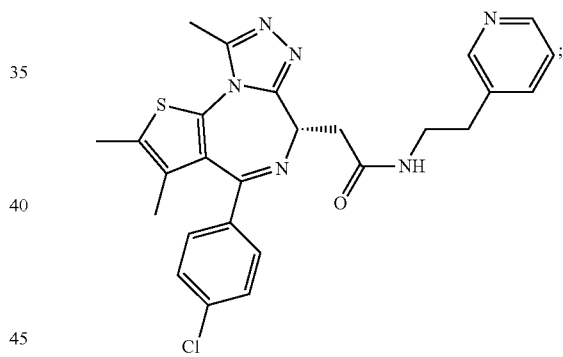
or a salt, solvate or hydrate thereof.
In another embodiment, the compound is represented by the structure:
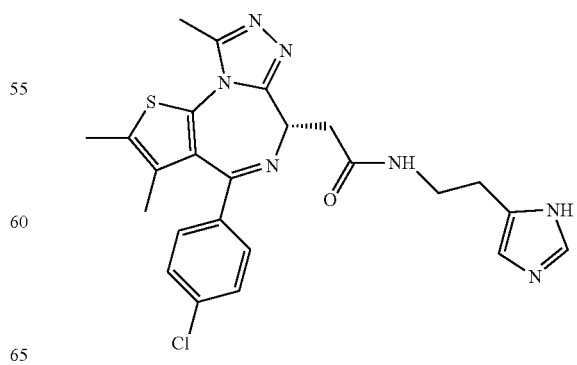
or a salt, solvate or hydrate thereof.

In another embodiment, the compound is represented by the structure:

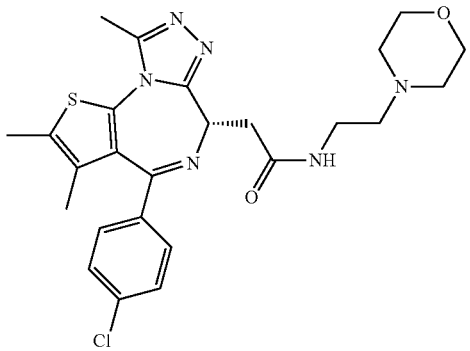 [SMILES: Cc1sc2c(c1C)C(c1ccc(Cl)cc1)=N[C@@H](CC(=O)NCCN1CCOCC1)c1nnc(C)n1-2]

or a salt, solvate or hydrate thereof.

In certain embodiments, a compound of the invention can have the opposite chirality of any compound shown herein.

In certain embodiments, the invention provides a compound represented by Formula (V), (VI), or (VII):

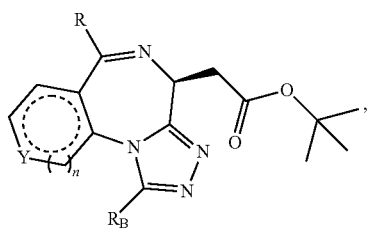
(V)

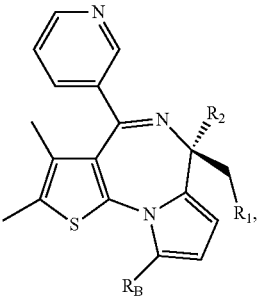
(VI)

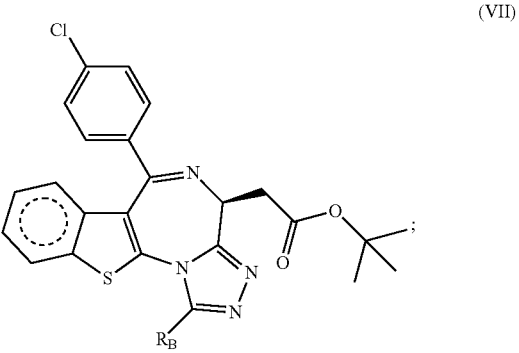
(VII)

in which R, $R_1$, and $R_2$ and $R_B$ have the same meaning as in Formula (I); Y is O, N, S, or $CR_5$, in which $R_5$ has the same meaning as in Formula (I); n is 0 or 1; and the dashed circle in Formula (VII) indicates an aromatic or non-aromatic ring; or a salt, solvate or hydrate thereof.

In certain embodiments of any of the Formulae I-IV and VI (or any formula herein), $R_6$ represents the non-carbonyl portion of an aldehyde shown in Table A, below (i.e., for an aldehyde of formula $R_6CHO$, $R_6$ is the non-carbonyl portion of the aldehyde). In certain embodiments, $R_4$ and $R_6$ together represent the non-carbonyl portion of a ketone shown in Table A (i.e., for a ketone of formula $R_6C(O)R_4$, $R_4$ and $R_6$ are the non-carbonyl portion of the ketone).

TABLE A

Plate 1

TABLE A-continued
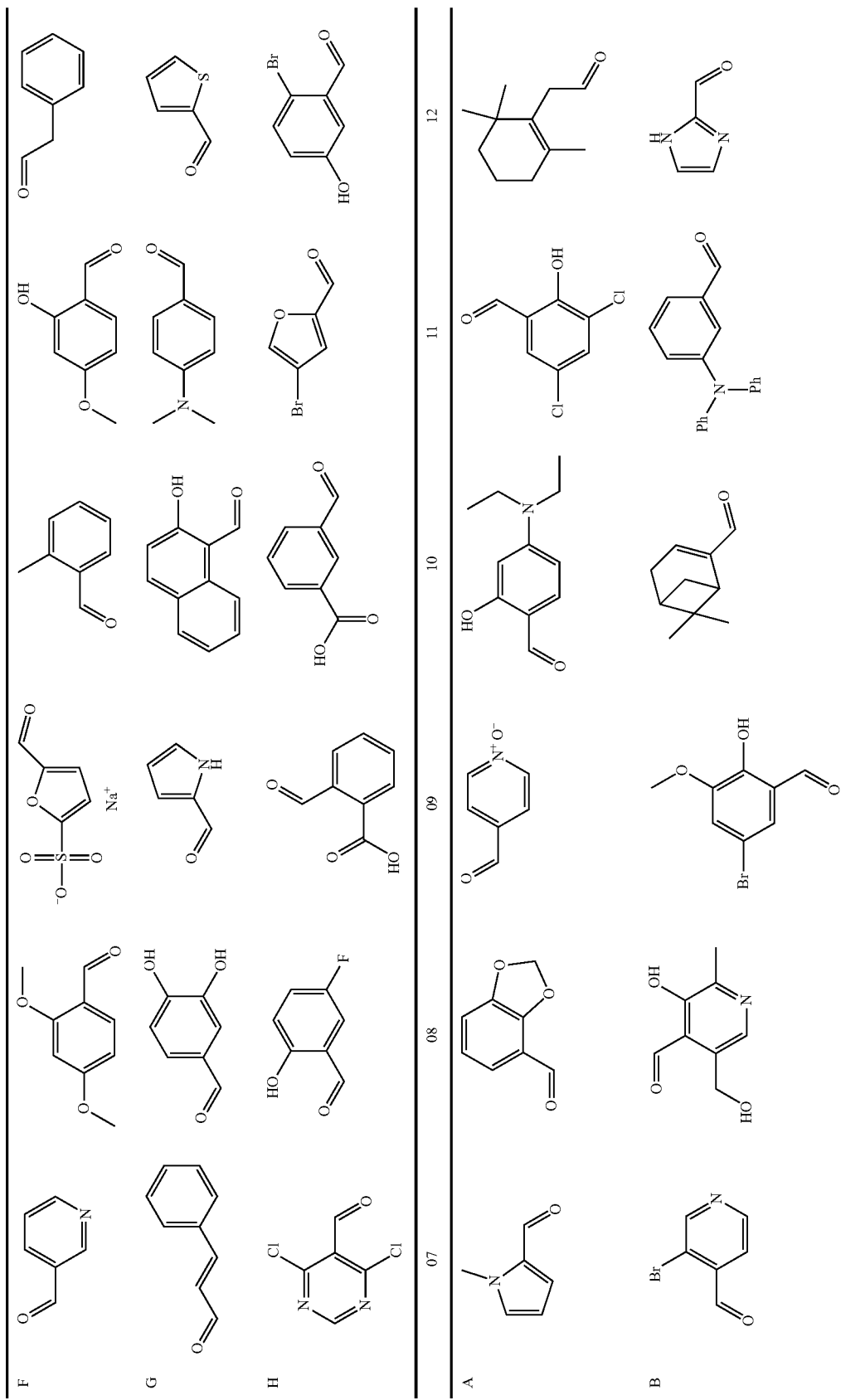

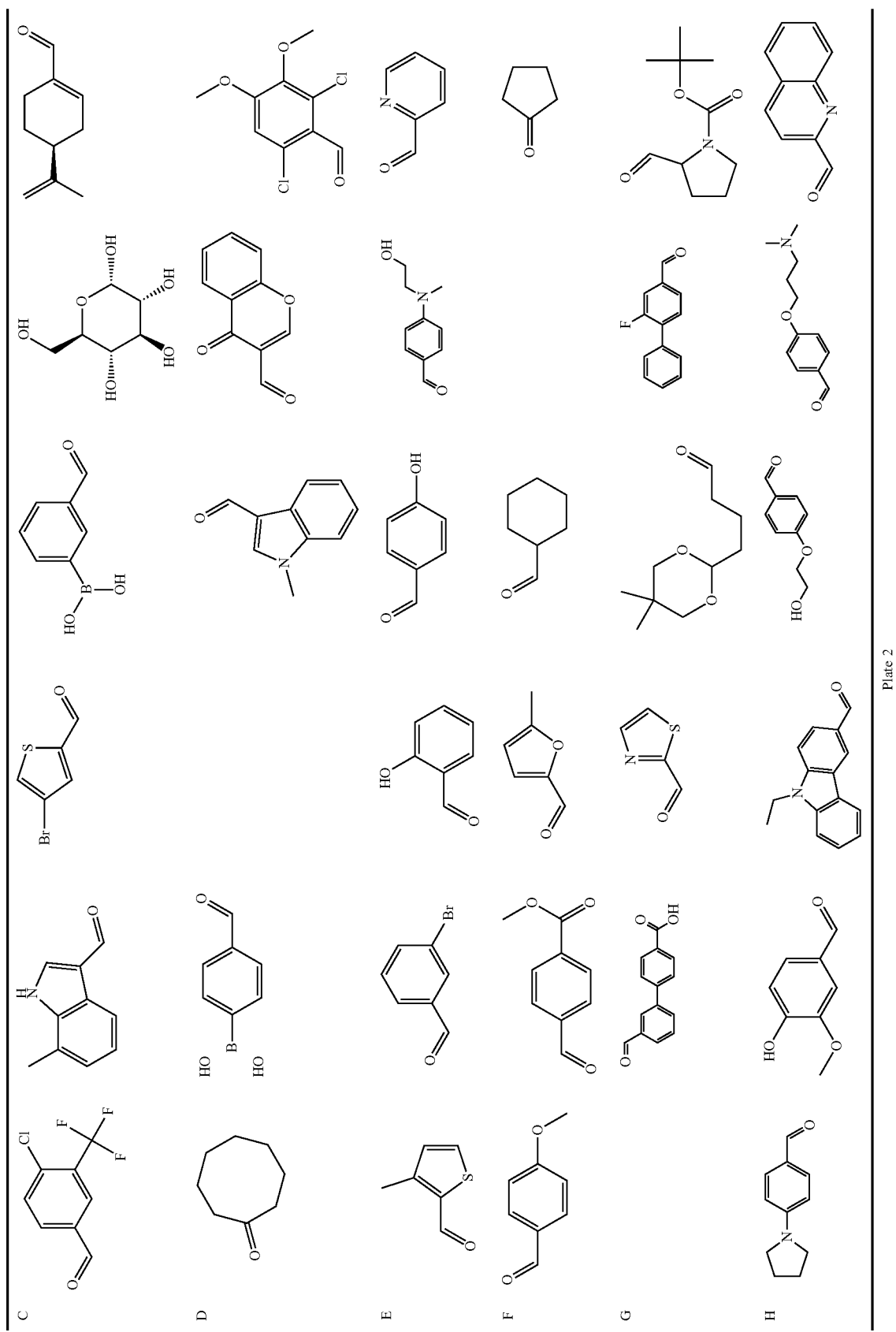

TABLE A-continued
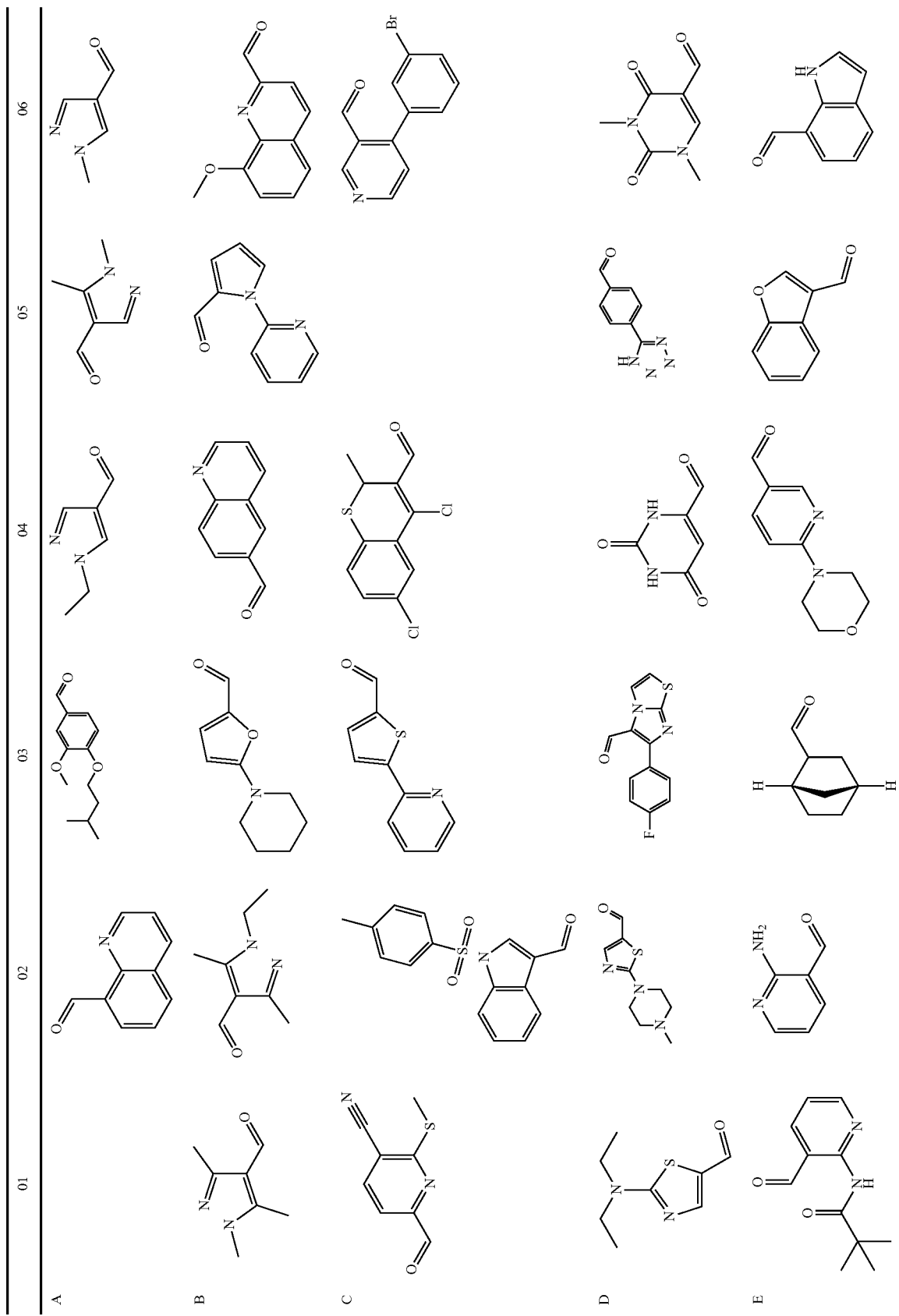

TABLE A-continued
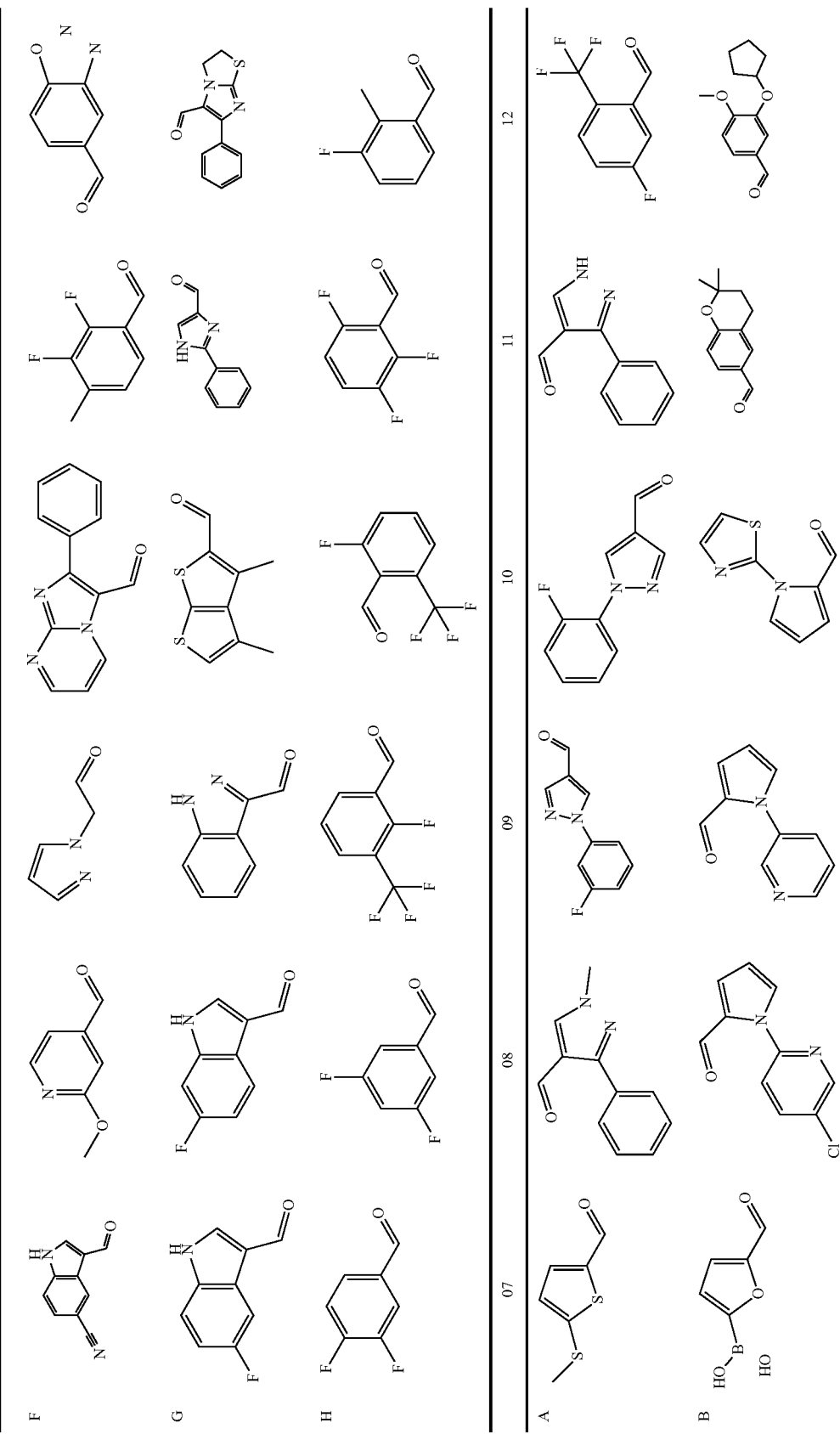

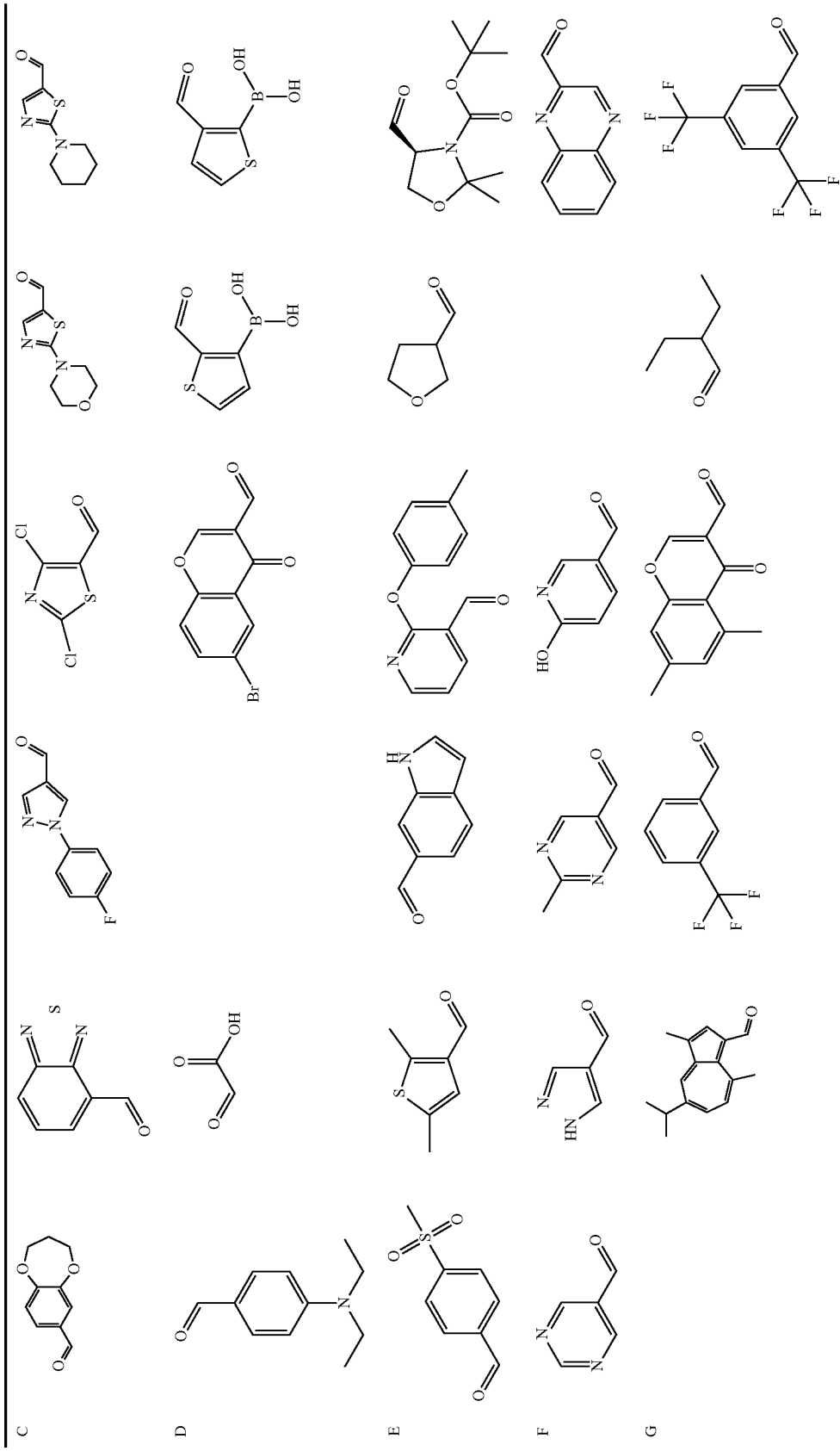

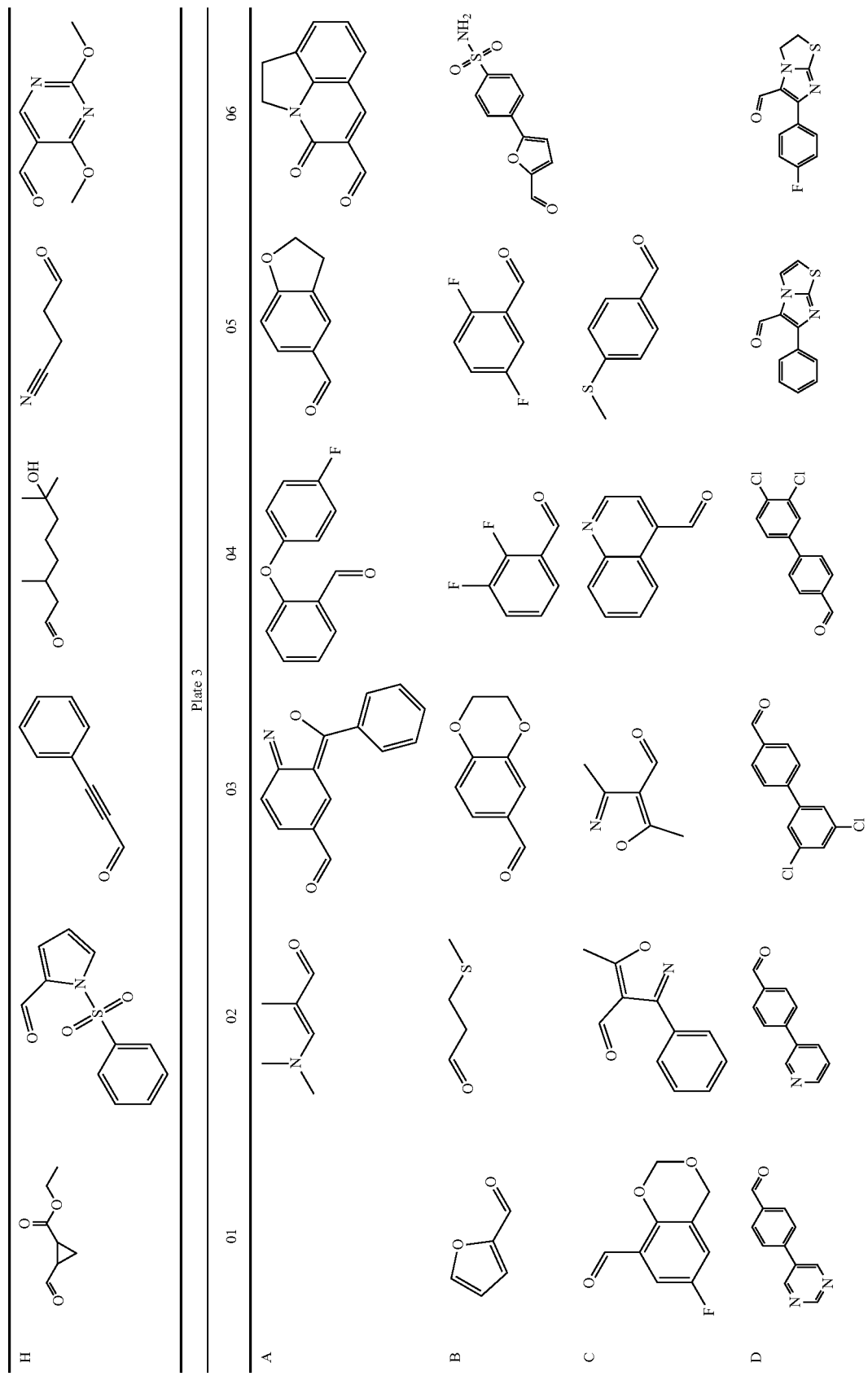

TABLE A-continued
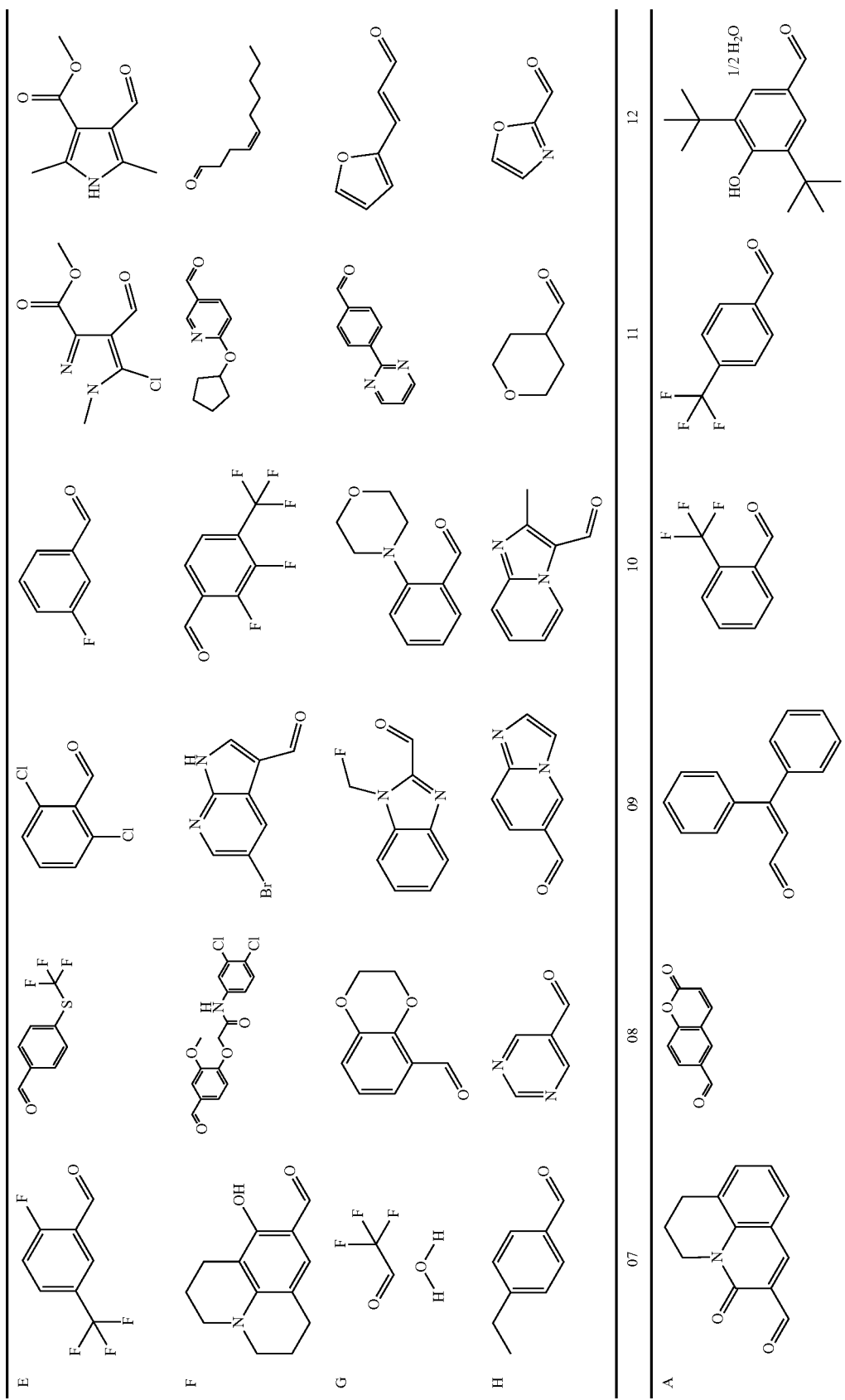

TABLE A-continued
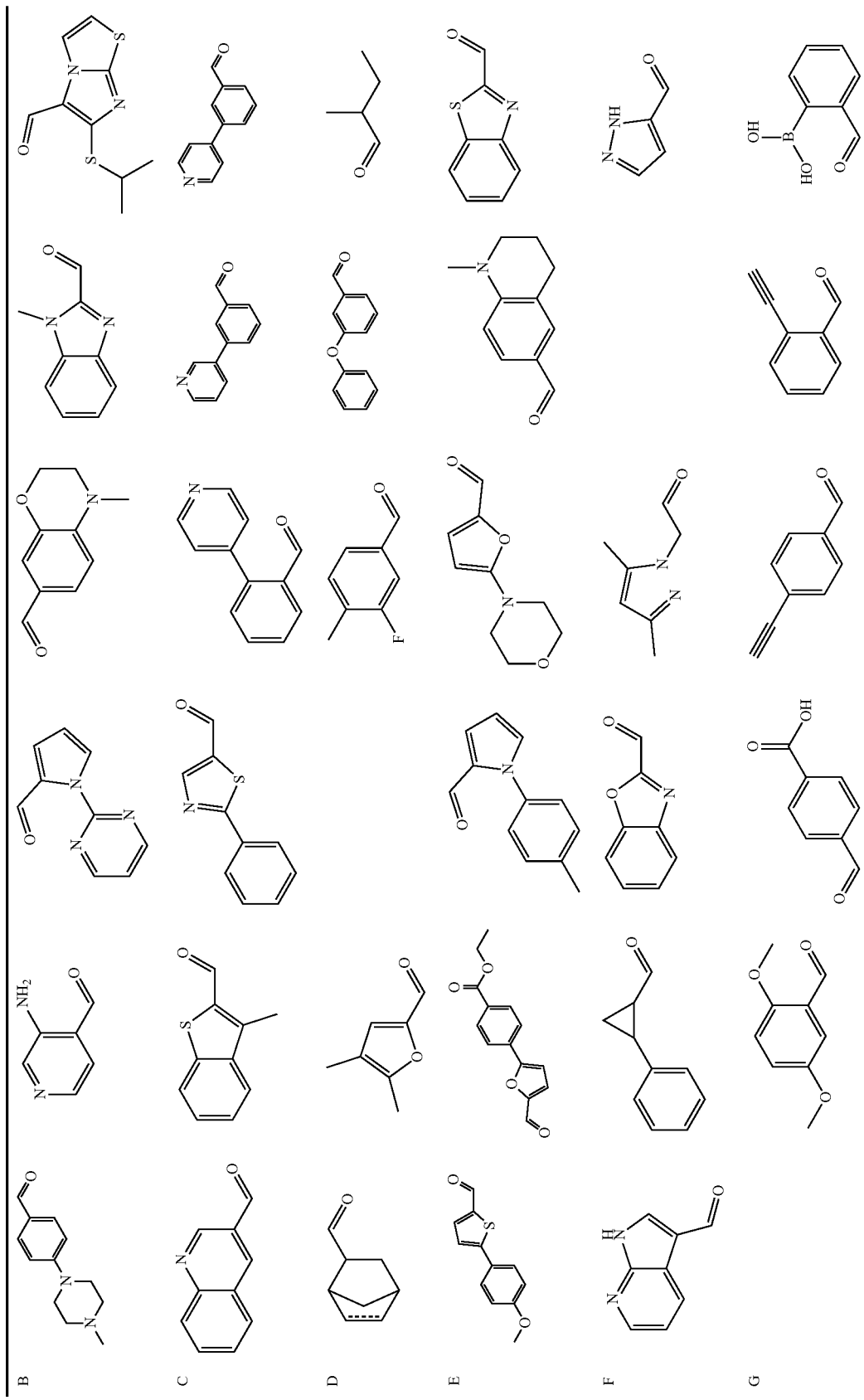

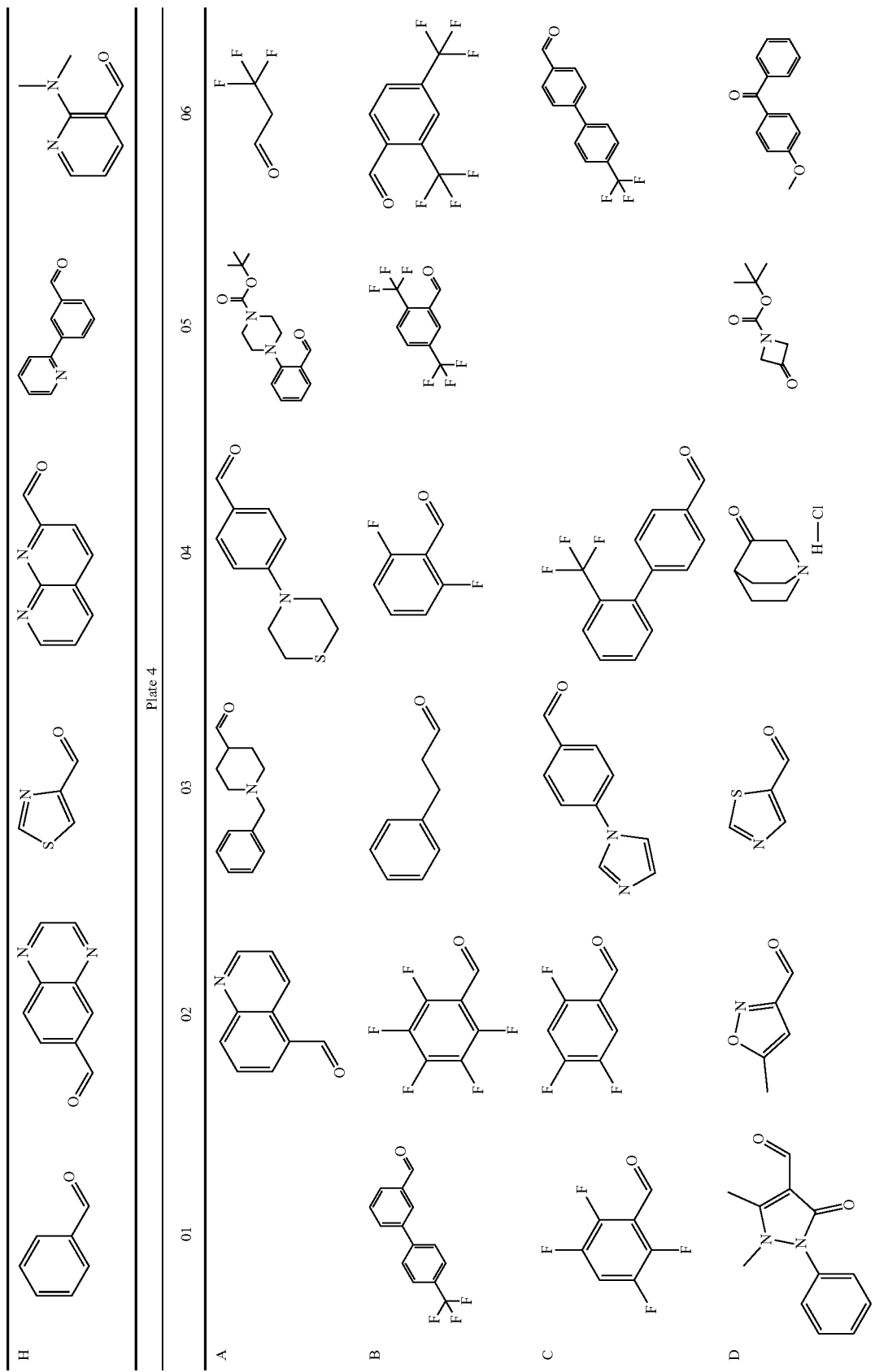

TABLE A-continued
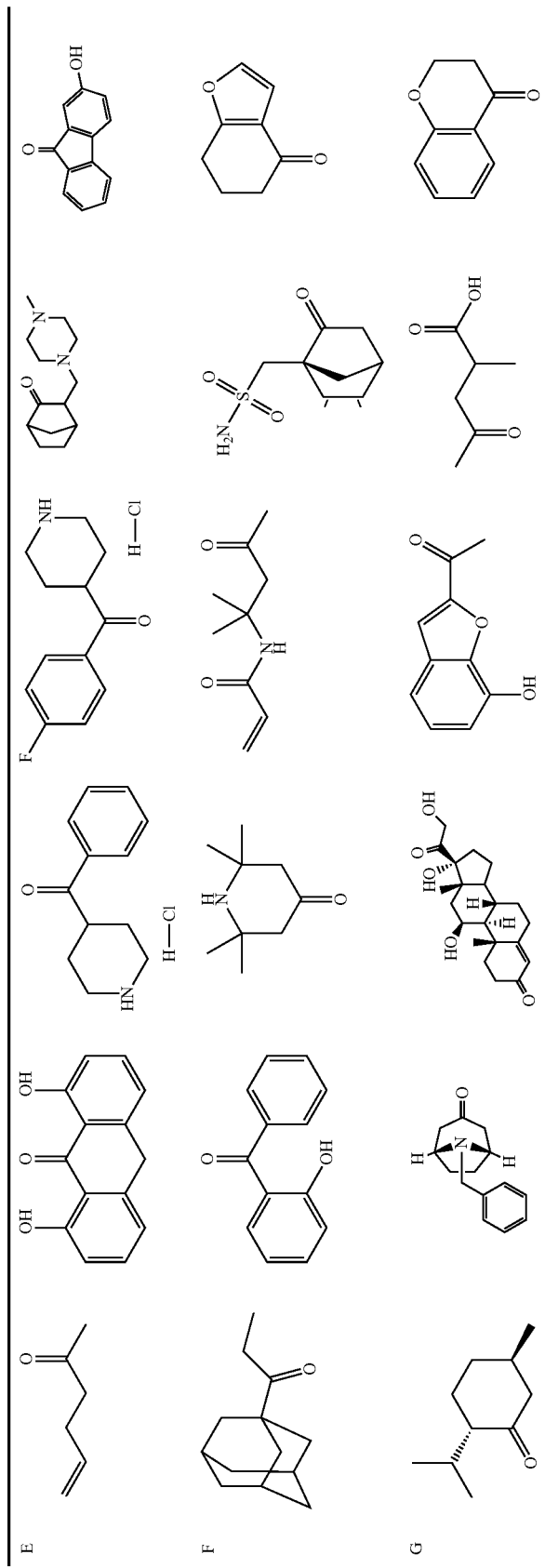
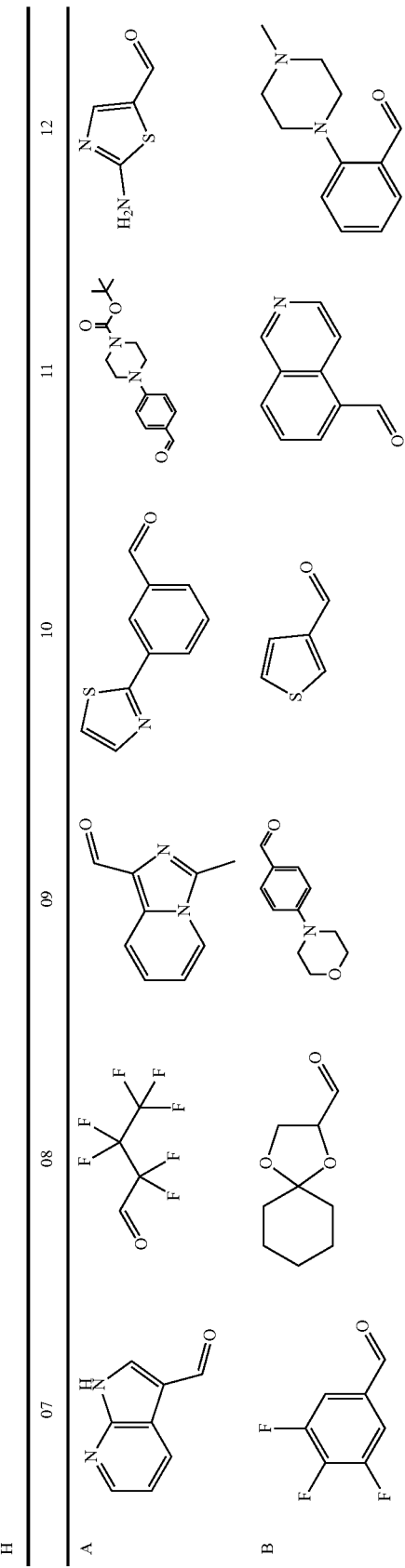

TABLE A-continued
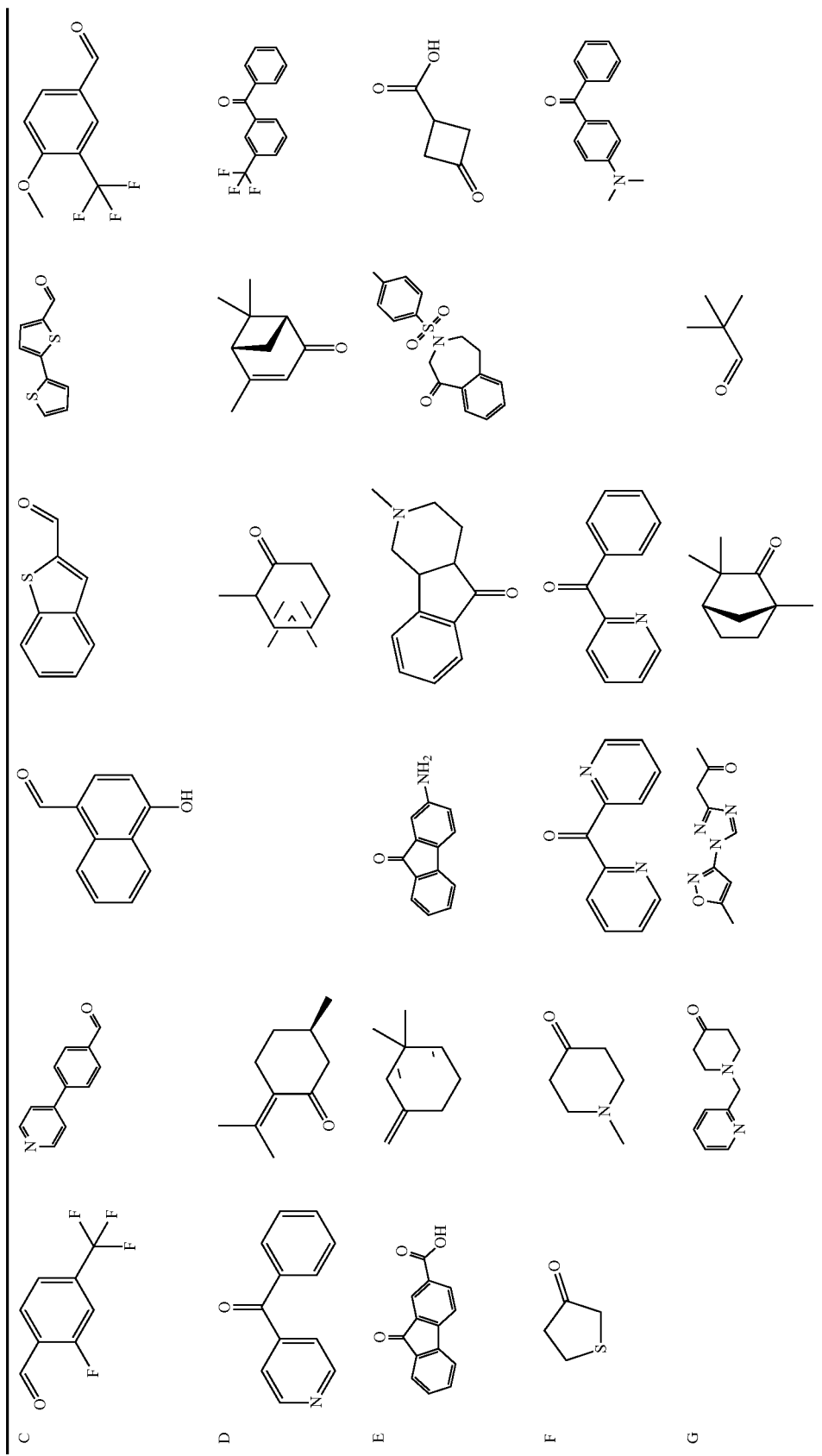

In one embodiment, a compound is represented by the formula:

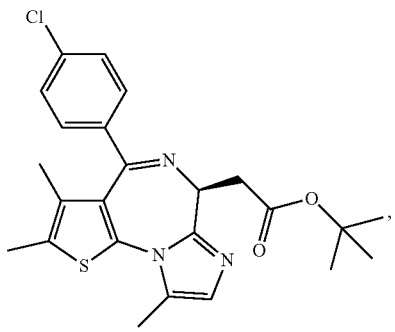
(VIII)

or a salt, solvate, or hydrate thereof.

In certain embodiments, the compound is (racemic) JQ1; in certain embodiments, the compound is (+)-JQ1. In certain embodiments, the compound is a compound selected from the group consisting of:

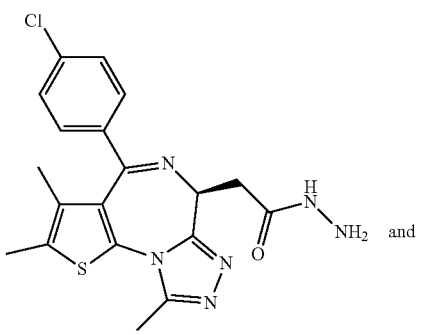
(3)

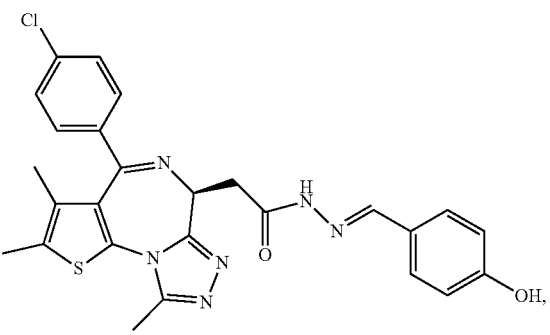
(4)

or a salt, solvate, or hydrate thereof.

Additional examples of compounds include compounds according to any of the following formulae:

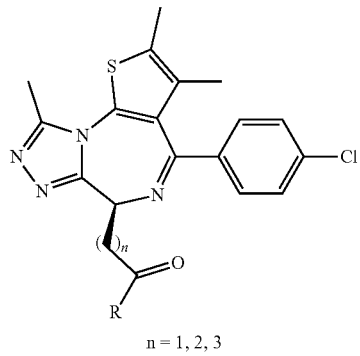
(IX)
n = 1, 2, 3

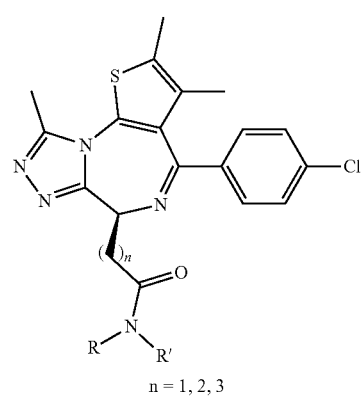
(X)
n = 1, 2, 3

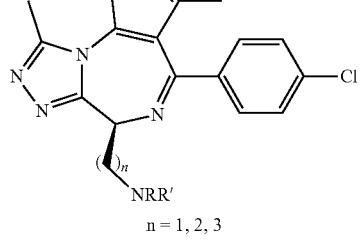
(XI)
n = 1, 2, 3

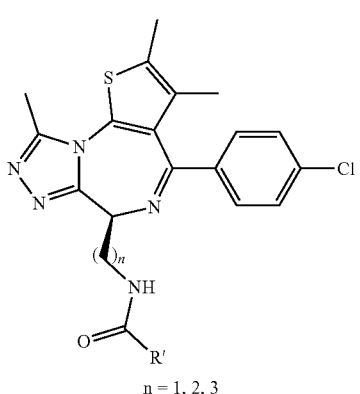
(XII)
n = 1, 2, 3

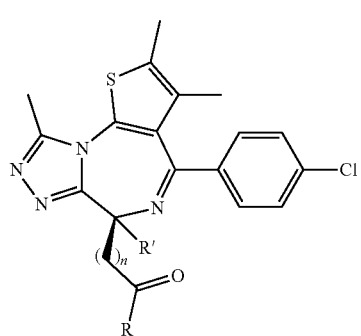
(XIII)
R' = H, D, Me
n = 1, 2, 3
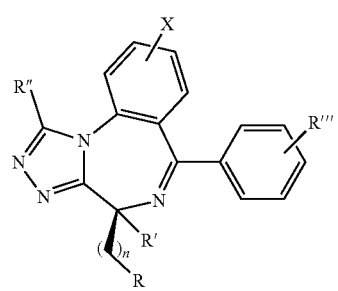
(XIV)
R' = H, D, Me
n = 1, 2, 3
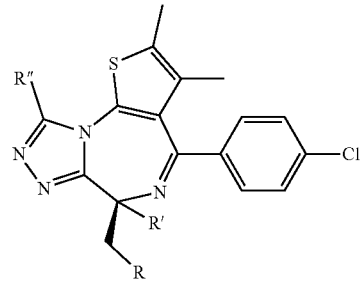
(XV)
R' = OMe, CH₂OH, CH₂NH₂, CH₂OMe
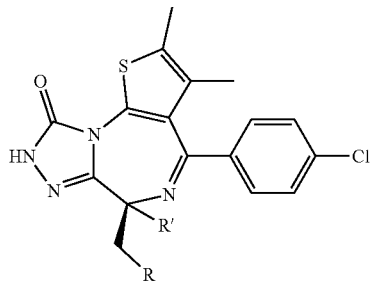
(XVI)
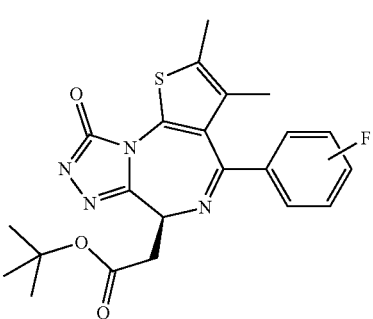
(XVII)
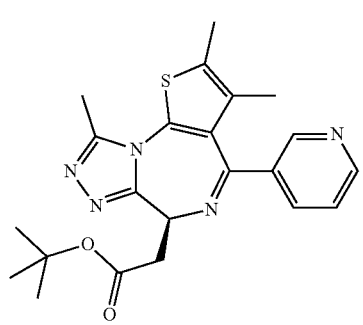
(XVIII)
Also 2- and 4-pyridyl
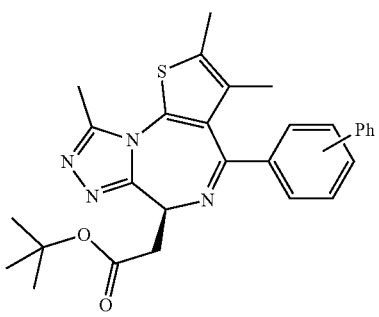
(XIX)
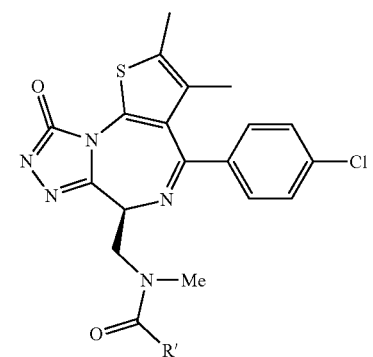
(XX)

-continued

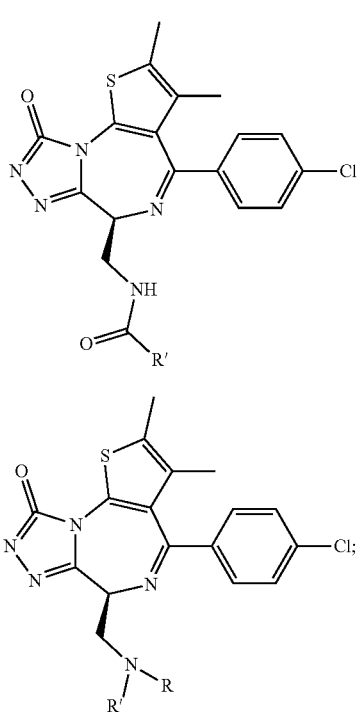

or a salt, solvate or hydrate thereof.

In Formulae IX-XXII, R and R' can be, e.g., H, aryl, substituted aryl, heteroaryl, heteroaryl, heterocycloalkyl, —$C_1$-$C_8$ alkyl, —$C_2$-$C_8$ alkenyl, —$C_2$-$C_8$ alkynyl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted. In Formulae XIV, X can be any substituent for an aryl group as described herein.

Compounds of the invention can be prepared by a variety of methods, some of which are known in the art. For instance, the chemical Examples provided hereinbelow provide synthetic schemes for the preparation of the compound JQ1 (as the racemate) and the enantiomers (+)-JQ1 and (−)-JQ1 (see Schemes S1 and S2). A variety of compounds of Formulae (I)-(XXII) can be prepared by analogous methods with substitution of appropriate starting materials.

For example, starting from JQ1, the analogous amine can be prepared as shown in Scheme 1, below.

Scheme 1

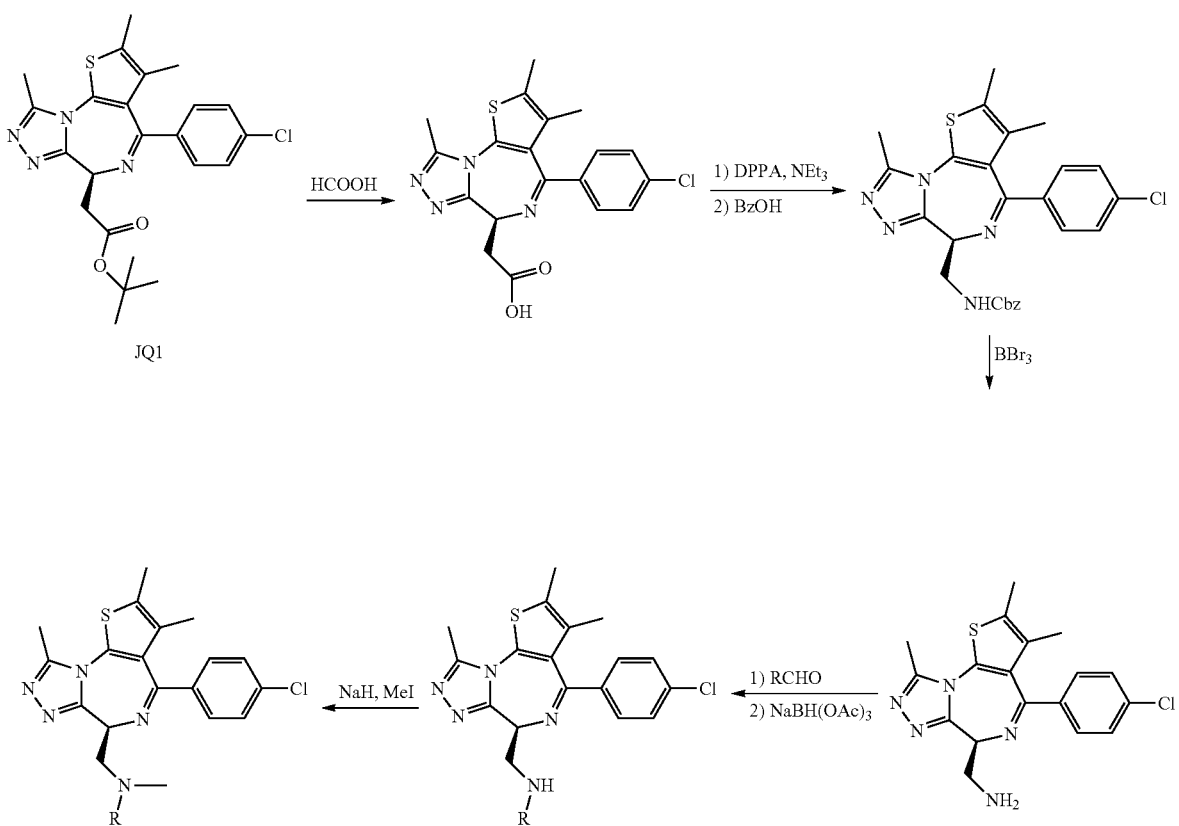

As shown in Scheme 1, hydrolysis of the t-butyl ester of JQ1 affords the carboxylic acid, which is treated with diphenylphosphoryl azide (DPPA) and subjected to Curtius rearrangement conditions to provide the Cbz-protected amine, which is then deprotected to yield the amine. Subsequent elaboration of the amine group, e.g., by reductive amination yields secondary amines, which can be further alkylated to provide tertiary amines.

Scheme 2

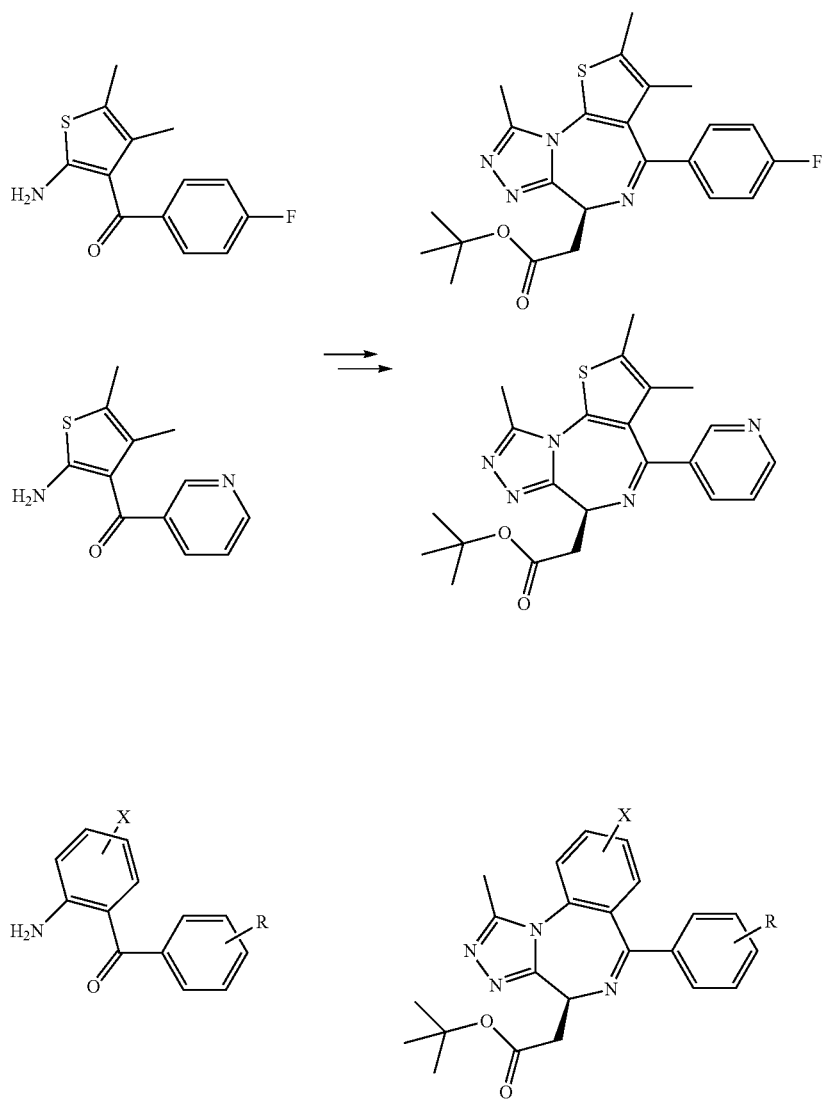

Scheme 2 shows the synthesis of further examples of the compounds of the invention, e.g., of Formula I, in which the fused ring core is modified (e.g., by substitution of a different aromatic ring as Ring A in Formula I). Use of aminodiarylketones having appropriate functionality (e.g., in place of the aminodiarylketone S2 in Scheme S1, infra) provides new compounds having a variety of fused ring cores and/or aryl group appendages (corresponding to group R in Formula I). Such aminodiarylketones are commercially available or can be prepared by a variety of methods, some of which are known in the art.

Scheme 3 provides additional exemplary synthetic schemes for preparing further compounds of the invention.

Scheme 3

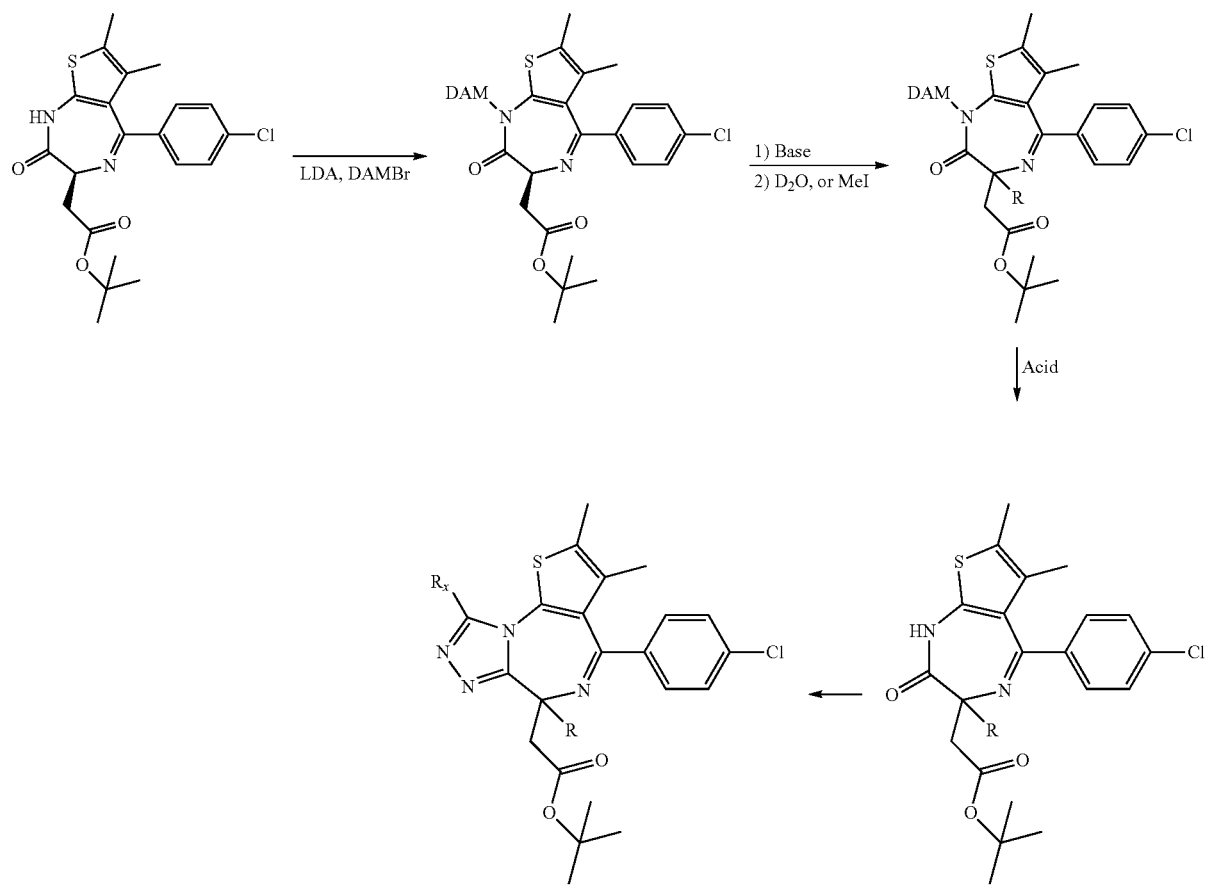

As shown in Scheme 3, a fused bicyclic precursor (see Scheme S1, infra, for synthesis of this compound) is functionalized with a moiety R (DAM=dimethylaminomethylene protecting group) and then elaborated by reaction with a hydrazide to form the tricyclic fused core. Substituent $R_x$ can be varied by selection of a suitable hydrazide.

Additional examples of compounds of the invention (which can be prepared by the methods described herein) include:

Amides:

Amides can be prepared, e.g., by preparation of a corresponding carboxylic acid or ester, followed by amidation with an appropriate amine using standard conditions. In certain embodiments, an amide provides a two-carbon "linker" with a terminal nitrogen-containing ring (e.g., pyridyl, piperidyl, piperazinyl, imidazolyl (including N-methyl-imidazolyl), morpholinyl, and the like. Exemplary amide structures include:

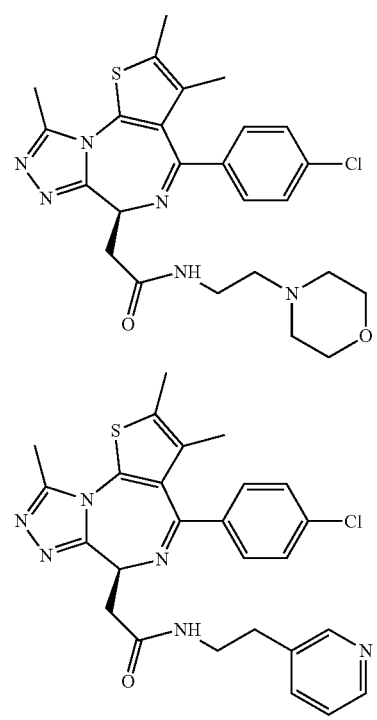

-continued
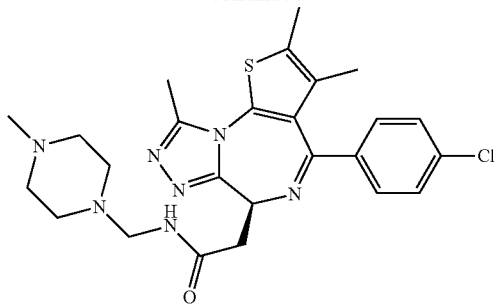
"Reverse amides":
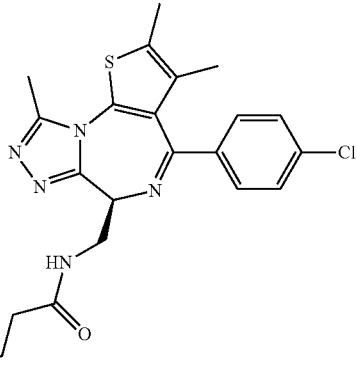
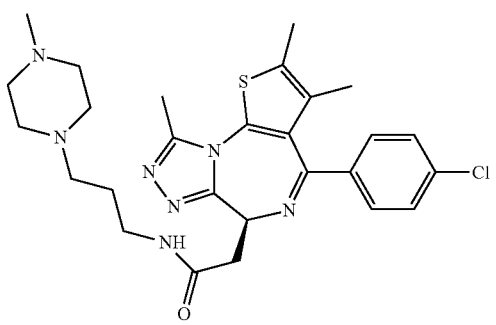
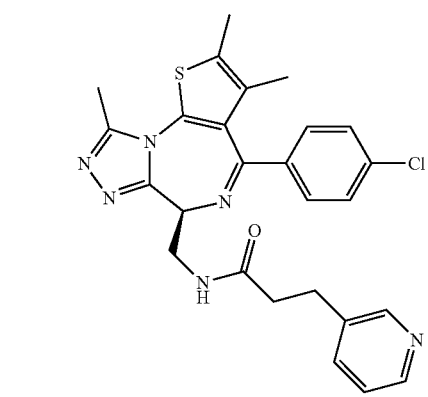
N position can be different
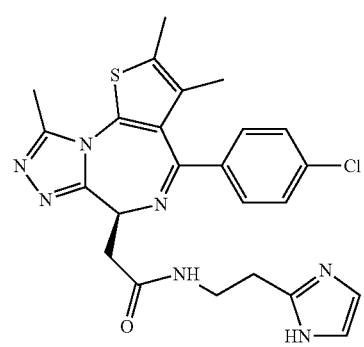
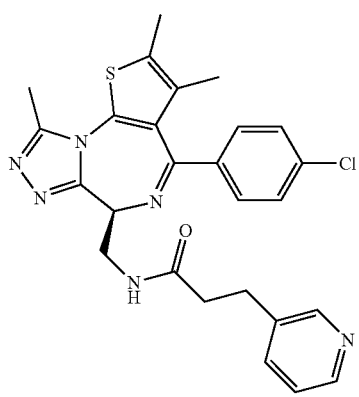
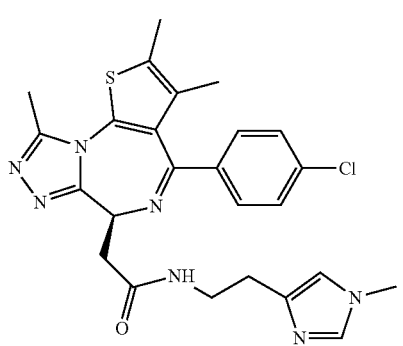 [SMILES: Cc1sc2c(c1C)C(c1ccc(Cl)cc1)=N[C@@H](CC(=O)NCCc1cn(C)cn1)c1nnc(C)n1-2]
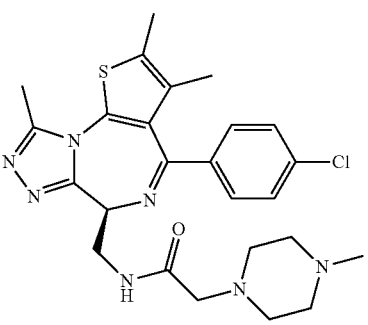
The use of a two-carbon linker between the amide moiety and the terminal-nitrogen-containing ring is preferred.
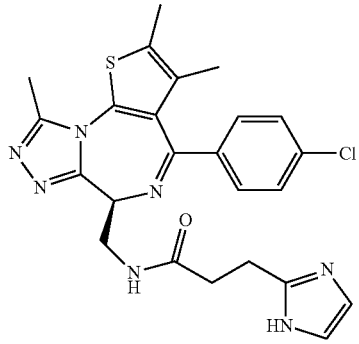

93
-continued
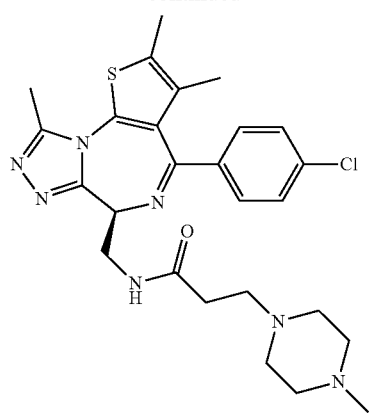
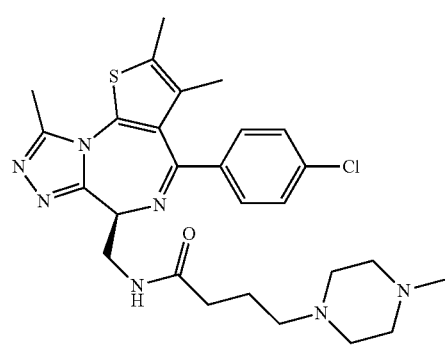
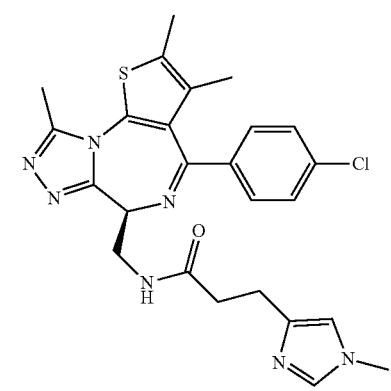
Secondary amines:
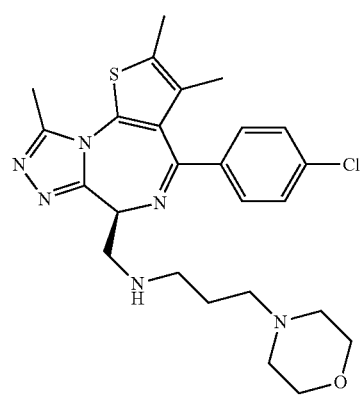
94
-continued
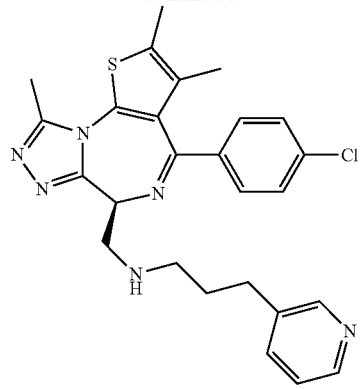
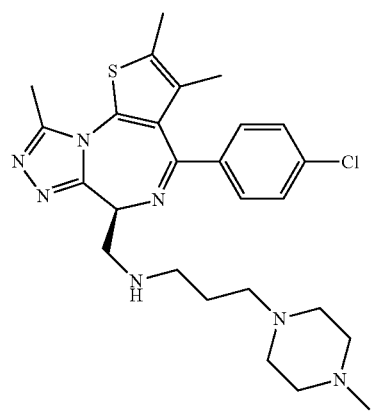
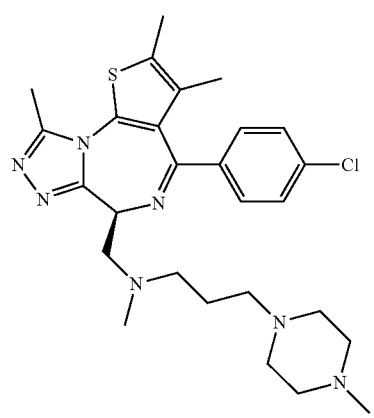
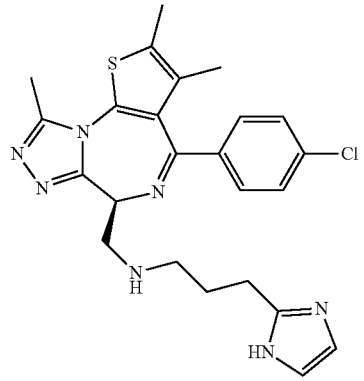 [SMILES: Cc1sc2c(c1C)C(c1ccc(Cl)cc1)=N[C@@H](CNCCCc1ncc[nH]1)c1nnc(C)n1-2]

Boronic acids:

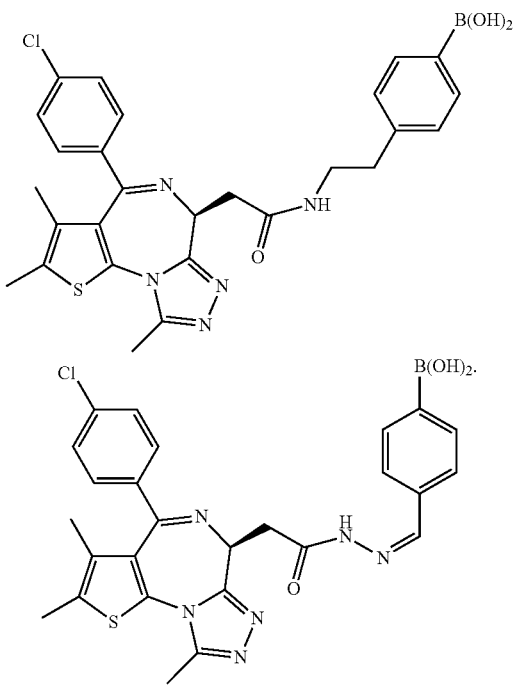

In certain embodiments, a compound having at least one chiral center is present in racemic form. In certain embodiments, a compound having at least one chiral center is enantiomerically enriched, i.e., has an enantiomeric excess (e.e.) of at least about 10%, 20%, 30%, 40%, 50%, 60%, 70%, 80%, 85%, 90%, 90%, 95%, 99%, 99% or 100%. In certain embodiments, a compound has the same absolute configuration as the compound (+)-JQ1 ((S)-tert-Butyl 2-(4-(4-chlorophenyl)-2,3,9-trimethyl-6H-thieno[3,2-f][1,2,4]triazolo[4,3-a][1,4]diazepin-6-yl)acetate) described herein.

In certain embodiments of any of the Formulae disclosed herein, the compound is not represented by the following structure:

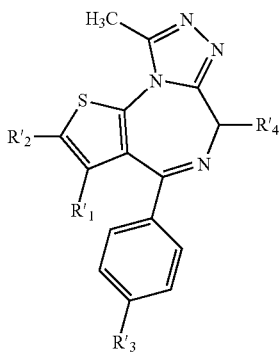

in which:
$R'_1$ is $C_1$-$C_4$ alkyl;
$R'_2$ is hydrogen, halogen, or $C_1$-$C_4$ alkyl optionally substituted with a halogen atom or a hydroxyl group;
$R'_3$ is a halogen atom, phenyl optionally substituted by a halogen atom, $C_1$-$C_4$ alkyl, $C_1$-$C_4$ alkoxy, or cyano; —$NR_5$—$(CH_2)_m$—$R_6$ wherein $R_5$ is a hydrogen atom or $C_1$-$C_4$ alkyl, m is an integer of 0-4, and $R_6$ is phenyl or pyridyl optionally substituted by a halogen atom; or —$NR_7$—$CO$—$(CH_2)_n$—$R_8$ wherein $R_7$ is a hydrogen atom or $C_1$-$C_4$ alkyl, n is an integer of 0-2, and $R_8$ is phenyl or pyridyl optionally substituted by a halogen atom; and $R'_4$ is —$(CH_2)_a$—$CO$—$NH$—$R_9$ wherein a is an integer of 1-4, and $R_9$ is $C_1$-$C_4$ alkyl; $C_1$-$C_4$ hydroxyalkyl; $C_1$-$C_4$ alkoxy; or phenyl or pyridyl optionally substituted by $C_1$-$C_4$ alkyl, $C_1$-$C_4$ alkoxy, amino or a hydroxyl group or —$(CH_2)_b$—$COOR_{10}$ wherein b is an integer of 1-4, and Rio is $C_1$-$C_4$ alkyl.

The term "pharmaceutically acceptable salt" refers to a salt prepared from a compound disclosed herein (e.g., JQ1, a compound of Formulas I-XXII) or any other compound delineated herein, having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, or any other compound delineated herein, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

In Silico Screening Methods and Systems

In another aspect, the invention provides a machine readable storage medium which comprises the structural coordinates of a BET family member polypeptide (e.g., BRD4 domain) binding site identified herein. This is the proposed binding site of JQ1. A storage medium encoded with these data is capable of displaying a three-dimensional graphical representation of a molecule or molecular complex which comprises such binding sites on a computer screen or similar viewing device.

The invention also provides methods for designing, evaluating and identifying compounds that bind to the aforementioned binding site. Such compounds are expected to be to inhibit the biological activity of a BET family member (e.g., BRD2, BRD3, BRD4, BRDT) and/or to disrupt the subcellular localization of a BET family member (e.g., BRD2, BRD3, BRD4, BRDT). The invention provides a computer for producing a) a three-dimensional representation of a molecule or molecular complex, wherein said molecule or molecular complex comprises a binding site; or b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms, wherein said computer comprises:

(i) a machine-readable data storage medium comprising a data storage material encoded with machine-readable data, wherein said data comprises the structure coordinates of amino acid residues in the bromodomain structural binding pocket or other BET family member binding site;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

Thus, the computer produces a three-dimensional graphical structure of a molecule or a molecular complex which comprises a binding site.

In another embodiment, the invention provides a computer for producing a three-dimensional representation of a molecule or molecular complex defined by structure coordinates of a BET family member (e.g., BRD2, BRD3, BRD4, BRDT) amino acids, or a three-dimensional representation of a homologue of said molecule or molecular complex, wherein said homologue comprises a binding site that has a root mean square deviation from the backbone atoms of said amino acids of not more than 2.0 (more preferably not more than 1.5) angstroms In exemplary embodiments, the computer or computer system can include components that are conventional in the art, e.g., as disclosed in U.S. Pat. Nos. 5,978,740 and/or 6,183,121 (incorporated herein by reference). For example, a computer system can include a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in a manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket may be used for a variety of purposes, such as drug discovery.

For example, the structure encoded by the data may be computationally evaluated for its ability to associate with chemical entities. Chemical entities that associate with a binding site of a BET family member (e.g., BRD2, BRD3, BRD4, BRDT) are expected to inhibit the proliferation or induce the differentiation of a neoplastic cell, to inhibit the biological activity of a BET family member (e.g., BRD2, BRD3, BRD4, BRDT), and/or to disrupt subcellular localization. Such compounds are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding site defined by structure coordinates of a BET family member (e.g., BRD2, BRD3, BRD4, BRDT), as described herein, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:

i) employing computational means to perform a fitting operation between the chemical entity and a binding site of a BET family member (e.g., BRD2, BRD3, BRD4, BRDT) polypeptide or fragment thereof or molecular complex; and ii) analyzing the results of the fitting operation to quantify the association between the chemical entity and the binding pocket. This embodiment relates to evaluating the potential of a chemical entity to associate with or bind to a binding site of a of a BET family member (e.g., BRD2, BRD3, BRD4, BRDT) or fragment thereof.

The term "chemical entity", as used herein, refers to chemical compounds, complexes of at least two chemical compounds, and fragments of such compounds or complexes.

In certain embodiments, the method evaluates the potential of a chemical entity to associate with a molecule or molecular complex defined by structure coordinates of all of the amino acids of a BET family member (e.g., BRD2, BRD3, BRD4, BRDT), as described herein, or a homologue of said molecule or molecular complex having a root mean square deviation from the backbone atoms of said amino acids of not more than 2.0 (more preferably not more than 1.5) angstroms.

In a further embodiment, the structural coordinates one of the binding sites described herein can be utilized in a method for identifying an antagonist of a molecule comprising a bromodomain binding site (e.g., a bromodomain structural binding pocket). This method comprises the steps of:

a) using the atomic coordinates of a BET family member; and b) employing the three-dimensional structure to design or select the potential agonist or antagonist. One may obtain the compound by any means available. By "obtaining" is meant, for example, synthesizing, buying, or otherwise procuring the agonist or antagonist. If desired, the method further involves contacting the agonist or antagonist with BET family member polypeptide or a fragment thereof to determine the ability of the potential agonist or antagonist to interact with the molecule. If desired, the method also further involves the step of contacting a neoplastic cell with a bromodomain binding compound and evaluating cytotoxicity, evaluating neoplastic cell proliferation, cell death, BET family member biological activity, or subcellular localization.

In another embodiment, the invention provides a method for identifying a potential antagonist of a BET family member (e.g., BRD2, BRD3, BRD4, BRDT), the method comprising the steps of:

a) using the atomic coordinates of a BET family member (e.g., BRD2, BRD3, BRD4, BRDT) (e.g., bromodomain structural binding pocket); and b) employing the three-dimensional structure to design or select the potential agonist or antagonist.

The present inventors' elucidation of heretofore unidentified binding sites of a bromodomain provides the necessary information for designing new chemical entities and compounds that may interact with bromodomains, in whole or in part, and may therefore modulate (e.g., inhibit) the activity of a BET family member (e.g., BRD2, BRD3, BRD4, BRDT).

The design of compounds that bind to a BET family member (e.g., BRD2, BRD3, BRD4 and BRDT) structural binding pocket sequence that reduce the biological activity of a bromodomain, or that disrupt the subcellular localization of a BET family member, according to this invention generally involves consideration of several factors. In one embodiment, the compound physically and/or structurally associates with at least a fragment of a BET family member (e.g., BRD2, BRD3, BRD4 and BRDT), such as a binding site within a bromodomain structural binding pocket sequence. Non-covalent molecular interactions important in this association include hydrogen bonding, van der Waals interactions, hydrophobic interactions and electrostatic interactions. Desirably, the compound assumes a conformation that allows it to associate with the bromodomain binding site(s) directly. Although certain portions of the compound may not directly participate in these associations, those portions of the entity may still influence the overall conformation of the molecule. This, in turn, may have a significant impact on the compound's potency. Such conformational requirements include the overall three-dimensional structure and orientation of the chemical compound in relation to all or a portion of the binding site, or the spacing between functional groups comprising several chemical compound that directly interact with the binding site or a homologue thereof.

The potential inhibitory or binding effect of a chemical compound on a bromodomain binding site may be analyzed prior to its actual synthesis and testing by the use of computer modeling techniques. If the theoretical structure of the given compound suggests insufficient interaction and association between it and the target binding site, testing of the compound is obviated. However, if computer modeling indicates a strong interaction, the molecule is synthesized and tested for its ability to bind a BET family member (e.g., BRD2, BRD3, BRD4 and BRDT) structural binding pocket sequence or to test its biological activity by assaying for example, cytotoxicity in a neoplastic cell, by assaying a reduction in the biological activity of a BET family member, or by assaying the subcellular localization of a BET family member (e.g., BRD2, BRD3, BRD4 and BRDT). Candidate compounds may be computationally evaluated by means of a series of steps in which chemical entities or fragments are screened and selected for their ability to associate with the bromodomain structural binding pocket.

One skilled in the art may use one of several methods to screen chemical compounds, or fragments for their ability to associate with a bromodomain binding site. This process may begin by visual inspection of, for example, a binding site on the computer screen based on the a BET family member's structure coordinates described herein, or other coordinates which define a similar shape generated from the machine-readable storage medium. Selected fragments or chemical compounds are then positioned in a variety of orientations, or docked, within that binding site as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding site.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention (see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once a compound has been designed or selected, the efficiency with which that entity may bind to a binding site may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein (see, e.g., Examples). Many thousands of compounds can be rapidly screened and the best virtual compounds can be selected for further screening (e.g., by synthesis and in vitro or in vivo testing). Small molecule databases can be screened for chemical entities or compounds that can bind, in whole or in part, to a bromodomain binding site of a BET family member (e.g., BRD2, BRD3, BRD4 and BRDT). In this screening, the quality of fit of such entities to the binding site may be judged either by shape complementarity or by estimated interaction energy.

A computer for producing a three-dimensional representation of
a) a molecule or molecular complex, wherein said molecule or molecular complex comprises a structural binding pocket of a BET family member defined by structure coordinates of amino acid residues in the structural binding pocket sequence of a bromodomain; or
b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms, wherein said computer comprises:
(i) a machine-readable data storage medium comprising a data storage material encoded with machine-readable data, wherein said data comprises the structure coordinates of structure coordinates of amino acid residues in the structural binding pocket sequence of a BET family member;
(ii) a working memory for storing instructions for processing said machine-readable data;
(iii) a central-processing unit coupled to said working memory and to said machine-readable data storage medium for processing said machine readable data into said three-dimensional representation; and
(iv) a display coupled to said central-processing unit for displaying said three-dimensional representation. As described in the Examples, compounds identified using in silico methods may optionally be tested in vitro or in vivo, for example, using the "Additional Screening Methods" described below, or any other method known in the art.

Additional Screening Methods

As described above, the invention provides specific examples of chemical compounds, including JQ1, as well as other substituted compounds that bind a bromodomain binding pocket and that induce cell differentiation or reduce cell proliferation in a neoplastic cell. However, the invention is not so limited. The invention further provides a simple means for identifying agents (including nucleic acids, peptides, small molecule inhibitors, and mimetics) that are capable of binding to a BET family member, that are cytotoxic to a neoplastic cell, that reduce the biological activity of a BET family member, or that disrupt the subcellular localization of a BET family member. Such compounds are also expected to be useful for the treatment or prevention of a neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency.

In particular, certain aspects of the invention are based at least in part on the discovery that agents that reduce the biological activity of a BET family member polypeptide are likely useful as therapeutics for the treatment or prevention of a neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency. In particular embodiments, the effect of a compound or other agent of the invention is analyzed by assaying cell proliferation, cell survival or cell death. In another approach, agents and compounds of the invention are assayed for their effect on transcriptional regulation or elongation. Agents and compounds of the invention that reduce the growth, proliferation, or invasiveness of a neoplasia are identified as useful for the treatment or prevention of a neoplasia. In yet another embodiment, compounds of the invention are assayed for their effect on an immunoresponsive cell, on cytokine or histamine release, or on any other marker of inflammatory disease.

Virtually any agent that specifically binds to a BET family member or that reduces the biological activity of a BET family member may be employed in the methods of the invention. Methods of the invention are useful for the high-throughput low-cost screening of candidate agents that reduce, slow, or stabilize the growth or proliferation of a neoplasia or for the treatment or prevention of inflammatory disease.

A candidate agent that specifically binds to a bromodomain of a BET family member is then isolated and tested for activity in an in vitro assay or in vivo assay for its ability to reduce neoplastic cell proliferation, induce differentiation, and/or increase neoplastic cell death. One skilled in the art appreciates that the effects of a candidate agent on a cell is typically compared to a corresponding control cell not contacted with the candidate agent. Thus, the screening methods include comparing the proliferation of a neoplastic cell contacted by a candidate agent to the proliferation of an untreated control cell.

In other embodiments, the expression or activity of a BET family member in a cell treated with a candidate agent is compared to untreated control samples to identify a candidate compound that decreases the biological activity of a BET family member in the contacted cell. Polypeptide expression or activity can be compared by procedures well known in the art, such as Western blotting, flow cytometry, immunocytochemistry, binding to magnetic and/or a bromodomain-specific antibody-coated beads, in situ hybridization, fluorescence in situ hybridization (FISH), ELISA, microarray analysis, RT-PCR, Northern blotting, or colorimetric assays, such as the Bradford Assay and Lowry Assay.

In one working example, one or more candidate agents are added at varying concentrations to the culture medium containing a neoplastic cell. An agent that reduces the expression of a BET family member expressed in the cell is considered useful in the invention; such an agent may be used, for example, as a therapeutic to prevent, delay, ameliorate, stabilize, or treat a neoplasia or inflammatory disease. Once identified, agents of the invention (e.g., agents that specifically bind to and/or antagonize a bromodomain) may be used to treat a neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency. An agent identified according to a method of the invention is locally or systemically delivered to treat neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility or for use in organ transplantation, modulation of cell state for regenerative medicine (i.e., by promoting or inhibiting cellular differentiation), or facilitating pluripotency in situ.

In one embodiment, the effect of a candidate agent may, in the alternative, be measured at the level of BET family member production using the same general approach and standard immunological techniques, such as Western blotting or immunoprecipitation with an antibody specific for the BET family member. For example, immunoassays may be used to detect or monitor the expression of a BET family member in a neoplastic cell. In one embodiment, the invention identifies a polyclonal or monoclonal antibody (produced as described herein) that is capable of binding to and blocking the biological activity or disrupting the subcellular localization of a BET family member. A compound that disrupts the subcellular localization, or reduces the biological activity of a BET family member is considered particularly useful. Again, such an agent may be used, for example, as a therapeutic to prevent or treat a neoplasia or inflammatory disease.

Alternatively, or in addition, candidate compounds may be identified by first assaying those that specifically bind to and antagonize a BET family member (e.g., BRD2, BRD3, BRD4 and BRDT) of the invention and subsequently testing their effect on neoplastic cells as described in the Examples.

In one embodiment, the efficacy of a candidate agent is dependent upon its ability to interact with the BET family member. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate neoplastic cell proliferation may be assayed by any standard assays (e.g., those described herein). In one embodiment, division of neoplastic cells is determined by assaying BrdU incorporation using flow cytometry analysis. In another embodiment, the expression of a BET family member is monitored immunohistochemically.

Potential bromodomain antagonists include organic molecules, peptides, peptide mimetics, polypeptides, nucleic acid ligands, aptamers, and antibodies that bind to a BET family member bromodomain and reduce its activity. In one particular example, a candidate compound that binds to a BET family member may be identified using a chromatography-based technique. For example, a recombinant BET family member polypeptide of the invention may be purified by standard techniques from cells engineered to express the polypeptide, or may be chemically synthesized, once purified the peptide is immobilized on a column. A solution of candidate agents is then passed through the column, and an agent that specifically binds the BET family member polypeptide or a fragment thereof is identified on the basis of its ability to bind to the BET family member polypeptide and to be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to reduce neoplastic cell proliferation or viability. Agents isolated by this approach may also be used, for example, as therapeutics to treat or prevent neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility or for use in organ transplantation, modulation of cell state for regenerative medicine (i.e., by promoting or inhibiting cellular differentiation), and facilitating pluripotency. Compounds that are identified as binding to a BET family member with an affinity constant less than or equal to 1 nM, 5 nM, 10 nM, 100 nM, 1 µM or 10 µM are considered particularly useful in the invention.

Test Compounds and Extracts

In certain embodiments, BET family member antagonists (e.g., agents that specifically bind and reduce the activity of a bromodomain) are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of a neoplasia or inflammatory disease. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have BET family member bromodomain binding activity further fractionation of the positive lead extract is necessary to isolate molecular constituents responsible for the observed effect. Thus, the goal of the extraction, fractionation, and purification process is the careful characterization and identification of a chemical entity within the crude extract that reduces neoplastic cell proliferation or viability. Methods of fractionation and purification of such heterogenous extracts are known in the art. If desired, compounds shown to be useful as therapeutics are chemically modified according to methods known in the art.

The present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof.

Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which neoplasia or inflammation may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Pharmaceutical Therapeutics

In other embodiments, agents discovered to have medicinal value (e.g., JQ1 or a compound of a formula delineated herein) using the methods described herein are useful as a drug or as information for structural modification of existing compounds, e.g., by rational drug design. Such methods are useful for screening agents having an effect on neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility or for use in organ transplantation, modulation of cell state for regenerative medicine (i.e., by promoting or inhibiting cellular differentiation), and facilitating pluripotency.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility or for use in organ transplantation, modulation of cell state for regenerative medicine (i.e., by promoting or inhibiting cellular differentiation), and facilitating pluripotency. Generally, amounts will be in the range of those used for other agents used in the treatment of other diseases associated with such diseases or states, although in certain instances lower amounts will be needed because of the increased specificity of the compound. A compound is administered at a dosage that is cytotoxic to a neoplastic cell, that reduces the biological activity of a BET family member, or that reduces the proliferation, survival, or invasiveness of a neoplastic cell as determined by a method known to one skilled in the art, or using any that assay that measures the expression or the biological activity of a BET family member. In another embodiment, the compound is administered at a dosage that reduces inflammation or a symptom of inflammatory disease.

Inflammatory Disease

Compositions of the invention, including compounds of formulas delineated herein, are useful for reducing inflammation and for the treatment of inflammatory disease. Inflammation is the result of a complex series of molecular signals involving the immune system, usually in response to infection or cellular or tissue damage. Inflammation normally constitutes the body's initiation of healing; however when it is not properly regulated inflammation can result in chronic diseases, such as arthritis.

By "inflammatory response" or "immune response" is meant the reaction of living tissues to injury, infection or irritation characterized by redness, warmth, swelling, pain, and loss of function produced, as the result of increased blood flow and an influx of immune cells and secretions. Inflammation is the body's reaction to invading infectious microorganisms and results in an increase in blood flow to the affected area, the release of chemicals that attract white blood cells, an increased flow of plasma, and the arrival of monocytes to clean up the debris. Anything that stimulates the inflammatory response is said to be inflammatory.

The innate cascade, or the innate immune response, is the non-specific response mounted by the immune system and is characterized by the infiltration of cells, such as leukocytes, natural killer cells, mast cells, eosinophils and basophils, as well as phagocytes, such as neutrophils, macrophages and dendritic cells in response to chemotatic signaling at the site of injury or infection. Molecules secreted by the aforementioned cells, such as histamine and various cytokines; and the complement system of circulating proteins contribute to inflammation.

Diseases characterized by inflammation are significant causes of morbidity and mortality in humans.

In certain embodiments, the inflammatory disorder is a rheumatoid disorder. Rheumatoid disorders, as used herein, refer to any of a variety of inflammatory disorders characterized by inflammation, and sometimes degeneration and/or metabolic derangement, of the connective tissue structures, especially the joints, ligaments, and tendons. Rheumatoid disorders typically result in pain, stiffness, and/or limitation of motion. The particular tissue or tissues effected depends on the rheumatoid disorder. Exemplary rheumatoid disorders include, but are not limited to, rheumatoid arthritis, juvenile arthritis, bursitis, spondylitis, gout, scleroderma, Still's disease, and vasculitis.

In certain embodiments, the rheumatoid disorder is rheumatoid arthritis and "treating" rheumatoid arthritis includes decreasing the severity, frequency, and/or occurrence of one or more of the symptoms of rheumatoid arthritis. In other embodiments, the rheumatoid disorder is juvenile arthritis, bursitis, spondylitis, gout, scleroderma, Still's disease, or vasculitis. Methods of the invention decrease the severity, frequency, and/or occurrence of any one or more of the symptoms of these conditions.

In various embodiments, symptoms of arthritis or other inflammatory diseases include redness, swelling, inflammation, fever, decreased range of motion, and pain. Examples of reducing the occurrence or severity of symptoms include, but are not limited to, decreasing the number of swollen joints, decreasing the number of painful joints, decreasing the reliance on pain medication, decreasing a patient's self-evaluation of the frequency or severity of their pain, increasing freedom of motion, increasing mobility, decreasing fever, and increasing the ability to perform daily tasks.

Neuroinflammation, characterized by activated microglia and astrocytes and local expression of a wide range of inflammatory mediators, is a fundamental reaction to brain injury, whether by trauma, stroke, infection, or neurodegeneration. This local tissue response is thought to be part of a repair and restorative process. Like many inflammatory conditions in peripheral diseases, neuroinflammation can contribute to the pathophysiology of CNS disorders.

In certain embodiment, the inflammatory disorder is an inflammatory skin disorder. Inflammatory skin disorders include but are not limited to rosacea, atopic dermatitis, acne, seborrheic dermatitis, and cellulitis.

In other embodiments, the inflammatory disease is an ischemic or inflammatory cardiovascular disease. An inflammatory cardiovascular disease or disorder may be, but is not limited to, an occlusive disease or disorder, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, or thrombosis. In other embodiments, the site is a secondary site of ischemic injury, such as the CNS or kidney.

In other embodiments, the inflammatory disease is an ischemic or inflammatory bowel disease.

Inflammatory bowel disease (IBD) refers to a chronic recurrent inflammatory disease of unclear etiology affecting the small intestine and colon that includes both Crohn's disease (CD) and ulcerative colitis (UC). Crohn's disease can involve any portion of the intestinal tract but most commonly involves the distal small intestine and/or the colon. Ulcerative colitis involves only the colon, generally limited to the rectum or distal colon. Studies of murine models of CD and UC strongly suggest that both of these diseases are due to dysregulation of the mucosal immune response to antigens in the mucosal microflora (Sartor, R. B. (1995). Gastroenterol Clin North Am 24, 475-507) (Strober W, et al. (2002) Annu. Rev. Immunol. 20:495-549).

Ulcerative colitis or indeterminate colitis refers to a condition of the colon characterized by a state of inflammation in which one or more of the following histological characteristics are detectable: a superficial inflammation characterized by the presence of epithelial cell loss and patchy ulceration, pronounced depletion of mucin producing-goblet cells, and reduction of the density of the tubular glands. In addition, in the lamina propia, a mixed inflammatory cell infiltrate consisting of lymphocytes and granulocytes (the latter consisting mostly of neutrophils and, to a lesser extent, eosinophils) associated with an exudation of cells into the bowel lumen is observed. Also, the submucosal level can display marked edema with few inflammatory cells, while in the outer muscle layer one of skill in the art would see little or no evidence of inflammation. See e.g. Boirivant et al. Journal of Experimental Medicine 188: 1929-1939 (1998). Clinical symptoms can include, but are not limited to, diarrhea, rectal prolapse, weight loss, abdominal pain, and dehydration.

Crohn's disease refers to inflammation affecting any part of the alimentary tract but most often affecting the terminal part of the small bowel and/or the adjacent ascending colon. Frequently, the inflammation is characterized by "skip lesions" consisting of areas of inflammation alternating with areas of normal mucosa. The affected area of bowel in Crohn's is marked by erythema, edema and increased friability; at times the bowel is structured and attached to other abdominal organs or to the bowel wall. Fistulae between the affected bowel and other structures including the skin are not infrequent. Microscopic examination of the tissue in Crohn's disease reveals epithelial erosions, loss of mucin-producing goblet cells and an extensive lymphocytic infiltration involving all layers of the mucosa; this infiltrate sometimes contains giant cells indicative of granuloma formation. When inflammation is present for a long time (chronic), it sometimes can cause scarring (fibrosis). Scar tissue is typically not as flexible as healthy tissue. Therefore, when fibrosis occurs in the intestines, the scarring may narrow the width of the passageway (lumen) of the involved segments of the bowel. These constricted areas are called strictures. The strictures may be mild or severe, depending on how much they block the contents of the bowel from passing through the narrowed area. Clinical signs/symptoms of Crohn's disease can include but are not limited to: cachexia, weight loss, poor growth, abdominal pain, draining fistulae, rectal prolapse and dehydration.

In certain embodiments, an inflammatory hepatic disease or disorder. For example, an inflammatory hepatic disease or disorder is selected from the group consisting of autoimmune hepatitis, hepatic cirrhosis, and biliary cirrhosis.

Formulation of Pharmaceutical Compositions

The administration of a compound for the treatment of a neoplasia or inflammatory disease may be by any suitable means that results in a concentration of the therapeutic that, combined with other components, is effective in ameliorating, reducing, or stabilizing a neoplasia or inflammatory disease. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia or inflammatory disease by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia or inflammatory disease, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutaminine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Encyclopedia of Pharmaceutical Technology, supra.

At least two therapeutics may be mixed together in the tablet, or may be partitioned. In one example, the first active anti-neoplasia therapeutic is contained on the inside of the tablet, and the second active therapeutic is on the outside, such that a substantial portion of the second therapeutic is released prior to the release of the first therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-neoplasia or anti-inflammatory therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Combination Therapies

Optionally, an anti-neoplasia or anti-inflammatory therapeutic may be administered in combination with any other standard anti-neoplasia or anti-inflammatory therapy known in the art; such methods are known to the skilled artisan and described in Remington's Pharmaceutical Sciences by E. W. Martin. If desired, agents of the invention (e.g., JQ1, compounds of formulas delineated herein, and derivatives thereof) are administered in combination with any conventional anti-neoplastic therapy, including but not limited to, surgery, radiation therapy, or chemotherapy. In preferred embodiments, a compound of the invention is administered in combination with an epigenetic or transcriptional modulator (e.g., DNA methyltransferase inhibitor, histone deacetylase inhibitor (HDAC inhibitor), lysine methyltransferase inhibitor), with antimitotic drugs (e.g., taxanes, vinca alkaloids), hormone receptor modulators (e.g., estrogen receptor modulators, androgen receptor modulators), cell signaling pathway inhibitors (e.g., tyrosine kinase inhibitors), modulators of protein stability (proteasome inhibitors), hsp90 inhibitors, conventional chemotherapeutics, glucocorticoids, all-trans retinoic acid or other agents that promote differentiation.

Kits or Pharmaceutical Systems

The present compositions may be assembled into kits or pharmaceutical systems for use in ameliorating a neoplasia or inflammatory disease. Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

I. Chemical Examples—Synthesis and Methods of Preparation

Compounds of the invention can be synthesized by methods described herein, and/or according to methods known to one of ordinary skill in the art in view of the description herein.

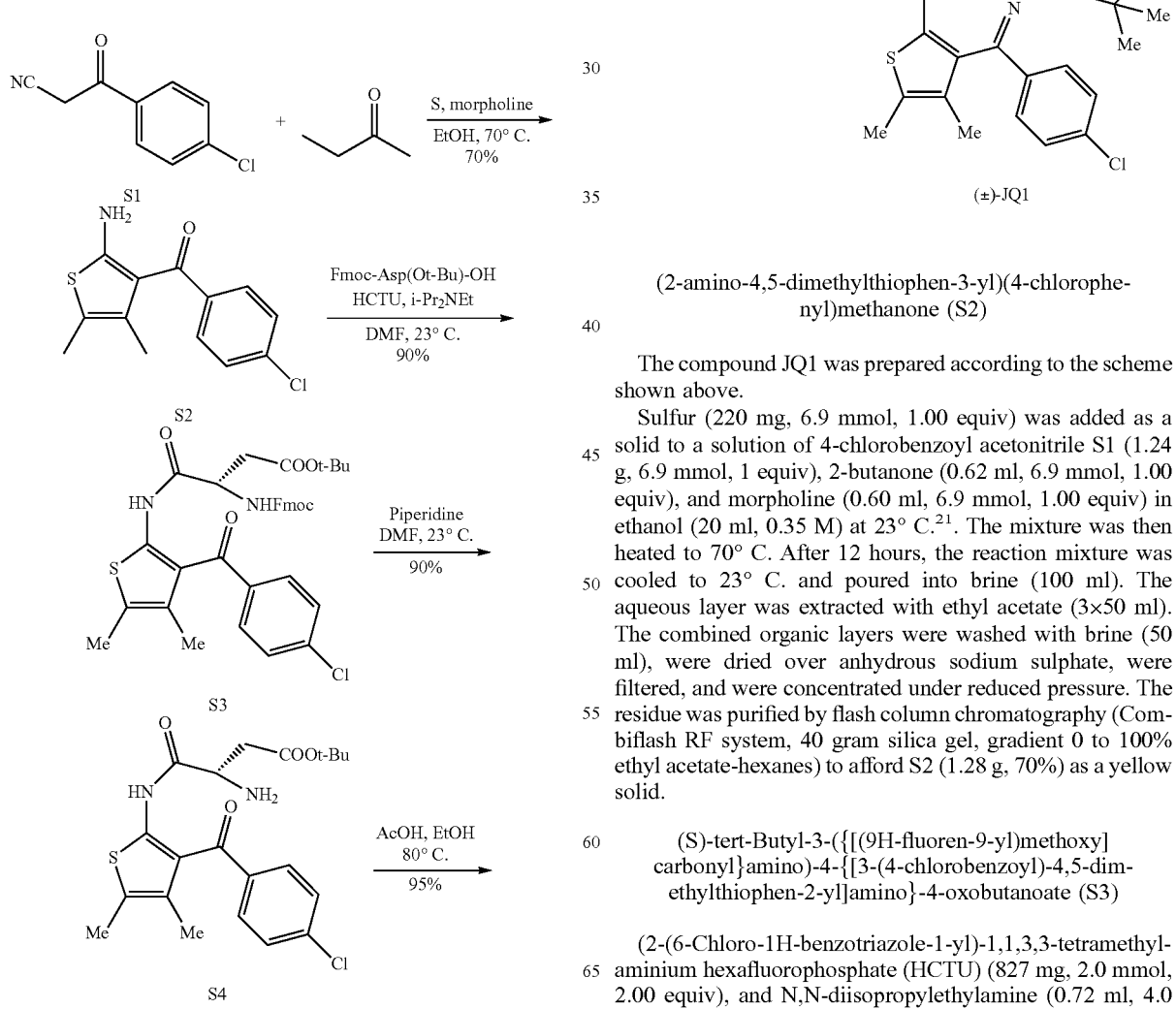

(2-amino-4,5-dimethylthiophen-3-yl)(4-chlorophenyl)methanone (S2)

The compound JQ1 was prepared according to the scheme shown above.

Sulfur (220 mg, 6.9 mmol, 1.00 equiv) was added as a solid to a solution of 4-chlorobenzoyl acetonitrile S1 (1.24 g, 6.9 mmol, 1 equiv), 2-butanone (0.62 ml, 6.9 mmol, 1.00 equiv), and morpholine (0.60 ml, 6.9 mmol, 1.00 equiv) in ethanol (20 ml, 0.35 M) at 23° C.[21]. The mixture was then heated to 70° C. After 12 hours, the reaction mixture was cooled to 23° C. and poured into brine (100 ml). The aqueous layer was extracted with ethyl acetate (3×50 ml). The combined organic layers were washed with brine (50 ml), were dried over anhydrous sodium sulphate, were filtered, and were concentrated under reduced pressure. The residue was purified by flash column chromatography (Combiflash RF system, 40 gram silica gel, gradient 0 to 100% ethyl acetate-hexanes) to afford S2 (1.28 g, 70%) as a yellow solid.

(S)-tert-Butyl-3-({[(9H-fluoren-9-yl)methoxy]carbonyl}amino)-4-{[3-(4-chlorobenzoyl)-4,5-dimethylthiophen-2-yl]amino}-4-oxobutanoate (S3)

(2-(6-Chloro-1H-benzotriazole-1-yl)-1,1,3,3-tetramethylaminium hexafluorophosphate (HCTU) (827 mg, 2.0 mmol, 2.00 equiv), and N,N-diisopropylethylamine (0.72 ml, 4.0 mmol, 4.00 equiv) were added sequentially to a solution of 9-fluorenylmethoxycarbonyl-aspartic acid β-tert-butyl ester [Fmoc-Asp(Ot-Bu)-OH] (864 mg, 2.1 mmol, 2.10 equiv) in N,N-dimethylformamide (1.5 ml, 1.0 M). The mixture was then stirred at 23° C. for 5 min. S2 (266 mg, 1.0 mmol, 1 equiv) was then added as a solid. The reaction mixture was stirred at 23° C. After 16 hours, ethyl acetate (20 ml) and brine (20 ml) were added. The two layers were separated, and the aqueous layer was extracted with ethyl acetate (2×20 ml). The combined organic layers were washed with brine (30 ml), were dried over with anhydrous sodium sulphate, were filtered, and were concentrated under reduced pressure. The residue was purified by flash column chromatography (Combiflash RF, 40 gram silica gel, gradient 0 to 100% ethyl acetate-hexanes) to afford S3 (625 mg, 90%) as brown oil.

(S)-tert-butyl 3-amino-4-((3-(4-chlorobenzoyl)-4,5-dimethylthiophen-2-yl)amino)-4-oxobutanoate (S4)

Compound S3 (560 mg, 0.85 mmol, 1 equiv) was dissolved into 20% piperidine in DMF solution (4.0 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexanes) to afford free amine S4 (370 mg, 90%) as yellow solid. The enantiomeric purity dropped to 75% (determined with Berger Supercritical Fluid Chromatography (SFC) using AS-H column).

(S)-tert-Butyl 2-(5-(4-chlorophenyl)-6,7-dimethyl-2-oxo-2,3-dihydro-1H-thieno[2,3-e][1,4]diazepin-3-yl) acetate (S5)

Amino ketone (S4) (280 mg, 0.63 mmol) was dissolved in 10% acetic acid ethanol solution (21 ml, 0.03 M). The reaction mixture was heated to 85° C. After 30 minutes, all solvents were removed under reduced pressure. The residue was purified by flash column chromatography (Combiflash RF system, 12 gram silica gel, gradient 0 to 100% ethyl acetate-hexanes) to afford compound S5 (241 mg, 95%) as white solid. Enantiomeric purity of S5 was 67% (determined with Berger Supercritical Fluid Chromatography (SFC) using an AS-H column).

tert-Butyl 2-(5-(4-chlorophenyl)-6,7-dimethyl-2-thioxo-2,3-dihydro-1H-thieno[2,3-e][1,4]diazepin-3-yl)acetate (S6)

Phosphorus pentasulfide (222 mg, 1.0 mmol, 2.00 equiv), sodium bicarbonate (168 mg, 2.0 mmol, 4.00 equiv) were added sequentially to a solution of S5 (210 mg, 0.5 mmol, 1 equiv) in diglyme (1.25 ml, 0.4M). The reaction mixture was heated to 90° C. After 16 h, brine (20 ml) and ethyl acetate (35 ml) were added. The two layers were separated, and the aqueous layer was extracted with ethyl acetate (3×30 ml). The combined organic layers were washed with brine (2×15 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexanes) to afford S6 (141 mg, 65%) as brown solid with recovered S5 (73 mg, 34%).

tert-Butyl 2-(4-(4-chlorophenyl)-2,3,9-trimethyl-6H-thieno[3,2-f][1,2,4]triazolo[4,3-a][1,4]diazepin-6-yl) acetate [(±)JQ1]

Hydrazine (0.015 ml, 0.45 mmol, 1.25 equiv) was added to a solution of S6 (158 mg, 0.36 mmol, 1 equiv) in THF (2.6 ml, 0.14 M) at 0° C. The reaction mixture was warmed to 23° C., and stirred at 23° C. for 1 h. All solvents were removed under reduced pressure. The resulting hydrazine was used directly without purification. The hydrazine was then dissolved in a 2:3 mixture of trimethyl orthoacetate and toluene (6 ml, 0.06 M). The reaction mixture was heated to 120° C. After 2 h, all the solvents were removed under reduced pressure. The residue was purified by flash column chromatography (Combiflash system, 4 g silica gel, gradient 0 to 100% ethyl acetate-hexanes) to afford JQ1 (140 mg, 85% in 2 steps) as white solid. The reaction conditions further epimerized the stereogenic center, resulting in the racemate, JQ1 (determined with Berger Supercritical Fluid Chromatography (SFC) with an AS-H column).

Scheme S2. Synthesis of enantiomerically enriched (+)-JQ1.

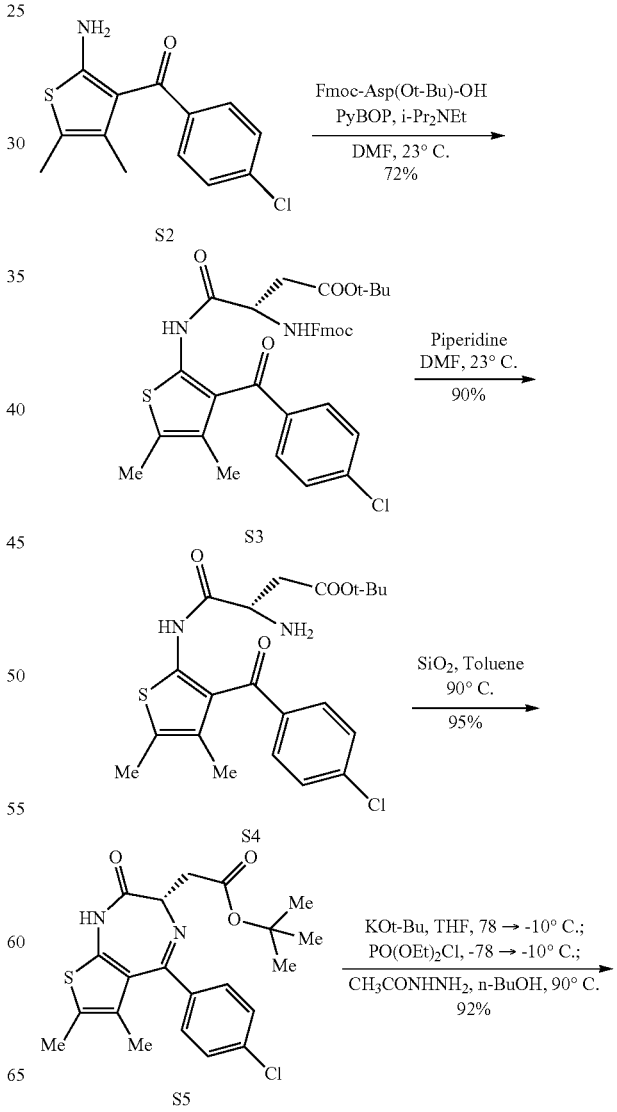

119

-continued

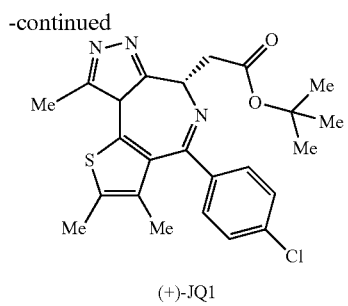

(+)-JQ1

(S)-tert-Butyl-3-({[(9H-fluoren-9-yl)methoxy]carbonyl}amino)-4-{[3-(4-chlorobenzoyl)-4,5-dimethylthiophen-2-yl]amino}-4-oxobutanoate (S3)

(Benzotriazol-1-yloxyl)tripyrrolidinophosphonium (PyBOP) (494 mg, 0.95 mmol, 0.95 equiv), N,N-diisopropylethylamine (0.50 ml, 2.8 mmol, 2.75 equiv) were added sequentially to a solution of 9-fluorenylmethoxycarbonyl-aspartic acid β-tert-butyl ester [Fmoc-Asp(Ot-Bu)-OH] (411 mg, 1.00 mmol, 1.0 equiv) in N,N-dimethylformamide (1.0 ml, 1.0 M). The mixture was then stirred at 23° C. for 5 min. S2 (266 mg, 1.0 mmol, 1 equiv) was then added as solid. The reaction mixture was stirred at 23° C. After 4 h, ethyl acetate (20 ml) and brine (20 ml) were added. The two layers were separated, and the aqueous layer was extracted with ethyl acetate (2×20 ml). The combined organic layers were washed with brine, were dried over with anhydrous sodium sulphate, were filtered, and were concentrated under reduced pressure. The residue was purified by flash column chromatography (Combiflash RF system, 40 gram silica gel, gradient 0 to 100% ethyl acetate-hexanes) to afford S3 (452 mg, 72%) as brown oil.

(S)-tert-butyl 3-amino-4-((3-(4-chlorobenzoyl)-4,5-dimethylthiophen-2-yl)amino)-4-oxobutanoate (S4)

Compound S3 (310 mg, 0.47 mmol, 1 equiv) was dissolved into 20% piperidine in DMF solution (2.2 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexane) to afford free amine S4 (184 mg, 90%) as yellow solid.

The enantiomeric purity was 91% (checked with Berger Supercritical Fluid Chromatography (SFC) using an AS-H column).

120

(S)-tert-Butyl 2-(5-(4-chlorophenyl)-6,7-dimethyl-2-oxo-2,3-dihydro-1H-thieno[2,3-e][1,4]diazepin-3-yl)acetate (S5)

Amino ketone (S4) (184 mg, 0.42 mmol) was dissolved in toluene (10 ml, 0.04 M). Silica gel (300 mg) was added, and the reaction mixture was heated to 90° C. After 3 h, the reaction mixture was cooled to 23° C. The silica gel was filtered, and washed with ethyl acetate. The combined filtrates were concentrated. The residue was purified by flash column chromatography (Combiflash RF system, 12 gram silica gel, gradient 0 to 100% ethyl acetate-hexanes) to afford compound S5 (168 mg, 95%) as white solid. Enantiomeric purity of S5 was 90% (determined with Berger Supercritical Fluid Chromatography (SFC) using an AS-H column).

(S)-tert-Butyl 2-(4-(4-chlorophenyl)-2,3,9-trimethyl-6H-thieno[3,2-f][1,2,4]triazolo[4,3-a][1,4]diazepin-6-yl)acetate [(+)JQ1]

Potassium tert-butoxide (1.0 M solution in THF, 0.3 ml, 0.30 mmol, 1.10 equiv) was added to a solution of S5 (114 mg, 0.27 mmol, 1 equiv) in THF (1.8 ml, 0.15 M) at −78° C. The reaction mixture was warmed to −10° C., and stirred at 23° C. for 30 min. The reaction mixture was cooled to −78° C. Diethyl chlorophosphate (0.047 ml, 0.32 mmol, 1.20 equiv) was added to reaction mixture[22]. The resulting mixture was warmed to −10° C. over 45 min. Acetic hydrazide (30 mg, 0.40 mmol, 1.50 equiv) was added to reaction mixture. The reaction mixture was stirred at 23° C. After 1 h, 1-butanol (2.25 ml) was added to reaction mixture, which was heated to 90° C. After 1 h, all solvents were removed under reduce pressure. The residue was purified with flash column chromatography (Combiflash system, 4 g silica gel, gradient 0 to 100% ethyl acetate-hexanes) to afford (+)-JQ1 (114 mg, 92%) as white solid with 90% enantiomeric purity (determined with Berger Supercritical Fluid Chromatography (SFC) using AS-H column, 85% hexanes-methanol, 210 nm, $t_R$ (R-enantiomer)=1.59 min, $t_R$ (S-enantiomer)=3.67 min). The product was further purified by chiral preparative HPLC (Agilent High Pressure Liquid Chromatography using an OD-H column) to provide the S-enantiomer in greater than 99% ee.

$^1$H NMR (600 MHz, CDCl$_3$, 25° C.) δ 7.39 (d, J=8.4 Hz, 2H), 7.31 (d, J=8.4 Hz, 2H), 4.54 (t, J=6.6 MHz, 1H), 3.54-3.52 (m, 2H), 2.66 (s, 3H), 2.39 (s, 3H), 1.67 (s, 3H), 1.48 (s, 9H).

$^{13}$C NMR (150 MHz, CDCl$_3$, 25° C.) δ 171.0, 163.8, 155.7, 150.0, 136.9, 131.1, 130.9, 130.6, 130.3, 128.9, 81.2, 54.1, 38.1, 28.4, 14.6, 13.5, 12.1.

HRMS(ESI) calc'd for $C_{21}H_{24}ClN_2O_3S$ [M+H]$^+$: 457.1460, found 457.1451 m/z.

TLC (EtOAc), Rf: 0.32 (UV)

$[\alpha]^{22}_D$=+75 (c 0.5, CHCl$_3$)

(−)-JQ1 was synthesized in a similar manner, employing Fmoc-D-Asp(Ot-Bu)-OH as a starting material, and was further purified by chiral preparative HPLC (Agilent High Pressure Liquid Chromatography using an OD-H column) to afford the R-enantiomer in greater than 99% ee. $[\alpha]^{22}_D$=−72 (c 0.5, CHCl$_3$)

Synthesis of Additional Compounds

Additional compounds of the invention were prepared as illustrated in Scheme S3.

Scheme S3. Synthesis of hydrazine derivatives.

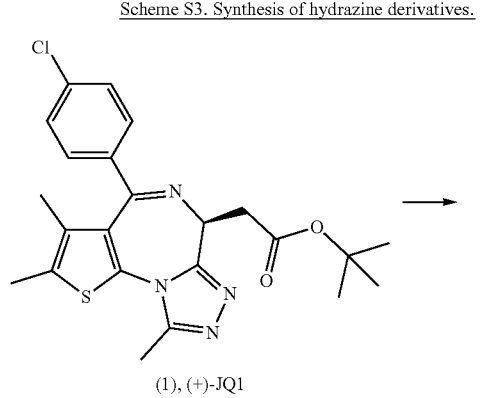

(1), (+)-JQ1

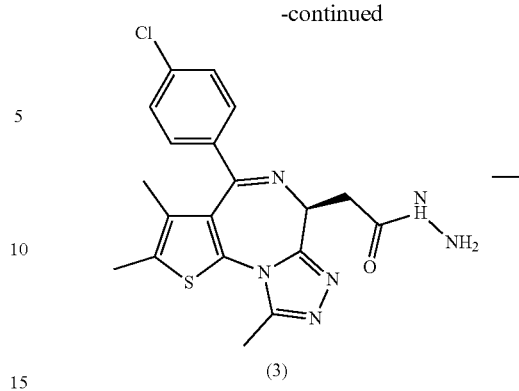

(3)

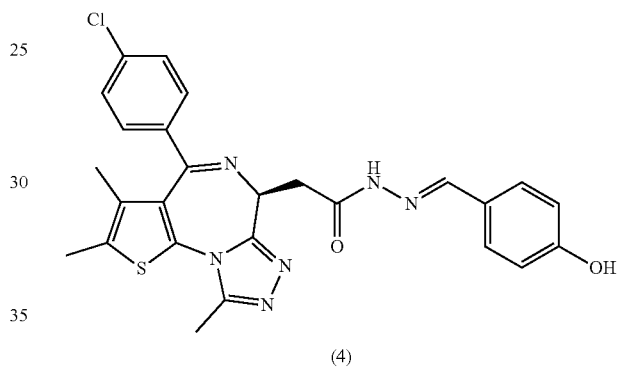

(4)

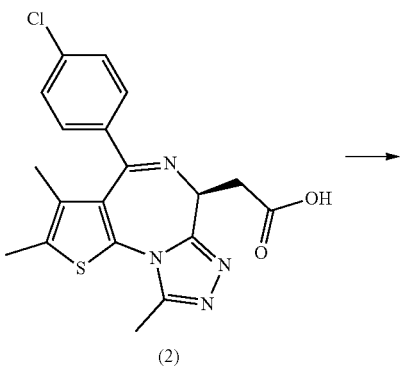

(2)

As shown in Scheme S3, the t-butyl ester of (+)-JQ1 (1) was cleaved to yield the free acid (2), which was coupled with hydrazine to yield the hydrazide (3). Reaction with 4-hydroxybenzaldehyde yielded the hydrazone (4).

Both hydrazide (3) and hydrazone (4) showed activity in at least one biological assay.

A library of compounds was prepared by reaction of the hydrazide (3) with a variety of carbonyl-containing compounds (see Table A, above).

Additional compounds were prepared for use, e.g., as probes for assay development. An exemplary synthesis is shown in Scheme S4, below.

Scheme S4. Synthesis of derivatives useful as probes.

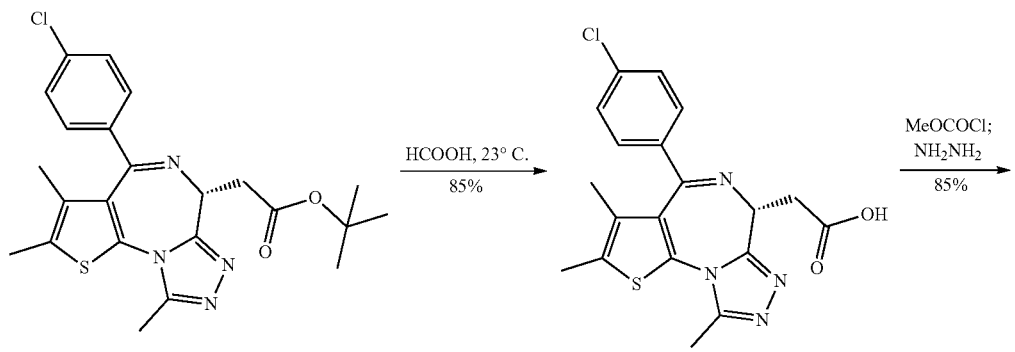

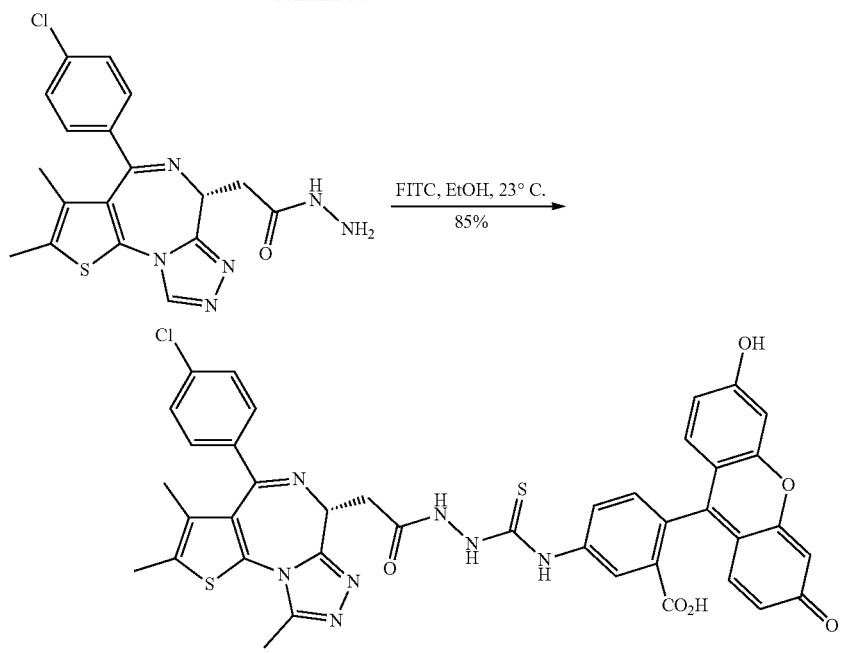
For FITC assay
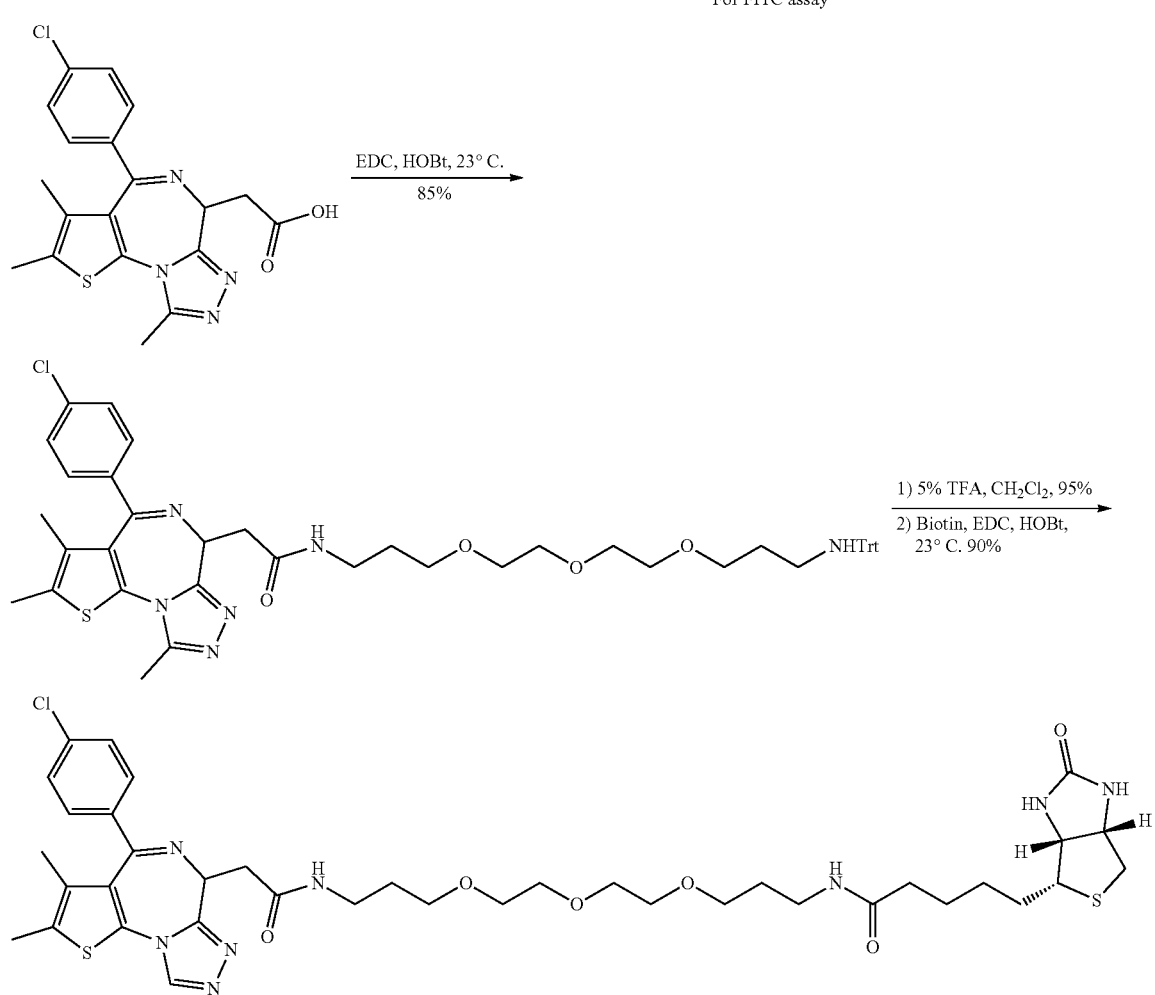
For Alpha assay

Additional compounds were prepared as shown in Table B, below:
| Compound Name | Structure | MS [M + H]+ m/z (Observed) |
|---|---|---|
| (S)-JQ1 | 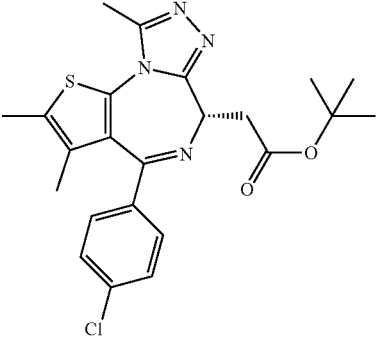 [SMILES: Cc1sc2c(c1C)C(c1ccc(Cl)cc1)=N[C@@H](CC(=O)OC(C)(C)C)c1nnc(C)n1-2] | 457.1 |
| (R)-JQ1 | 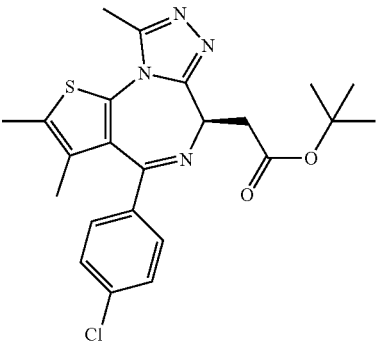 [SMILES: Cc1sc2c(c1C)C(c1ccc(Cl)cc1)=N[C@H](CC(=O)OC(C)(C)C)c1nnc(C)n1-2] | 457.1 |
| JQ3 | 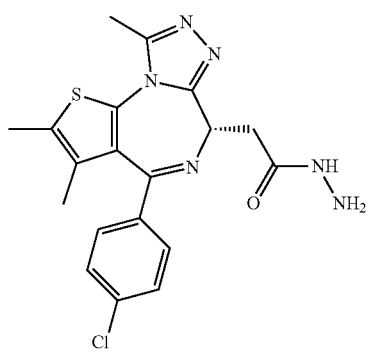 [SMILES: Cc1sc2c(c1C)C(c1ccc(Cl)cc1)=N[C@@H](CC(=O)NN)c1nnc(C)n1-2] | 415.1 |
| JQ4 | 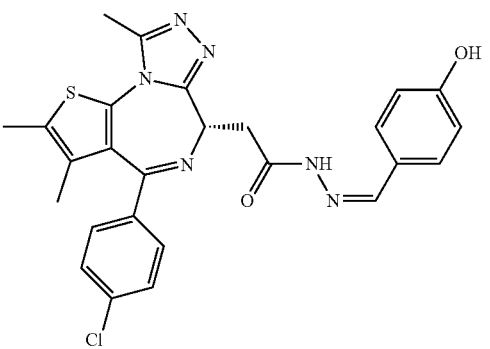 [SMILES: Cc1sc2c(c1C)C(c1ccc(Cl)cc1)=N[C@@H](CC(=O)N/N=C\c1ccc(O)cc1)c1nnc(C)n1-2] | 519.1 |

-continued

| Compound Name | Structure | MS [M + H]+ m/z (Observed) |
|---|---|---|
| JQ6 | 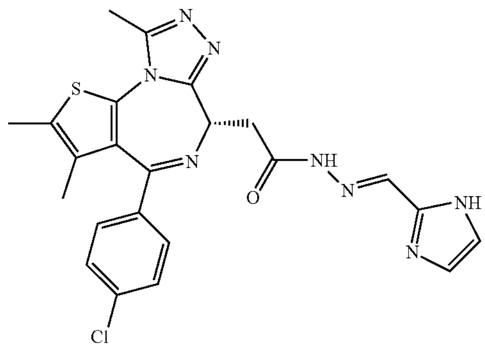 [SMILES: Cc1sc2c(c1C)C(c1ccc(Cl)cc1)=N[C@@H](CC(=O)N/N=C/c1ncc[nH]1)c1nnc(C)n1-2] | 493.1 |
| JQ7 | 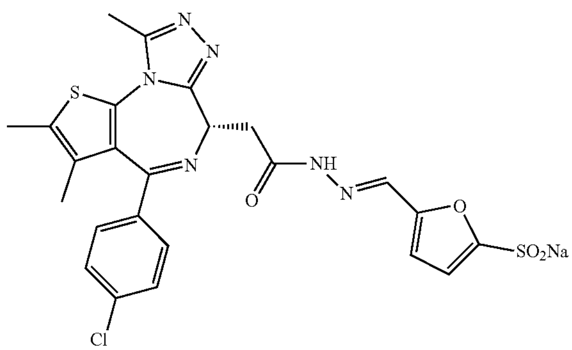 | 579.0 |
| JQ8 | 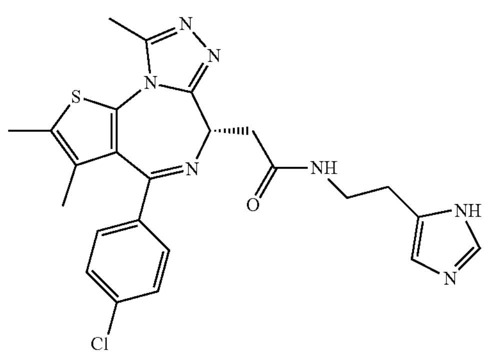 [SMILES: Cc1sc2c(c1C)C(c1ccc(Cl)cc1)=N[C@@H](CC(=O)NCCc1cnc[nH]1)c1nnc(C)n1-2] | 494.1 |
| JQ10 | 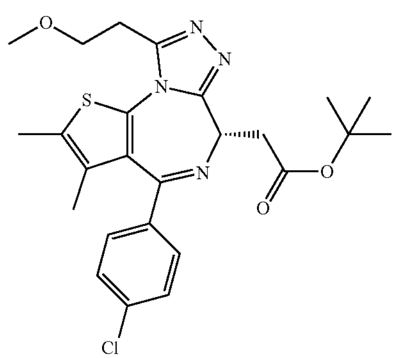 [SMILES: COCCc1nnc2n1-c1sc(C)c(C)c1C(c1ccc(Cl)cc1)=N[C@H]2CC(=O)OC(C)(C)C] | 501.1 |

-continued
| Compound Name | Structure | MS [M + H]+ m/z (Observed) |
|---|---|---|
| JQ11 | 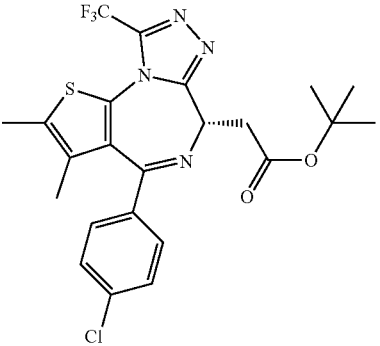 [SMILES: Cc1sc2c(c1C)C(c1ccc(Cl)cc1)=N[C@@H](CC(=O)OC(C)(C)C)c1nnc(C(F)(F)F)n1-2] | 511.1 |
| JQ1-FITC | 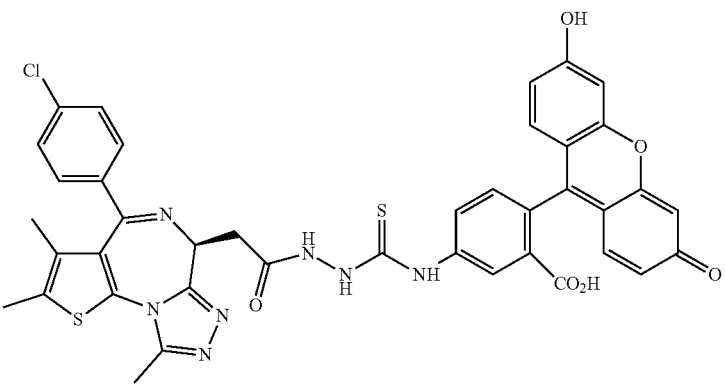 [SMILES: Cc1sc2c(c1C)C(c1ccc(Cl)cc1)=N[C@@H](CC(=O)NNC(=S)Nc1ccc(-c3c4ccc(=O)cc-4oc4cc(O)ccc34)c(C(=O)O)c1)c1nnc(C)n1-2] | 804.1 |
| JQ1-Biotin | 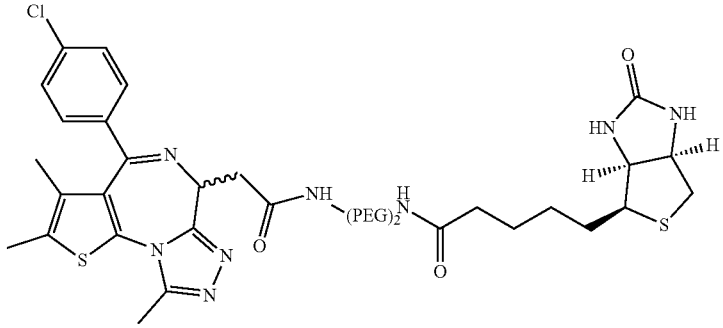 | 829.3 |
| JQ13 | 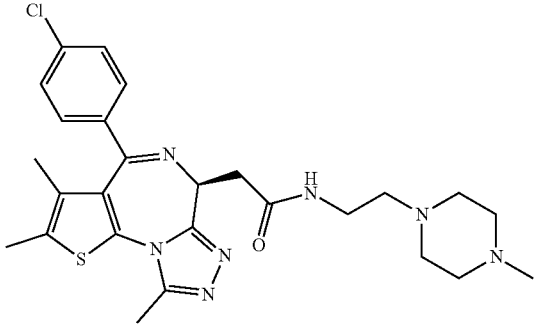 | 526.2 |

-continued
| Compound Name | Structure | MS [M + H]+ m/z (Observed) |
|---|---|---|
| KS1 | 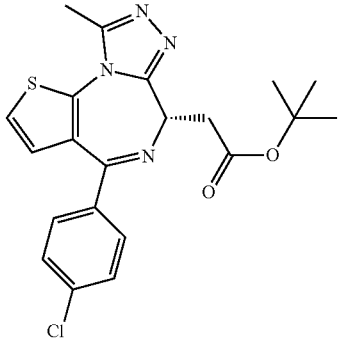 [SMILES: Cc1nnc2n1-c1sccc1C(c1ccc(Cl)cc1)=N[C@H]2CC(=O)OC(C)(C)C] | 429.1 |
| JQ18 | 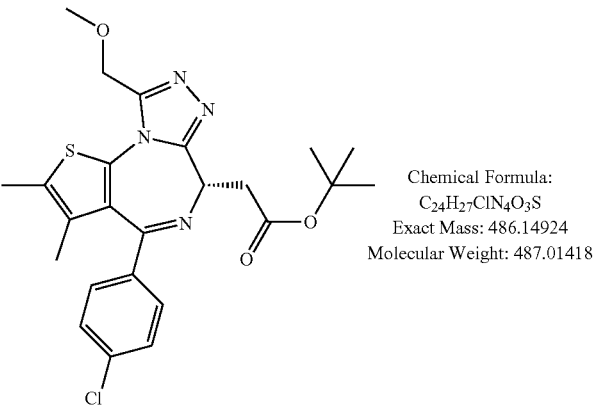 [SMILES: COCc1nnc2n1-c1sc(C)c(C)c1C(c1ccc(Cl)cc1)=N[C@H]2CC(=O)OC(C)(C)C] Chemical Formula: $C_{24}H_{27}ClN_4O_3S$ Exact Mass: 486.14924 Molecular Weight: 487.01418 | 487.1 |
| JQ19 | 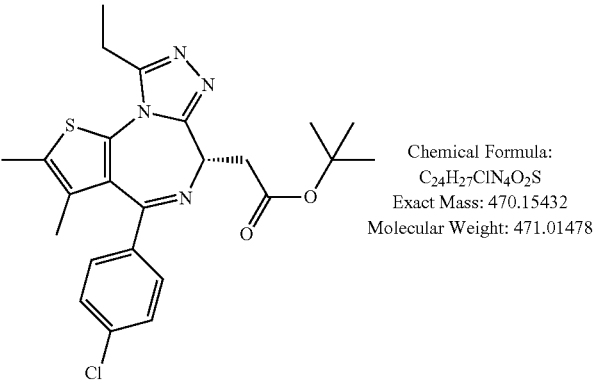 [SMILES: CCc1nnc2n1-c1sc(C)c(C)c1C(c1ccc(Cl)cc1)=N[C@H]2CC(=O)OC(C)(C)C] Chemical Formula: $C_{24}H_{27}ClN_4O_2S$ Exact Mass: 470.15432 Molecular Weight: 471.01478 | 471.1 |
| JQ20 JQI-II-023 | 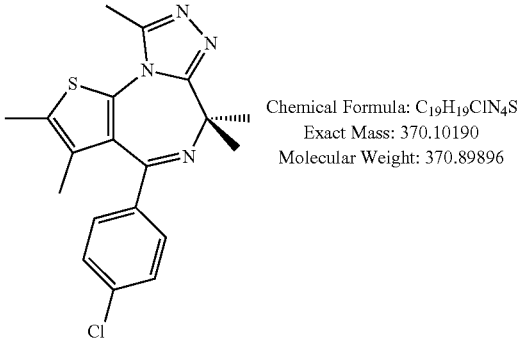 Chemical Formula: $C_{19}H_{19}ClN_4S$ Exact Mass: 370.10190 Molecular Weight: 370.89896 | 370.1 |

-continued

| Compound Name | Structure | MS [M + H]+ m/z (Observed) |
|---|---|---|
| JQ21 | 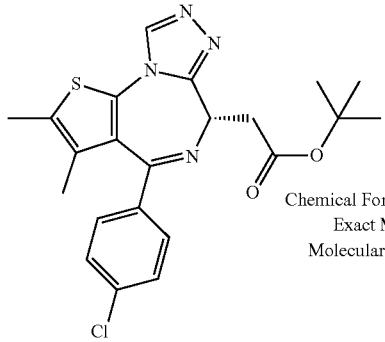 Chemical Formula: C$_{22}$H$_{23}$ClN$_4$O$_2$S<br>Exact Mass: 442.12302<br>Molecular Weight: 442.96162<br>JQI-II-024 | 443.1 |
| JQ24A | 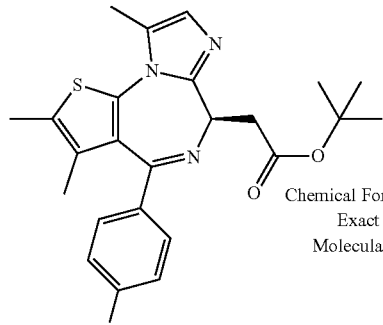 Chemical Formula: C$_{24}$H$_{26}$ClN$_3$O$_2$S<br>Exact Mass: 455.1434<br>Molecular Weight: 456.0001 | 456.1 |
| JQ24B | 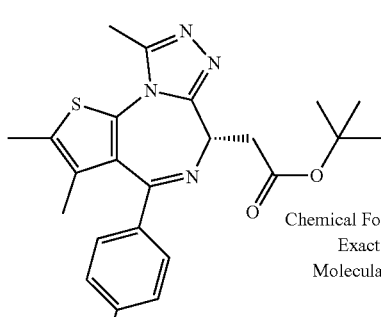 Chemical Formula: C$_{24}$H$_{26}$ClN$_3$O$_2$S<br>Exact Mass: 455.1434<br>Molecular Weight: 456.0001 | 456.1 |
| JQ25 | 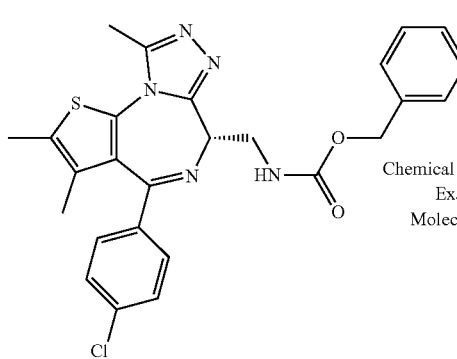 Chemical Formula: C$_{26}$H$_{24}$ClN$_5$O$_2$S<br>Exact Mass: 505.1339<br>Molecular Weight: 506.0191 | 506.1 |

-continued
| Compound Name | Structure | MS [M + H]+ m/z (Observed) |
|---|---|---|
| JQB | 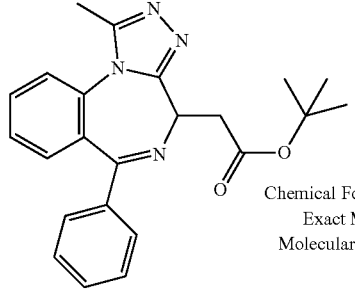 Chemical Formula: C₂₃H₂₄N₄O₂<br>Exact Mass: 388.1899<br>Molecular Weight: 388.4623 | 389.2 |
| JQ30 | 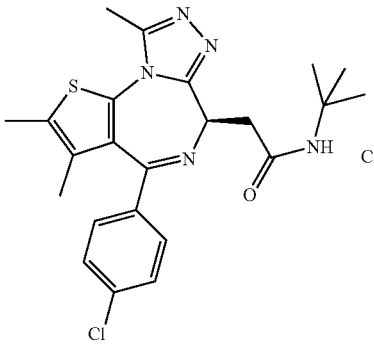 Chemical Formula: C₂₃H₂₆ClN₅OS<br>Exact Mass: 455.1547<br>Molecular Weight: 456.0034 | 456.2 |
| JQ31 | 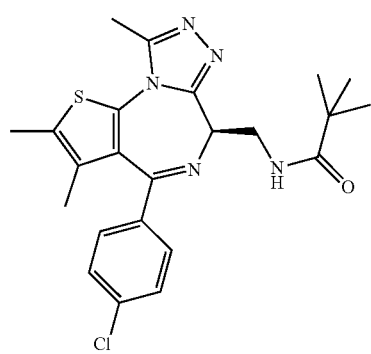 Chemical Formula: C₂₃H₂₆ClN₅OS<br>Exact Mass: 455.1547<br>Molecular Weight: 456.0034 | 456.2 |
| JQ32 | 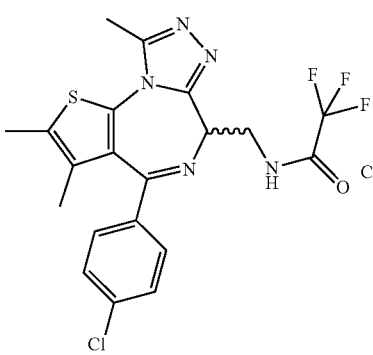 Chemical Formula: C₂₀H₁₇ClF₃N₅OS<br>Exact Mass: 467.0794<br>Molecular Weight: 467.8951 | 468.1 |

-continued
| Compound Name | Structure | MS [M + H]+ m/z (Observed) |
|---|---|---|
| JQ33 | 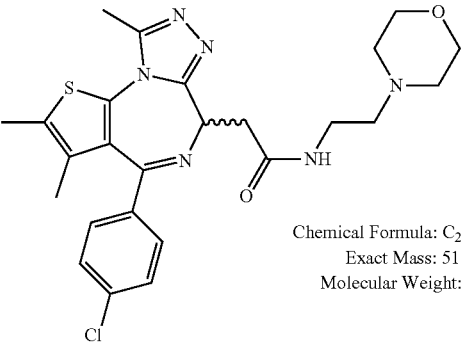<br>Chemical Formula: C25H29ClN6O2S<br>Exact Mass: 512.1761<br>Molecular Weight: 513.0548 | 512.2 |
| JQ34 | 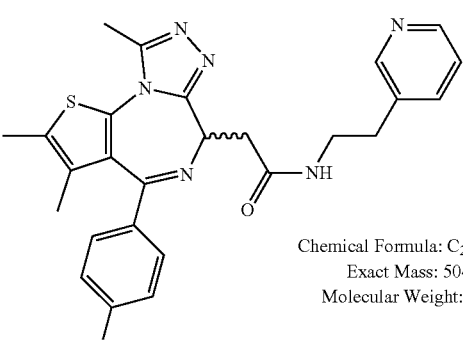<br>Chemical Formula: C26H25ClN6OS<br>Exact Mass: 504.1499<br>Molecular Weight: 505.0343 | 505.1 |
| JQ35 | 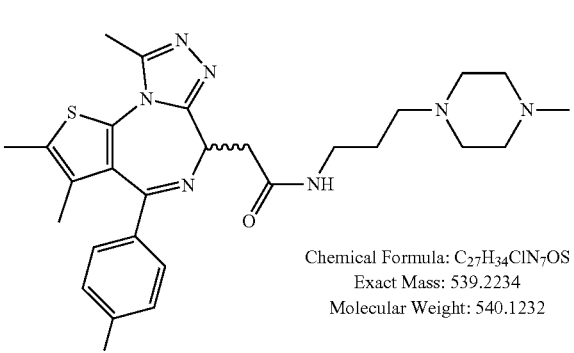<br>Chemical Formula: C27H34ClN7OS<br>Exact Mass: 539.2234<br>Molecular Weight: 540.1232 | 540.2 |
| JQ36 | 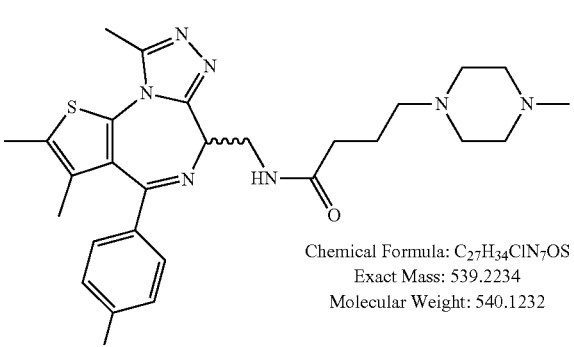<br>Chemical Formula: C27H34ClN7OS<br>Exact Mass: 539.2234<br>Molecular Weight: 540.1232 | 540.2 |

-continued
| Compound Name | Structure | MS [M + H]+ m/z (Observed) |
|---|---|---|
| JQ37 | 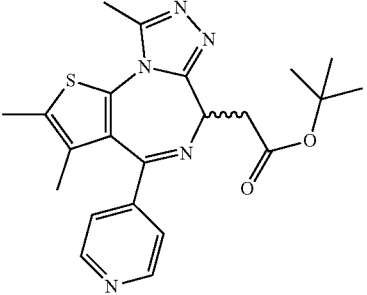 Chemical Formula: C22H25N5O2S<br>Exact Mass: 423.1729<br>Molecular Weight: 423.5312 | 424.2 |
| JQ38 | 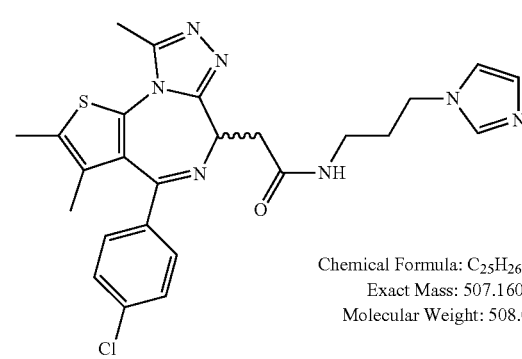 Chemical Formula: C25H26ClN7OS<br>Exact Mass: 507.1608<br>Molecular Weight: 508.0382 | 508.2 |
| JQ39 | 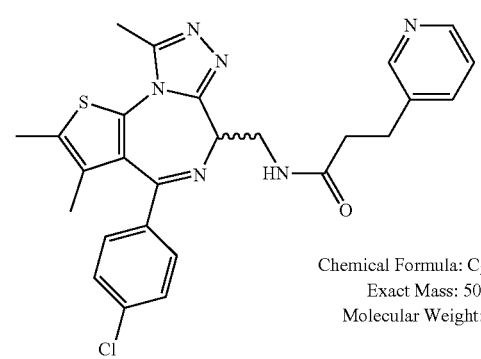 Chemical Formula: C26H25ClN6OS<br>Exact Mass: 504.1499<br>Molecular Weight: 505.0343 | 505.1 |
| JQ40 | 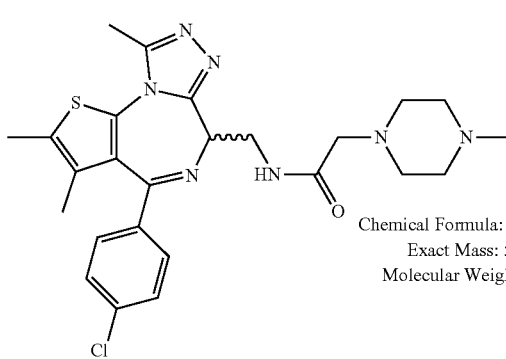 Chemical Formula: C25H30ClN7OS<br>Exact Mass: 511.1921<br>Molecular Weight: 512.0700 | 512.2 |

-continued
| Compound Name | Structure | MS [M + H]+ m/z (Observed) |
|---|---|---|
| JQ41 | 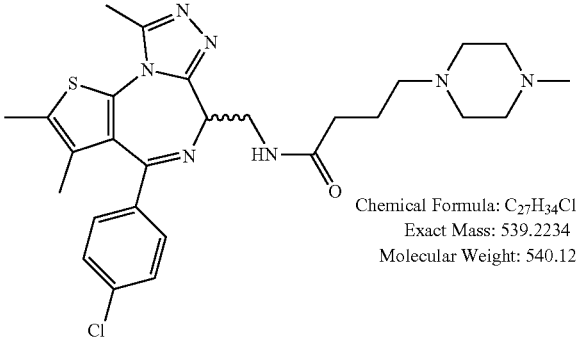 Chemical Formula: C$_{27}$H$_{34}$ClN$_7$OS<br>Exact Mass: 539.2234<br>Molecular Weight: 540.1232 | 540.2 |
| JQ42 | 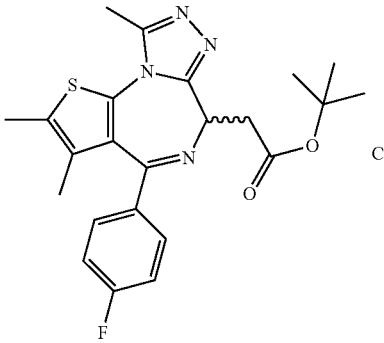 Chemical Formula: C$_{23}$H$_{25}$FN$_4$O$_2$S<br>Exact Mass: 440.1682<br>Molecular Weight: 440.5336 | 441.2 |
| JQ43 | 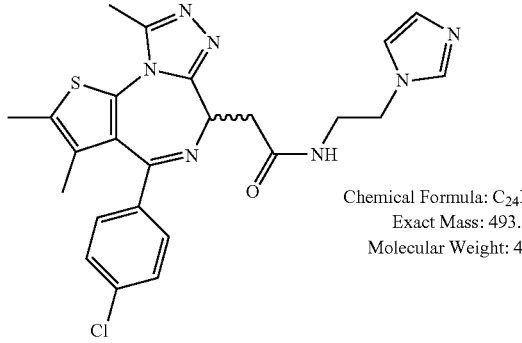 Chemical Formula: C$_{24}$H$_{24}$ClN$_7$OS<br>Exact Mass: 493.1452<br>Molecular Weight: 494.0117 | 494.1 |
| JQ44 | 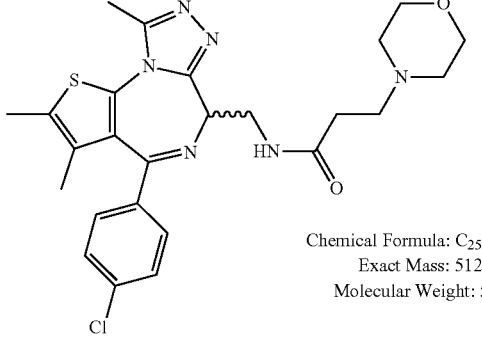 Chemical Formula: C$_{25}$H$_{29}$ClN$_6$O$_2$S<br>Exact Mass: 512.1761<br>Molecular Weight: 513.0548 | 513.2 |

-continued
| Compound Name | Structure | MS [M + H]+ m/z (Observed) |
|---|---|---|
| JQ45 | 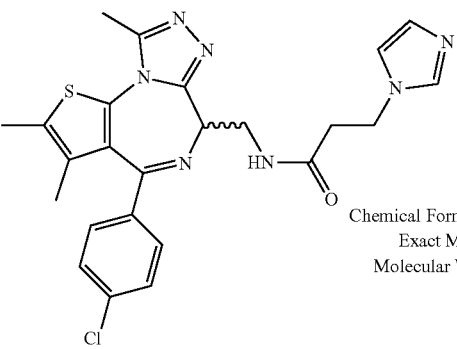 Chemical Formula: C$_{24}$H$_{24}$ClN$_7$OS<br>Exact Mass: 493.1452<br>Molecular Weight: 494.0117 | 494.1 |
| JQ46 | 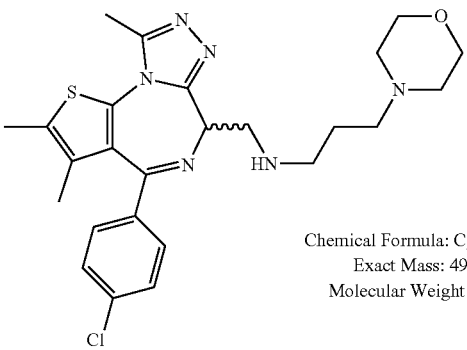 Chemical Formula: C$_{25}$H$_{31}$ClN$_6$OS<br>Exact Mass: 498.1969<br>Molecular Weight: 499.0712 | 499.2 |
| JQ47 | 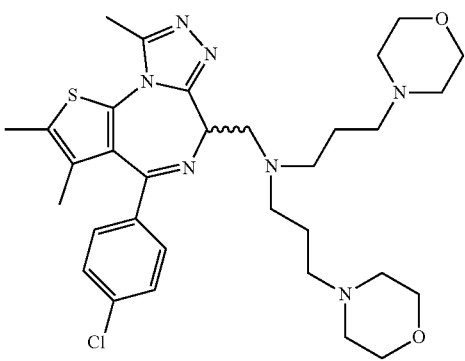 Chemical Formula: C$_{32}$H$_{44}$ClN$_7$O$_2$S<br>Exact Mass: 625.2966<br>Molecular Weight: 626.2555 | 626.3 |
| JQ48 | 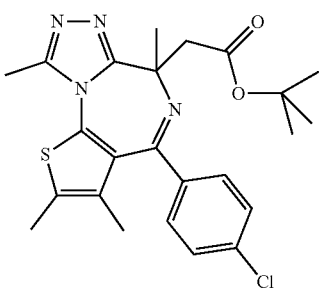 Exact Mass: 470.1543<br>Molecular Weight: 471.0148 | 471.2 |

-continued
| Compound Name | Structure | MS [M + H]+ m/z (Observed) |
|---|---|---|
| JQ49 | 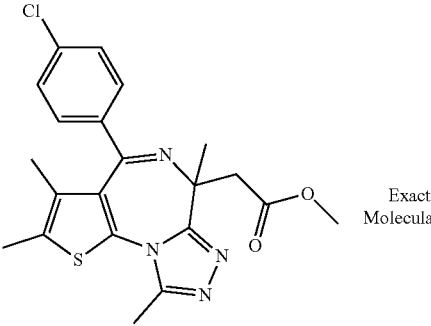<br>Exact Mass: 428.1074<br>Molecular Weight: 428.9350 | 429.1 |
| JQ50 | 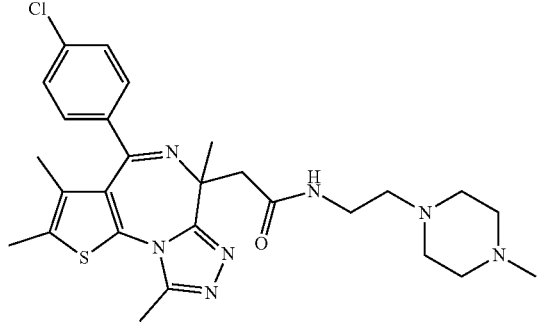<br>Exact Mass: 539.2234<br>Molecular Weight: 540.1232 | 540.2 |
| JQ51 | 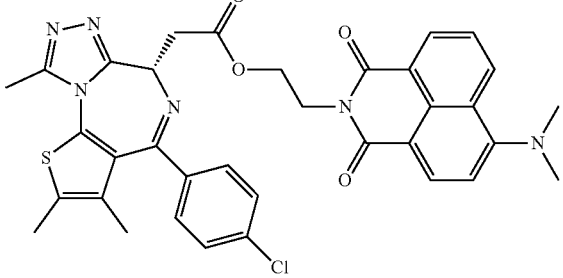<br>JQI-II-114<br>Exact Mass: 666.1816<br>Molecular Weight: 667.1764 | 667.2 |
| JQ52 | 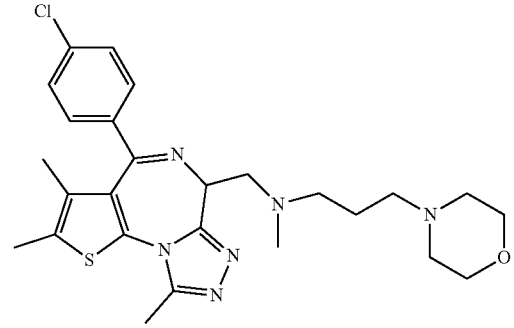<br>Exact Mass: 512.2125<br>Molecular Weight: 513.0978 | 513.2 |

| Compound Name | Structure | MS [M + H]+ m/z (Observed) |
|---|---|---|
| JQ53 | 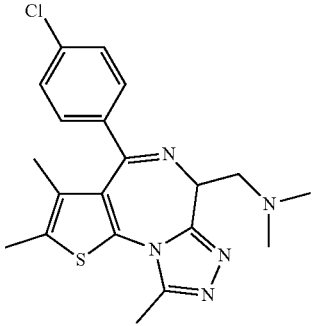 Exact Mass: 399.1284<br>Molecular Weight: 399.9402 | 400.1 |

Spectral data for each compound were consistent with the assigned structure.

II. Biological Activity

Example 1: JQ1

FIG. 1 shows JQ1 enantiomers.

Example 2: JQ1 Displaces BRD4 from Nuclear Chromatin in Cells

Figure 2A:
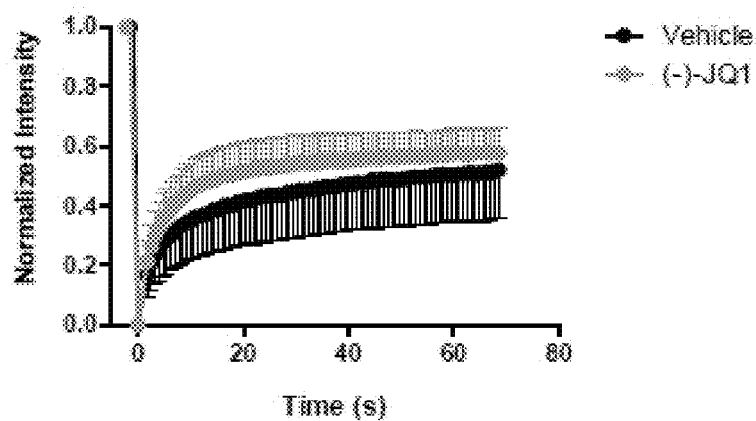
FIGS. 2A, 2B, and 2C are graphs showing that that the (−)-JQ1 enantiomer does not bind competitively to BRD4-NUT in cells.
Figure 2B:
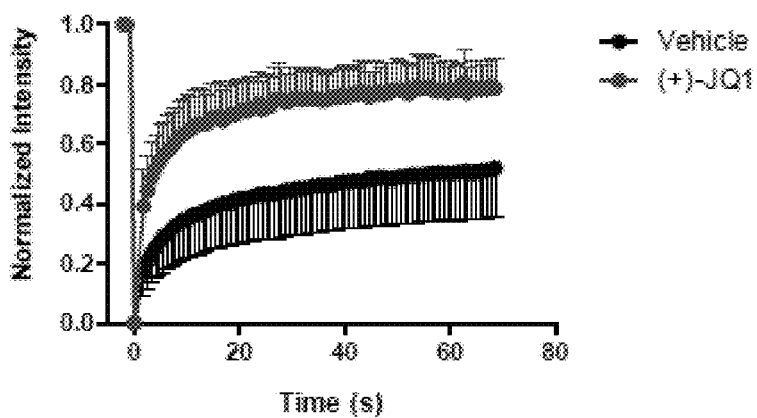
Figure 2C:
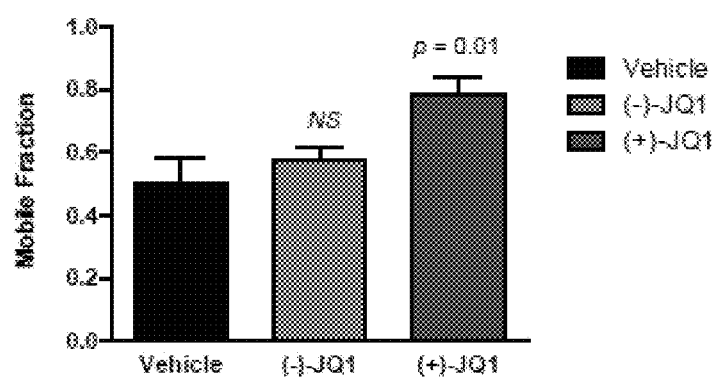
Figure 3A:
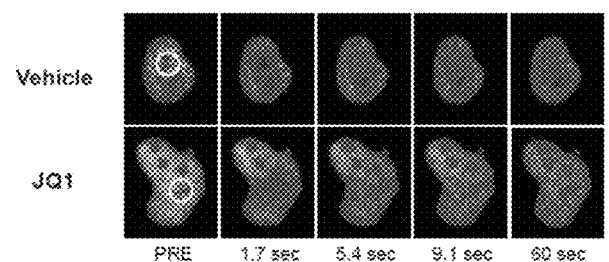
FIGS. 3A-3J show that JQ1 binds BRD4 competitively with chromatin and differentiates human NUT midline carcinoma cells.
Figure 3B:
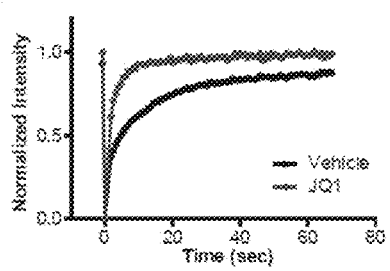

To establish whether JQ1 binds bromodomains competitively with chromatin in a cellular environment, fluorescence recovery after photobleaching (FRAP) experiments were performed on BRD4. Prior research has demonstrated the utility of FRAP in assessing the pace of lateral redistribution of bromodomain-containing fluorescent chimera following selective photobleaching of discrete regions of nuclear chromatin[27]. Human osteosarcoma cells (U2OS) transfected with a GFP-BRD4 exhibit a time-dependent recovery of fluoresce intensity (FIGS. 2A and 2B). In the presence of JQ1 (500 nM), observed recovery is immediate consistent with displaced nuclear BRD4 (FIGS. 3A and 3B). Cellular FRAP studies confirmed that effects on the mobile fraction of BRD4 are limited to the biochemically active (+)-JQ1 stereoisomer (FIGS. 2A-2C).

Figure 3C:
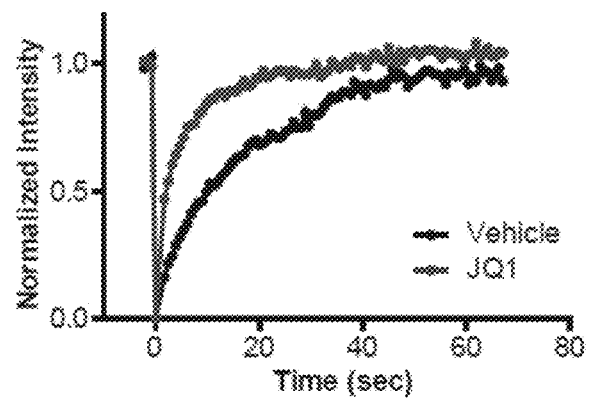
Figure 3D:
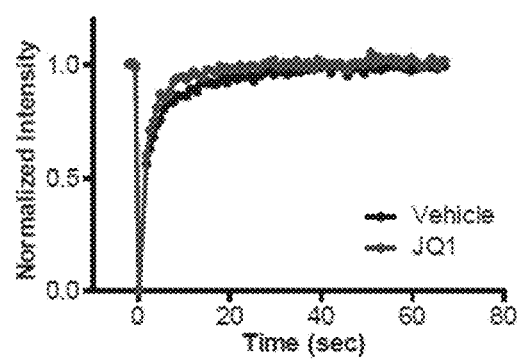
Figure 3E:
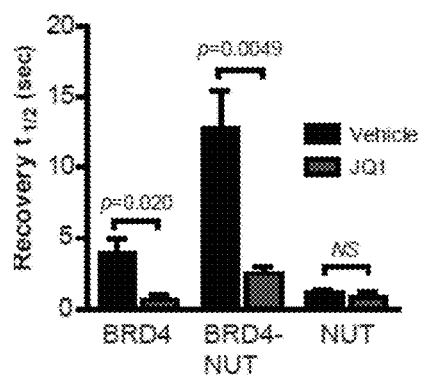

Having demonstrated potent, selective binding to BRD4 in homogeneous and cell-based assays, the effect of JQ1 on disease-relevant, BRD4-dependent cellular phenotypes was assessed. The pathogenic BRD4-NUT fusion protein arising from t(15; 19) translocation in NMC binds avidly to discrete foci of acetylated chromatin, conferring a proliferative advantage and differentiation block. Using FRAP, the ability of JQ1 to target directly the BRD4-NUT oncoprotein was assessed. Compared to a vehicle control, JQ1 (500 nM) markedly accelerated time-to-recovery of fluorescence intensity in photobleached regions of cells transfected with GFP-BRD4-NUT (FIGS. 3C and 3E). Importantly, no effect was observed on redistribution of GFP-NUT (FIGS. 3D and 3E). In summary, these data are consistent with competitive binding of JQ1 to BRD4 in cultured cells.

Figure 3F:
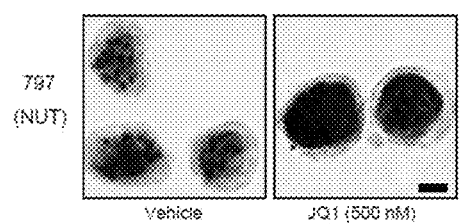
Figure 3G:
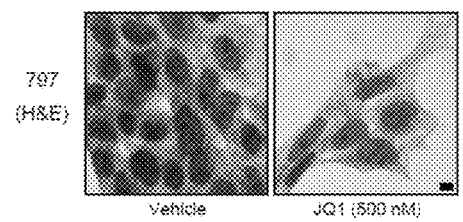

Example 5: JQ1 Induces Squamous Differentiation and Growth Arrest in BRD4-Dependent Carcinoma Direct inhibition of gene products expressed from recurrent, oncogenic translocations is a validated therapeutic approach in cancer[28,29]. The phenotypic consequences of chemical inhibition of BET-family bromodomains on the BRD4-dependent NUT midline carcinoma was explored. BRD4-NUT chromatin localization is mechanistically linked to the preserved tandem bromodomains of BRD4 in the fusion protein[17]. A characteristic feature of NMC is the appearance of discrete nuclear speckles of the BRD4-NUT oncoprotein by NUT-directed immunohistochemistry (IHC)[30]. Treatment of the patient-derived 797 NMC cell line for 48 hours with JQ1 (500 nM) effaced nuclear foci, producing diffuse nuclear NUT staining by IHC (FIG. 3F).

Figure 3H:
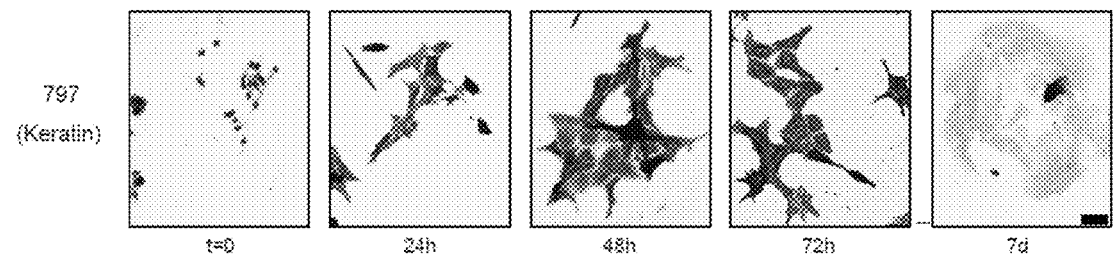
Figure 3I:
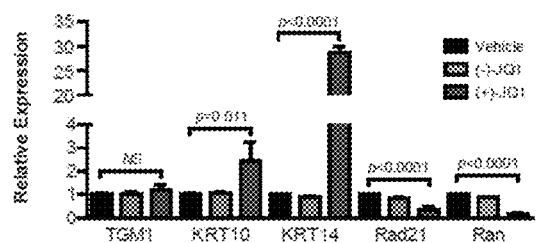
Figure 3J:
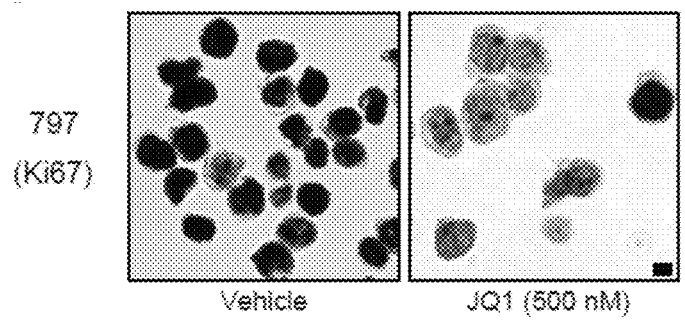
Figure 4A:
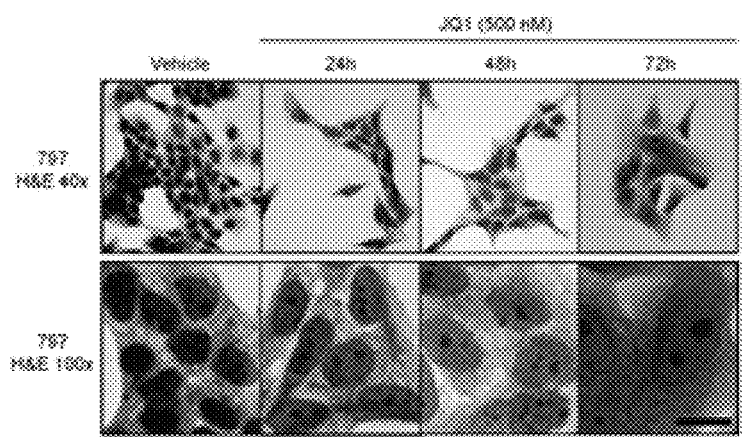
FIGS. 4A, 4B, and 4C are micrographs showing that JQ1 selectively induces squamous differentiation in NUT midline carcinoma.
Figure 4B:
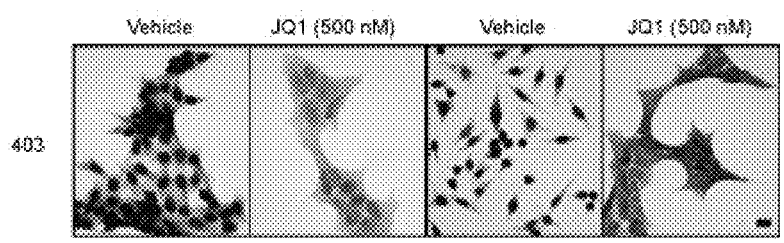
Figure 4C:
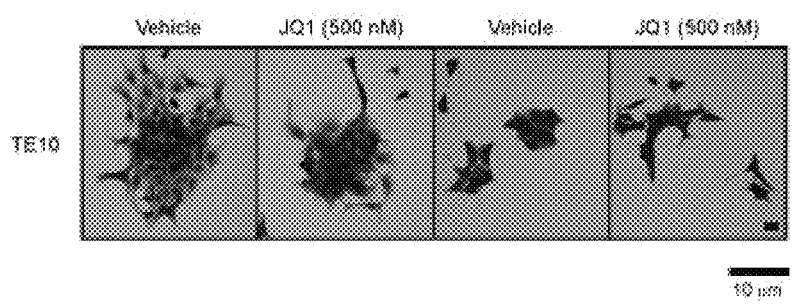

A striking differentiation phenotype is observed with knock-down of BRD4-NUT in NMC cell lines[17]. JQ1 produced an equivalent, dose- and time-dependent differentiation phenotype, characterized by cell spreading and flattening, open chromatin and spindle morphology in NMC 797 and Per403 cells (FIG. 3G and FIGS. 4A, 4B, and 4C). Differentiation was prompt (<24 hours) and characterized by markedly augmented expression of cytokeratin, a hallmark of squamous differentiation (FIG. 3H). After seven days in culture with sub-micromolar exposures to JQ1, terminal differentiation was observed. Importantly, non-BRD4-dependent squamous carcinoma cell lines (TE10 and TT) fail to exhibit differentiation effects of JQ1 (FIGS. 4A, 4B, and 4C). In BRD4-dependent NMC cells, differentiation is expectedly accompanied by growth arrest, evidenced by reduced Ki67 staining (FIGS. 3I-3J and other figures described herein). Further supporting an on-target mechanism of action, differentiation and growth arrest phenotypes are prompted only by (+)-JQ1, whereas (−)-JQ1 shows no observable effect (FIGS. 4E-4I)

Figure 4D:
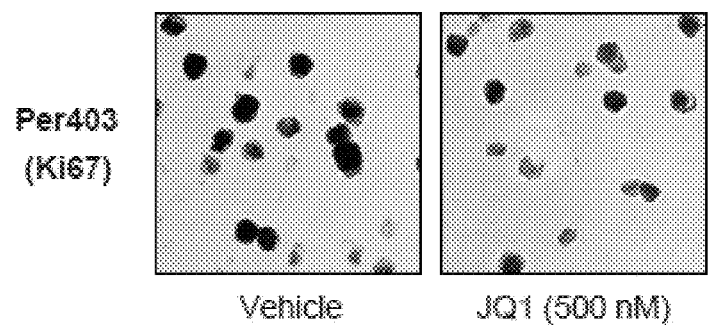
FIGS. 4D and 4E show that JQ1 impairs NMC cellular proliferation.
Figure 4E:
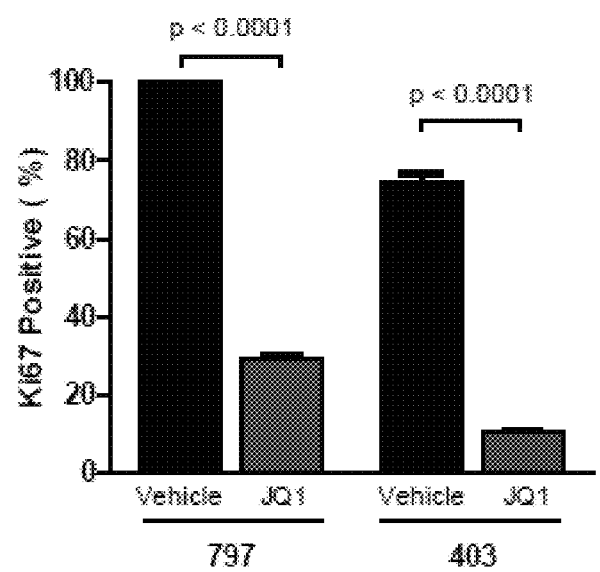
Figure 4F:
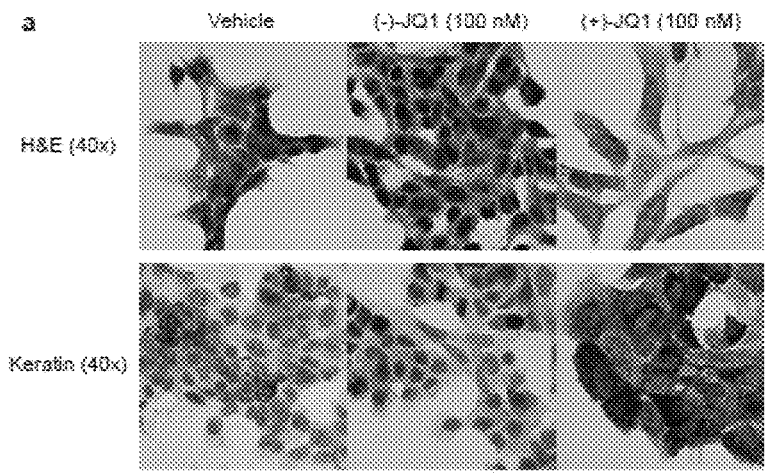
FIGS. 4F-4I show that the induction of squamous differentiation in NUT midline carcinoma cells by JQ1 is stereo-specific and time-dependent.
Figure 4G:
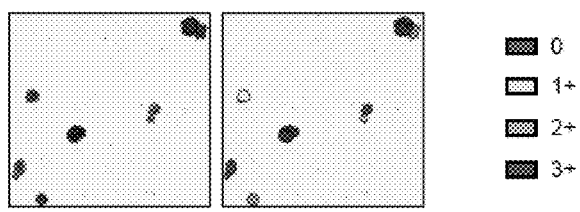
Figure 4H:
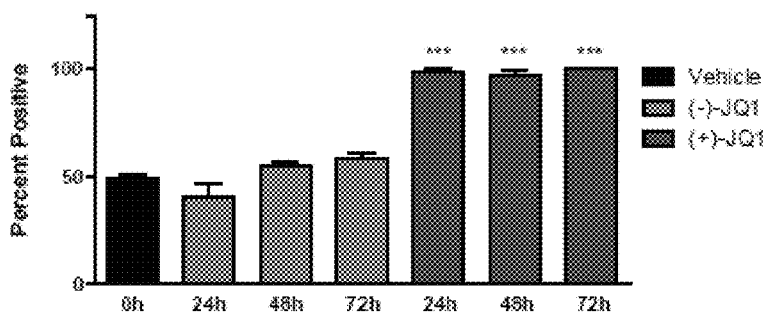
Figure 4I:
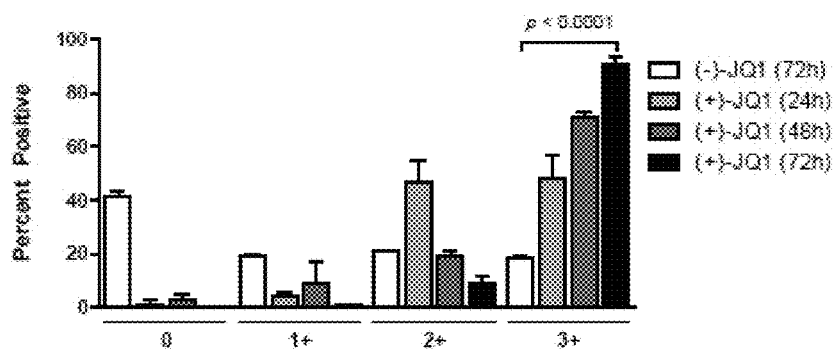
Figure 4J:
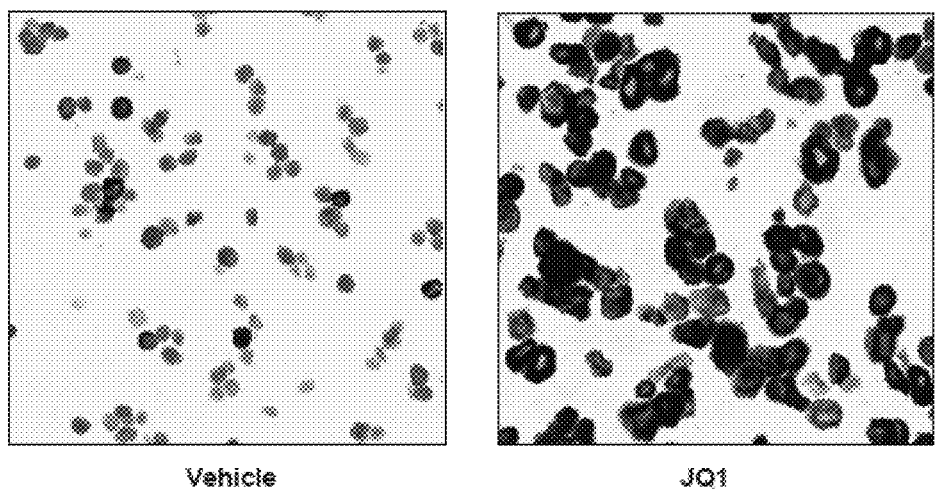
Figure 4K:
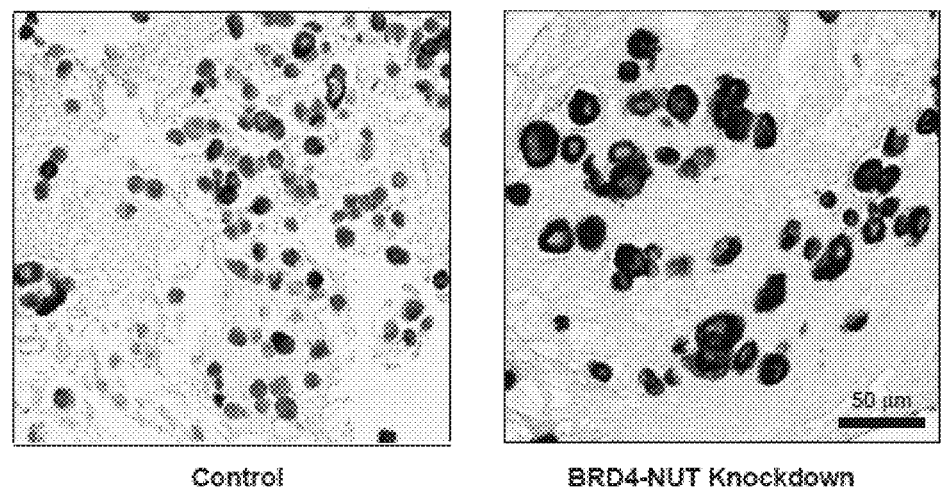

Notably, JQ1 treatment phenocopies the morphologic changes and increased keratin expression observed with BRD4-NUT silencing by RNA interference (FIGS. 4J-4K). Corroborating these morphologic and IHC studies, expression analysis of three canonical squamous tissue genes by RT-PCR identified marked (30-fold) induction of Keratin-14 by (+)-JQ1 in NMC 797 cells (FIG. 3I). The modest induction of Keratin-10 and absent effect on epidermal transglutaminase (TGM1) are consistent with progressive differentiation toward thoracic squamous epithelium, consistent with the mediastinal primary tumor from which NMC 797 cells derive[28]. Induction of differentiation with strong (3+) keratin staining by IHC is progressive over 72 h, as determined by quantitative IHC analysis (FIG. 4I). Supporting an on-target mechanism-of-action, the differentiation phenotype is prompted only by (+)-JQ1 whereas (−)-JQ1 shows no observable effect. Importantly, a non-BRD4-dependent squamous carcinoma cell line (TE10) fails to exhibit differentiation effects from JQ1 treatment (FIG. 4C). In BRD4-dependent NMC cells, differentiation is expectedly accompanied by growth arrest, evidenced by reduced Ki67 staining (FIGS. 4D and 4E).

Figure 5A:
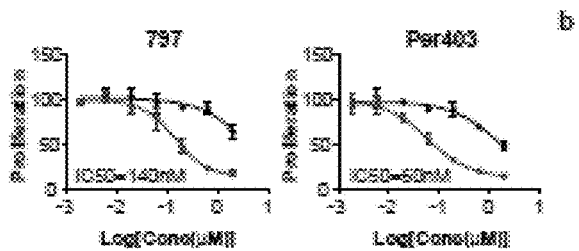
FIGS. 5A-5K show that JQ1 treatment inhibits proliferation, prompting differentiation and cell death in vitro and in vivo.
Figure 5B:
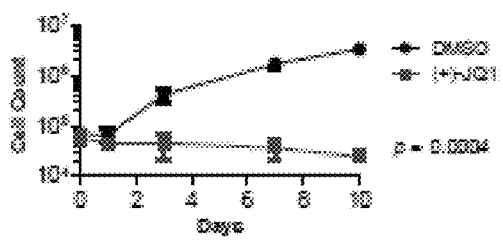
Figure 7A:
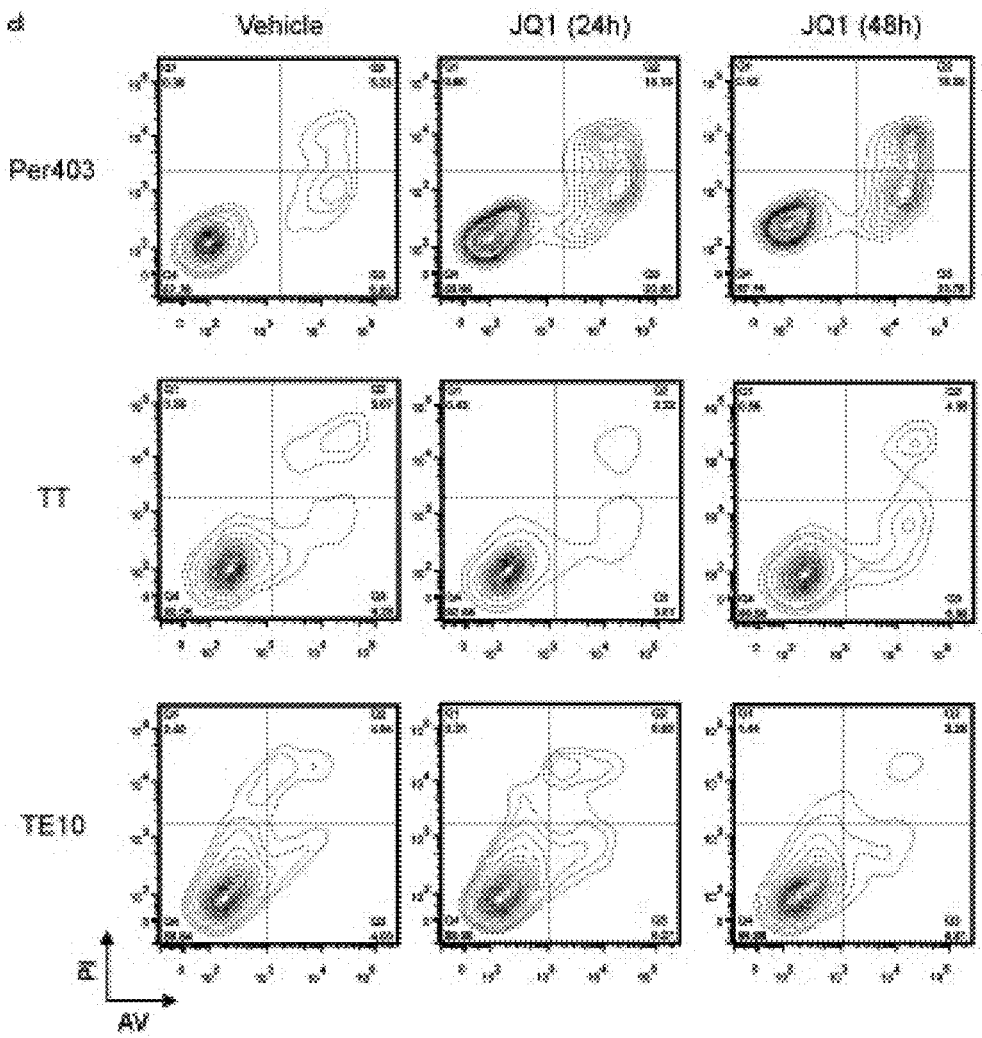
FIGS. 7A and 7B show that JQ1 selectively induces apoptosis in NMC among human squamous carcinoma cell lines.
Figure 7B:
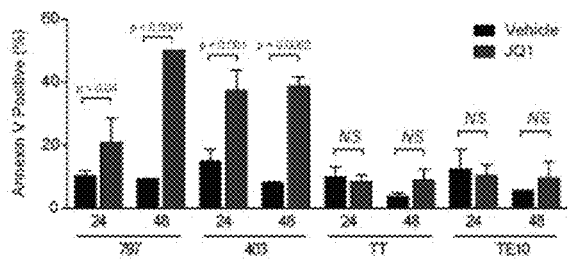

Antiproliferative activity of the JQ1 enantiomers was next assessed in BRD4-dependent (797 and Per403) and BRD4-independent (TE10 and TT) human squamous carcinoma cell lines. As shown in FIG. 5A and FIGS. 4K and 4L, (+)-JQ1 uniquely exhibited a dose-dependent inhibition of cell growth only in BRD4-dependent cell lines (797 $IC_{50}$=140 nM; Per403 $IC_{50}$=60 nM). The potent anti-proliferative effect and irreversible differentiation observed by IHC suggested induction of cell death. Thus, early and late apoptosis was assessed with annexin-V and propidium iodide staining by flow cytometry. As expected, JQ1 induced immediate and progressive apoptosis in BRD4-dependent human carcinoma cells but at the concentration used significant levels of apoptotic cells in cell lines that do not carry the BRD-NUT fusion were not detected (FIG. 5B and FIG. 7).

Figure 5C:
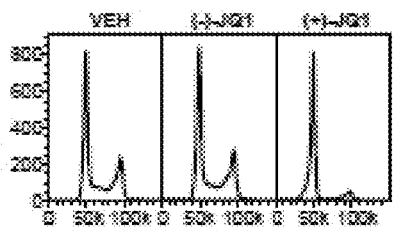
Figure 5D:
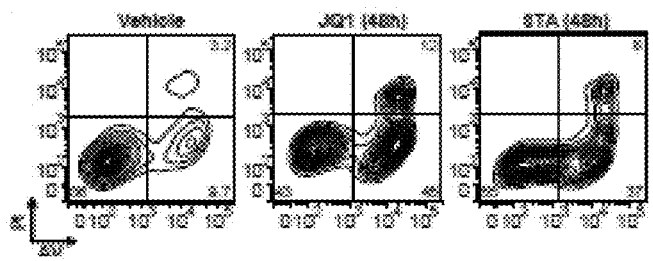
Figure 5E:
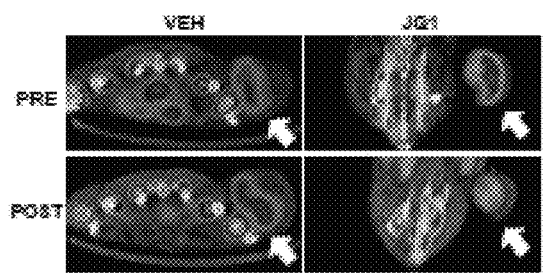
Figure 5F:
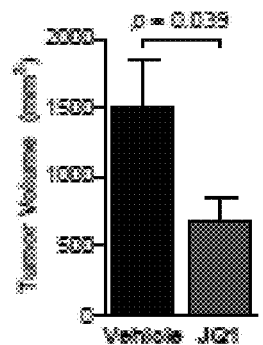
Figure 5G:
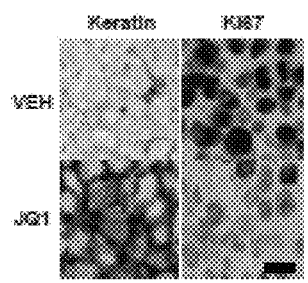

Example 6: In Vivo Efficacy and Pharmacodynamic Effect of JQ1 in a Murine Model of NMC To establish whether JQ1 could attenuate the growth of BRD4-dependent carcinoma as a single agent in vivo, a mouse xenograft model of NMC was developed in mice using the NMC 797 cell line. Short-term treatment studies were performed with PET imaging as a primary endpoint to explore whether anti-tumor activity of JQ1 could be demonstrated and later followed by non-invasive imaging. Matched cohorts of mice with established and comparable burdens of measurable disease were randomized to treatment with JQ1 (50 mg $kg^{-1}$) or vehicle, administered by daily intraperitoneal injection. Prior to randomization and after four days of therapy, mice were evaluated by PET imaging. A marked response on FDG uptake was observed with JQ1 treatment, whereas vehicle-treated animals demonstrated evident, progressive disease (FIG. 5E).

Figure 5H:
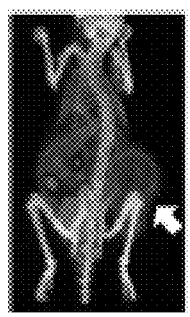
Figure 5I:
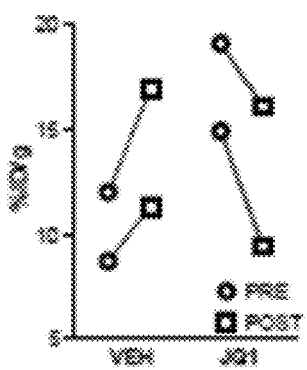
Figure 5J:
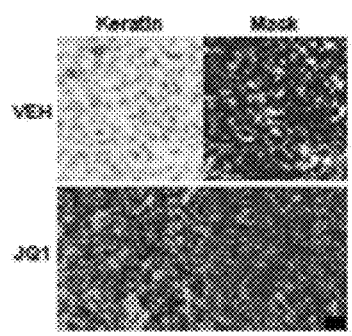
Figure 5K:
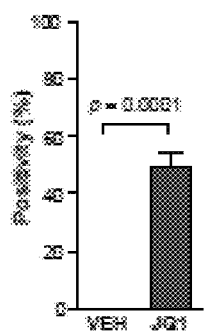
Figure 5L:
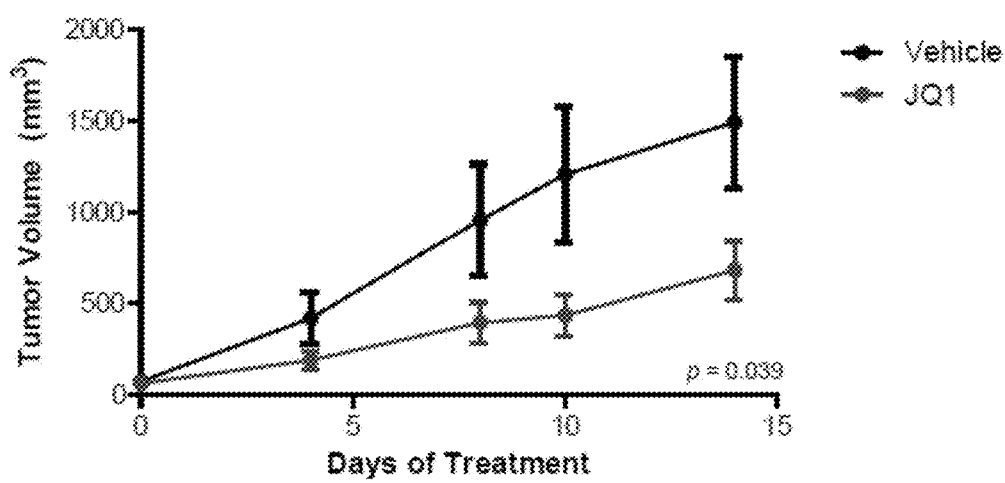
FIGS. 5L and 5M are graphs showing that mice bearing NMC 797 xenografts tolerate JQ1 therapy, which elicits and anti-tumor effect.
Figure 5M:
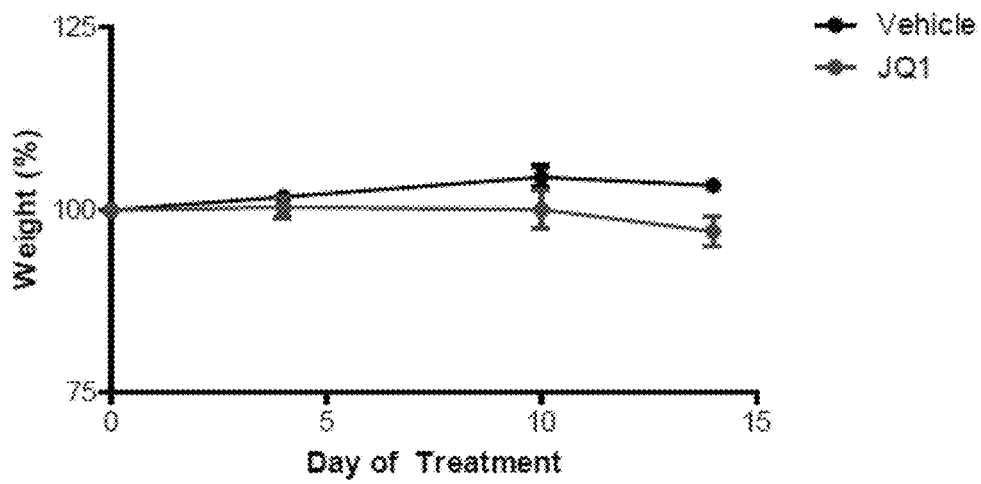

In parallel, matched cohorts of NMC 797 tumor-bearing mice were studied for effects of JQ1 on tumor volume by caliper measurement and pharmacodynamic effect by quantitative IHC. The aggressive growth of NMC 797 xenografts prompted termination of the study at day fourteen of treatment, by which point all vehicle-treated animals had approached institutional tumor size limits. Animals receiving JQ1 exhibited a statistically-significant reduction in tumor growth (FIG. 5C, p=0.039; two-tailed t-test). To capture comparative mechanistic and pharmacodynamic data, all animals were sacrificed and tumors were explanted for histopathologic analysis. Notably, JQ1 was well tolerated at this dose and schedule without adverse signs of toxicity or evident weight loss (FIGS. 5D and 5L).

Figure 6A:
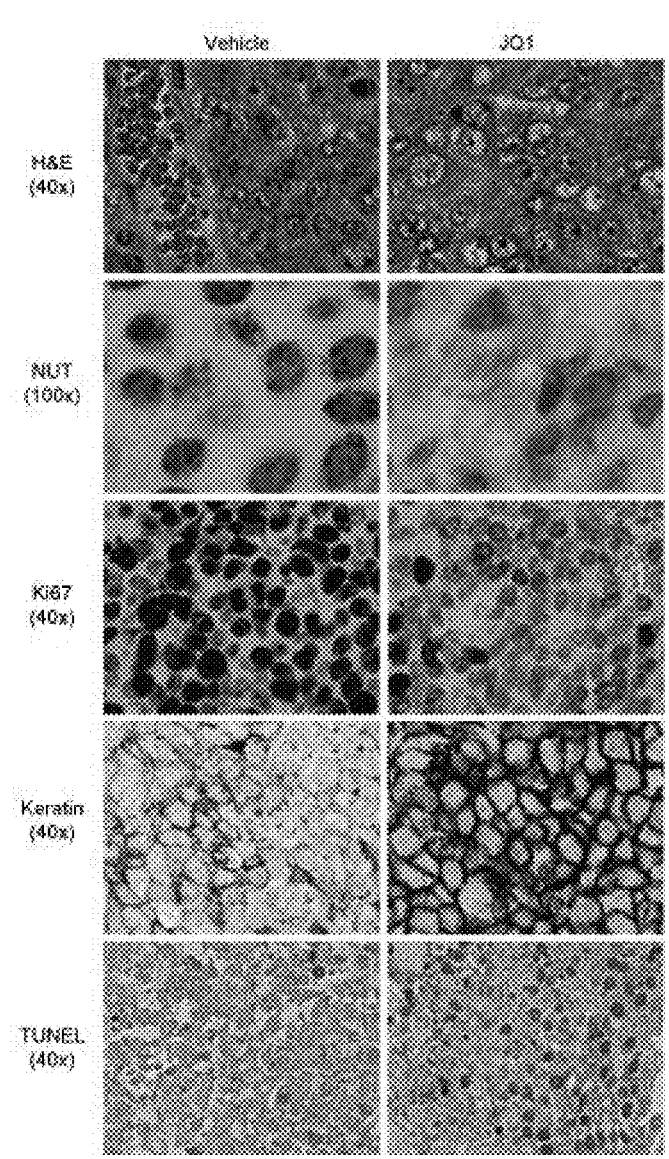
FIGS. 6A and 6B-6F provide micrographs showing that JQ1 prompts squamous differentiation, growth arrest and apoptosis in vivo, as determined by IHC. Histopathological analysis of NMC tumors excised from animals treated with JQ1 (right panel) reveals squamous differentiation (H&E, 40×), effacement of nuclear NUT foci (NUT, 100×), impaired proliferation (Ki67, 40×), induction of keratin expression (AE1/AE3, 40×) and an apoptotic response (TUNEL, 40×), all as compared to vehicle-treated animals (left panel).
Figure 6B:
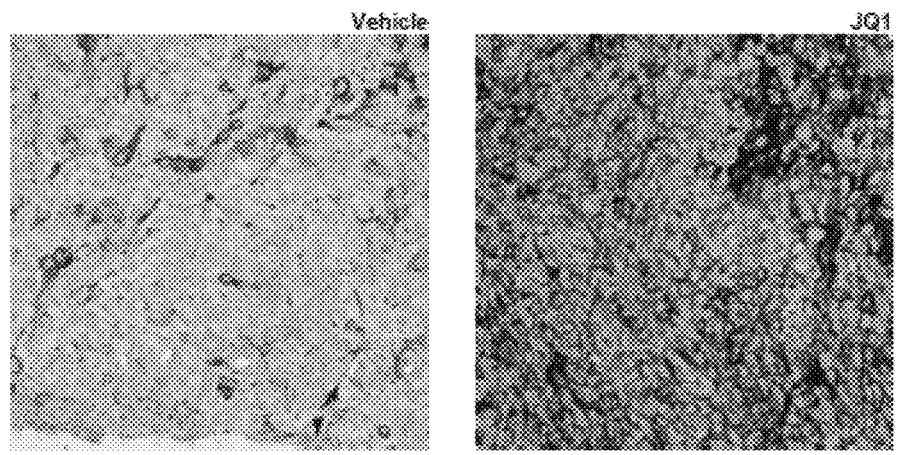
Figure 6C:
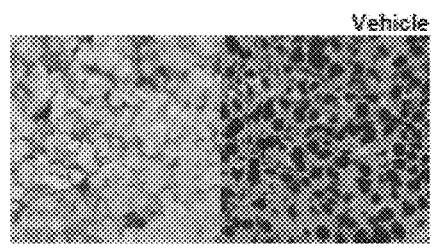
Figure 6D:
Figure 6E:
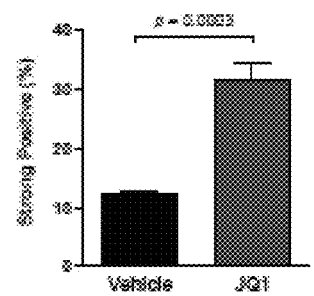
Figure 6F:
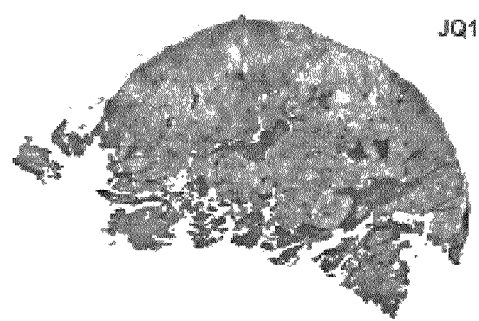

To confirm that the anti-neoplastic effect observed with JQ1 treatment was associated with target engagement, sectioned tumor tissue was examined for the BRD4-NUT oncoprotein. As presented in FIG. 5E and FIG. 6A, JQ1 treatment resulted in effacement of NUT nuclear speckles, consistent with competitive binding to nuclear chromatin. Cell spreading and increased keratin expression confirmed pharmacodynamic squamous differentiation. Decreased nuclear staining for Ki67 and increased TUNEL staining in treated animals confirmed an ongoing anti-proliferative, apoptotic effect. Together, these data provide a mechanistic link between BRD4 inhibition and a therapeutic response to JQ1 in vivo.

In an effort to report the pharmacodynamic (PD) biomarker of tumor keratin expression in an unbiased manner, protocols were established for quantitative IHC image acquisition and analysis. Paired samples from treated and untreated animals were prepared and analyzed using standardized protocols and commercially-available software (ImageScope; Aperio Technologies). JQ1 elicited strong (3+) keratin expression in NMC 797 xenografts, uniformly within excised tumor specimens (FIGS. 6B-6F).

Figure 8A:
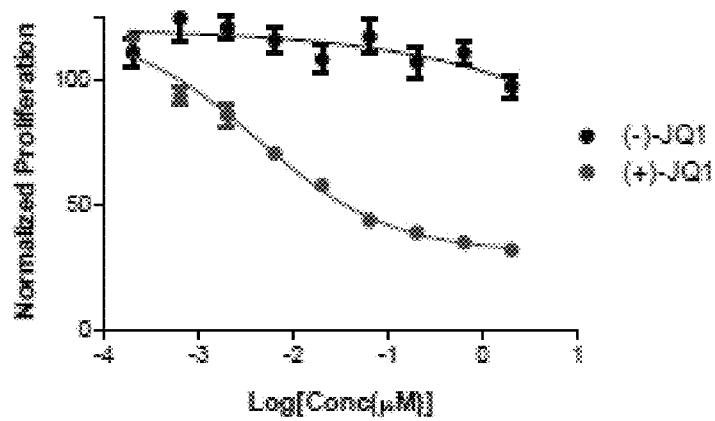
FIGS. 8A-8C are graphs showing that NMC patient-derived tissue is sensitive to the antiproliferative effects of (+)-JQ1 in vitro.
Figure 8B:
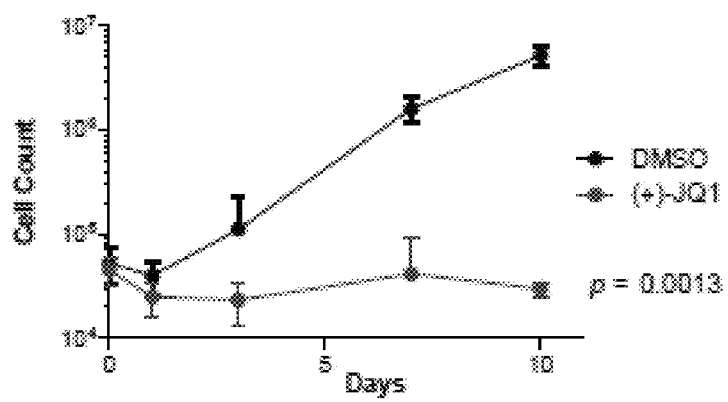
Figure 8C:
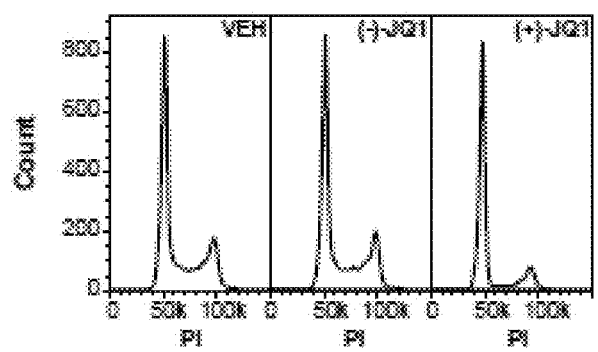
Figure 9A:
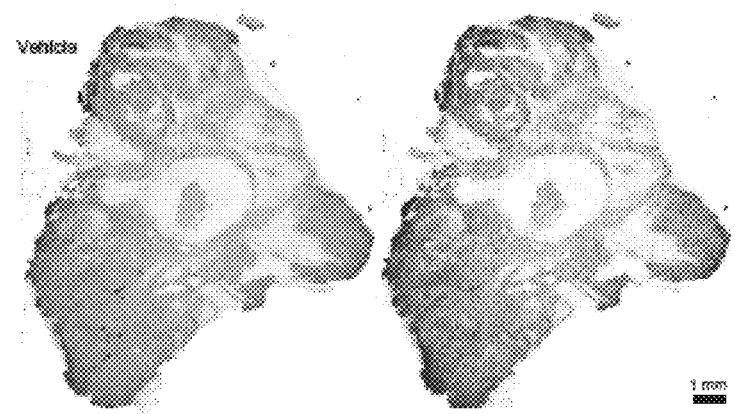
FIGS. 9A and 9B provides a quantification of diffuse, strong keratin expression induced by jq1 in patient-derived nmc 11060 primary xenograft tumors.
Figure 9B:
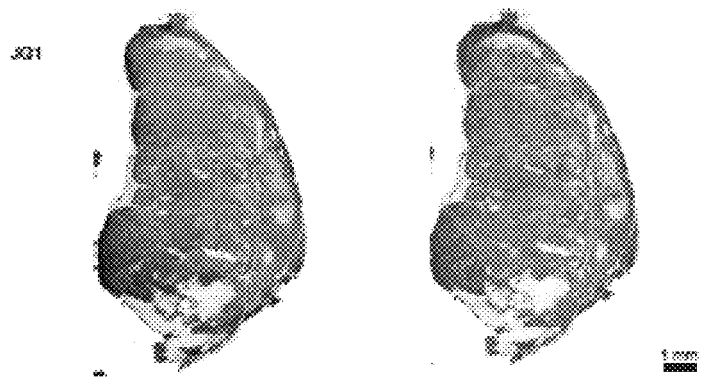

In parallel with these studies, a 29 year-old patient with widely metastatic BRD4-NUT positive NMC arising from the mediastinum was identified. With the goal of developing a more clinically-relevant disease model, short-term cultures were established using discarded clinical material obtained from pleural fluid draining from a palliative chest tube in the patient. As presented in FIG. 8, in vitro studies confirmed the stereoselective, potent effect of (+)-JQ1 on cellular viability (IC50=4 nM), growth and cell cycle progression. Four animals engrafted with patient-derived tumor material developed measurable disease, which was strongly PET positive (FIG. 5H). Animals were randomly assigned to vehicle or (+)-JQ1 treatment cohorts. Prior to treatment assignment and after four days of therapy, mice were evaluated by PET imaging. A marked response on FDG uptake was observed with (+)-JQ1 treatment, whereas vehicle-treated animals demonstrated evident, progressive disease (FIG. 5I). Again, tumor material was prepared for quantitative IHC analysis, which demonstrated induction of keratin expression following (+)-JQ1 treatment (FIGS. 5J, 5K, and FIG. 9). Together, these data provide a mechanistic link between BRD4 inhibition and a therapeutic response to JQ1 in vivo.

Across the emerging, complex mutational landscape of the cancer genome, recurrent chromosomal rearrangements comprise a compelling subset of clear, genetic targets in cancer. As evidenced by the successful development of kinase inhibitors targeting BCR-ABL in CML, well-characterized probe compounds[31,32], high-resolution crystallographic data[33], translational research studies[34], and informative murine models[35], where available, provide an optimal platform for ligand discovery and target validation. As reported herein, a novel BRD4-directed small molecule inhibitor is likely to be useful for the treatment of genetically-defined human squamous carcinoma associated with the NUT-BRD4 fusion.

Beyond NUT-midline carcinoma, BET-family bromodomains contribute to numerous other neoplastic and non-neoplastic diseases. BRD4 targets the P-TEFb complex to mitotic chromosomes resulting in expression of growth promoting genes such as c-Myc[11][9] and the well established cancer target Aurora B[13]. In addition, BRD4 is amplified in breast cancer[36] and is a predictive marker of survival among breast cancer patients[37]. Apart from these functions in cancer biology, BET family members have been recognized as essential genes for the replication of viruses[38,39] and in mediating inflammatory responses[14]. Thus, the availability of (+)-JQ1 and (−)-JQ1 as paired chemical probes will prompt informative research broadly in transcriptional, developmental and disease biology. JQ1 was also found to exhibit few off-target effects on cellular receptors and excellent pharmacokinetic properties including 49% oral bioavailability (FIG. 10), establishing the plausibility of developing drug-like derivatives for therapeutic application.

The discovery and optimization of small-molecule inhibitors of epigenetic targets is a major focus of current biomedical research. Successful approaches to date are limited to the identification of ligands for chromatin-modifying enzymes[40]. Perhaps most studied are modulators of lysine side-chain deacetylation, for which numerous pharmaceutical inhibitors have been clinically developed. The present invention provides compositions and methods for developing potent, selective inhibitors of epigenetic readers, including the first, thoroughly characterized inhibitor of the BET-family of bromodomains. In view of this discovery, the approach outlined herein can be used for the identification of additional candidates for identifying additional inhibitors having selectivity within the BET-family.

Example 7: JQ1 Enantiomers Bind and Inhibit BRD4.1 and BRD4.2

Figure 11:
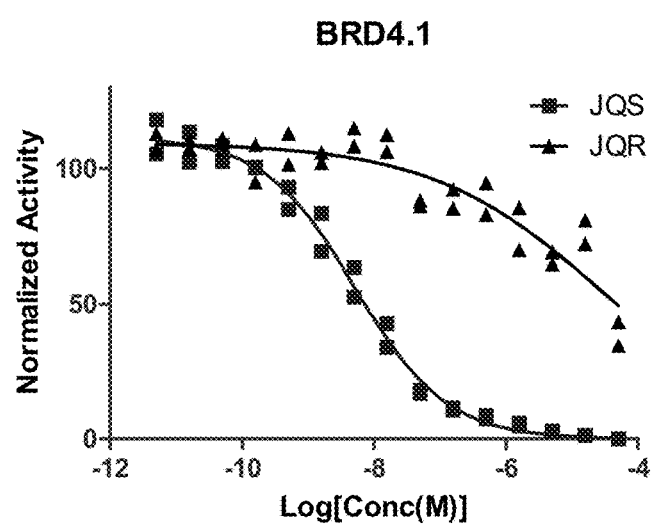
FIG. 11 is a graph showing AlphaScreen binding data for JQ1 enantiomers inhibiting BRD4.1.
Figure 12:
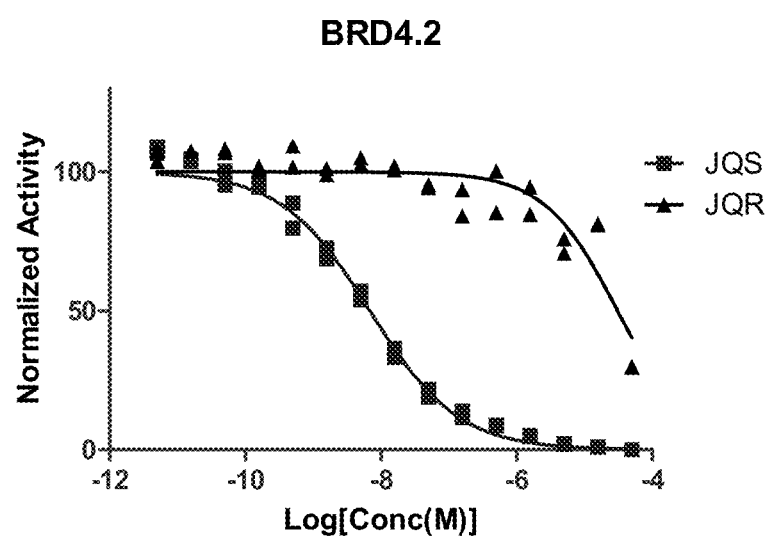
FIG. 12 is a graph showing AlphaScreen binding data for JQ1 enantiomers inhibiting BRD4.2.
Figure 13:
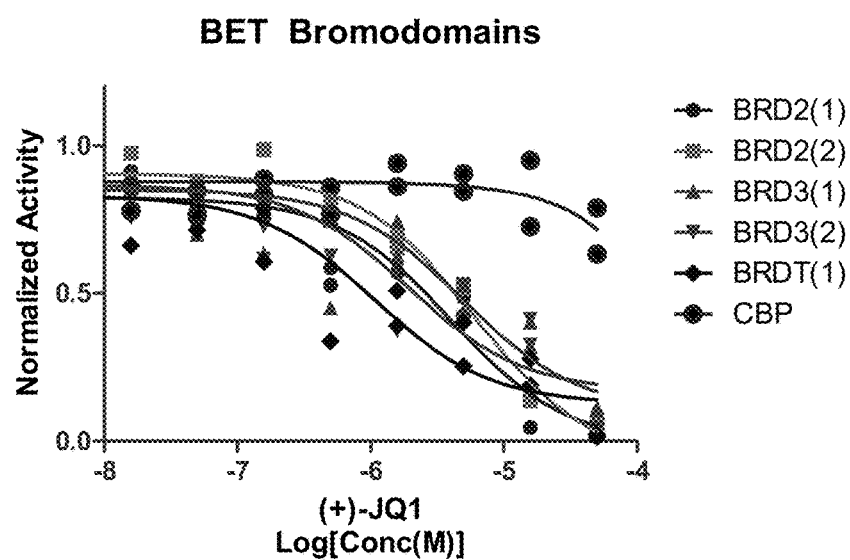
FIG. 13 is a graph showing profiling of JQ1S against other BET family members (active) and CBP (inactive).
Figure 14:
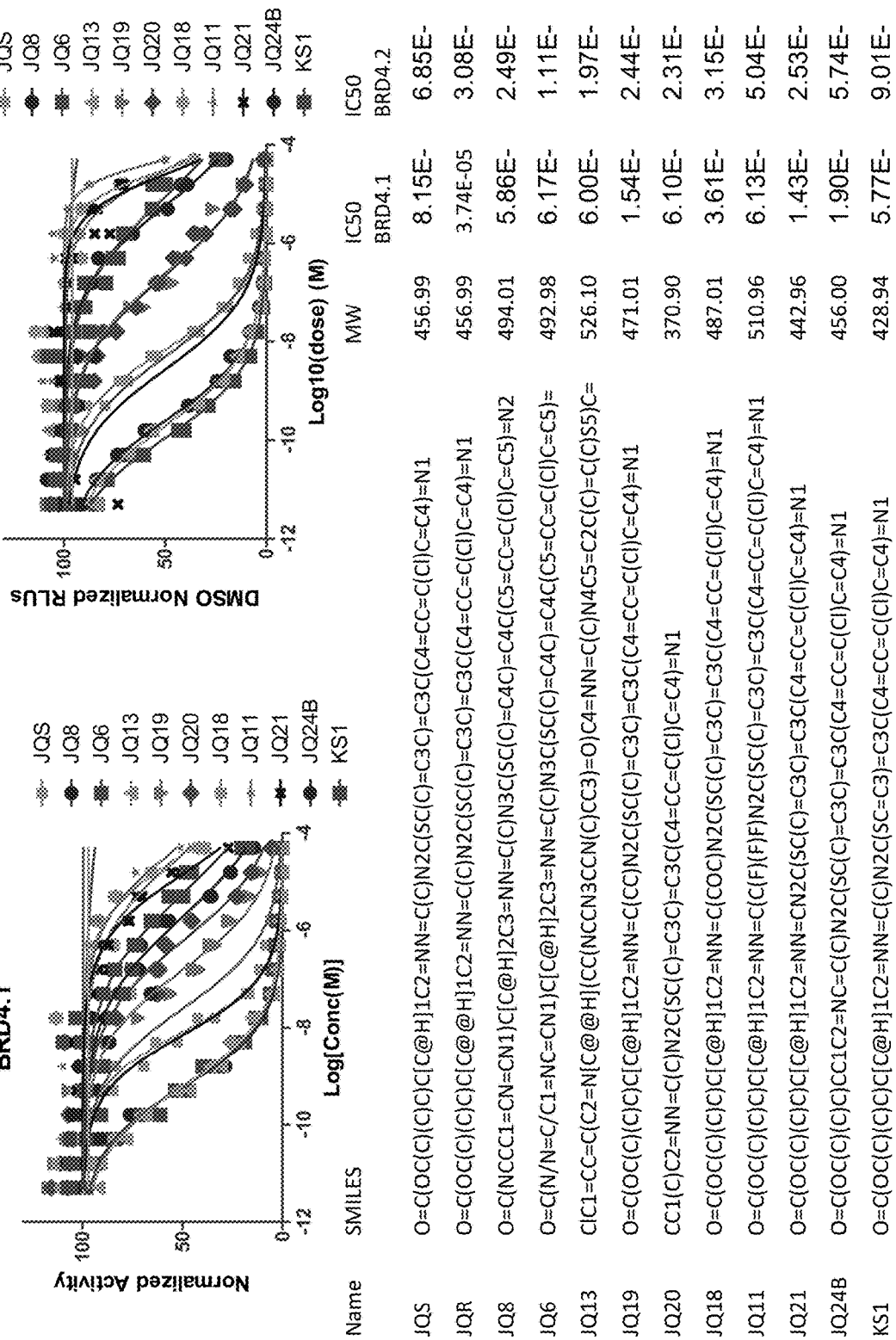
FIG. 14 is a graph showing dose-ranging studies of a focused library of JQ1 derivatives.

FIGS. 11 and 12 show that JQ1 enantiomers bind and inhibit BRD4.1 and BRD4.2. FIG. 13 shows a comparison of JQ1S binding and inhibition of BET family members (active) and CBP (inactive). FIG. 14 shows the results of dose-ranging studies of a focused library of JQ1 derivatives (for compound structures, see Table B, above).

Example 8: JQ1 is Effective for the Treatment of BRD3-NUT Cancer

Figure 15A:
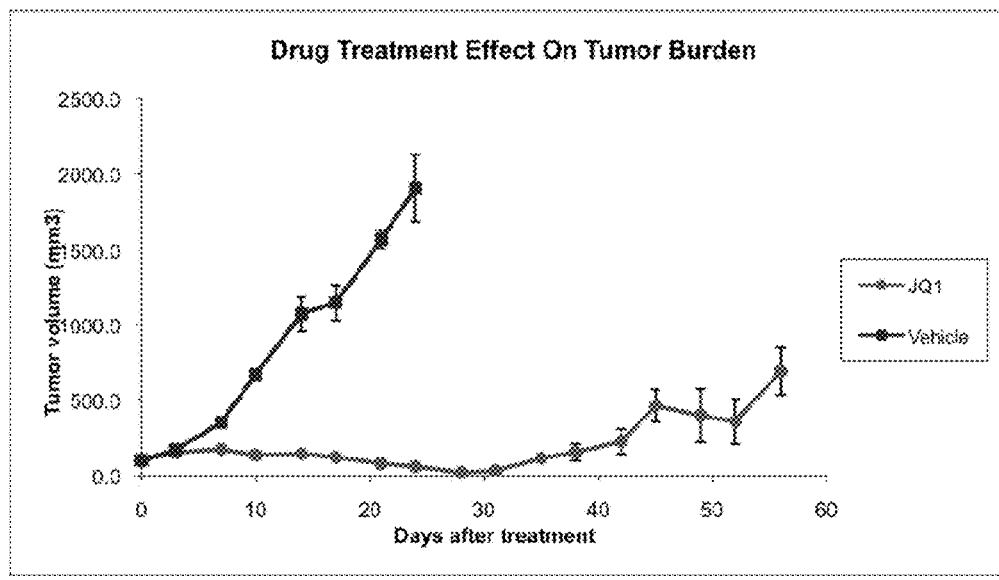
FIGS. 15A and 15B are graphs.
Figure 15B:
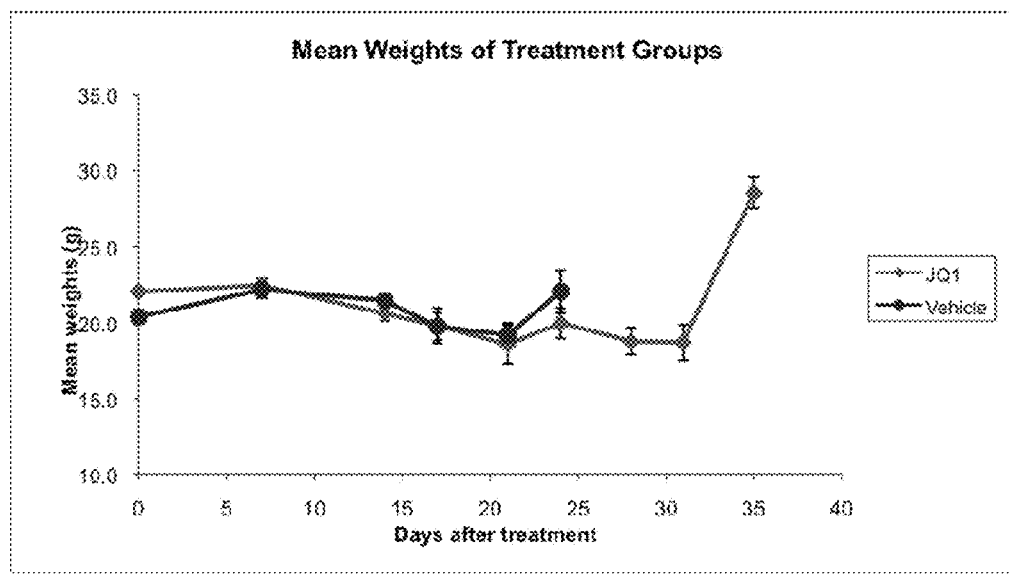
Figure 18:
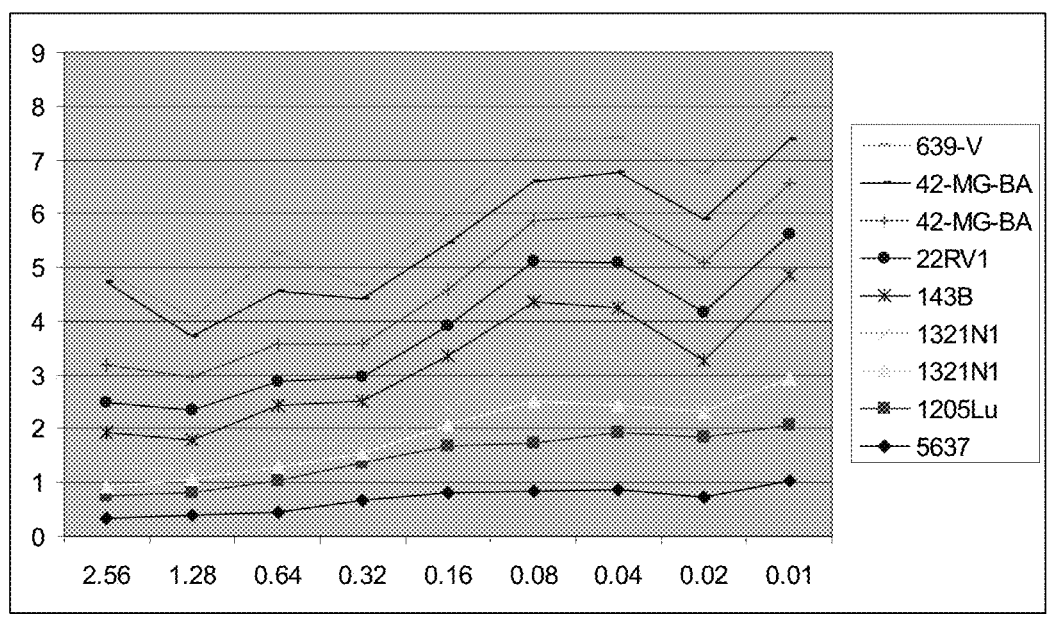
FIGS. 18-55 show dose response viability for a variety of cancer cell lines treated with JQ1 and derivatives thereof.
Figure 19:
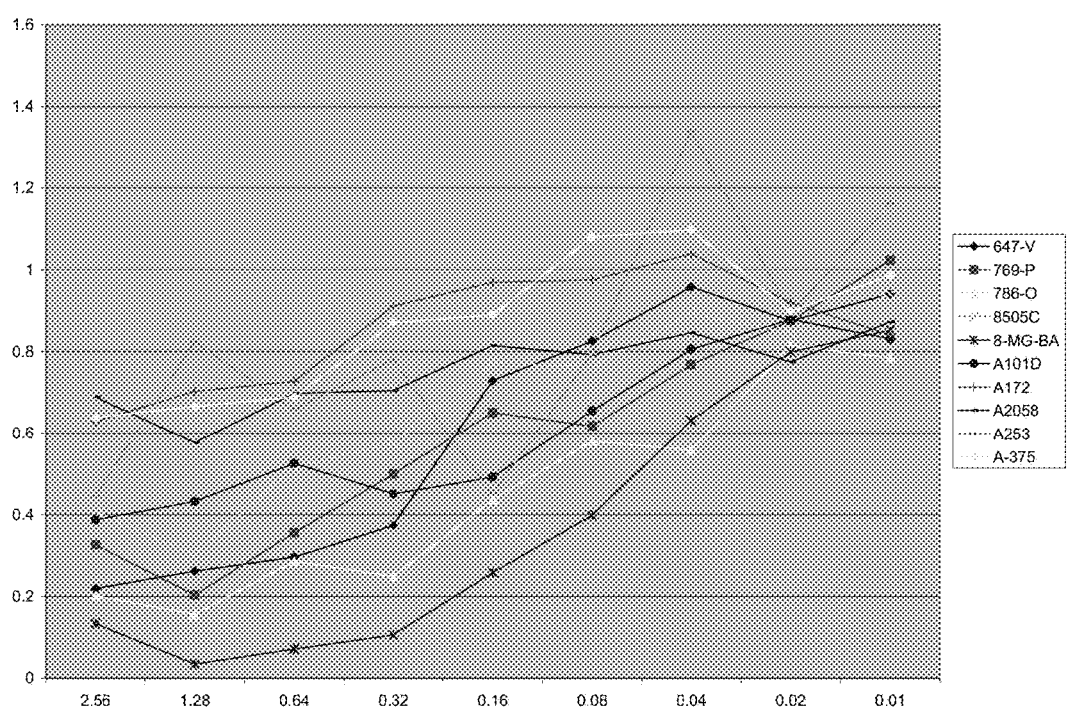
Figure 20:
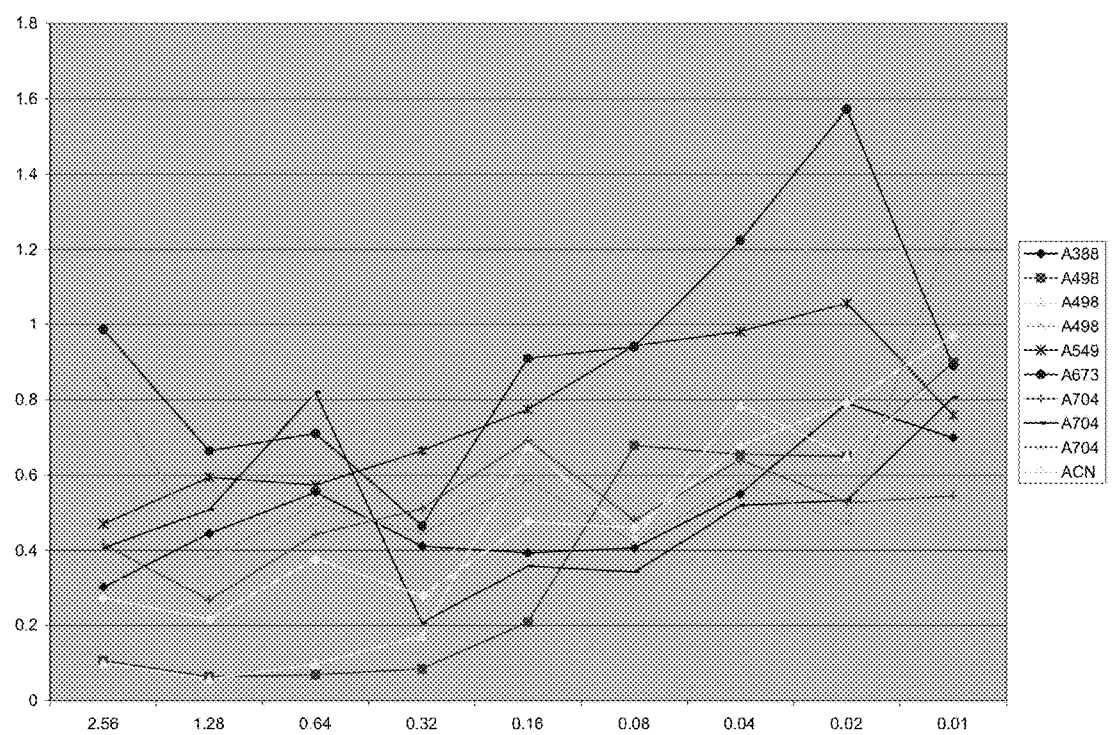
Figure 21:
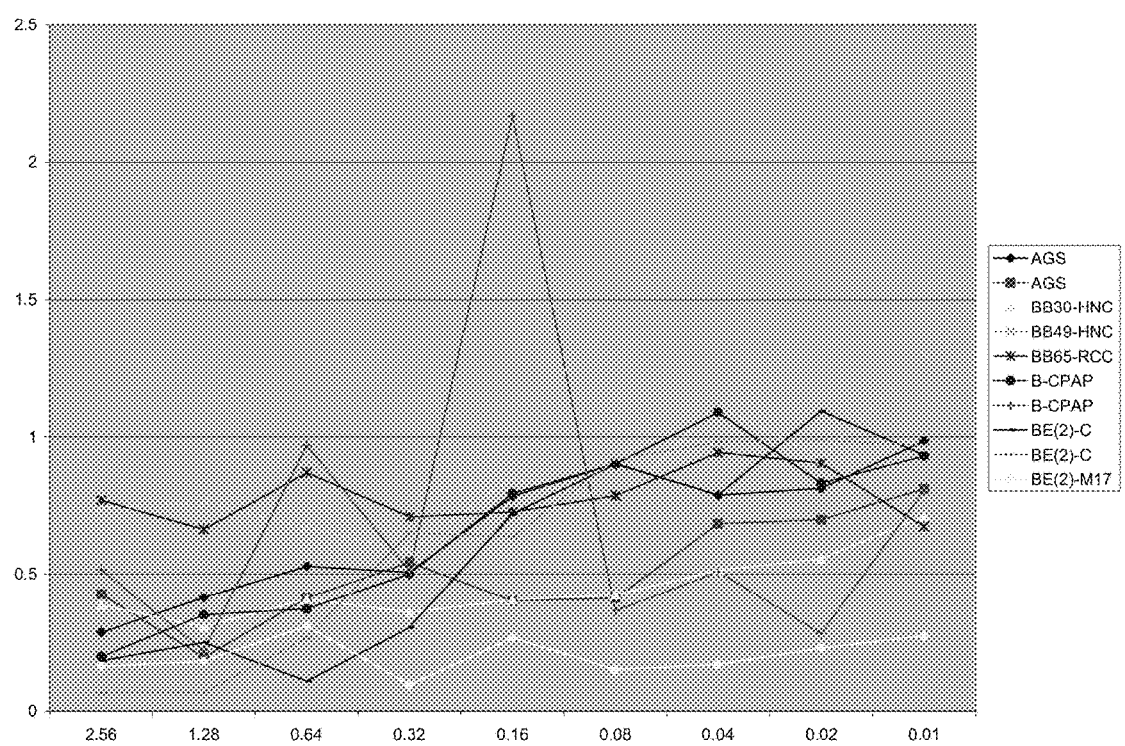
Figure 22:
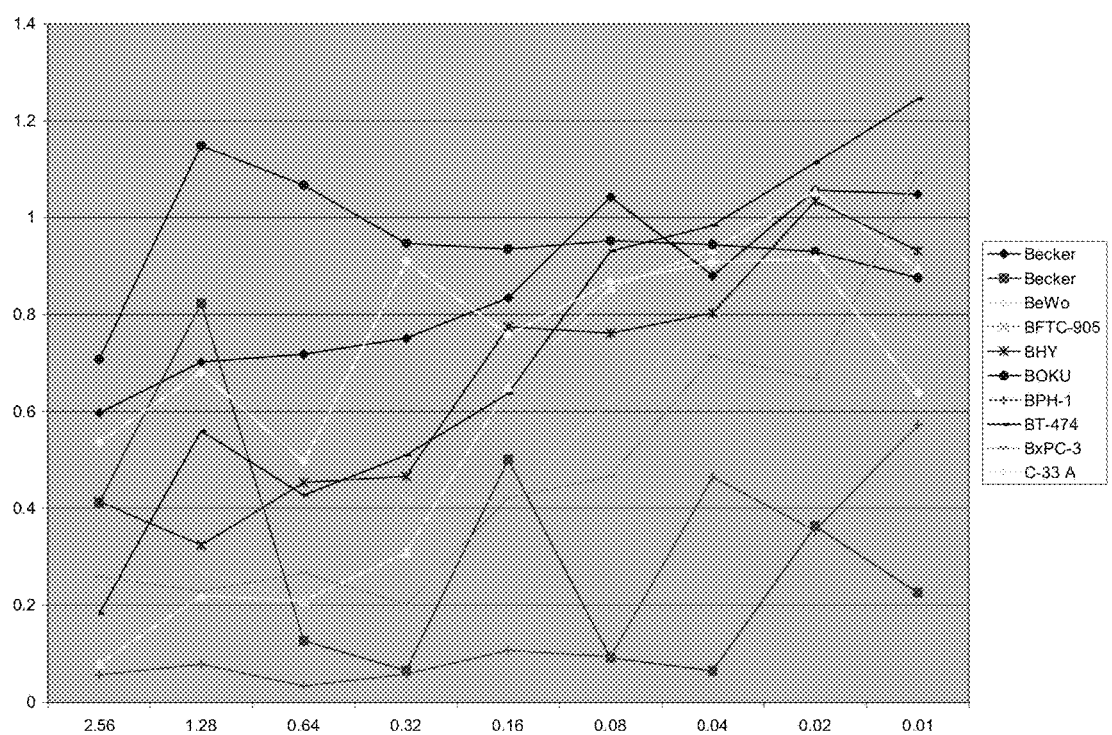
Figure 23:
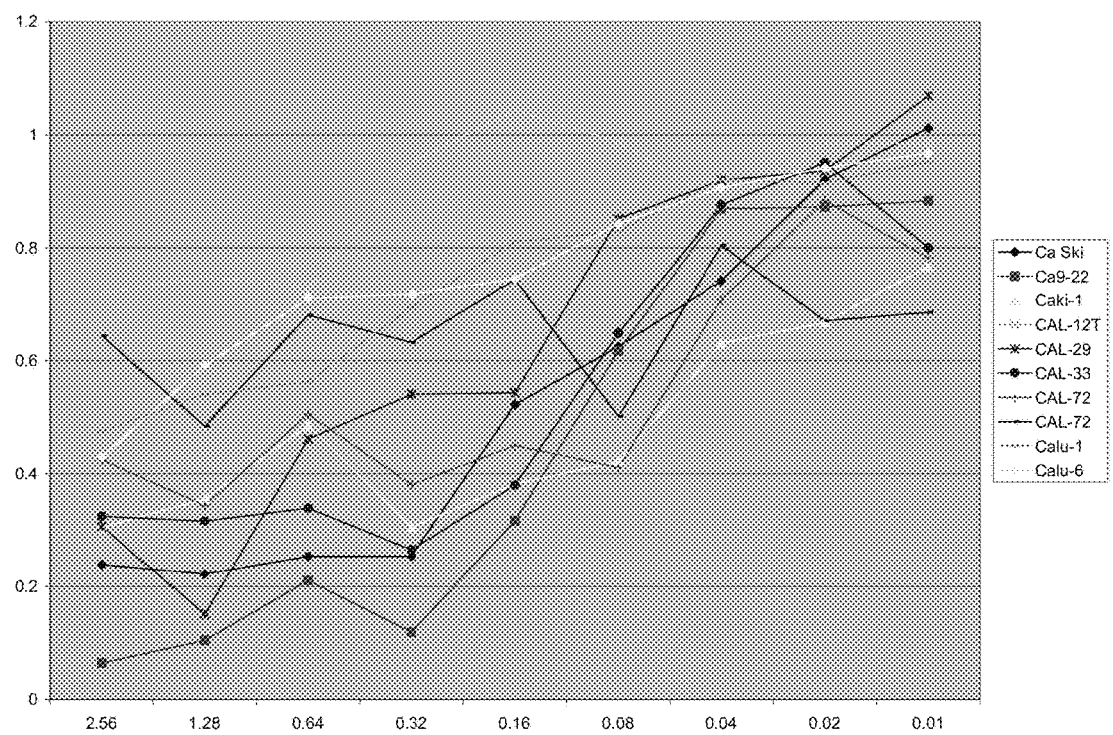
Figure 24:
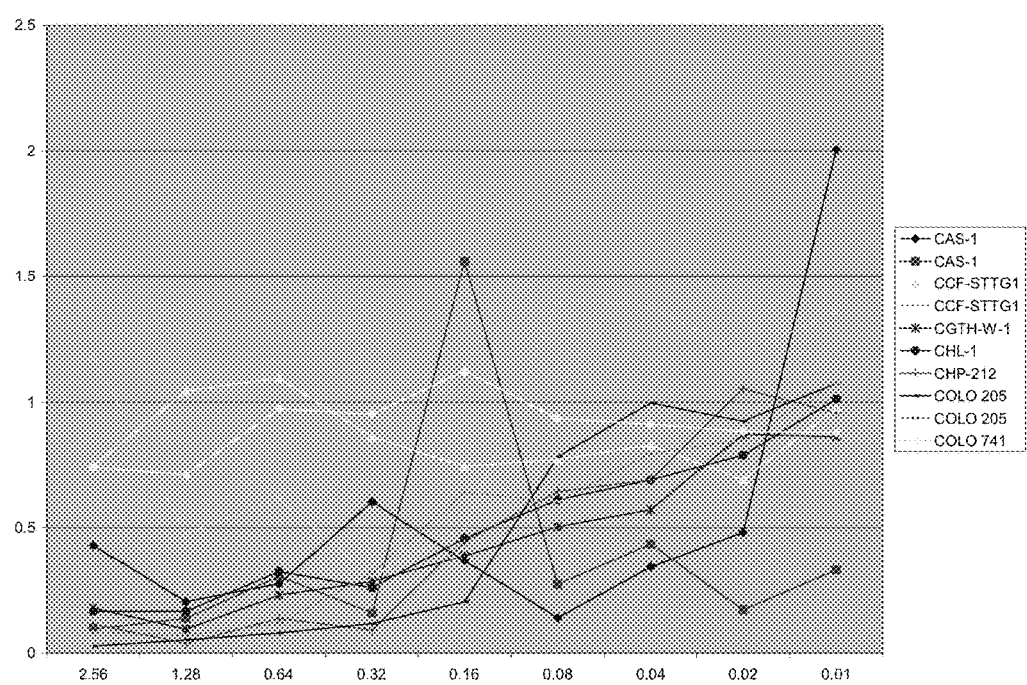
Figure 25:
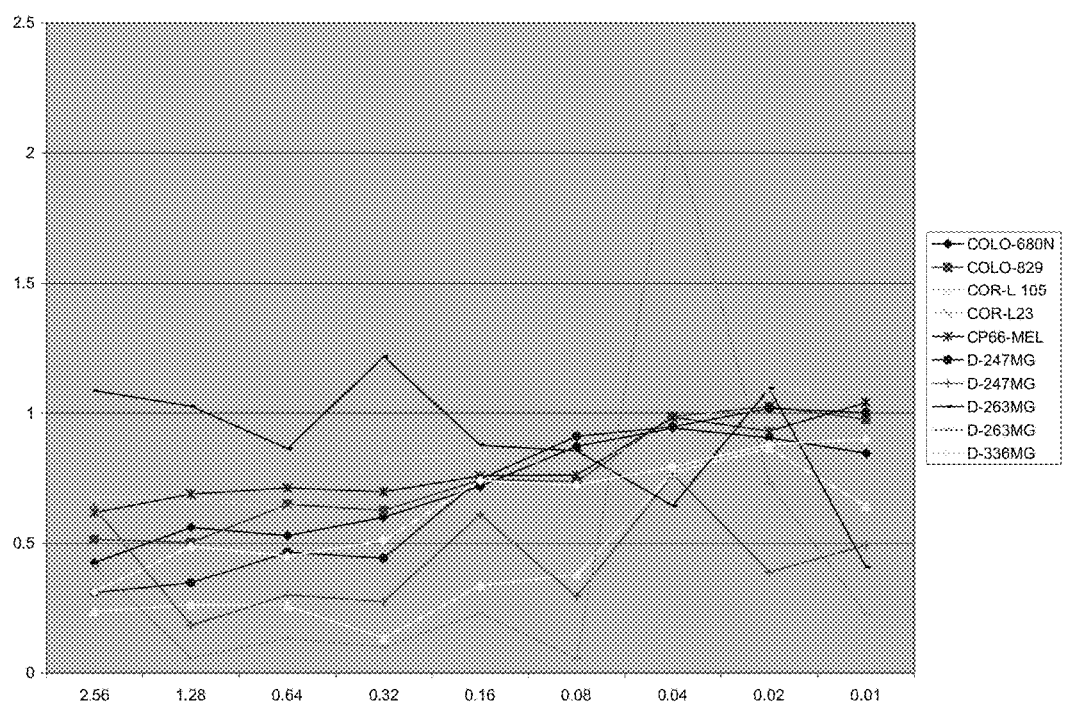
Figure 26:
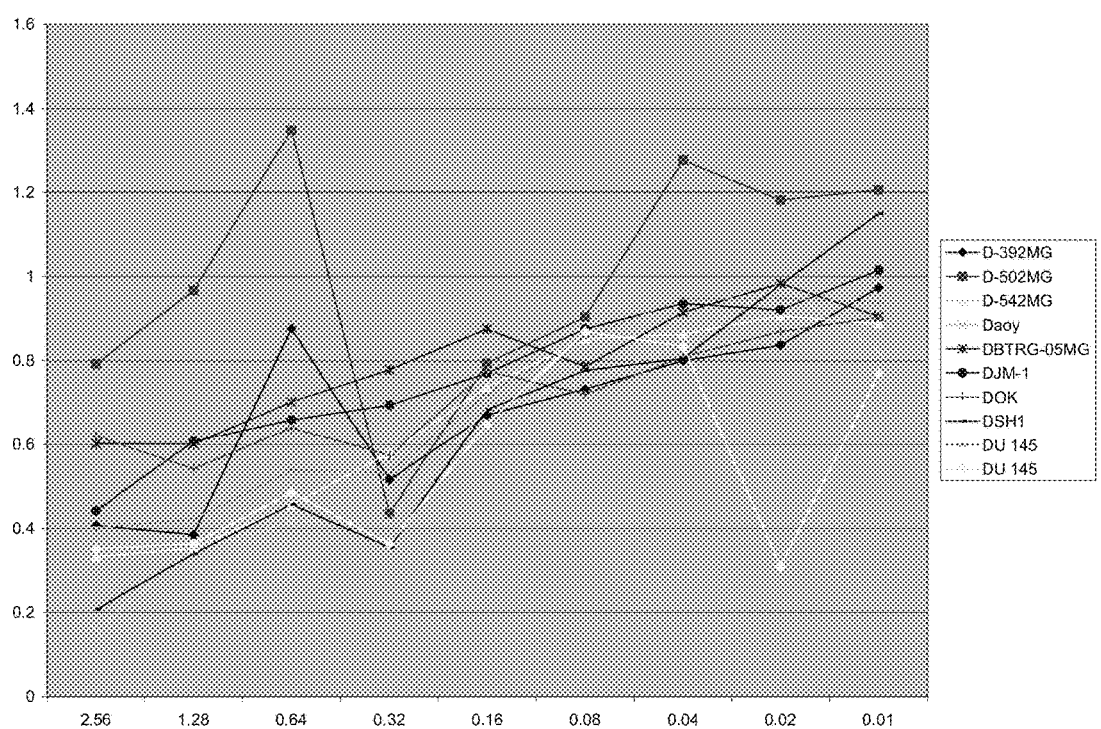
Figure 27:
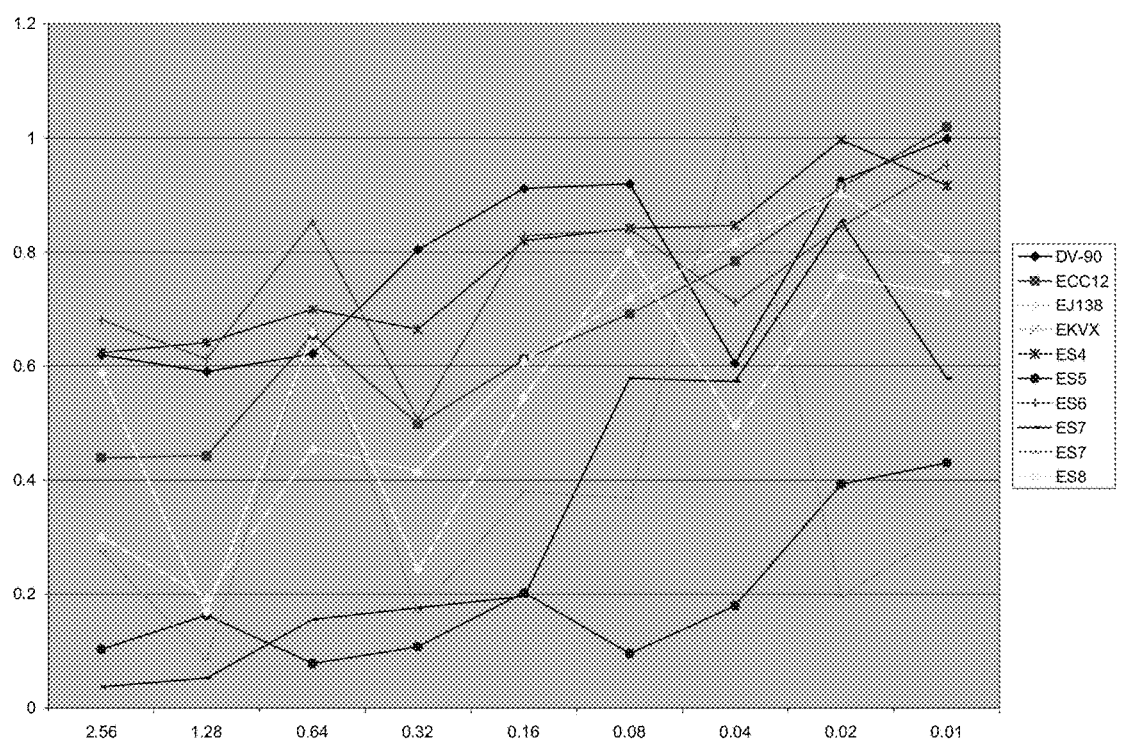
Figure 28:
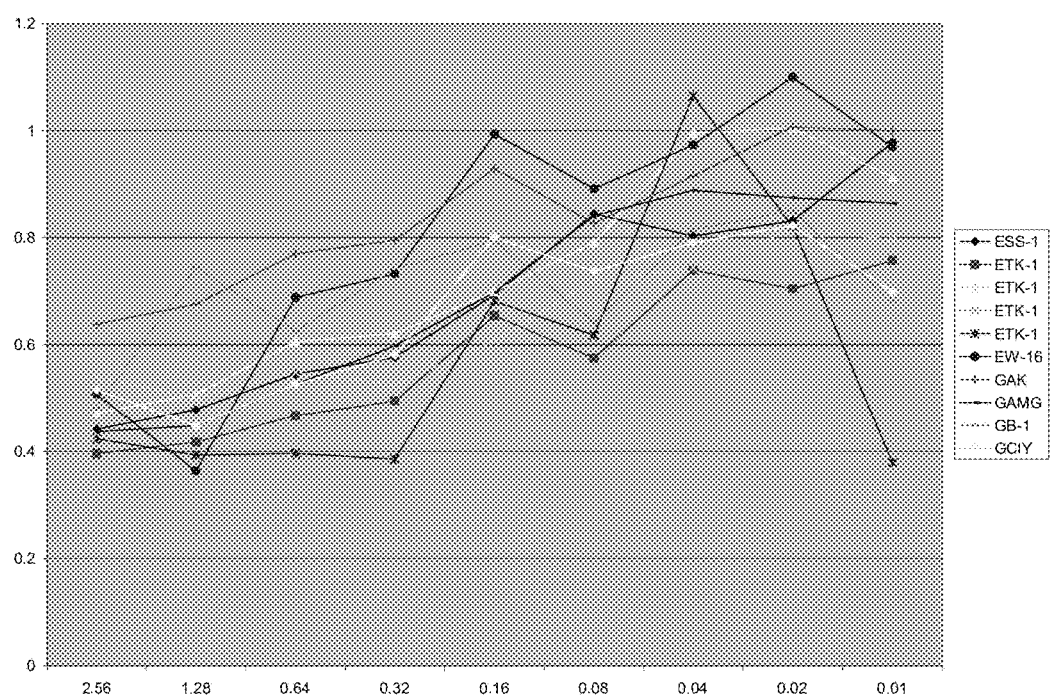
Figure 29:
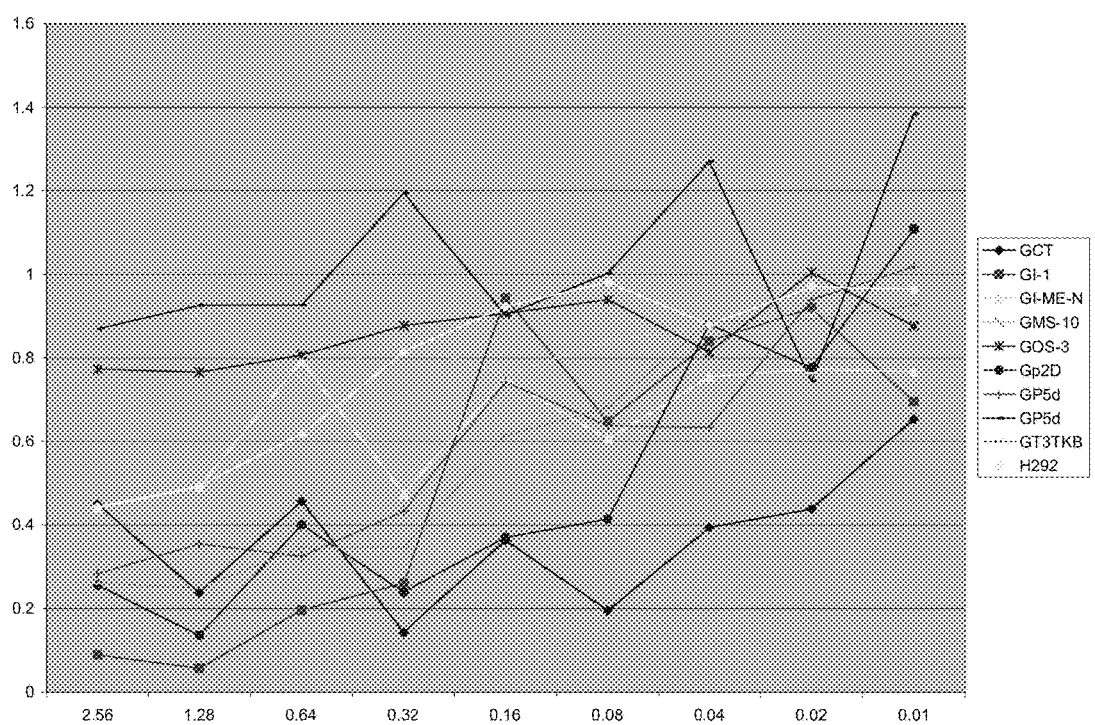
Figure 30:
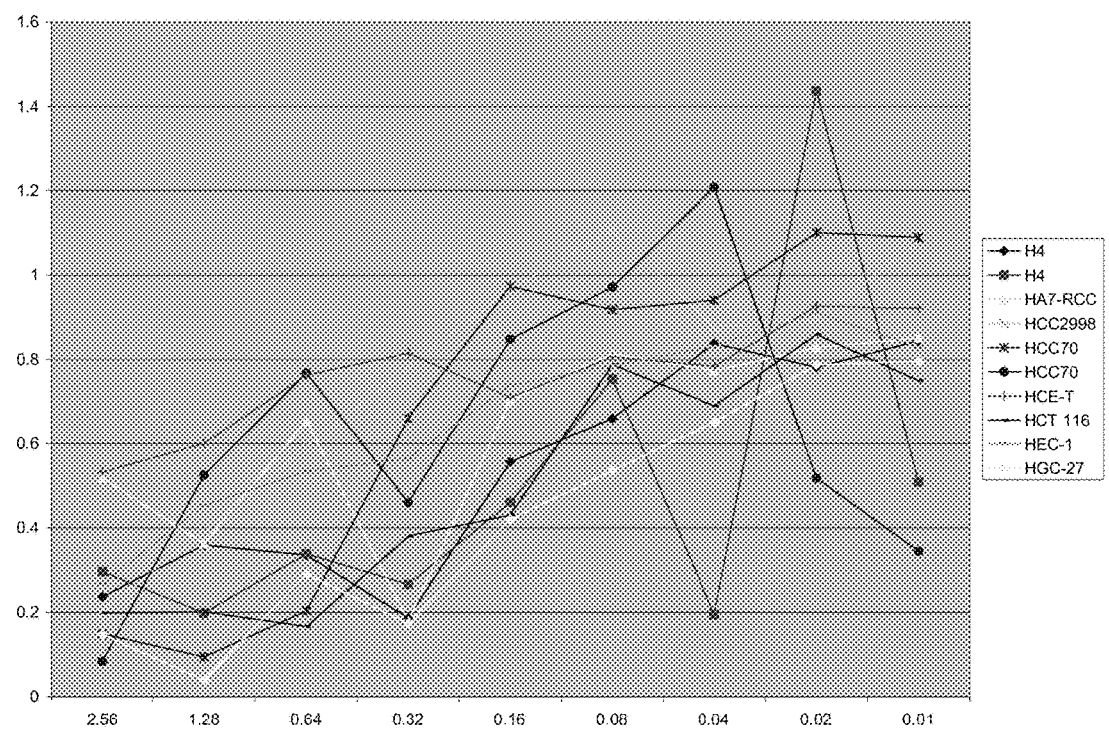
Figure 31:
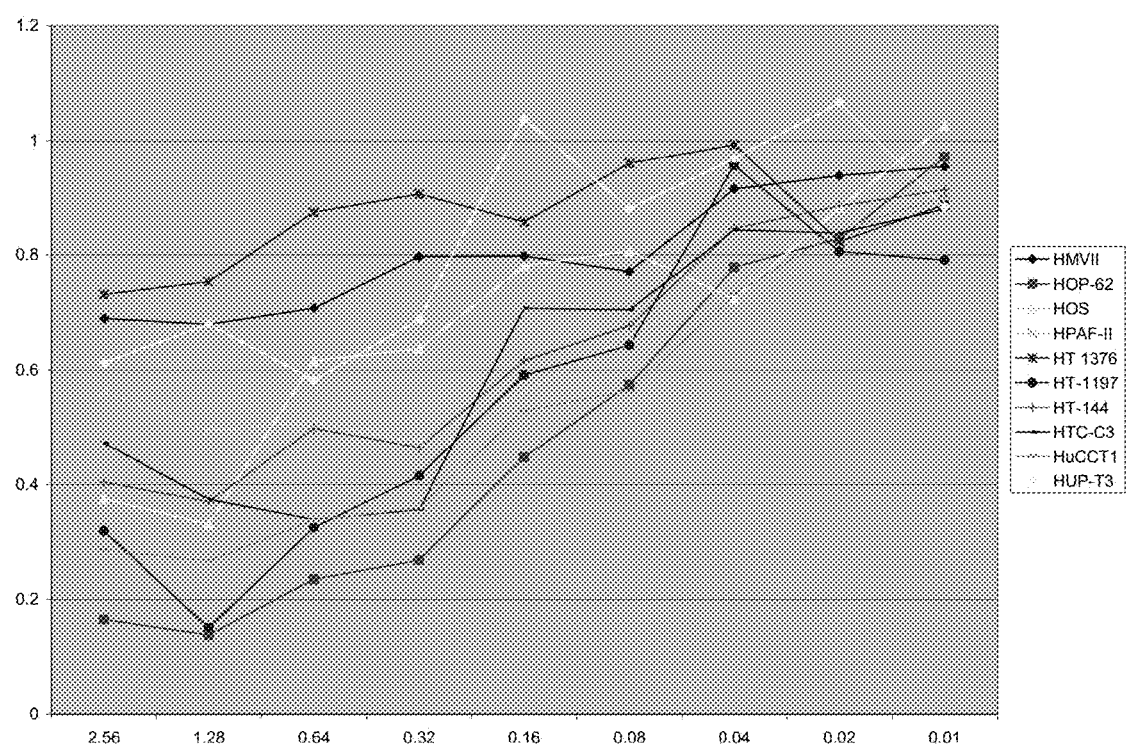
Figure 32:
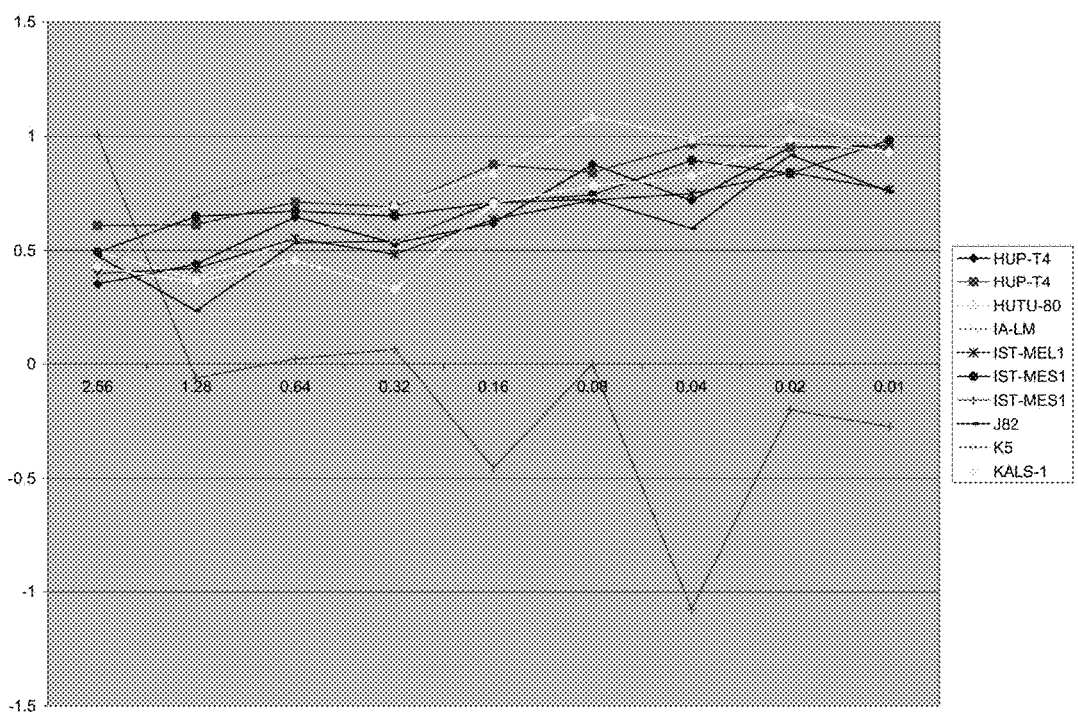
Figure 33:
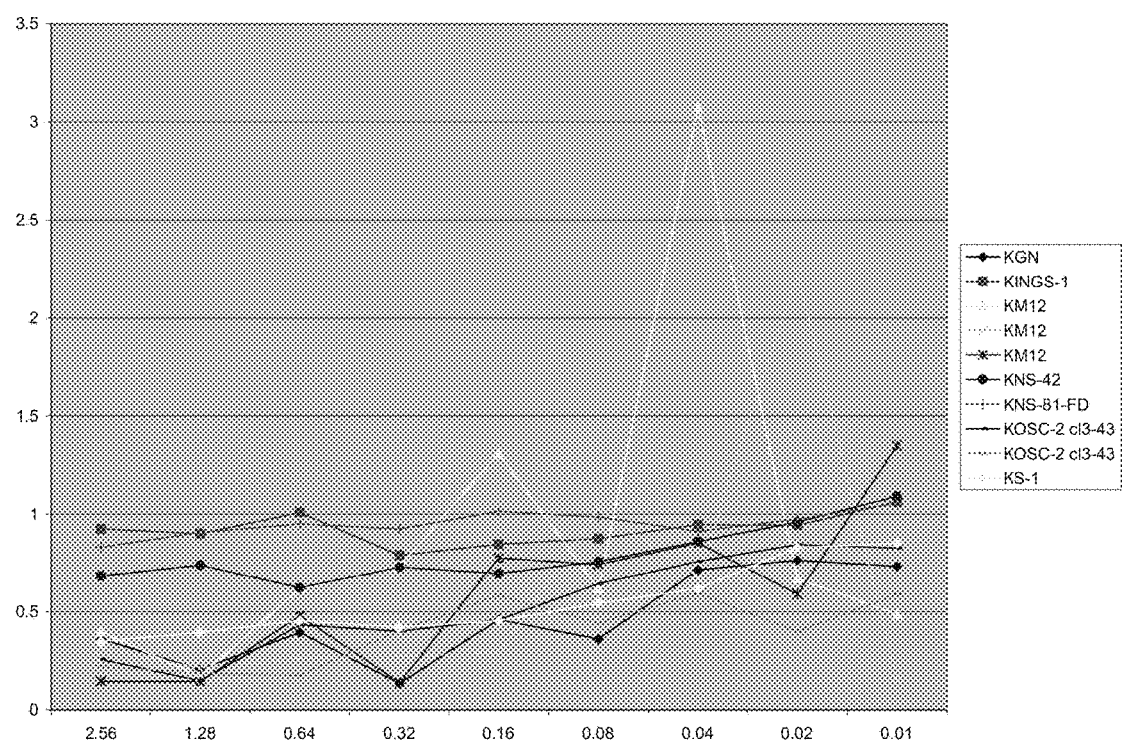
Figure 34:
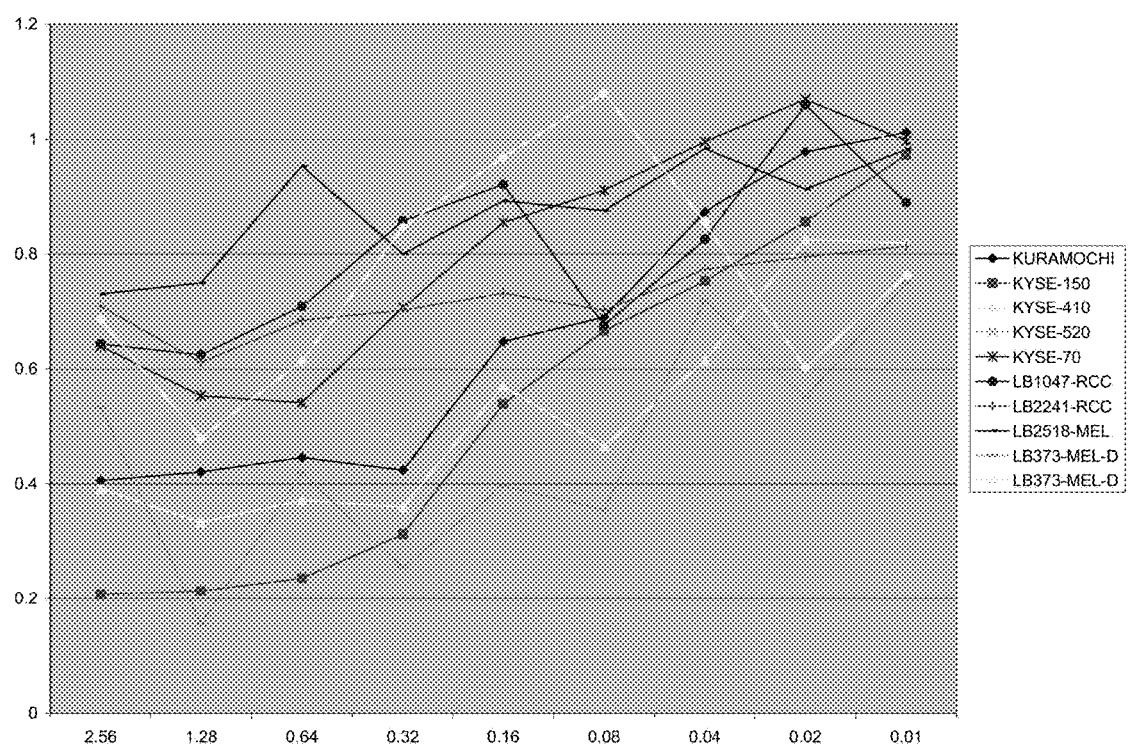
Figure 35:
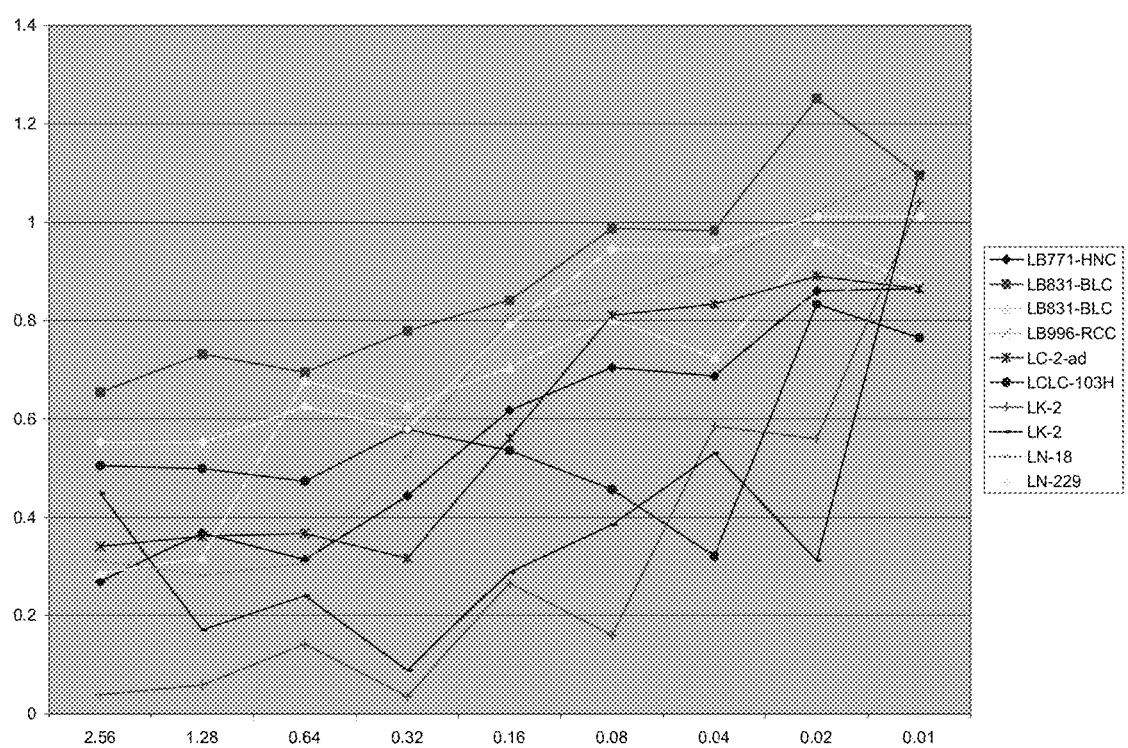
Figure 36:
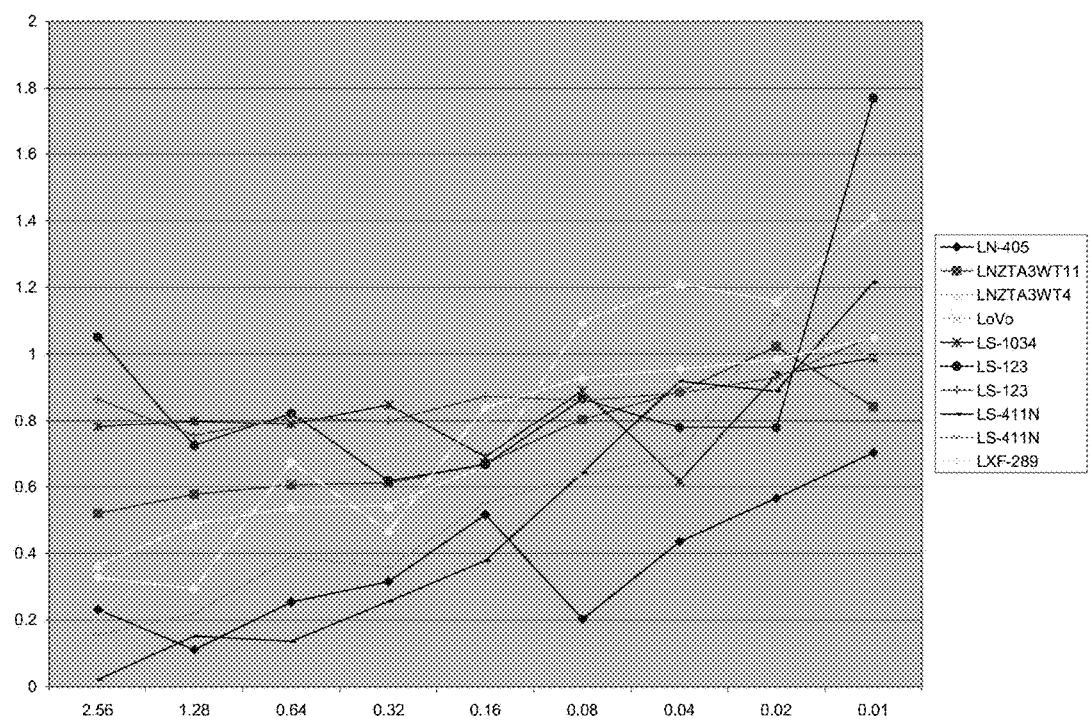
Figure 37:
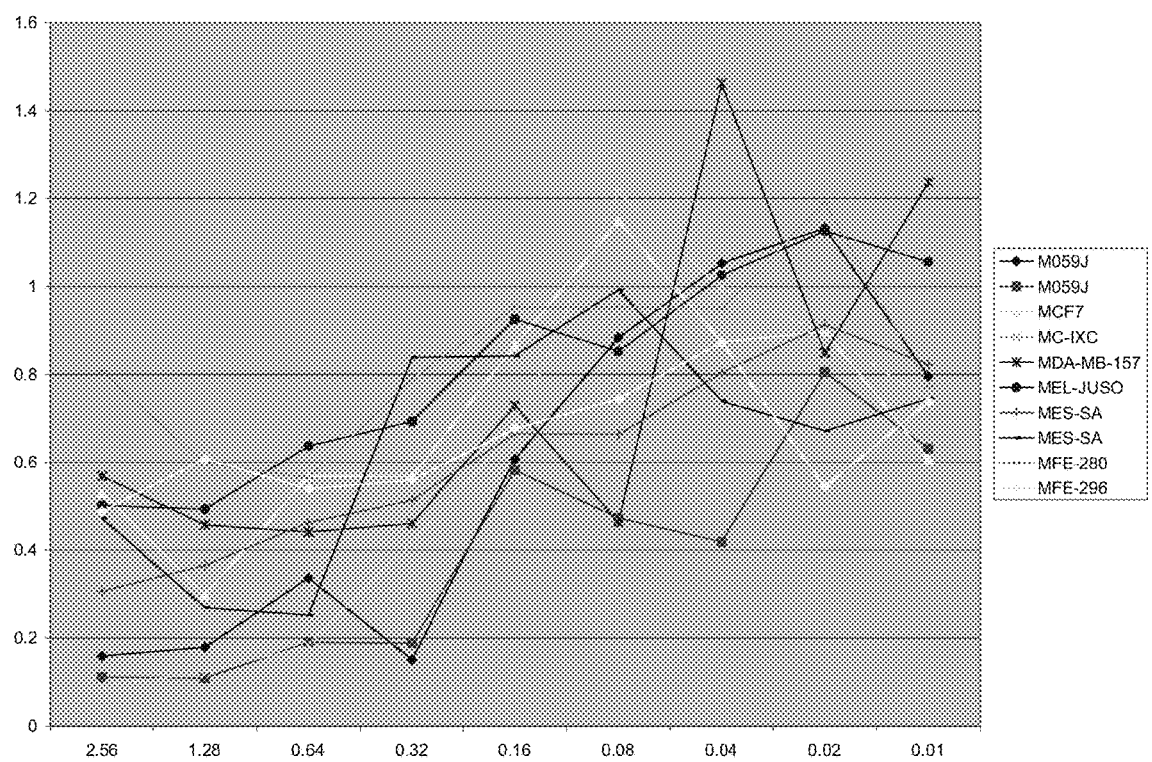
Figure 38:
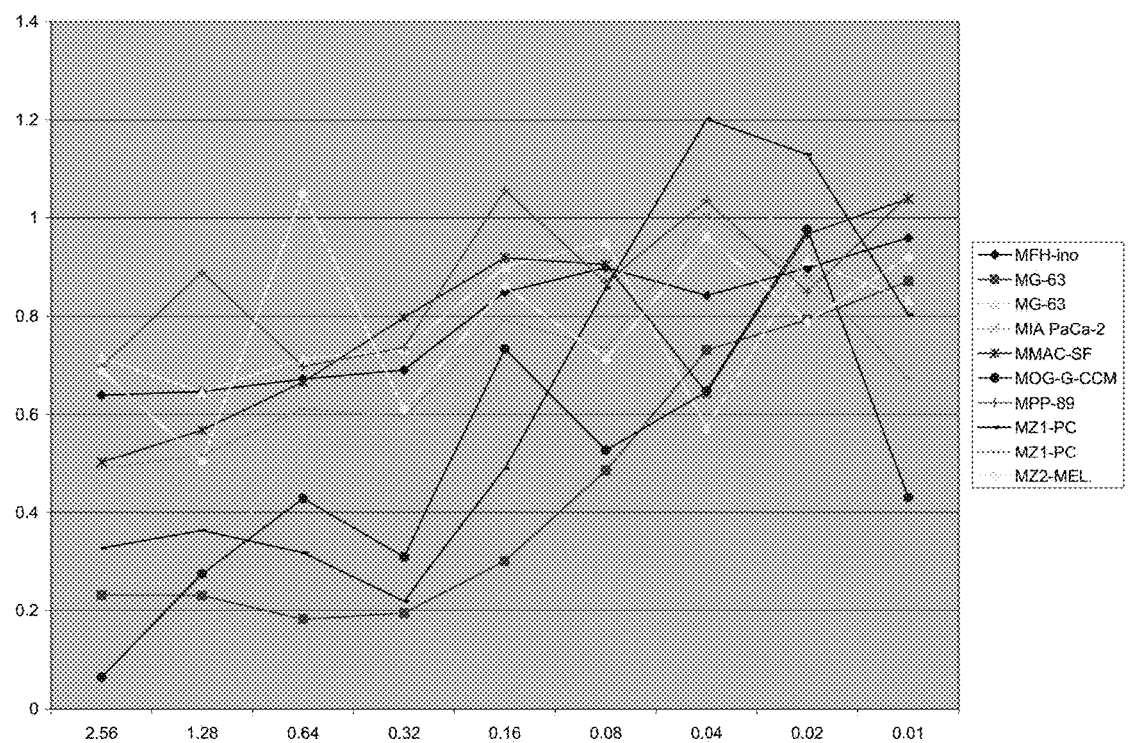
Figure 39:
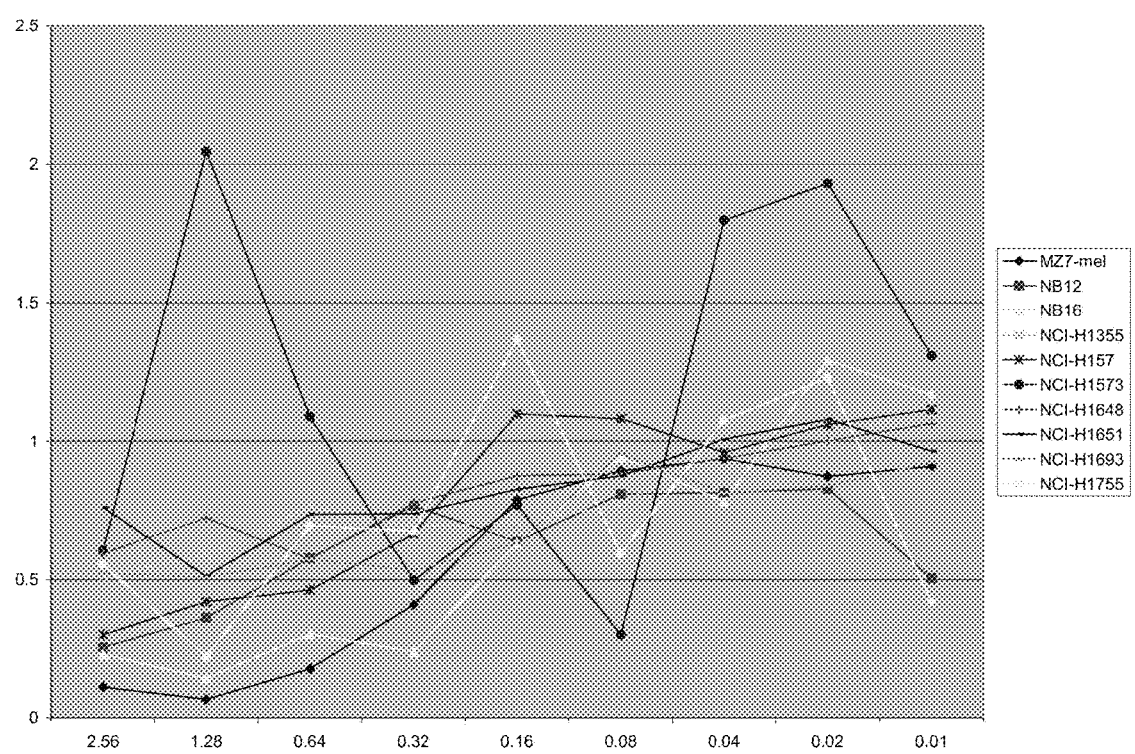
Figure 40:
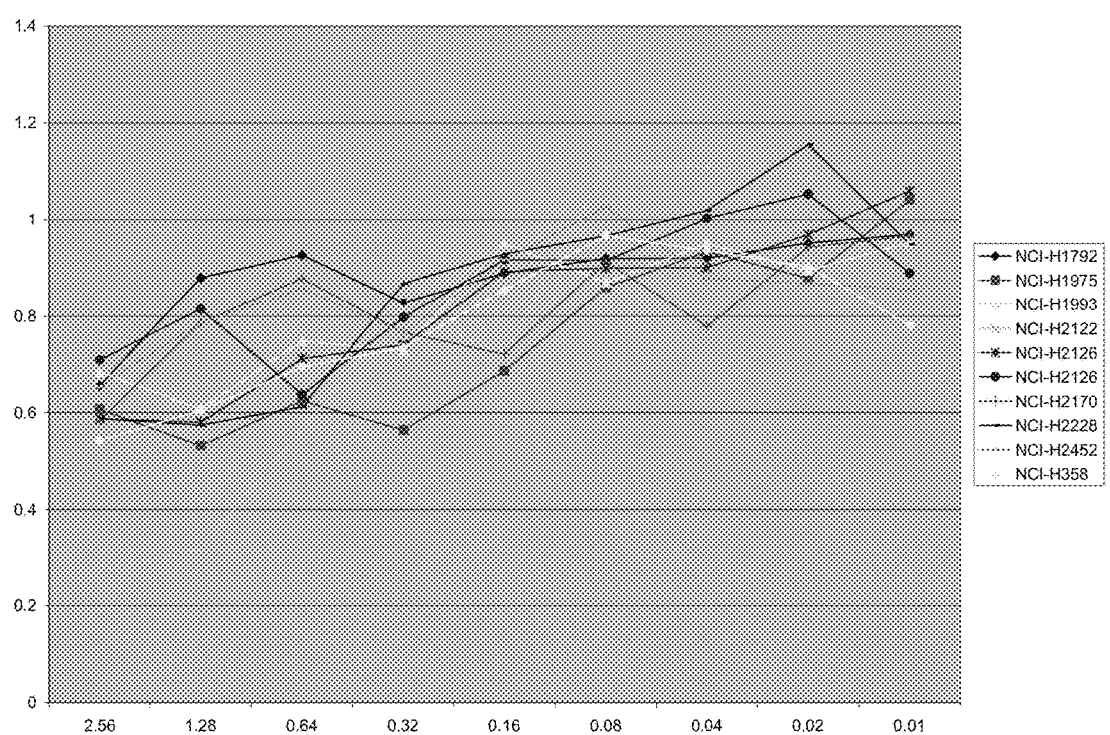
Figure 41:
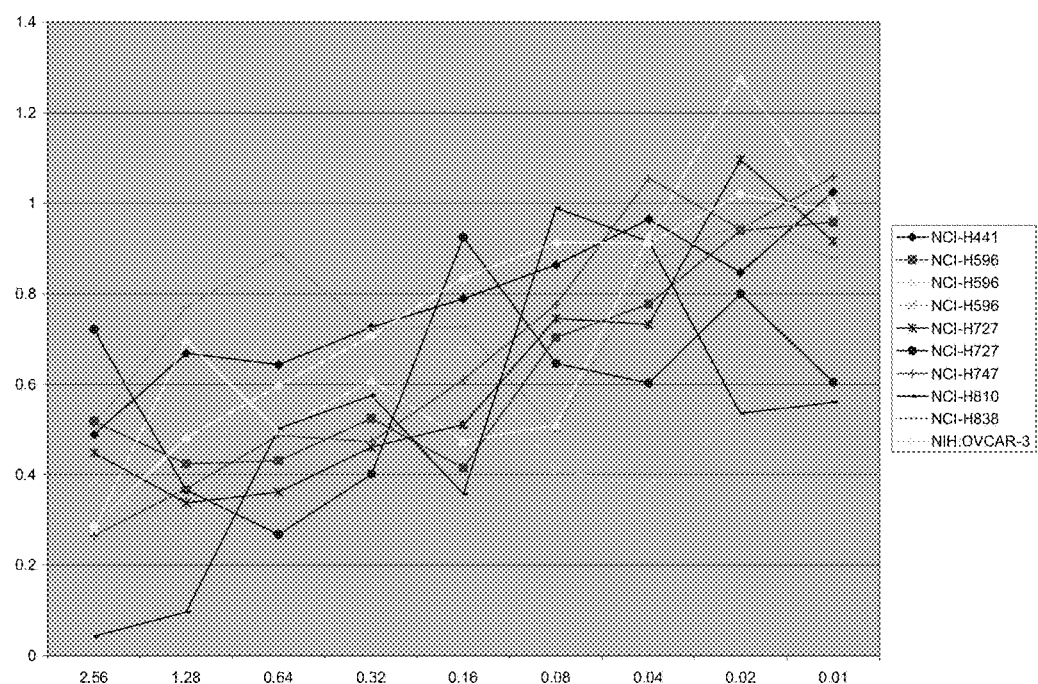
Figure 42:
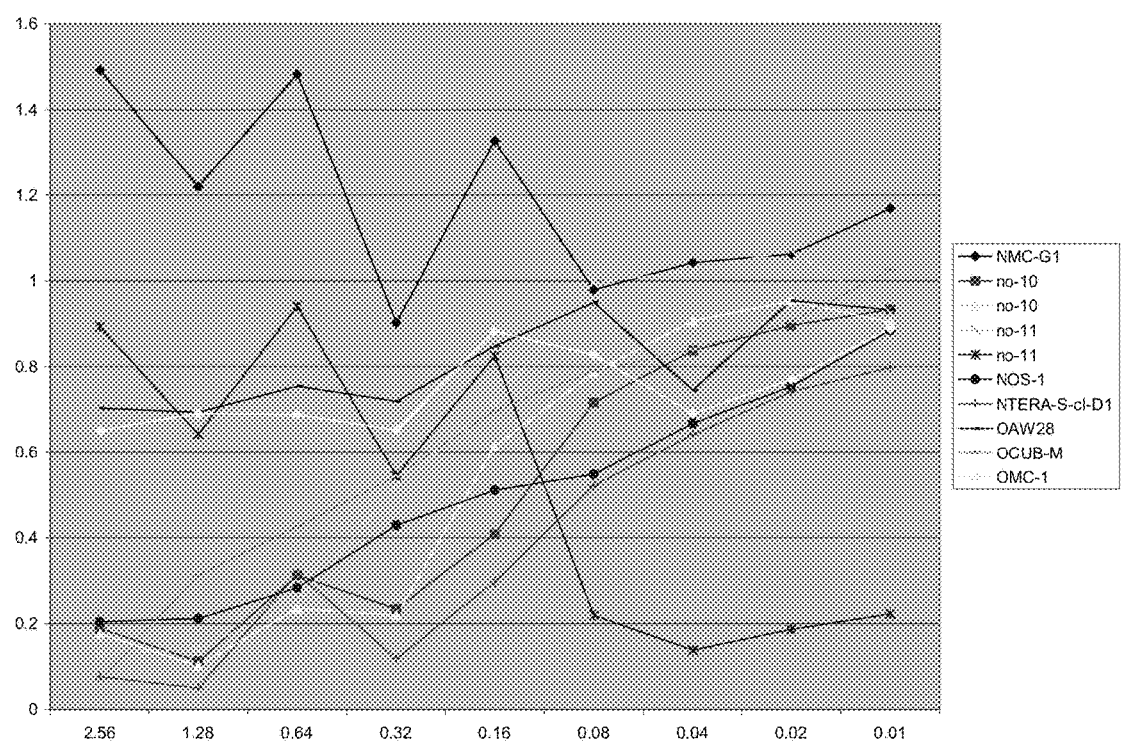
Figure 43:
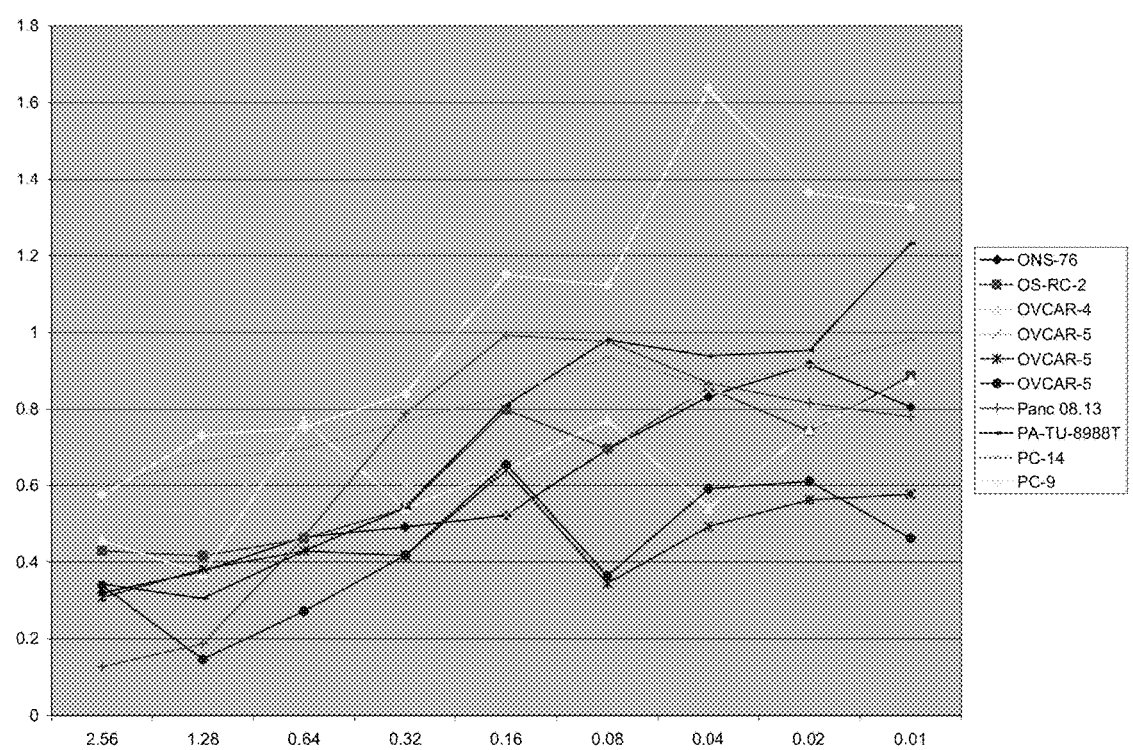
Figure 44:
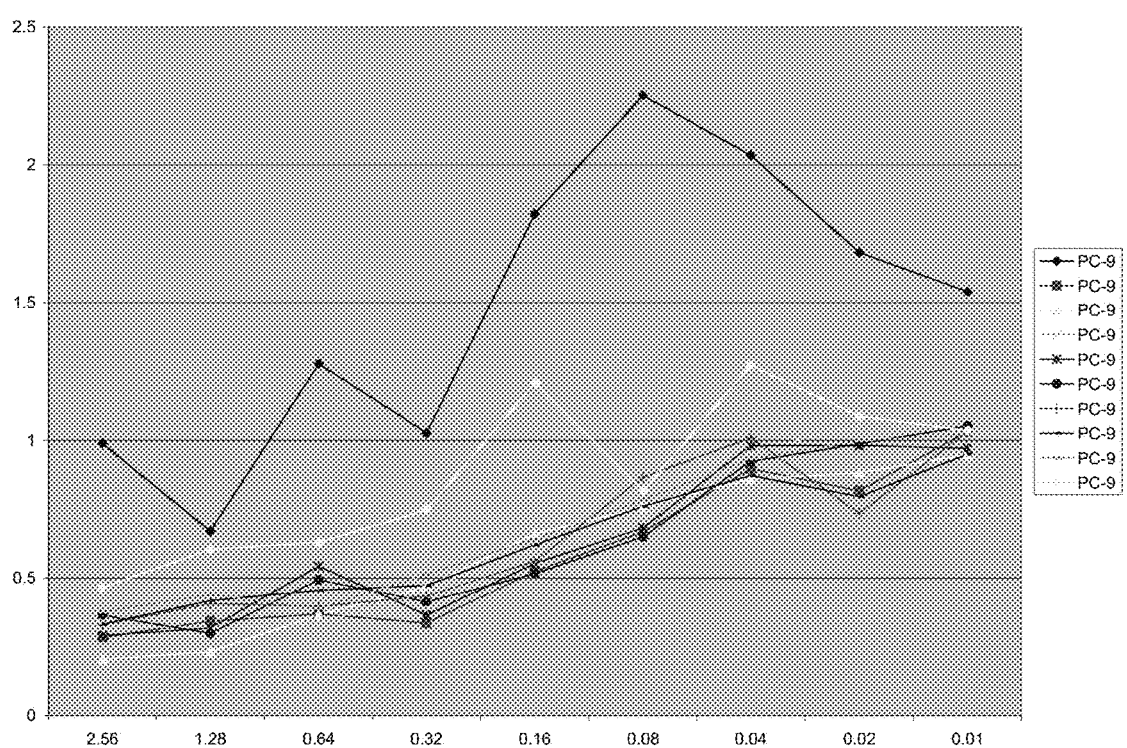
Figure 45:
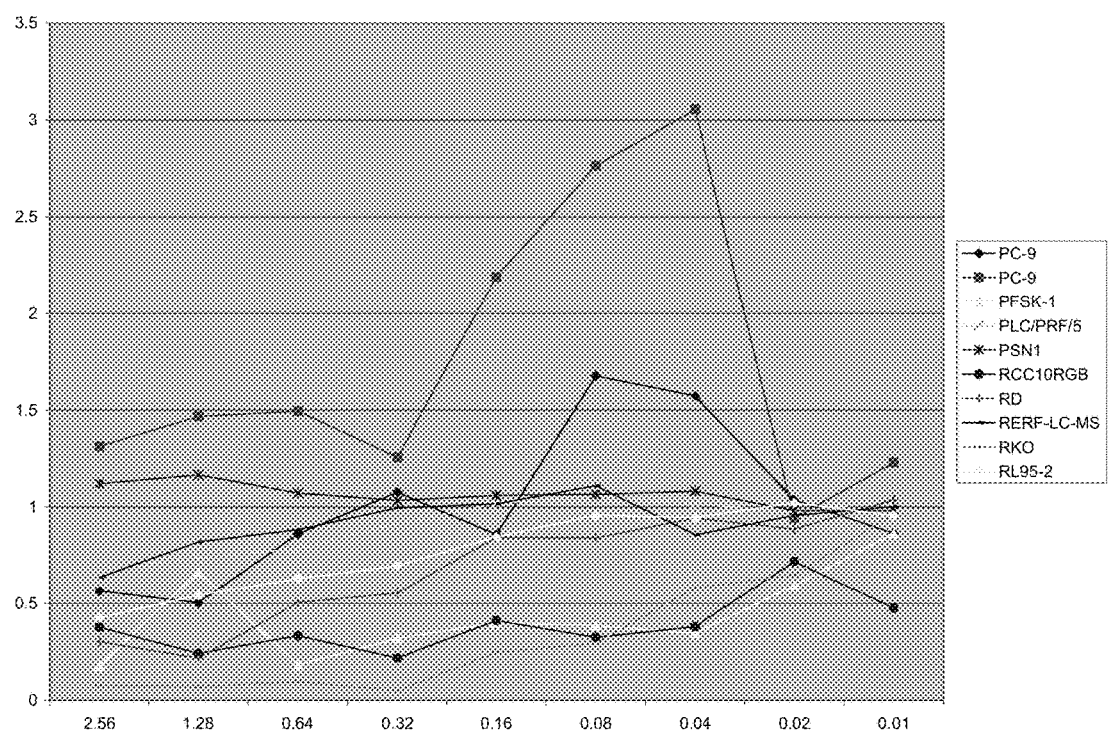
Figure 46:
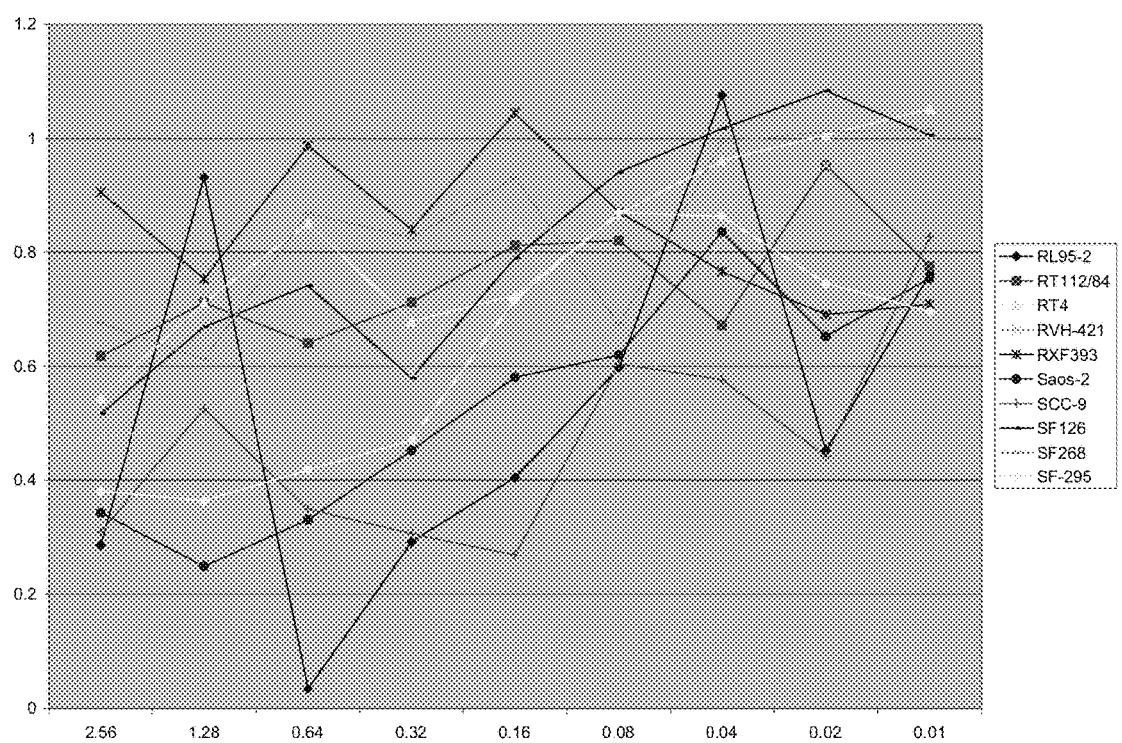
Figure 47:
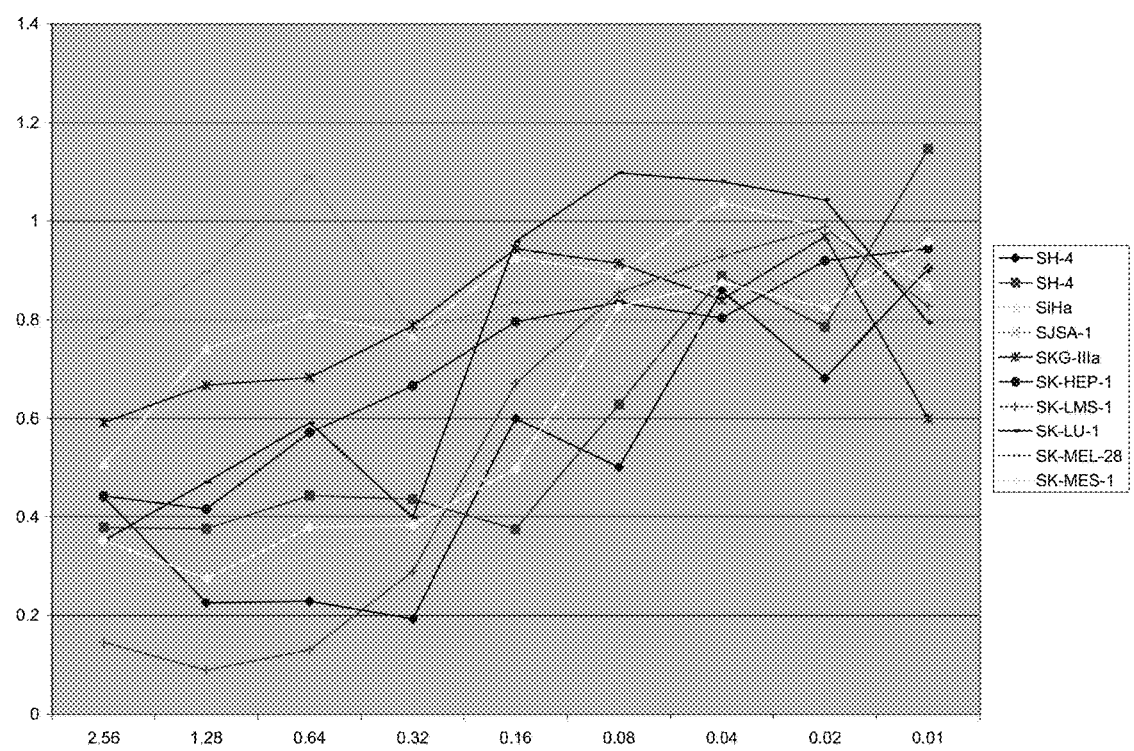
Figure 48:
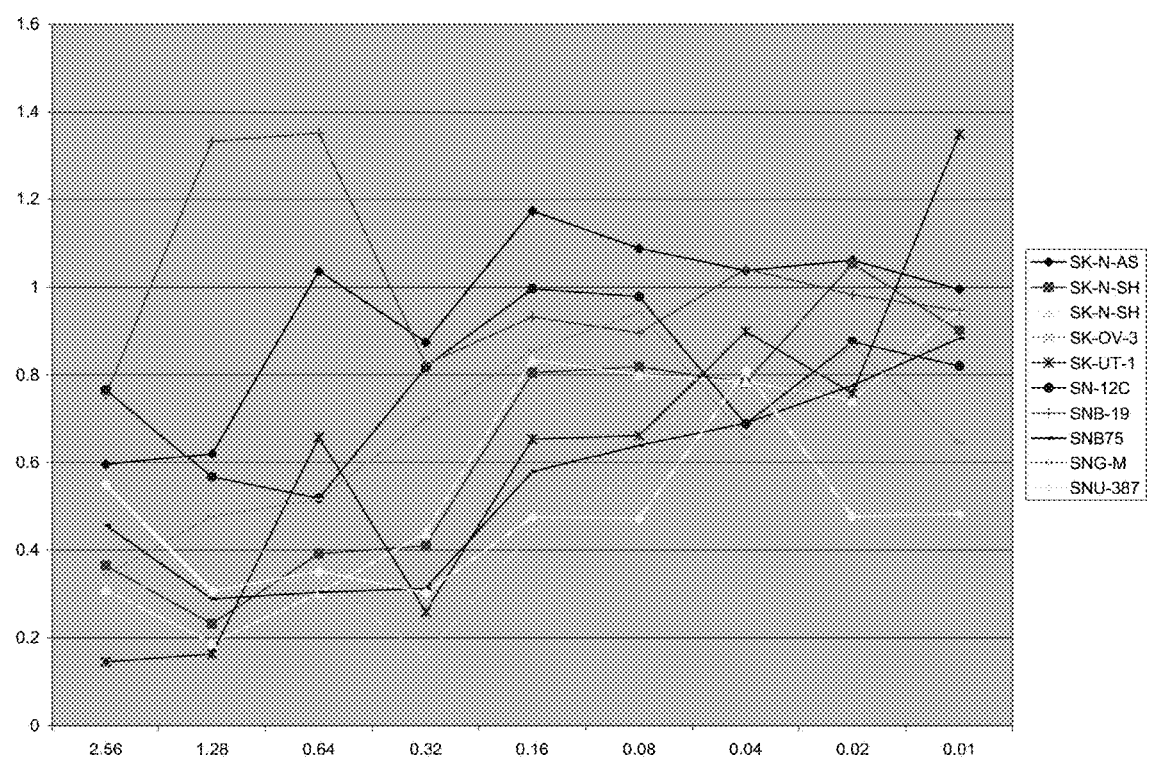
Figure 49:
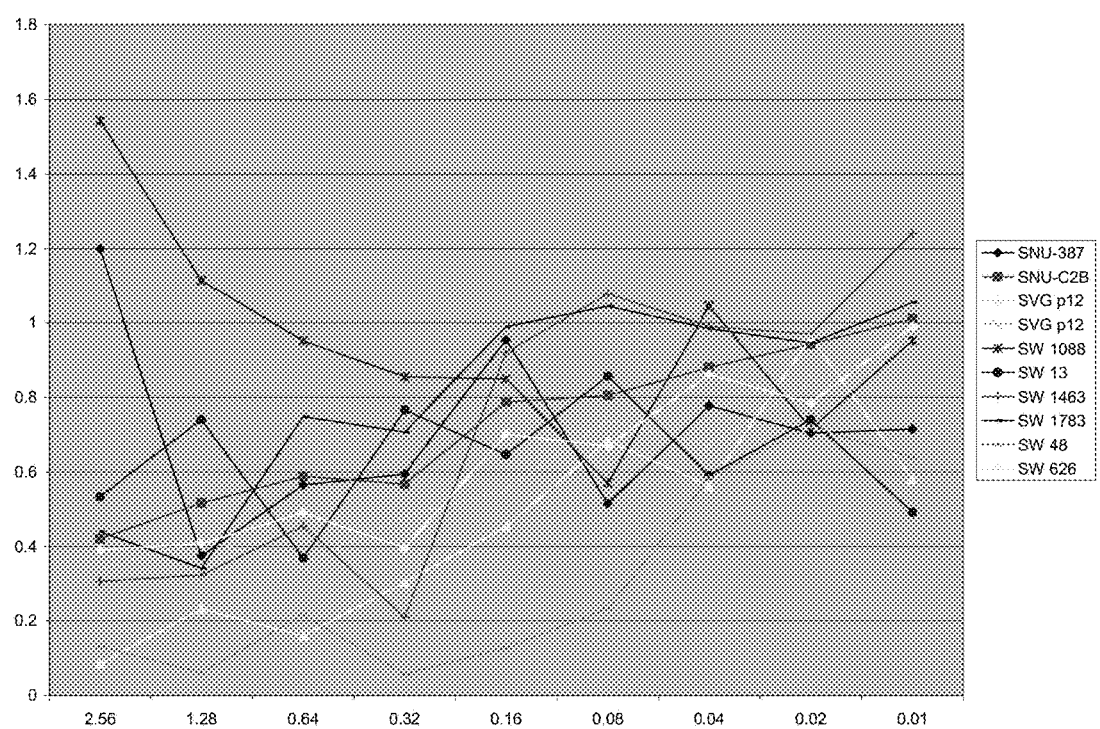
Figure 50:
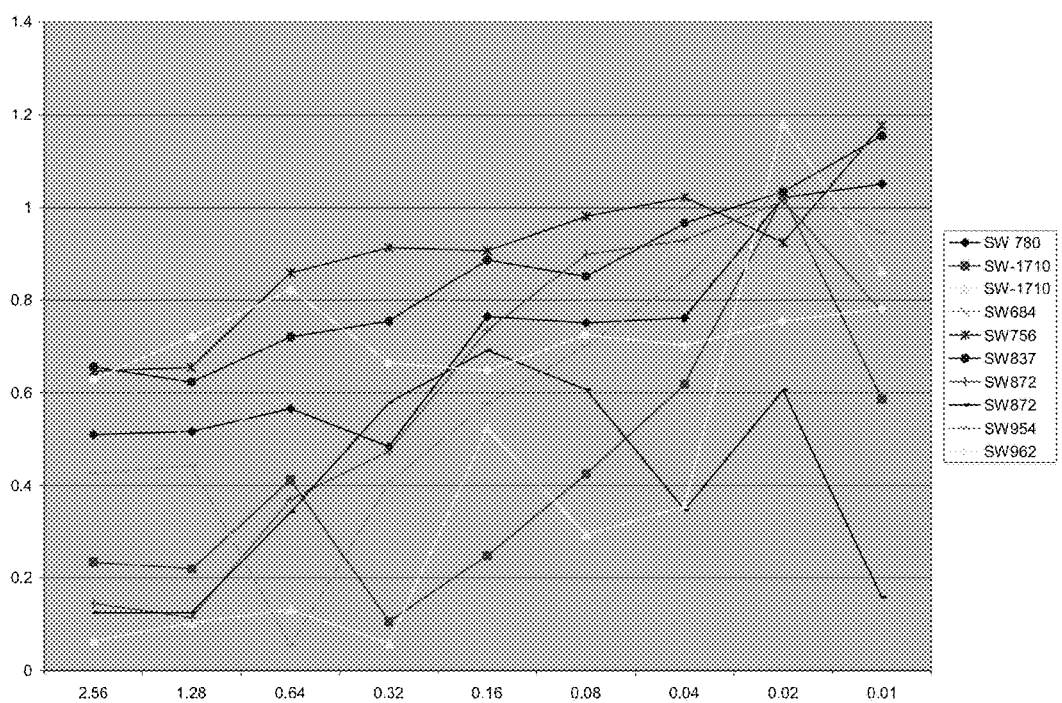
Figure 51:
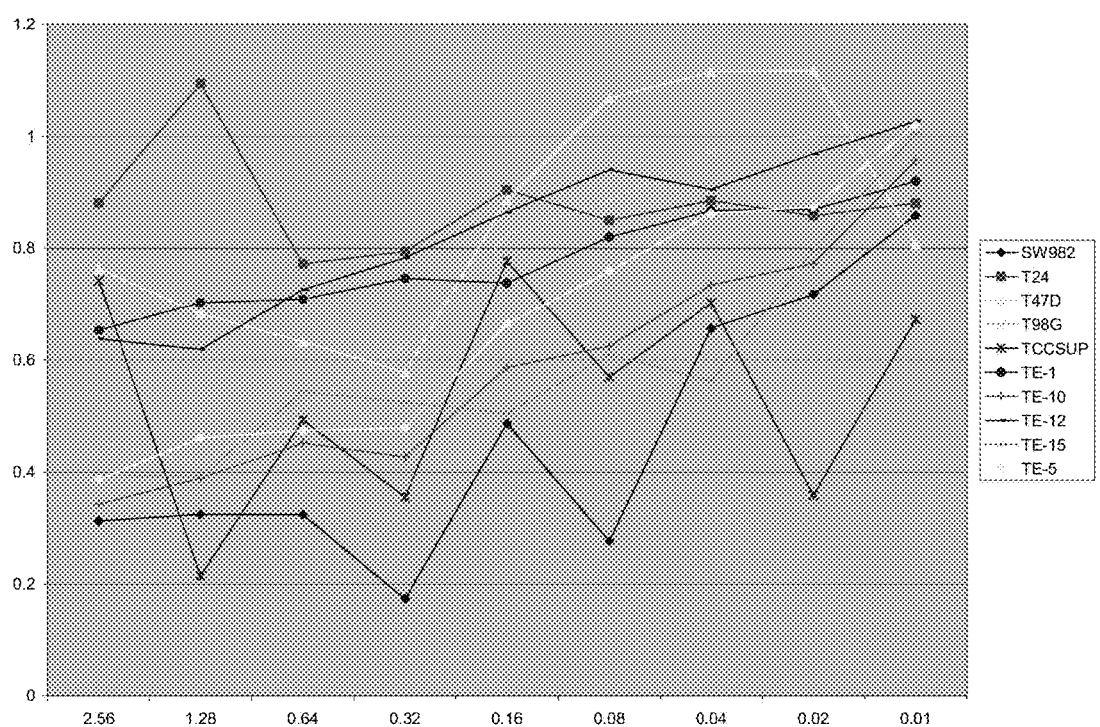
Figure 52:
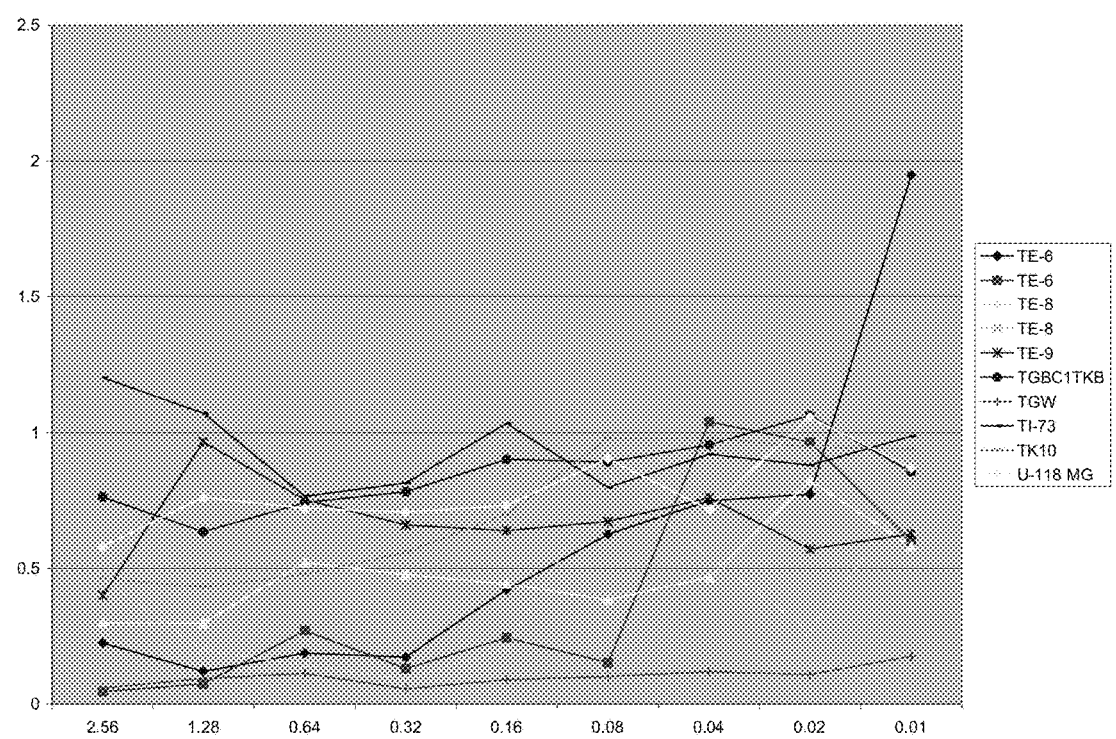
Figure 53:
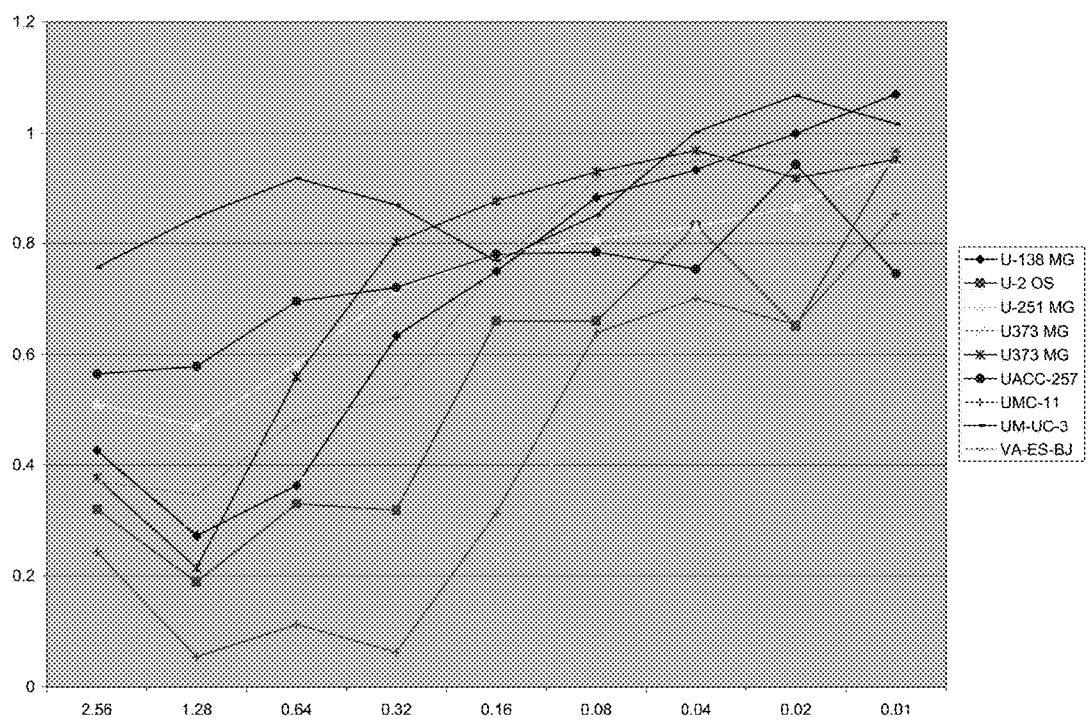
Figure 54:
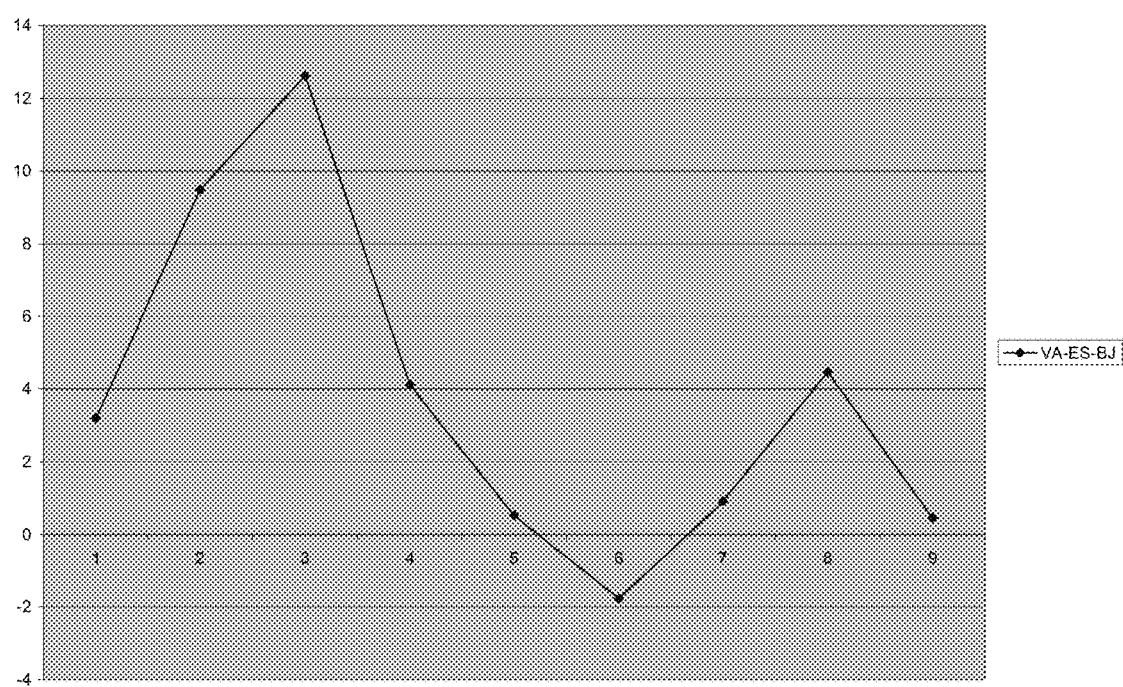
Figure 55:
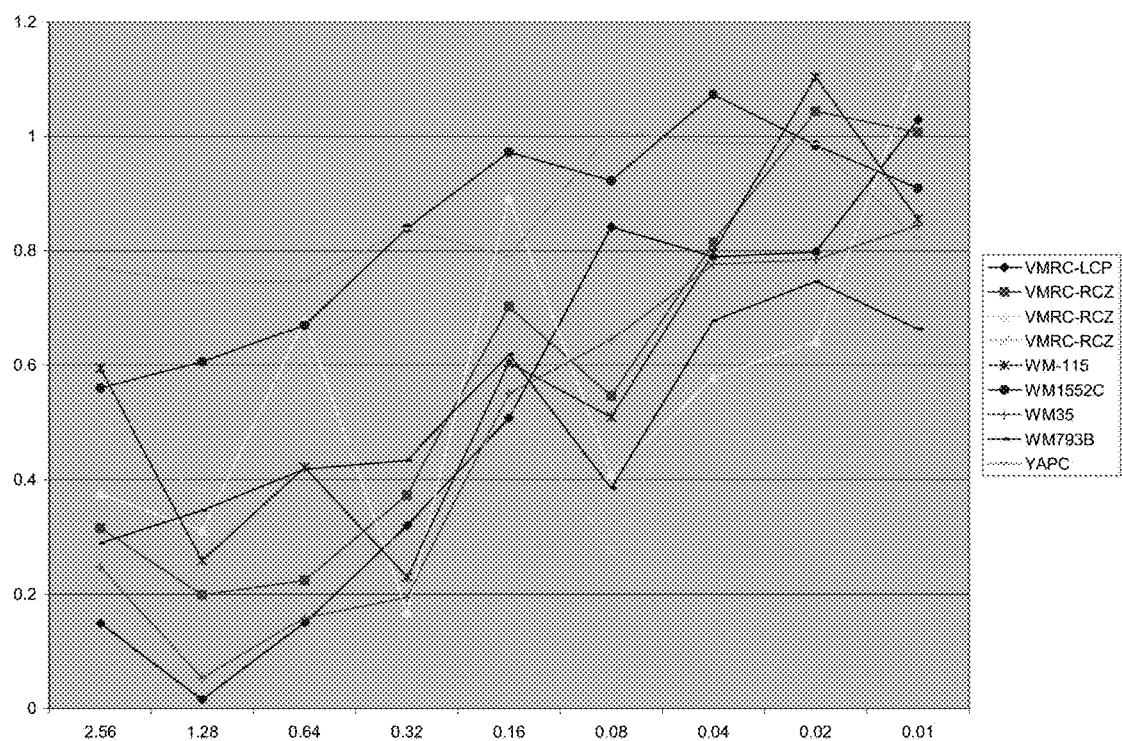

Mice were implanted subcutaneously with BRD3-NUT cells. Tumor measurement data were collected weekly. When the tumors became palpable, the mice were divided into 2 treatment groups (n=10): JQ1 was administered at 50 mg/kg intraperitoneally (IP) 7 days/week and vehicle was administered IP 7 days/week. On day 24 post-injection, five mice from each group were euthanized and tumor samples were collected to be sent for lab analysis. Throughout the remainder of the study tumor samples were collected as mice were sacrificed. For all samples one half of the tumor was fixed in 10% formalin and the other half was flash frozen on dry ice. Treatment ended on day 32. Tumor volume and weights were collected weekly until all mice either became moribund or tumors reached 2 cm in any dimension. FIG. 15A is a graph showing that JQ1 showed in vivo efficacy against BRD3-NUT in a murine xenograph model. Treatment with JQ1 resulted in tumor regression while on therapy. Upon cessation of therapy, tumor growth resumed. Tumor volume differences were significant at all points (p=7.65274E-09 at Day 24). JQ1 was administered at 50 mg/kg. FIG. 15B shows that mice treated with JQ1 showed mild weight loss with rapid recovery after cessation of therapy.

Example 9: JQ1 and Analogs Thereof are Effective Against a Variety of Cancers FIGS. 16A-16D show that JQ1 and derivatives thereof inhibit Brd4.1 and Brd4.2 binding at 5 µM JQ1 (for compound structures, see Table A, above). FIGS. 17A-17D show NUT midline carcinoma (NMC) cell viability following treatment with JQ1 and derivatives thereof at 2 µM compound (for compound structures, see Table A, above). FIGS. 18-55 show dose response viability for a variety of cancer cell lines. These data indicate that JQ1 and derivatives thereof show anti-cancer efficacy against a broad range of cancers.

The results reported herein were obtained using the following methods and materials.

Example 10: Binding Assay Results

Results of a binding assay are shown below at Table C.

TABLE C

| Compound | | Bio-assay IC$_{50}$ (µM) | | Cell-assay IC$_{50}$ (µM) | |
| --- | --- | --- | --- | --- | --- |
| Name | Structure | BRD4(1) | BRD4(2) | 797 cells | 10326 cells |
| (S)-JQ1 | 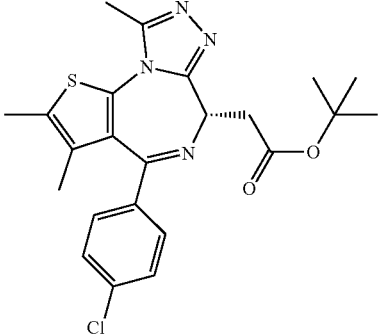 [SMILES: Cc1sc2c(c1C)C(c1ccc(Cl)cc1)=N[C@@H](CC(=O)OC(C)(C)C)c1nnc(C)n1-2] | 0.018 | 0.014 | 0.0056 | 0.0015 |

TABLE C-continued
Bio-assay IC$_{50}$ and Cell-assay IC$_{50}$
| Compound | | Bio-assay IC$_{50}$ (μM) | | Cell-assay IC$_{50}$ (μM) | |
| --- | --- | --- | --- | --- | --- |
| Name | Structure | BRD4(1) | BRD4(2) | 797 cells | 10326 cells |
| (R)-JQ1 | 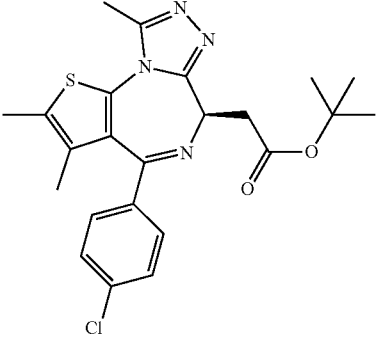 [SMILES: Cc1sc2c(c1C)C(c1ccc(Cl)cc1)=N[C@H](CC(=O)OC(C)(C)C)c1nnc(C)n1-2] | 8,354 | 52,120 | 1,543 | 11.82 |
| JQ6 | 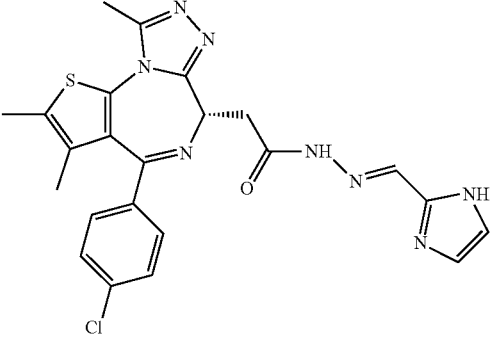 [SMILES: Cc1sc2c(c1C)C(c1ccc(Cl)cc1)=N[C@@H](CC(=O)N/N=C/c1ncc[nH]1)c1nnc(C)n1-2] | 0.00348 | 0.00024 | 0.0010 | 0.000051 |
| JQ8 | 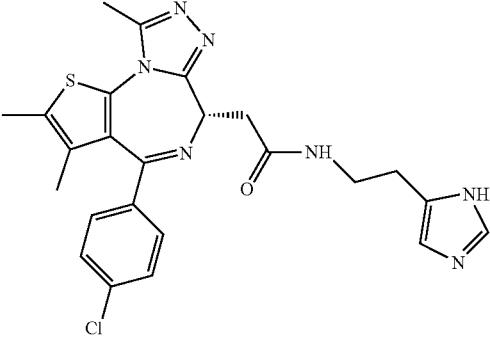 [SMILES: Cc1sc2c(c1C)C(c1ccc(Cl)cc1)=N[C@@H](CC(=O)NCCc1cnc[nH]1)c1nnc(C)n1-2] | 0.002189 | 0.000427 | 0.6 | 0.0028 |
| JQ13 | 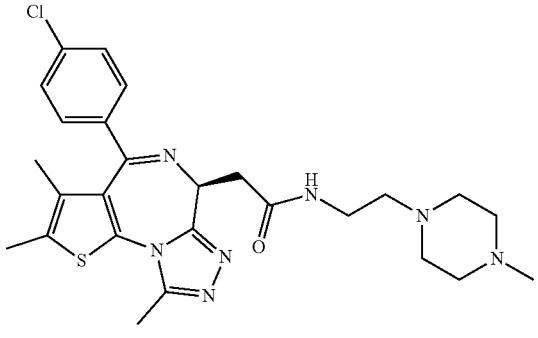 | 0.002493 | 0.0005843 | 10,860 | 0.00000031 |

TABLE C-continued

Bio-assay IC$_{50}$ and Cell-assay IC$_{50}$

| Compound Name | Structure | Bio-assay IC$_{50}$ (μM) BRD4(1) | BRD4(2) | Cell-assay IC$_{50}$ (μM) 797 cells | 10326 cells |
|---|---|---|---|---|---|
| JQ33 | Chemical Formula: C$_{25}$H$_{29}$ClN$_6$O$_2$S; Exact Mass: 512.1761; Molecular Weight: 513.0548 | 0.085 | 0.0295 | 0.00297 | 0.0080 |
| JQ35 | Chemical Formula: C$_{27}$H$_{34}$ClN$_7$OS; Exact Mass: 539.2234; Molecular Weight: 540.1232 | 0.0243 | 0.00613 | 0.00609 | 0.0030 |

Figure 56A:
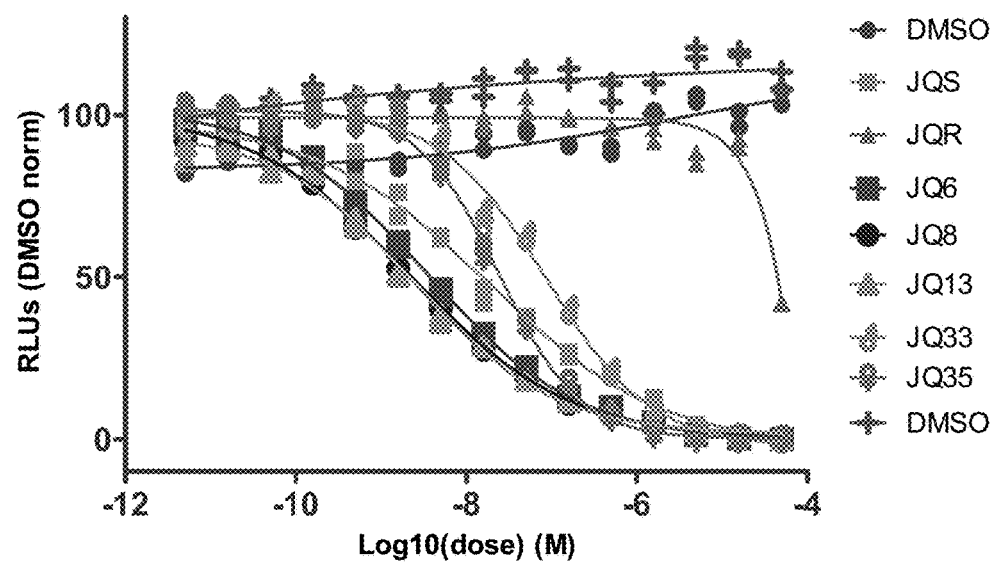
FIGS. 56A-56D are graphs showing results of lead compound binding assays.
Figure 56B:
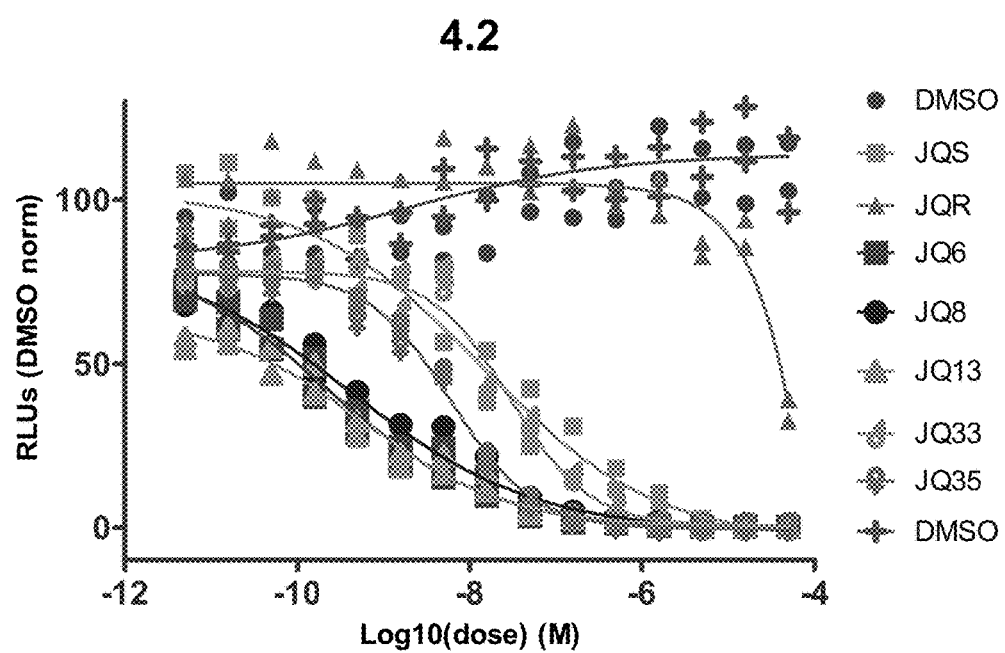

The binding activity of lead compounds with the BRD4 site 1 was determined by Alpha-assay with a 12-point dose response curve (FIG. 56A). Compound (S)-JQ1 (JQS) was used as a positive control. (R)-JQ1 (JQR) was used as a negative control. Compounds JQ6, JQ8, JQ13, JQ33 and JQ35 exhibited excellent binding activity. The results of binding activity of all lead compounds with the BRD4 site 2 was also determined by Alpha-assay with a 12-point dose response curve (FIG. 56B). Compounds JQ6, JQ8, JQ13, JQ33 and JQ35 exhibited excellent binding activity.

Figure 56C:
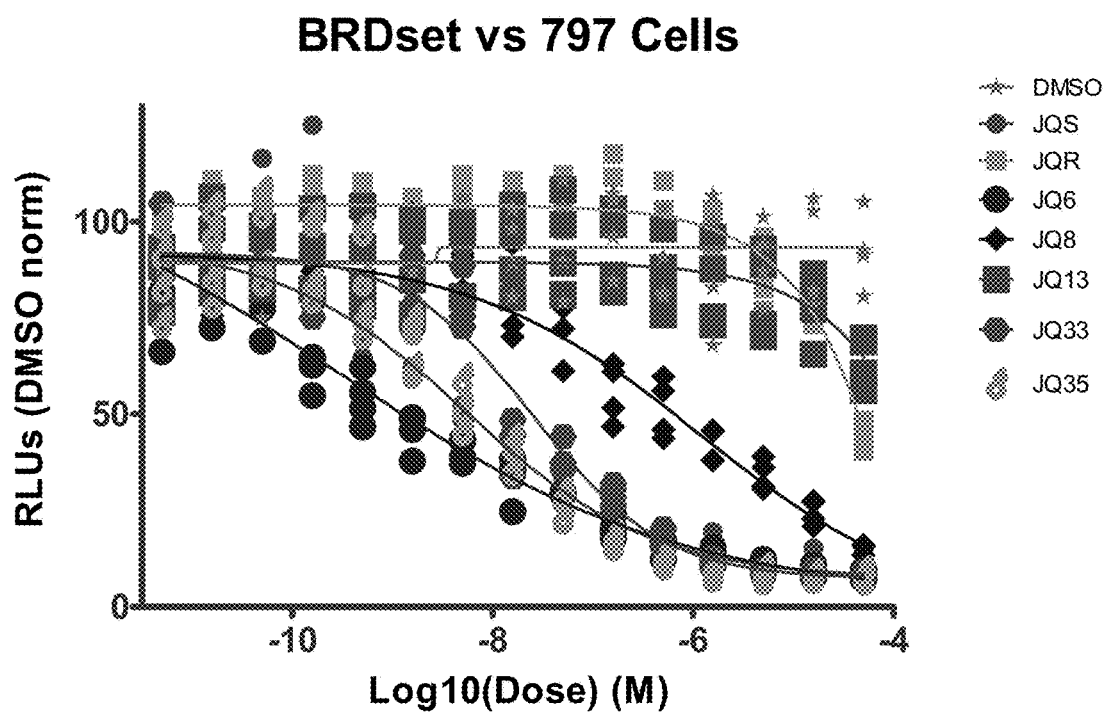
Figure 56D:
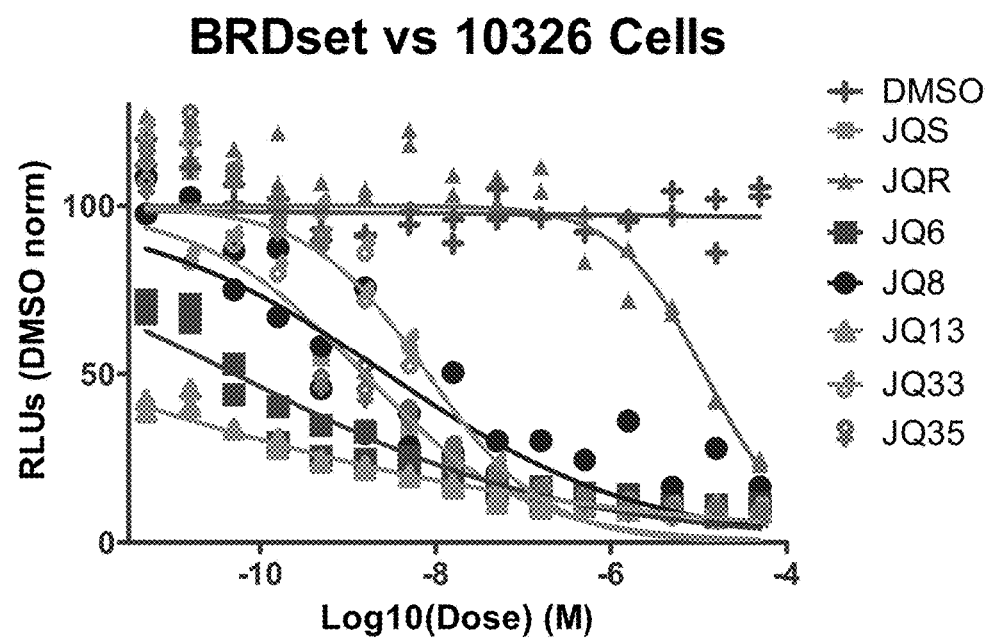

The activity of the lead compounds was examined in a cell-assay with the 797 cell line (derived from patient) to determine the growth effects of BRD4 inhibition on BRD4-NUTdependent cell lines. Cells were incubated with compounds and monitored for proliferation after 72 hours. Curve fit was calculated by logistical regression (FIG. 56C). All the lead compounds were examined in cell-assays with 10326 cell line that directly derived from a patient to determine the growth effects of BRD4 inhibition on BRD4-NUTdependent cell lines (FIG. 56D). Cells were incubated with compounds and monitored for proliferation after 72 hours. Curve fit was calculated by logistical regression.

Reagents.

Endogenous BRD4-NUT-expressing midline carcinoma cell lines, 797[1] and PER-403[2], were described previously. The non-NMC human squamous carcinoma cell lines TE10 and TT were obtained from Drs. Anil Rustgi (University of Pennsylvania) and Adam Bass (Dana-Farber Cancer Institute). U2OS cells were obtained from the ATCC. Mammalian overexpression constructs for GFP-BRD4, GFP-NUT and GFP-BRD4-NUT have been previously described[3]. Media, trypsin, and antibiotics for tissue culture were purchased from Mediatech. Antibodies and stains for immunohistochemistry and flow cytometry were obtained from Dako (Cytokeratin AE1/AE3 antibody Cat# N1590), Millipore (TUNEL Cat# S7100), Vector (Ki67 Cat#VP-RM04), Cell Signaling Technologies (NUT Cat#3625), BD Pharmingen (Annexin V-FITC Cat#556547) and Invitrogen (propidium iodide Cat# P3566).

Acetyl-Histone Binding Assay.

Assays were performed as described previously[8] with minor modifications from the manufacturer's protocol (PerkinElmer, USA). All reagents were diluted in 50 mM HEPES, 100 mM NaCl, 0.1% BSA, pH 7.4 supplemented with 0.05% CHAPS and allowed to equilibrate to room temperature prior to addition to plates. A 24-point 1:2 serial dilution of the ligands was prepared over the range of 150-0 μM and 4 μl transferred to low-volume 384-well plates (ProxiPlate™-384 Plus, PerkinElmer, USA), followed by 4 μl of HIS-tagged protein (BRD4/1, 250 nM, BRD4/2 and CREBBP, 2000 nM). Plates were sealed and incubated at room temperature for 30 minutes, before the addition of 4 μl of biotinylated peptide at equimolar concentration to the protein [peptide for BRD4(1) & BRD4(2): H4K5acK8acK12acK16ac, H-SGRGK(Ac)GGK(Ac)GLGK(Ac)GGAK(Ac)RHRK(Biotin)-OH (SEQ ID NO: 5); peptide for CREBBP: H3K36ac, Biotin-KSAPATGGVK(Ac)KPHRYRPGT-OH (SEQ ID NO: 6) (Cambridge Research Biochemicals, UK)]. Plates were sealed and incubated for a further 30 minutes, before the addition of 4 μl of streptavidin-coated donor beads (25 μg/ml) and 4 μl nickel chelate acceptor beads (25 μg/ml) under low light conditions. Plates were foil-sealed to protect from light, incubated at room temperature for 60 minutes and read on a PHERAstar FS plate reader (BMG Labtech, Germany) using an AlphaScreen 680 excitation/570 emission filter set. IC$_{50}$ values were calculated in Prism 5 (GraphPad Software, USA) after normalization against corresponding DMSO controls and are given as the final concentration of compound in the 20 μl reaction volume.

Sequence Alignment.

Amino acid sequences for full length human bromodomains were obtained from the NCBI (BRD2 Acession No. NP_005095, BRD3 Acession No. NP_031397.1, BRD4 Acession No. NP_055114.1, BRD-T Acession No. NP_001717.2). Multiple sequence alignment of individual bromodomains was performed using ClustalW[19].

Fluorescence Recovery After Photobleaching (FRAP).

FRAP studies were performed on U2OS cells as previously described[3,20]. In brief, U2OS cells were transfected (lipofectamine; Invitrogen) with mammalian overexpression constructs encoding GFP chimera with BRD4, NUT and BRD4-NUT. A 5 μm$^2$ nuclear region was bleached with high laser intensity in one cell within each field, and measured for recovery with low laser intensity and a 150 μm pinhole. Images of identical fields were acquired using a Nikon C1 Plus confocal microscope equipped with a 37° C. heated chamber and FRAP modules over 90 seconds. Average intensities of the bleached region were measured over time and using MetaMorph v7, and normalized to an independent region of interest before bleaching. Data were then analyzed to assess the time to half-maximal fluorescence recovery in Microsoft Excel Mac 12.2.4.

Differentiation and Proliferation Immunohistochemistry.

Cultured cancer cell lines (797, Per403, TT and TE10) were grown in chamber slides at $1.0 \times 10^4$ cells per chamber (4-chamber slides) or $5.0 \times 10^3$ cells per chamber (8-chamber slides). Cells were treated with JQ1-racemic, (+)-JQ1, (−)-JQ1, or vehicle (DMSO) and incubated for various time intervals. Media was then removed and chambers were washed with cold PBS. Cells were then fixed in 4% formaldehyde for 20 minutes at 4° C., washed with PBS and transferred to the Dana-Farber/Harvard Cancer Center (DF/HCC) Specialized Histopathology Services Core at Brigham and Women's Hospital for staining, as described below. Immunohistochemical studies of cell pellets were performed by first growing cancer cell lines (797 and Per403) in T-75 flasks, treated with either JQ1 or vehicle (DMSO) for 48 hours. Cells were then trypsinized and cell pellets were formed by centrifugation at 2,000 rpm for 10 minutes, stabilized with ½ volume of HistoGel (Richard-Allen Scientific) and 10% bovine serum albumin. Cell pellets were washed with PBS and fixed in 4% formaldehyde for 20 minutes at 4° C. The cells were then washed with PBS and transferred to the DF/HCC Core Laboratory at the Brigham and Women's Hospital for staining, as described below. Quantitative analysis of Ki67 staining (cell scoring) was performed by light microscopy using five high-powered (40×) fields-of-view per experiment. All fixed material was embedded, sectioned and stained by the DF/HCC Core Laboratory at Brigham and Women's Hospital, using established optimized protocols. Images were obtained using an Olympus BX40 microscope (Olympus Imaging America, Center Valley, Pa.) and a Micropublisher 3.3 RTV color camera (QImaging, Surrey, BC).

Cell Proliferation Assay.

Cells were seeded into white, 384-well microtiter plates (Nunc) at 500 cells per well in a total volume of 50 μL media. The 797, TT and TE10 cells were grown in DMEM containing 1% penicillin/streptomycin and 10% FBS. The Per403 cells were grown in DMEM containing 1% penicillin/streptomycin and 20% FBS. Compounds were delivered to microtiter assay plates by robotic pin transfer (PerkinElmer JANUS equipped with a V&P Scientific 100 nL pin tool). Following a 48 h incubation at 37° C., cells were lysed and wells were assessed for total ATP content using a commercial proliferation assay (Cell TiterGlo; Promega). Replicate measurements were analyzed with respect to dose and estimates of $IC_{50}$ were calculated by logistic regression (GraphPad Prism).

Flow Cytometry.

Cultured human cancer cells (797, Per403, TT and TE10) were grown in 6-well tissue culture plates (BD Falcon) at a starting concentration of $5.0 \times 10^4$ cells per well. Cells were treated with JQ1 (500 nM), staurosporine (50 nM) or vehicle (DMSO 0.05%) for 24 or 48 hours. Trypsinized cells were mixed 1:1 on ice with Annexin-V/propidium iodide buffer (10 mM HEPES pH 7.4, 140 mM NaCl, 2.5 mM CaCl2) containing Annexin V-FITC (BD Pharmingen, 1:500) and propidium iodide (Invitrogen, 1:1000). Samples were immediately analyzed on a BD FACS Canto II. Visualizations and analyses of apoptotic fractions were generated using FlowJo flow cytometry analysis software (Tree Star, Inc.).

Xenograft Efficacy Studies.

NMC xenografts were established by injecting 797 NMC cells ($10^7$) in 30% Matrigel (BD Biosciences) into the flank of 6 week-old female NCr nude mice (Charles River Laboratories). Twelve days after injection, mice with measureable tumors were divided into cohorts to be treated with JQ1 at 50 mg/kg IP or vehicle (5% DMSO in 5% dextrose). The average size of tumors in the JQ1 treatment group (n=8) and vehicle group (n=7) were similar (63.8+/−17.1 and 73.6+/−14.4 mm3 respectively) at the start of treatment. Animals were followed daily for clinical symptoms. Tumor measurements were assessed by caliper measurements, and volume calculated using the formula Vol=$0.5 \times L \times W^2$. After 2 weeks of treatment, all mice were humanely euthanized, and tumors were fixed in 10% formalin for histopathological examination. Statistical significance of tumor volumes was calculated by two-sided Students t-test. All animal studies were approved by the IACUC of the DFCI.

Instrumentation.

Proton and carbon-13 nuclear magnetic resonance ($^1$H NMR and $^{13}$C NMR) spectra were recorded with a Varian inverse probe 600 INOVA spectrometer at the Harvard Medical School East Quad NMR Facility. Chemical shifts are recorded in parts per million on the δ scale and are referenced from the residual protium in the NMR solvent (CHCl$_3$: δ 7.24) for $^1$H NMR, the carbon resonances of the solvent (CDCl$_3$: δ 77.2) for $^{13}$C NMR respectively. Data is reported as follows: chemical shift [multiplicity (s=singlet, d=doublet, t=triplet, q=quartet, m=multiplet, br=broad), coupling constant(s) in Hertz, integration]. High resolution mass spectra (HRMS) were recorded on a Bruker APEX 4.7 Tesler FTMS spectrometer using eletronspray ion source (ESI) at the Instrumentation Facility of the Department of Chemistry, Massachusetts Institute of Technology. The intermediates and final product were purified with a CombiFlash RF system (Teledyne Isco). Organic solutions were concentrated on Büchi R-205 rotary evaporators. The enantiomeric purities were checked with Berger Supercritical Fluid Chromatography (SFC) and an AS-H column. The enantiomeric preparative purification was performed with Agilent High Pressure Liquid Chromatography and an OD-H column (Broad Institute of Harvard and MIT).

REFERENCES

1 Ptashne, M. Binding reactions: epigenetic switches, signal transduction and cancer. *Curr Biol* 19, R234-241, (2009).

2 Schreiber, S. L. & Bernstein, B. E. Signaling network model of chromatin. *Cell* 111, 771-778, (2002).
3 Marushige, K. Activation of chromatin by acetylation of histone side chains. *Proc Natl Acad Sci USA* 73, 3937-3941, (1976).
4 Dey, A., Nishiyama, A., Karpova, T., McNally, J. & Ozato, K. Brd4 marks select genes on mitotic chromatin and directs postmitotic transcription. *Mol Biol Cell* 20, 4899-4909, (2009).
5 Owen, D. J. et al. The structural basis for the recognition of acetylated histone H4 by the bromodomain of histone acetyltransferase gcn5p. *Embo J* 19, 6141-6149, (2000).
6 Zeng, L. & Zhou, M. M. Bromodomain: an acetyl-lysine binding domain. *FEBS Lett* 513, 124-128, (2002).
7 Yang, X. J. Multisite protein modification and intramolecular signaling. *Oncogene* 24, 1653-1662, (2005).
8 Yang, Z. et al. Recruitment of P-TEFb for stimulation of transcriptional elongation by the bromodomain protein Brd4. *Mol Cell* 19, 535-545, (2005).
9 Phelps, M. A. et al. Clinical response and pharmacokinetics from a phase 1 study of an active dosing schedule of flavopiridol in relapsed chronic lymphocytic leukemia. *Blood* 113, 2637-2645, (2009).
10 Rahl, P. B. et al. c-Myc Regulates Transcriptional Pause Release. *Cell* 141, 4323-4445, (2010).
11 Yang, Z., He, N. & Zhou, Q. Brd4 recruits P-TEFb to chromosomes at late mitosis to promote G1 gene expression and cell cycle progression. *Mol Cell Biol* 28, 967-976, (2008).
12 Mochizuki, K. et al. The bromodomain protein Brd4 stimulates G1 gene transcription and promotes progression to S phase. *J Biol Chem* 283, 9040-9048, (2008).
13 You, J. et al. Regulation of aurora B expression by the bromodomain protein Brd4. *Mol Cell Biol* 29, 5094-5103, (2009).
14 Huang, B., Yang, X. D., Zhou, M. M., Ozato, K. & Chen, L. F. Brd4 coactivates transcriptional activation of NF-kappaB via specific binding to acetylated RelA. *Mol Cell Biol* 29, 1375-1387, (2009).
15 French, C. A., Miyoshi, I., Aster, J. C. & et al. BRD4 bromodomain gene rearrangement in aggressive carcinoma with translocation t (15; 19). *Am J Pathol* 159(6), 1987-1992, (2001).
16 French, C. A. et al. BRD4-NUT fusion oncogene: a novel mechanism in aggressive carcinoma. *Cancer Res* 63, 304-307, (2003).
17 French, C. A. et al. BRD-NUT oncoproteins: a family of closely related nuclear proteins that block epithelial differentiation and maintain the growth of carcinoma cells. *Oncogene* 27, 2237-2242, (2008).
18 Miyoshi, S., Ooike, S., Iwata, K., Hikawa, H. & Sugaraha, K. ANTITUMOR AGENT. (2009).
19 Adachi, K. et al. (2006).
20 Sueoka, H., Komatsu, H., Kobayashi, H. & Ehara, S. Thienotriazolodiazepine compounds and medicinal uses thereof. (1998).
21 VonVoigtlander, P. F. & Straw, R. N. Alprazolam: Review of Pharmacological, Pharmacokinetic and Clinical Data. *Drug Development Research* 6, 1-12, (1985).
22 Niesen, F. H., Berglund, H. & Vedadi, M. The use of differential scanning fluorimetry to detect ligand interactions that promote protein stability. *Nat Protoc* 2, 2212-2221, (2007).
23 Fedorov, O. et al. A systematic interaction map of validated kinase inhibitors with Ser/Thr kinases. *Proc Natl Acad Sci USA* 104, 20523-20528, (2007).
24 Bullock, A. N. et al. Structural basis of inhibitor specificity of the human protooncogene proviral insertion site in moloney murine leukemia virus (PIM-1) kinase. *J Med Chem* 48, 7604-7614, (2005).
25 Quinn, A. M. et al. A homogeneous method for investigation of methylation-dependent protein-protein interactions in epigenetics. *Nucleic Acids Res* 38, e11, (2010).
26 Vollmuth, F., Blankenfeldt, W. & Geyer, M. Structures of the dual bromodomains of the P-TEFb-activating protein Brd4 at atomic resolution. *J Biol Chem* 284, 36547-36556, (2009).
27 French, C. A. Molecular pathology of NUT midline carcinomas. *J Clin Pathol*, (2008).
28 Huang, M. E. et al. Use of all-trans retinoic acid in the treatment of acute promyelocytic leukemia. *Blood* 72, 567-572, (1988).
29 Druker, B. J. et al. Efficacy and safety of a specific inhibitor of the BCR-ABL tyrosine kinase in chronic myeloid leukemia. *N Engl J Med* 344, 1031-1037, (2001).
Haack, H. et al. Diagnosis of NUT Midline Carcinoma Using a NUT-specific Monoclonal Antibody. *Am J Surg Pathol*, (2009).
31 Buchdunger, E. et al. Selective inhibition of the platelet-derived growth factor signal transduction pathway by a protein-tyrosine kinase inhibitor of the 2-phenylaminopyrimidine class. *Proc Natl Acad Sci USA* 92, 2558-2562, (1995).
32 Buchdunger, E. et al. Inhibition of the Abl protein-tyrosine kinase in vitro and in vivo by a 2-phenylaminopyrimidine derivative. *Cancer Res* 56, 100-104, (1996).
33 Schindler, T. et al. Structural mechanism for STI-571 inhibition of abelson tyrosine kinase. *Science* 289, 1938-1942, (2000).
34 Druker, B. J. et al. Effects of a selective inhibitor of the Abl tyrosine kinase on the growth of Bcr-Abl positive cells. *Nat Med* 2, 561-566, (1996).
35 le Coutre, P. et al. In vivo eradication of human BCR/ABL-positive leukemia cells with an ABL kinase inhibitor. *J Natl Cancer Inst* 91, 163-168, (1999).
36 Kadota, M. et al. Identification of novel gene amplifications in breast cancer and coexistence of gene amplification with an activating mutation of PIK3CA. *Cancer Res* 69, 7357-7365, (2009).
37 Crawford, N. P. et al. Bromodomain 4 activation predicts breast cancer survival. *Proc Natl Acad Sci USA* 105, 6380-6385, (2008).
38 You, J. et al. Kaposi's sarcoma-associated herpesvirus latency-associated nuclear antigen interacts with bromodomain protein Brd4 on host mitotic chromosomes. *J Virol* 80, 8909-8919, (2006).
39 Abbate, E. A., Voitenleitner, C. & Botchan, M. R. Structure of the papillomavirus DNA-tethering complex E2:Brd4 and a peptide that ablates HPV chromosomal association. *Mol Cell* 24, 877-889, (2006).
40 Cole, P. A. Chemical probes for histone-modifying enzymes. *Nat Chem Biol* 4, 590-597, (2008).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application is related to U.S. Provisional Patent Applications Nos. 61/334,991, filed May 14, 2010; 61/370,745, filed Aug. 4, 2010; and 61/375,863, filed Aug. 22, 2010. The contents of each of these applications are incorporated herein by reference.

All patents and publications mentioned in this specification are herein incorporated by reference to the same extent as if each independent patent and publication was specifically and individually indicated to be incorporated by reference.

What is claimed is:

1. A method of treating a condition in a subject in need thereof, the method comprising administering to the subject an effective amount of a compound of formula III:

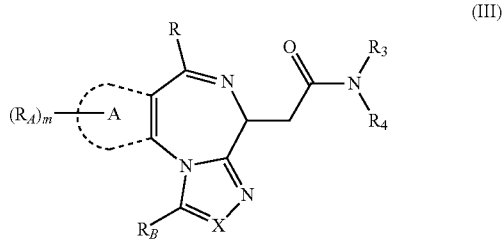

wherein
X is N or $CR_5$;
  $R_5$ is H, alkyl, cycloalkyl, heterocycloalkyl, aryl, or heteroaryl, each of which is optionally substituted;
  $R_B$ is H, alkyl, hydroxylalkyl, aminoalkyl, alkoxyalkyl, haloalkyl, hydroxy, alkoxy, or —COO—$R_3$, each of which is optionally substituted; ring A is aryl or heteroaryl;
  each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
  R is alkyl, cycloalkyl, heterocycloalkyl, aryl, or heteroaryl, each of which is optionally substituted;
  each $R_3$ is independently selected from the group consisting of:
    (i) H, aryl, substituted aryl, heteroaryl, or substituted heteroaryl;
    (ii) heterocycloalkyl or substituted heterocycloalkyl;
    (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
    (iv) $NH_2$, N=$CR'_4R_6$;
  $R_4$ and $R'_4$, each independently is H, alkyl, cycloalkyl, heterocycloalkyl, aryl, or heteroaryl, each of which is optionally substituted; or
  $R_3$ and $R_4$ are taken together with the nitrogen atom to which they are attached to form a 4-10-membered ring;
  $R_6$ is alkyl, alkenyl, cycloalkyl, cycloalkenyl, heterocycloalkyl, aryl, or heteroaryl, each of which is optionally substituted; or
  $R'_4$ and $R_6$ are taken together with the carbon atom to which they are attached to form a 4-10-membered ring;
  m is 0, 1, 2, or 3;
  provided that:
    (a) if ring A is thienyl, X is N, R is phenyl or substituted phenyl, and $R_B$ is methyl, then $R_3$ and $R_4$ are not taken together with the nitrogen atom to which they are attached to form a morpholino ring; and
    (b) if ring A is thienyl, X is N, R is substituted phenyl, $R_B$ is methyl, and one of $R_3$ and $R_4$ is H, then the other of $R_3$ and $R_4$ is not methyl, hydroxyethyl, alkoxy, phenyl, substituted phenyl, pyridyl or substituted pyridyl; and
  or a salt, solvate or hydrate thereof,
wherein the condition is selected from Ewing's sarcoma, medulloblastoma, mesothelioma, pancreatic cancer, small cell lung cancer, or melanoma.

2. The method of claim 1, wherein R is aryl or heteroaryl, each of which is optionally substituted.

3. The method of claim 2, wherein R is phenyl or pyridyl, each of which is optionally substituted.

4. The method of claim 2, wherein R is p-Cl-phenyl, o-Cl-phenyl, m-Cl-phenyl, p-F-phenyl, o-F-phenyl, m-F-phenyl or pyridinyl.

5. The method of claim 1, wherein $R_3$ is H, $NH_2$, or N=$CR'_4R_6$.

6. The method of claim 1, wherein $R_4$ and $R'_4$, each independently, is H, alkyl, cycloalkyl, heterocycloalkyl, aryl, heteroaryl; each of which is optionally substituted.

7. The method of claim 1, wherein $R_6$ is alkyl, alkenyl, cycloalkyl, cycloalkenyl, heterocycloalkyl, aryl, or heteroaryl, each of which is optionally substituted.

8. The method of claim 1, wherein the compound is represented by the formula:

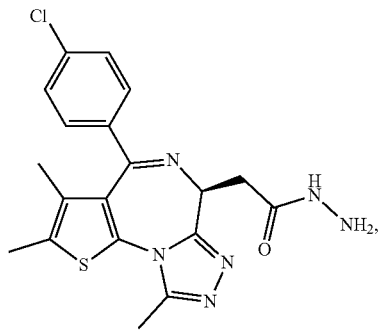

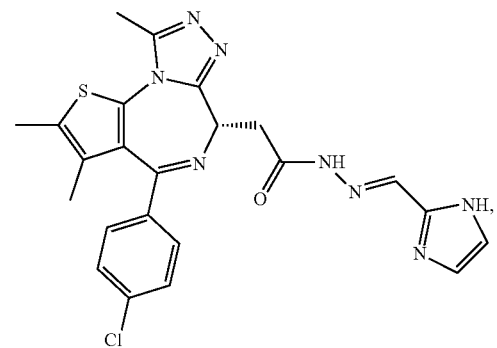

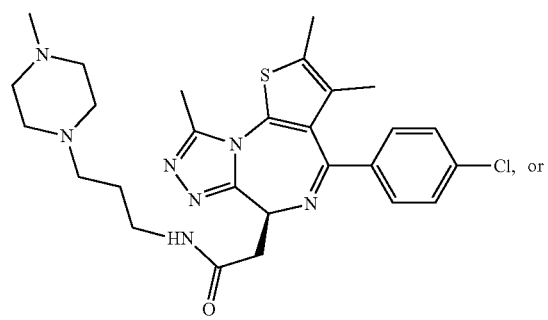

-continued
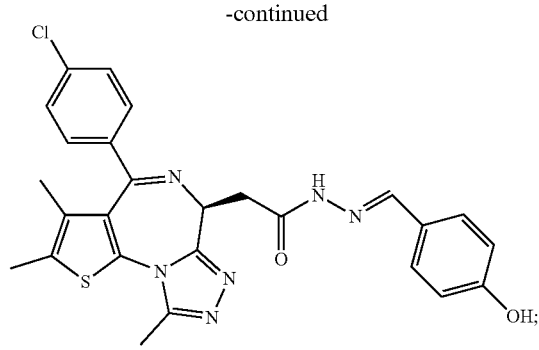
or a salt, solvate or hydrate thereof.
9. The method of claim 1, wherein the compound is represented by a structural formula selected from:
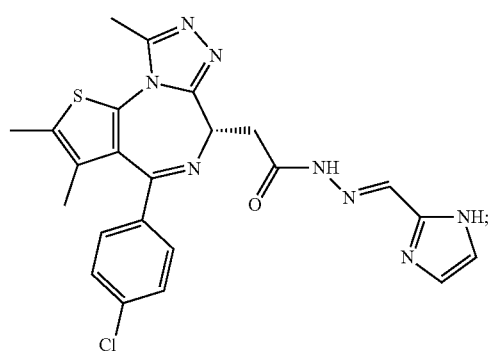
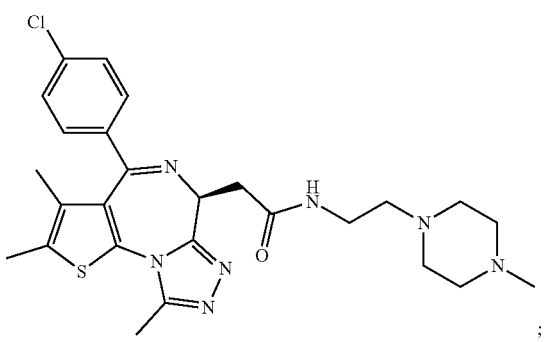
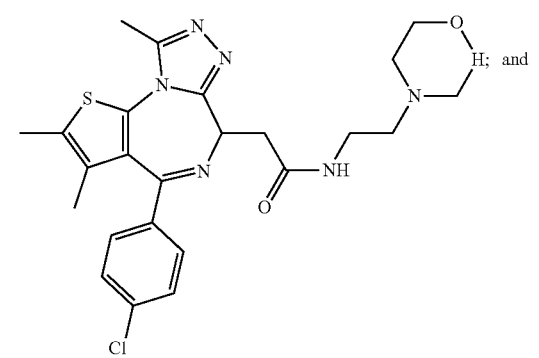
-continued
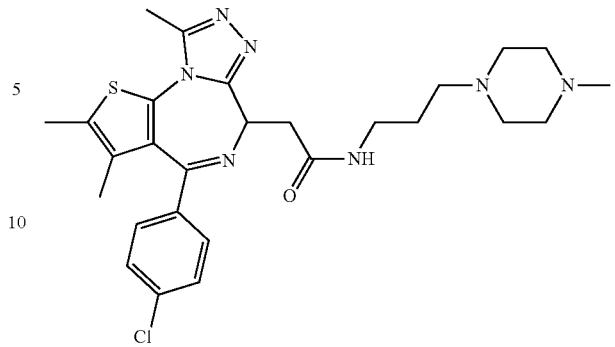
or a pharmaceutically acceptable salt thereof.
10. The method of claim 1, wherein the compound is represented by a structural formula selected from:
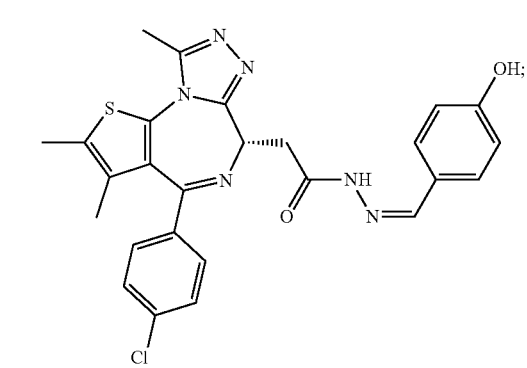
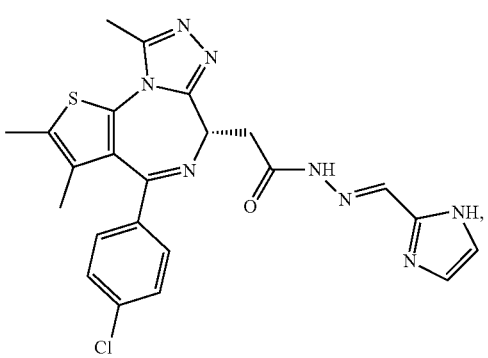

183
-continued

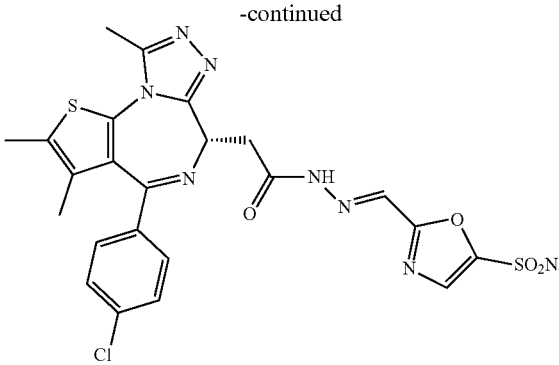

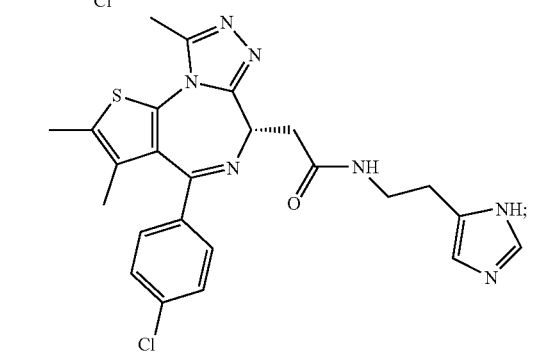

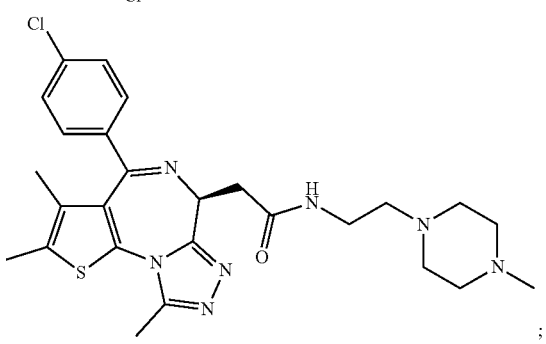

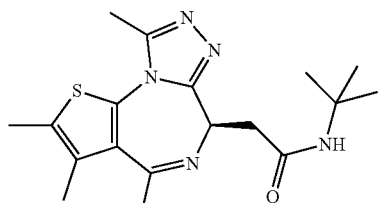

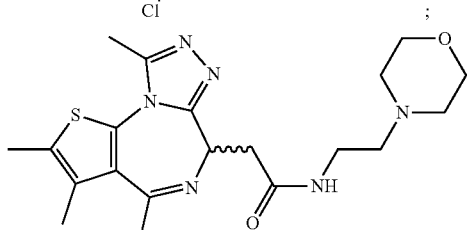

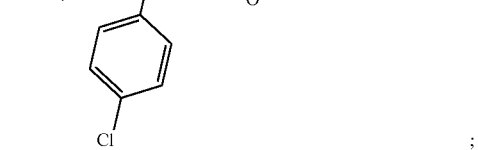
;

184
-continued

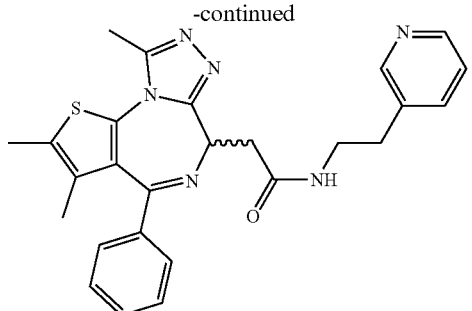
;

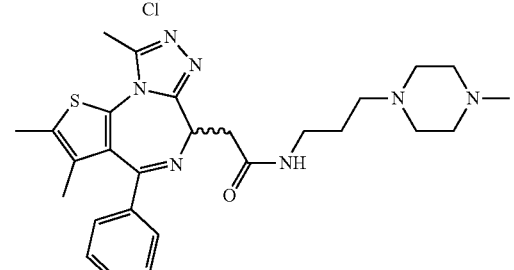
;

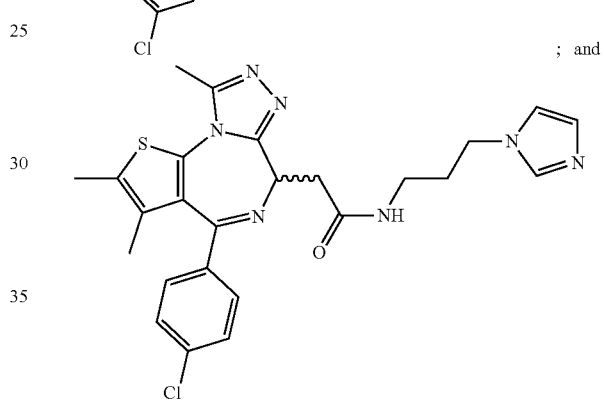
; and

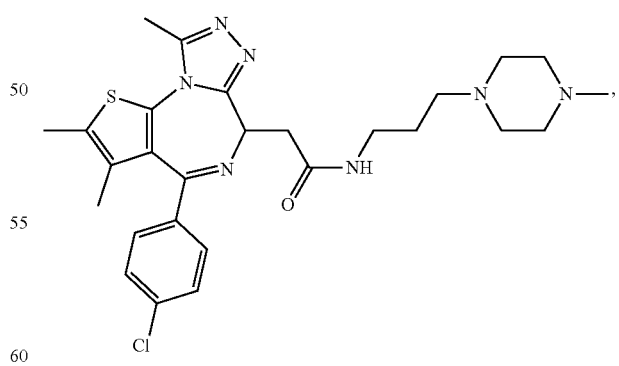

or a pharmaceutically acceptable salt thereof.

11. A method of treating a condition in a subject in need thereof, the method comprising administering to the subject an effective amount of a compound represented by the following structural:

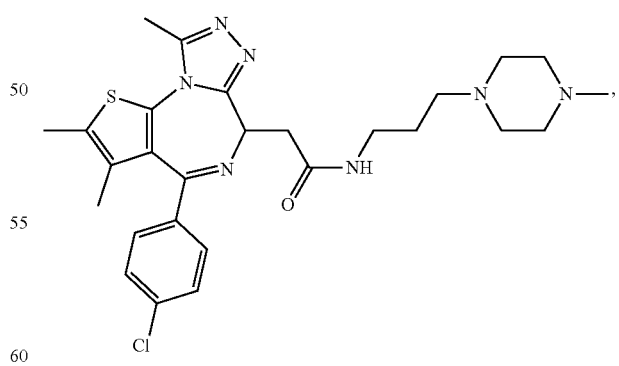

or a pharmaceutically acceptable salt thereof,
wherein the condition is selected from ovarian cancer, Ewing's sarcoma, medulloblastoma, mesothelioma, pancreatic cancer, small cell lung cancer, or melanoma.

12. The method of claim 11, wherein the condition is ovarian cancer.

13. The method of claim 11, wherein the condition is Ewing's sarcoma.

14. The method of claim 11, wherein the condition is medulloblastoma.

15. The method of claim 11, wherein the condition is mesothelioma.

16. The method of claim 11, wherein the condition is pancreatic cancer.

17. The method of claim 11, wherein the condition is small cell lung cancer.

18. The method of claim 11, wherein the condition is melanoma.

* * * * *